US009181245B2

(12) United States Patent
Rombouts et al.

(10) Patent No.: US 9,181,245 B2

(45) Date of Patent: Nov. 10, 2015

(54) SUBSTITUTED PYRIDO[1,2-A]PYRAZINES AND SUBSTITUTED PYRIDO[1,2-A][1,4]DIAZEPINES FOR THE TREATMENT OF (INTER ALIA) ALZHEIMER'S DISEASE

(71) Applicants: Janssen Pharmaceuticals, Inc., Titusville, NJ (US); Cellzome Limited, Brentford, Middlesex (GB)

(72) Inventors: Frederik Jan Rita Rombouts, Antwerpen (BE); Andrés Avelino Trabanco-Suarez, Toldeo (ES); Henricus Jacobus Maria Gijsen, Breda (BE); Gregor James MacDonald, Zoersel (BE); François Paul Bischoff, Vosselaar (BE); Sergio-Alvar Alonso-de-Diego, Toledo (ES); Adriana Ingrid Velter, Antwerpen (BE); Yves Emiel Maria Van Roosbroeck, Antwerpen (BE)

(73) Assignees: Janssen Pharmaceuticals, Inc., Titusville, NJ (US); Cellzome Limited, Cambridgeshire (GB)

( * ) Notice: Subject to any disclaimer, the term of this patent is extended or adjusted under 35 U.S.C. 154(b) by 0 days.

(21) Appl. No.: 14/400,663

(22) PCT Filed: May 16, 2013

(86) PCT No.: PCT/IB2013/054014

§ 371 (c)(1),
(2) Date: Nov. 12, 2014

(87) PCT Pub. No.: WO2013/171712

PCT Pub. Date: Nov. 21, 2013

(65) Prior Publication Data

US 2015/0141411 A1 May 21, 2015

(30) Foreign Application Priority Data

May 16, 2012 (EP) .................................... 12168186
Dec. 6, 2012 (EP) .................................... 12195875
Dec. 13, 2012 (EP) .................................... 12197010
Mar. 14, 2013 (EP) .................................... 13159178

(51) Int. Cl.

| | |
|---|---|
| *A61K 31/4985* | (2006.01) |
| *A61K 31/551* | (2006.01) |
| *C07D 241/36* | (2006.01) |
| *C07D 243/10* | (2006.01) |
| *C07D 471/04* | (2006.01) |

(52) U.S. Cl.

CPC .................................... *C07D 471/04* (2013.01)

(58) Field of Classification Search

CPC ............. A61K 31/4985; A61K 31/551; C07D 241/36; C07D 243/10

USPC .................. 514/221, 249; 540/567; 544/349; 548/335.1, 469

See application file for complete search history.

(56) References Cited

U.S. PATENT DOCUMENTS

| | | | |
|---|---|---|---|
| 5,767,144 | A | 6/1998 | Winn et al. |
| 6,114,334 | A | 9/2000 | Kerrigan et al. |
| 7,923,563 | B2 | 4/2011 | Kushida et al. |
| 8,598,353 | B2 | 12/2013 | Mjalli et al. |
| 2002/0128319 | A1 | 9/2002 | Koo et al. |
| 2006/0004013 | A1 | 1/2006 | Kimura et al. |
| 2008/0280948 | A1 | 11/2008 | Baumann et al. |
| 2009/0062529 | A1 | 3/2009 | Kimura et al. |
| 2010/0137320 | A1 | 6/2010 | Huang et al. |
| 2011/0015175 | A1 | 1/2011 | Marchin et al. |

FOREIGN PATENT DOCUMENTS

| | | |
|---|---|---|
| CN | 101142194 | 3/2008 |
| EP | 1757591 | 2/2007 |
| EP | 1992618 A1 | 11/2008 |
| JP | 2003/502313 | 1/2003 |

(Continued)

OTHER PUBLICATIONS

Jordan, V. C. Nature Reviews: Drug Discovery, 2, 2003, 205.*

(Continued)

*Primary Examiner* — Douglas M Willis

(74) *Attorney, Agent, or Firm* — Baker & Hostetler LLP

(57) ABSTRACT

The present invention is concerned with novel substituted 3,4-dihydro-2H-pyrido[1,2- a]pyrazine-1,6-dione derivatives of Formula (I) wherein $R^1$, $R^2$, $R^3$, $R^4$, $R^5$, Z and X have the meaning defined in the claims. The compounds according to the present invention are useful as gamma secretase modulators. The invention further relates to processes for preparing such novel compounds, pharmaceutical compositions comprising said compounds as an active ingredient as well as the use of said compounds as a medicament.

(I)

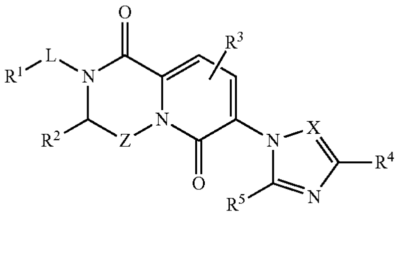

14 Claims, No Drawings

(56) References Cited

FOREIGN PATENT DOCUMENTS

| | | | |
|---|---|---|---|
| WO | WO 01/78721 | | 10/2001 |
| WO | WO 01/87845 | | 11/2001 |
| WO | WO 02/069946 | | 9/2002 |
| WO | WO 2004/017963 | | 3/2004 |
| WO | WO 2004/076448 | | 9/2004 |
| WO | WO 2004/110350 | | 12/2004 |
| WO | WO 2005/016892 | | 5/2005 |
| WO | WO 2005/085245 | | 9/2005 |
| WO | WO 2005/115990 | | 12/2005 |
| WO | WO 2006/135667 | | 12/2006 |
| WO | WO 2007/034252 | | 3/2007 |
| WO | WO 2007/038314 | | 4/2007 |
| WO | WO 2007/043786 | | 4/2007 |
| WO | WO 2007/044895 | | 4/2007 |
| WO | WO 2007/058942 | | 5/2007 |
| WO | WO 2007/102580 | | 9/2007 |
| WO | WO 2007/105053 | | 9/2007 |
| WO | WO 2007/113276 | | 10/2007 |
| WO | WO 2007/131991 | | 11/2007 |
| WO | WO 2008/065199 | | 6/2008 |
| WO | WO 2008/073370 | | 6/2008 |
| WO | WO 2008/082490 | | 7/2008 |
| WO | WO 2008/097538 | | 8/2008 |
| WO | WO 2008/099210 | | 8/2008 |
| WO | WO 2008/100412 | | 8/2008 |
| WO | WO 2008/137139 | | 11/2008 |
| WO | WO 2008/156580 | | 12/2008 |
| WO | WO 2009/005729 | | 1/2009 |
| WO | WO 2009/028588 | | 3/2009 |
| WO | WO 2009/032277 | | 3/2009 |
| WO | WO 2009/050227 | | 4/2009 |
| WO | WO 2009/073777 | | 6/2009 |
| WO | WO 2009/076352 | | 6/2009 |
| WO | WO 2009/103652 | | 8/2009 |
| WO | WO 2009/155551 | | 12/2009 |
| WO | WO 2010/010188 | | 1/2010 |
| WO | WO 2010/052199 | A1 | 5/2010 |
| WO | WO 2010/054067 | | 5/2010 |
| WO | WO 2010/065310 | | 6/2010 |
| WO | WO 2010/070008 | | 6/2010 |
| WO | WO 2010/083141 | | 7/2010 |
| WO | WO 2010/089292 | | 8/2010 |
| WO | WO 2010/094647 | | 8/2010 |
| WO | WO 2010/098487 | | 9/2010 |
| WO | WO 2010/098488 | | 9/2010 |
| WO | WO 2010/098495 | | 9/2010 |
| WO | WO 2010/100606 | | 9/2010 |
| WO | WO 2010/106745 | | 9/2010 |
| WO | WO 2010/126745 | | 11/2010 |
| WO | WO 2010/137320 | | 12/2010 |
| WO | WO 2010/145883 | | 12/2010 |
| WO | WO 2011/006903 | | 1/2011 |
| WO | WO 2011/086098 | | 7/2011 |
| WO | WO 2011/086099 | | 7/2011 |
| WO | WO 2012/131539 | | 4/2012 |
| WO | WO 2012/126984 | | 9/2012 |
| WO | WO 2013/010904 | | 1/2013 |
| WO | WO 2013/171712 | * | 11/2013 |

OTHER PUBLICATIONS

Vippagunta, et al. Advanced Drug Delivery Reviews, 48, 2001, 18.*
Hackam, et al. JAMA, 296(14), 2006, 1731-1732.*
"Crystallization", Kirk-Othmer Encyclopedia of Chemical Technology, 2002, 8, 95-147.
Citron et al. "Mutant Presenilins of Alzheimer's Disease Increase Production of 42-Residue Amyloid β-Protein in Both Transfected Cells and Transgenic Mice", Nature Medicine, Jan. 1997, 3(1), 67-72.
Dyatkin et al., "Determination of the Absolute Configuration of a Key Tricyclic Component of a Novel Vasopressin Receptor Antagonist by Use of Vibrational Circular Dichroism", Chirality, 2002, 14, 215-219.
Eriksen et al., "NSAIDs and Enantiomers of Flurbiprofen Target Gamma-Secretase and Lower A-beta-42 In Vivo", J. Clin Invest, 2003, 112(3), 440-449.
Garofalo, "Patents Targeting Gamma-Secretase Inhibition and Modulation for the Treatment of Alzheimer's Disease: 2004-2008", Expert Opinion Ther. Patents, 2008, 18(7), 693-703.
Greene et al., "Protective Groups in Organic Synthesis", John Wiley & Sons, Inc., Third Edition, 1999, 3 pages.
Guillory (Brittain Ed.). "Polymorphism in Pharmaceutical Solids" Marcel Dekker. Inc., NY, 1999, 50 pages.
International Patent Application No. PCT/EP2011/050350: International Search Report dated Feb. 23, 2011, 3 pages.
Jadhav et al. "Ammonium Metavanadate: A Novel Catalyst for Synthesis of 2-Substituted Benzimidazole Derivatives", Chinese Chemical Letters, 2009, 20, 292-295.
Jain et al., "Polymorphism in Pharmacy", Indian Drugs, 1986, 23(6), 315-329.
Larner, "Secretases as Therapeutic Targets in Alzheimer's Disease: Patents 2000-2004", Exp. Opinion Ther. Patents, 2004, 14, 1403-1420.
Marjaux et al., "γ-Secretase Inhibitors: Still in the running as Alzheimer's Therapeutics", Drug Discovery Today: Therapeutics Strategies, 2004, 1(1), 6 pages.
Matthews et al., "A Convenient Procedure for the Preparation of 4(5)-Cyanoimidazoles", J. Org. Chem., 1986 51, 3228-3231.
Moechars et al., "Early Phenotypic Changes in Transgenic Mice That Overexpress Different Mutants of Amyloid Precursor Protein in Brain", J. Biol. Chem., 1999, 274(10), 6483-6492.
Morihara et al., "Selective Inhibition of Aβ42 Production by NSAID R-Enantiomers", Journal of Neurochemistry, 2002, 83, 1009-1012.
Oumata et al., "Roscovitine-Derived, Dual-Specificity Inhibitors of Cyclin-Dependent Kinases and Casein Kinases 1", J. Med. Chem., 2008, 51, 5229-5242.
Peretto et al., "Synthesis and Biological Activity of Fluriprofen Analogues as Selective Inhibitors of β-Amyloid 1-42 Secretion", J Med Chem 2005, 48, 5705.
Schweisguth et al., "Regulation of Notch Signaling Activity", Current Biology, Feb. 3, 2004, 14, R129-R138.
Sechi et al., "Design and Synthesis of Novel Indole β-Diketo Acid Derivatives as HIV-1 Integrase Inhibitors", J. Med. Chem., 2004, 47, 5298-5310.
Steiner, "Uncovering γ-Secretase", Current Alzheimer Research, 2004, 1(3), 175-181.
Tanzi et al., "Twenty Years of the Alzheimer's Disease Amyloid Hypothesis: A Genetic Perspective", Cell, 2005, 120, 545-555.
Vippagunta et al., "Crystalline Solids", Advanced Drug Delivery Reviews, 2001, 48, 3-26.
Wang et al., "Preparation of a-Chloroketones by the Chloracetate Claisen Reaction", Synlett, 2000, 6, 902-904.
Weggen et al., "A Subset of NSAIDs Lower Amyloidegenic Aβ42 Independently of Cyclooxygenase Activity", Nature, Nov. 2001, 414, 212-216.
Wermuth, "Chapter 13—Molecular Variations Based on Isosteric Replacements", The Practice of Medicinal Chemistry, 1996, 35 pages.
West, "Solid State Chemistry and its Applications", Wiley, New York, 1988, 16 pages (see pp. 358 & 365).
Yu et al. "Physical Characterization of Polymorphic Drugs: An Integrated Characterization Strategy", PSTT, 1998, 1(3), 118-127.
Zettl et al., "Exploring the Chemical Space of γ-Secretase Modulators" ,Trends in Pharmaceutical Sciences, 2010, 31(9), 402-410.
Dorwald, "Side Reactions in Organic Synthesis", Wiley: VCH Weinheim Preface, Chapter 8, 45 pages, 2005.

* cited by examiner

SUBSTITUTED PYRIDO[1,2-A]PYRAZINES AND SUBSTITUTED PYRIDO[1,2-A][1,4]DIAZEPINES FOR THE TREATMENT OF (INTER ALIA) ALZHEIMER'S DISEASE

CROSS REFERENCE TO RELATED APPLICATIONS

This application is the National Stage of International Application No. PCT/IB2013/054014, filed May 16, 2013, which claims the benefit of European Patent Application No. 12168186.0, filed May 16, 2012; European Patent Application No. 12195875.5, filed Dec. 6, 2012; European Patent Application No. 12197010.7, filed Dec. 13, 2012; and European Patent Application No. 13159178.6, filed Mar. 14, 2013, the entire disclosures of each of which are incorporated herein by reference.

FIELD OF THE INVENTION

The present invention is concerned with novel substituted 3,4-dihydro-2H-pyrido[1,2- α]pyrazine-1,6-dione derivatives useful as gamma secretase modulators. The invention further relates to processes for preparing such novel compounds, pharmaceutical compositions comprising said compounds as an active ingredient as well as the use of said compounds as a medicament.

BACKGROUND OF THE INVENTION

Alzheimer's Disease (AD) is a progressive neurodegenerative disorder marked by loss of memory, cognition, and behavioral stability. AD afflicts 6-10% of the population over age 65 and up to 50% over age 85. It is the leading cause of dementia and the third leading cause of death after cardiovascular disease and cancer. There is currently no effective treatment for AD. The total net cost related to AD in the U.S. exceeds $100 billion annually.

AD does not have a simple etiology, however, it has been associated with certain risk factors including (1) age, (2) family history and (3) head trauma; other factors include environmental toxins and low levels of education. Specific neuropathological lesions in the limbic and cerebral cortices include intracellular neurofibrillary tangles consisting of hyperphosphorylated tau protein and the extracellular deposition of fibrillar aggregates of amyloid beta peptides (amyloid plaques). The major components of amyloid plaques are the amyloid beta (A-beta, Abeta or Aβ) peptides of various lengths. A variant thereof, which is the Aβ1-42-peptide (Abeta-42), is believed to be the major causative agent for amyloid formation. Another variant is the Aβ1-40-peptide (Abeta-40). Aβ is the proteolytic product of a precursor protein, beta amyloid precursor protein (beta-APP or APP).

Familial, early onset autosomal dominant forms of AD have been linked to missense mutations in the β-amyloid precursor protein (β-APP or APP) and in the presenilin proteins 1 and 2. In some patients, late onset forms of AD have been correlated with a specific allele of the apolipoprotein E (ApoE) gene, and, more recently, the finding of a mutation in alpha2-macroglobulin, which may be linked to at least 30% of the AD population. Despite this heterogeneity, all forms of AD exhibit similar pathological findings. Genetic analysis has provided the best clues for a logical therapeutic approach to AD. All mutations found to date, affect the quantitative or qualitative production of the amyloidogenic peptides known as Abeta-peptides (Aβ), specifically Aβ42, and have given strong support to the "amyloid cascade hypothesis" of AD (Tanzi and Bertram, 2005, Cell 120, 545). The likely link between Aβ peptide generation and AD pathology emphasizes the need for a better understanding of the mechanisms of Aβ production and strongly warrants a therapeutic approach at modulating Aβ levels.

The release of Aβ peptides is modulated by at least two proteolytic activities referred to as β- and γ-secretase cleavage at the N-terminus (Met-Asp bond) and the C-terminus (residues 37-42) of the Aβ peptide, respectively. In the secretory pathway, there is evidence that β-secretase cleaves first, leading to the secretion of s-APPβ (sβ) and the retention of a 11 kDa membrane-bound carboxy terminal fragment (CTF). The latter is believed to give rise to Aβ peptides following cleavage by γ-secretase. The amount of the longer isoform, Aβ42, is selectively increased in patients carrying certain mutations in the region of a particular gene coding in a particular protein (presenilin), and these mutations have been correlated with early-onset familial AD. Therefore, Aβ42 is believed by many researchers to be the main culprit of the pathogenesis of AD.

It has now become clear that the γ-secretase activity cannot be ascribed to a single protein, but is in fact associated with an assembly of different proteins.

The gamma (γ)-secretase activity resides within a multiprotein complex containing at least four components: the presenilin (PS) heterodimer, nicastrin, aph-1 and pen-2. The PS heterodimer consists of the amino- and carboxyterminal PS fragments generated by endoproteolysis of the precursor protein. The two aspartates of the catalytic site are at the interface of this heterodimer. It has recently been suggested that nicastrin serves as a gamma-secretase-substrate receptor. The functions of the other members of gamma-secretase are unknown, but they are all required for activity (Steiner, 2004. Curr. Alzheimer Research 1(3): 175-181).

Thus, although the molecular mechanism of the second cleavage-step has remained elusive until now, the γ-secretase-complex has become one of the prime targets in the search for compounds for the treatment of AD.

Various strategies have been proposed for targeting γ-secretase in AD, ranging from targeting the catalytic site directly, developing substrate-specific inhibitors and modulators of γ-secretase activity (Marjaux et al., 2004. Drug Discovery Today: Therapeutic Strategies, Volume 1, 1-6). Accordingly, a variety of compounds were described that have secretases as targets (Lamer, 2004. Secretases as therapeutics targets in AD: patents 2000-2004. Expert Opin. Ther. Patents 14, 1403-1420).

Indeed, this finding was supported by biochemical studies in which an effect of certain Non-Steroidal Anti-Inflammatory Drugs (NSAIDs) on γ-secretase was shown (US 2002/0128319; Eriksen (2003) J. Clin. Invest. 112, 440). Potential limitations for the use of NSAIDs to prevent or treat AD are their inhibition activity of cyclooxygenase (COX) enzymes, which can lead to unwanted side effects, and their low CNS penetration (Peretto et al., 2005, J. Med. Chem. 48, 5705-5720). More recently the NSAID R-flurbiprofen, an enantiomer lacking Cox-inhibitory activity and related gastric toxicity, has failed in large phase III trial since the drug did not improve thinking ability or the ability of patients to carry out daily activities significantly more than those patients on placebo.

WO-2010/100606 discloses phenyl imidazoles and phenyl triazoles for use as gamma-secretase modulators.

US20090062529 relates to polycyclic compounds effective as therapeutic or prophylactic agents for a disease caused by Aβ.

WO-2010/070008 is concerned with novel substituted bicyclic imidazole derivatives useful as γ-secretase modulators.

WO-2010/089292 is concerned with novel substituted bicyclic heterocyclic compounds useful as γ-secretase modulators.

WO-2011/006903 is concerned with novel substituted triazole and imidazole derivatives useful as γ-secretase modulators.

WO-2012/131539 relates to novel bicyclic pyridinones useful as brain-penetrable γ-secretase modulators.

There is a strong need for novel compounds which modulate γ-secretase activity thereby opening new avenues for the treatment of AD. It is an object of the present invention to overcome or ameliorate at least one of the disadvantages of the prior art, or to provide a useful alternative. The compounds of the present invention or part of the compounds of the present invention may have improved metabolic stability properties, improved central brain availability, improved solubilities, or reduced CYP inhibition compared with the compounds disclosed in the prior art. It is accordingly an object of the present invention to provide such novel compounds.

SUMMARY OF THE INVENTION

It has been found that the compounds of the present invention are useful as γ-secretase modulators. The compounds according to the invention and the pharmaceutically acceptable compositions thereof, may be useful in the treatment or prevention of AD.

The present invention concerns novel compounds of Formula (I):

(I)

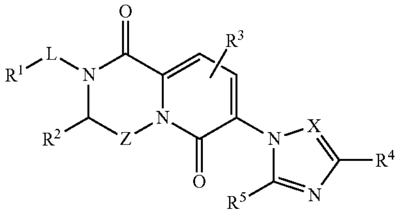

tautomers and stereoisomeric forms thereof, wherein $R^1$ is hydrogen, $C_{1-4}$alkyl or Ar;

provided however that $R^1$ is $C_{1-4}$alkyl or Ar when L is a covalent bond;

$R^2$ is hydrogen, phenyl, cyclo$C_{3-7}$alkyl, tetrahydro-2H-pyranyl, tetrahydro-2H-thiopyranyl, piperidinyl, or $C_{1-4}$alkyl optionally substituted with one or more substituents each independently selected from the group consisting of halo, hydroxyl, $C_{1-4}$alkyloxy and $NR^7R^8$;

Z is methylene or 1,2-ethanediyl, wherein methylene or 1,2-ethanediyl is optionally substituted with one or two $C_{1-4}$alkyl substituents;

L is a covalent bond, $—(CH_2)_{m-n}—Y—(CH_2)_n—$, 1,2-cyclopropanediyl, $C_{1-6}$alkanediyl optionally substituted with one or more substituents selected from the group consisting of tetrahydro-2H-pyranyl, phenyl and $C_{1-4}$alkyloxy$C_{1-4}$alkyl, or $C_{1-6}$alkanediyl wherein two geminal hydrogen atoms are replaced by $C_{2-6}$alkanediyl;

m represents 3, 4, 5, 6 or 7;

n represents 1, 2 or 3;

Y is O or NH;

Ar is a ring system selected from the group consisting of phenyl, indolyl, oxazolyl, benzo[b]thienyl, 1,3-benzodioxolyl, 1,4-benzodioxanyl, 3,4-dihydro-2H-1,5-benzodioxepinyl, pyridyl, indanyl, 1,2,3,4-tetrahydro-1-naphthalenyl, and naphthalenyl;

wherein said ring system is optionally substituted with one or more substituents each independently selected from the group consisting of halo, $Ar^2$, $R^0$, $C_{1-4}$alkyl optionally substituted with one or more substituents each independently selected from the group consisting of halo, $C_{1-4}$alkyloxy and cyclo$C_{3-7}$alkyl, and $C_{1-4}$alkyloxy optionally substituted with one or more substituents each independently selected from the group consisting of halo and cyclo$C_{3-7}$alkyl;

$Ar^2$ is phenyl optionally substituted with one or more substituents each independently selected from the group consisting of halo and $C_{1-4}$alkyl optionally substituted with one or more halo substituents;

$R^3$ is hydrogen, halo or $C_{1-4}$alkyl;

$R^4$ is hydrogen, halo or $C_{1-4}$alkyl;

$R^5$ is hydrogen or $C_{1-4}$alkyl;

X is $CR^6$ or N;

$R^6$ is hydrogen or $C_{1-4}$alkyl;

$R^7$ is hydrogen or $C_{1-4}$alkyl;

$R^8$ is hydrogen or $C_{1-4}$alkyl;

$R^0$ is a ring system selected from the group consisting of piperidinyl, morpholinyl, cyclo$C_{3-7}$alkyl, pyrazolyl and pyrrolidinyl; wherein said ring system is optionally substituted with one or more substituents each independently selected from the group consisting of halo or $C_{1-4}$alkyl optionally substituted with one or more halo atoms;

and the pharmaceutically acceptable addition salts, and the solvates thereof.

The present invention also concerns methods for the preparation of compounds of Formula (I) and pharmaceutical compositions comprising them.

The present compounds were found to modulate the γ-secretase activity in vitro and in vivo, and therefore may be useful in the treatment or prevention of AD, traumatic brain injury (TBI), dementia pugilistica, mild cognitive impairment (MCI), senility, dementia, dementia with Lewy bodies, cerebral amyloid angiopathy, multi-infarct dementia, Down's syndrome, dementia associated with Parkinson's disease and dementia associated with beta-amyloid; preferably AD and other disorders with Beta-amyloid pathology (e.g. glaucoma).

In view of the aforementioned pharmacology of the compounds of Formula (I), it follows that they may be suitable for use as a medicament.

More especially the compounds may be suitable in the treatment or prevention of AD, cerebral amyloid angiopathy, multi-infarct dementia, dementia pugilistica and Down syndrome.

The present invention also concerns the use of compounds according to the general Formula (I), the tautomers and the stereoisomeric forms thereof, and the pharmaceutically acceptable acid or base addition salts and the solvates thereof, for the manufacture of a medicament for the modulation of γ-secretase activity.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

Whenever a radical or group is defined as "optionally substituted" in the present invention, it is meant that said radical or group is unsubstituted or is substituted. For instance, when Ar is defined as "Ar is a ring system selected from the group consisting of phenyl, indolyl, oxazolyl, benzo[b]thienyl, 1,3-benzodioxolyl, 1,4-benzodioxanyl, 3,4-dihydro-2H-1,5-benzodioxepinyl, pyridyl, indanyl, 1,2,3,4-tetrahydro-1-naphthalenyl, and naphthalenyl; wherein said ring system is optionally substituted with one or more substituents each independently selected from the group consisting of halo, $Ar^2$, $R^0$, $C_{1-4}$alkyl optionally substituted with one or more substituents each independently selected from the group consisting of halo, $C_{1-4}$alkyloxy and cyclo$C_{3-7}$alkyl, and $C_{1-4}$alkyloxy optionally substituted with one or more substituents each independently selected from the group consisting of halo and cyclo$C_{3-7}$alkyl;" it is meant that:

"Ar is a ring system selected from the group consisting of phenyl, indolyl, oxazolyl, benzo[b]thienyl, 1,3-benzodioxolyl, 1,4-benzodioxanyl, 3,4-dihydro-2H-1,5-benzodioxepinyl, pyridyl, indanyl, 1,2,3,4-tetrahydro-1-naphthalenyl, and naphthalenyl; or Ar is a ring system selected from the group consisting of phenyl, indolyl, oxazolyl, benzo[b]thienyl, 1,3-benzodioxolyl, 1,4-benzodioxanyl, 3,4-dihydro-2H-1,5-benzodioxepinyl, pyridyl, indanyl, 1,2,3,4-tetrahydro-1-naphthalenyl, and naphthalenyl; wherein said ring system is substituted with one or more substituents each independently selected from the group consisting of halo, $Ar^2$, $R^0$, $C_{1-4}$alkyl optionally substituted with one or more substituents each independently selected from the group consisting of halo, $C_{1-4}$alkyloxy and cyclo$C_{3-7}$ alkyl, and $C_{1-4}$ alkyloxy optionally substituted with one or more substituents each independently selected from the group consisting of halo and cyclo$C_{3-7}$ alkyl".

Whenever the term "substituted" is used in the present invention, it is meant, unless otherwise is indicated or is clear from the context, to indicate that one or more hydrogens, in particular from 1 to 4 hydrogens, preferably from 1 to 3 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

The term "halo" as a group or part of a group is generic for fluoro, chloro, bromo, iodo unless otherwise is indicated or is clear from the context.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, more preferably 1 to 2 carbon atoms. $C_{1-4}$alkyl groups may be linear or branched and may be substituted as indicated herein. When a subscript is used herein following a carbon atom, the subscript refers to the number of carbon atoms that the named group may contain. $C_{1-4}$alkyl includes all linear, or branched alkyl groups with between 1 and 4 carbon atoms, and thus includes such as for example methyl, ethyl, n-propyl, i-propyl, 2-methyl-ethyl, butyl and its isomers (e.g. n-butyl, isobutyl and tert-butyl), and the like.

The term "$C_{1-4}$alkyloxy" as a group or part of a group refers to a radical having the Formula $OR^b$ wherein $R^b$ is $C_{1-4}$alkyl. Non-limiting examples of suitable $C_{1-4}$alkyloxy include methyloxy (also methoxy), ethyloxy (also ethoxy), propyloxy, isopropyloxy, butyloxy, isobutyloxy, sec-butyloxy and tert-butyloxy.

The term "cyclo$C_{3-7}$alkyl" alone or in combination, refers to a cyclic saturated hydrocarbon radical having from 3 to 7 carbon atoms. Non-limiting examples of suitable cyclo$C_{3-7}$alkyl include cyclopropyl, cyclobutyl, cyclopentyl, cyclohexyl and cycloheptyl.

The term "$C_{1-6}$alkanediyl" as a group or part of a group defines bivalent straight or branched chained saturated hydrocarbon radicals having from 1 to 6 carbon atoms such as, for example, methylene or methanediyl, ethan-1,2-diyl, ethan-1,1-diyl or ethylidene, propan-1,3-diyl, propan-1,2-diyl, butan-1,4-diyl, pentan-1,5-diyl, pentan-1,1-diyl, hexan-1,6-diyl, 2-methylbutan-1,4-diyl, 3-methylpentan-1,5-diyl and the like.

The term "$C_{2-6}$alkanediyl" as a group or part of a group defines bivalent straight or branched chained saturated hydrocarbon radicals having from 2 to 6 carbon atoms such as, for example, ethan-1,2-diyl, ethan-1,1-diyl or ethylidene, propan-1,3-diyl, propan-1,2-diyl, butan-1,4-diyl, pentan-1,5-diyl, pentan-1,1-diyl, hexan-1,6-diyl, 2-methylbutan-1,4-diyl, 3-methylpentan-1,5-diyl and the like; in particular "$C_{2-6}$alkanediyl" as a group or part of a group defines ethan-1,2-diyl.

Similarly, the term "$C_{1-3}$alkanediyl" as a group or part of a group defines bivalent straight or branched chained saturated hydrocarbon radicals having from 1 to 3 carbon atoms.

Whenever variable 1' represents $-(CH_2)_{m-n}-Y-(CH_2)_n-$, it is intended that $-(CH_2)_{m-n}-$ is attached to '$R^1$' and $-(CH_2)_n-$ is attached via the nitrogen atom to the remainder of the molecule. This is illustrated by formula (I'):

(I')

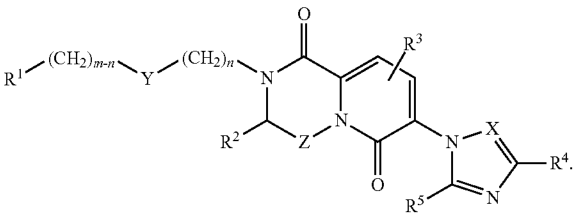

The chemical names of the compounds of the present invention were generated according to the nomenclature rules agreed upon by the Chemical Abstracts Service, using Advanced Chemical Development, Inc., nomenclature software (ACD/Labs Release 12.00 Product version 12.01; Build 33104, 27 May 2009). In case of tautomeric forms, the name of the depicted tautomeric form was generated. It should be clear that the other non-depicted tautomeric form is also included within the scope of the present invention.

Hereinbefore and hereinafter, the term "compound of formula (I)" is meant to include the tautomers and stereoisomeric forms thereof, and the pharmaceutically acceptable addition salts, and the solvates thereof.

The terms "stereoisomers", "stereoisomeric forms" or "stereochemically isomeric forms" hereinbefore or hereinafter are used interchangeably.

The invention includes all stereoisomers of the compound of Formula (I) and tautomers thereof, either as a pure stereoisomer or as a mixture of two or more stereoisomers. Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the invention includes enantiomers, diastereomers, racemates, E isomers, Z isomers, cis isomers, trans isomers and mixtures thereof, whenever chemically possible.

The absolute configuration is specified according to the Cahn-Ingold-Prelog system. The configuration at an asymmetric atom is specified by either R or S. Resolved compounds whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other isomers. Thus, when a compound of formula (I) is for instance specified as (R), this means that the compound is substantially free of the (S) isomer; when a compound of formula (I) is for instance specified as E, this means that the compound is substantially free of the Z isomer; when a compound of formula (I) is for instance specified as cis, this means that the compound is substantially free of the trans isomer.

For indications of stereochemistry in compounds of formula (I) wherein L is $CH(CH_3)$ or $CH(CH_2CH_3)$, the following numbering has been used to indicate the stereocenters of the diastereomers:

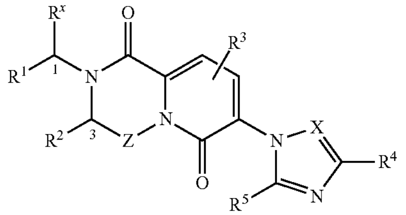

$R^x$ is methyl or ethyl

Some of the compounds according to formula (I) may also exist in their tautomeric form. Such forms although not explicitly indicated in the above formula are intended to be included within the scope of the present invention.

For therapeutic use, salts of the compounds of Formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds of Formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds of Formula (I) are able to form, as well as the salts thereof. Examples of such forms are e.g. hydrates, alcoholates and the like.

The compounds of Formula (I) as prepared in the processes described below may be synthesized in the form of mixtures of enantiomers, in particular racemic mixtures of enantiomers, that can be separated from one another following art-known resolution procedures. An manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the framework of this application, a compound according to the invention is inherently intended to comprise all isotopic combinations of its chemical elements. In the framework of this application, a chemical element, in particular when mentioned in relation to a compound according to Formula (I), comprises all isotopes and isotopic mixtures of this element. For example, when hydrogen is mentioned, it is understood to refer to $^1H$, $^2H$, $^3H$ and mixtures thereof.

A compound according to the invention therefore inherently comprises a compound with one or more isotopes of one or more element, and mixtures thereof, including a radioactive compound, also called radiolabelled compound, wherein one or more non-radioactive atoms has been replaced by one of its radioactive isotopes. By the term "radiolabelled compound" is meant any compound according to Formula (I) which contains at least one radioactive atom. For example, a compound can be labelled with positron or with gamma emitting radioactive isotopes. For radioligand-binding techniques, the $^{3}H$-atom or the $^{125}I$-atom is the atom of choice to be inserted. For imaging, the most commonly used positron emitting (PET) radioactive isotopes are $^{11}C$, $^{18}F$, $^{15}O$ and $^{13}N$, all of which are accelerator produced and have half-lives of 20, 100, 2 and 10 minutes (min) respectively. Since the half-lives of these radioactive isotopes are so short, it is only feasible to use them at institutions which have an accelerator on site for their production, thus limiting their use. The most widely used of these are $^{18}F$, $^{99m}Tc$, $^{201}Tl$ and $^{123}I$. The handling of these radioactive isotopes, their production, isolation and incorporation in a molecule are known to the skilled person.

In particular, the radioactive atom is selected from the group of hydrogen, carbon, nitrogen, sulfur, oxygen and halogen. In particular, the radioactive isotope is selected from the group of $^{3}H$, $^{11}C$, $^{18}F$, $^{122}I$, $^{123}I$, $^{125}I$, $^{131}I$, $^{75}Br$, $^{76}Br$, $^{77}Br$ and $^{82}Br$.

As used in the specification and the appended claims, the singular forms "a", "an," and "the" also include plural referents unless the context clearly dictates otherwise. For example, "a compound" means 1 compound or more than 1 compound.

It should be understood that the term "compounds of Formula (I)" or "a compound of Formula (I)" as used in the specification, also covers the tautomers and stereoisomeric forms thereof, and the pharmaceutically acceptable addition salts, and the solvates thereof.

The terms described above and others used in the specification are well understood to those in the art.

Preferred features of the compounds of this invention are now set forth.

In an embodiment, the present invention concerns novel compounds of Formula (I):

(I)

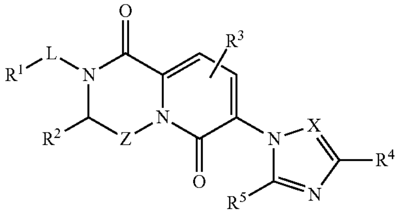

tautomers and stereoisomeric forms thereof, wherein $R^1$ is hydrogen, $C_{1-4}$alkyl or Ar;
- provided however that $R^1$ is $C_{1-4}$alkyl or Ar when L is a covalent bond;

$R^2$ is hydrogen, phenyl, cyclo$C_{3-7}$alkyl, tetrahydro-2H-pyranyl, tetrahydro-2H-thiopyranyl, piperidinyl, or $C_{1-4}$alkyl optionally substituted with one or more substituents each independently selected from the group consisting of hydroxyl, $C_{1-4}$alkyloxy and $NR^7R^8$;

Z is methylene or 1,2-ethanediyl, wherein methylene or 1,2-ethanediyl is optionally substituted with one or two $C_{1-4}$alkyl substituents;

L is a covalent bond, $—(CH_2)_{m-n}—Y—(CH_2)_n—$, 1,2-cyclopropanediyl,
- $C_{1-6}$alkanediyl optionally substituted with one or more substituents selected from the group consisting of tetrahydro-2H-pyranyl, phenyl and $C_{1-4}$alkyloxy$C_{1-4}$alkyl, or $C_{1-6}$alkanediyl wherein two geminal hydrogen atoms are replaced by $C_{2-6}$alkanediyl;

m represents 3, 4, 5, 6 or 7;

n represents 1, 2 or 3;

Y is O or NH;

Ar is a ring system selected from the group consisting of phenyl, indolyl, oxazolyl, benzo[b]thienyl, 1,3-benzodioxolyl, 1,4-benzodioxanyl, 3,4-dihydro-2H-1,5-benzodioxepinyl, pyridyl, indanyl, 1,2,3,4-tetrahydro-1-naphthalenyl, and naphthalenyl;

wherein said ring system is optionally substituted with one or more substituents each independently selected from the group consisting of halo, $Ar^2$, $R^0$, $C_{1-4}$alkyl optionally substituted with one or more substituents each independently selected from the group consisting of halo, $C_{1-4}$alkyloxy and cyclo$C_{3-7}$alkyl, and $C_{1-4}$alkyloxy optionally substituted with one or more substituents each independently selected from the group consisting of halo and cyclo$C_{3-7}$alkyl;

$Ar^2$ is phenyl optionally substituted with one or more substituents each independently selected from the group consisting of halo and $C_{1-4}$alkyl optionally substituted with one or more halo substituents;

$R^3$ is hydrogen, halo or $C_{1-4}$alkyl;

$R^4$ is hydrogen, halo or $C_{1-4}$alkyl;

$R^5$ is hydrogen or $C_{1-4}$alkyl;

X is $CR^6$ or N;

$R^6$ is hydrogen or $C_{1-4}$alkyl;

$R^7$ is hydrogen or $C_{1-4}$alkyl;

$R^8$ is hydrogen or $C_{1-4}$alkyl;

$R^0$ is a ring system selected from the group consisting of piperidinyl, morpholinyl, cyclo$C_{3-7}$alkyl, pyrazolyl and pyrrolidinyl; wherein said ring system is optionally substituted with one or more substituents each independently selected from the group consisting of halo or $C_{1-4}$alkyl optionally substituted with one or more halo atoms;

and the pharmaceutically acceptable addition salts, and the solvates thereof.

In an embodiment, the present invention concerns novel compounds of Formula (I), tautomers and stereoisomeric forms thereof, wherein $R^1$ is hydrogen, $C_{1-4}$alkyl or Ar;
- provided however that $R^1$ is $C_{1-4}$alkyl or Ar when L is a covalent bond;

$R^2$ is hydrogen, phenyl, cyclo$C_{3-7}$alkyl, tetrahydro-2H-pyranyl, tetrahydro-2H-thiopyranyl, piperidinyl, or $C_{1-4}$alkyl optionally substituted with one or more substituents each independently selected from the group consisting of halo, hydroxyl, $C_{1-4}$alkyloxy and $NR^7R^8$;

Z is methylene or 1,2-ethanediyl, wherein methylene or 1,2-ethanediyl is optionally substituted with one or two $C_{1-4}$alkyl substituents;

L is a covalent bond, 1,2-cyclopropanediyl,
- $C_{1-6}$alkanediyl optionally substituted with one or more substituents selected from the group consisting of tetrahydro-2H-pyranyl, phenyl and $C_{1-4}$alkyloxy$C_{1-4}$alkyl, or $C_{1-6}$alkanediyl wherein two geminal hydrogen atoms are replaced by $C_{2-6}$alkanediyl;

Ar is a ring system selected from the group consisting of phenyl, indolyl, oxazolyl, benzo[b]thienyl, 1,3-benzodioxolyl, 1,4-benzodioxanyl, 3,4-dihydro-2H-1,5-benzodioxepinyl, pyridyl, indanyl, 1,2,3,4-tetrahydro-1-naphthalenyl, and naphthalenyl;
- wherein said ring system is optionally substituted with one or more substituents each independently selected from the group consisting of halo, $Ar^2$, $R^0$,
- $C_{1-4}$alkyl optionally substituted with one or more substituents each independently selected from the group consisting of halo, $C_{1-4}$alkyloxy and cyclo$C_{3-7}$alkyl, and $C_{1-4}$alkyloxy optionally substituted with one or more substituents each independently selected from the group consisting of halo and cyclo$C_{3-7}$alkyl;

$Ar^2$ is phenyl optionally substituted with one or more substituents each independently selected from the group consisting of halo and $C_{1-4}$alkyl optionally substituted with one or more halo substituents;

$R^3$ is hydrogen, halo or $C_{1-4}$alkyl;

$R^4$ is hydrogen, halo or $C_{1-4}$alkyl;

$R^5$ is hydrogen or $C_{1-4}$alkyl;

X is $CR^6$ or N;

$R^6$ is hydrogen or $C_{1-4}$alkyl;

$R^7$ is hydrogen or $C_{1-4}$alkyl;

$R^8$ is hydrogen or $C_{1-4}$alkyl;

$R^0$ is a ring system selected from the group consisting of piperidinyl, morpholinyl, cyclo$C_{3-7}$alkyl, pyrazolyl and pyrrolidinyl; wherein said ring system is optionally substituted with one or more substituents each independently selected from the group consisting of halo or $C_{1-4}$alkyl optionally substituted with one or more halo atoms;

and the pharmaceutically acceptable addition salts, and the solvates thereof.

In an embodiment, the present invention concerns novel compounds of Formula (I), tautomers and stereoisomeric forms thereof, wherein $R^1$ is hydrogen, $C_{1-4}$alkyl or Ar;

provided however that $R^1$ is $C_{1-4}$alkyl or Ar when L is a covalent bond;

$R^2$ is hydrogen, phenyl, cyclo$C_{3-7}$alkyl, tetrahydro-2H-pyranyl, tetrahydro-2H-thiopyranyl, piperidinyl, or $C_{1-4}$alkyl optionally substituted with one or more substituents each independently selected from the group consisting of halo, hydroxyl, $C_{1-4}$alkyloxy and $NR^7R^8$;

Z is methylene or 1,2-ethanediyl, wherein methylene or 1,2-ethanediyl is optionally substituted with one or two $C_{1-4}$alkyl substituents;

L is a covalent bond, 1,2-cyclopropanediyl, $C_{1-6}$alkanediyl optionally substituted with one or more substituents selected from the group consisting of tetrahydro-2H-pyranyl, phenyl and $C_{1-4}$alkyloxy$C_{1-4}$alkyl, or $C_{1-6}$alkanediyl wherein two geminal hydrogen atoms are replaced by $C_{2-6}$alkanediyl;

in particular L is $C_{1-6}$alkanediyl;

Ar is indolyl optionally substituted with one or more substituents each independently selected from the group consisting of halo, $Ar^2$, $R^0$, $C_{1-4}$alkyl optionally substituted with one or more substituents each independently selected from the group consisting of halo, $C_{1-4}$alkyloxy and cyclo$C_{3-7}$alkyl, and $C_{1-4}$alkyloxy optionally substituted with one or more substituents each independently selected from the group consisting of halo and cyclo$C_{3-7}$alkyl;

$Ar^2$ is phenyl optionally substituted with one or more substituents each independently selected from the group consisting of halo and $C_{1-4}$alkyl optionally substituted with one or more halo substituents;

$R^3$ is hydrogen, halo or $C_{1-4}$alkyl;

$R^4$ is hydrogen, halo or $C_{1-4}$alkyl;

$R^5$ is hydrogen or $C_{1-4}$alkyl;

X is $CR^6$ or N;

$R^6$ is hydrogen or $C_{1-4}$alkyl;

$R^7$ is hydrogen or $C_{1-4}$alkyl;

$R^8$ is hydrogen or $C_{1-4}$alkyl;

$R^0$ is a ring system selected from the group consisting of piperidinyl, morpholinyl, cyclo$C_{3-7}$alkyl, pyrazolyl and pyrrolidinyl; wherein said ring system is optionally substituted with one or more substituents each independently selected from the group consisting of halo or $C_{1-4}$alkyl optionally substituted with one or more halo atoms;

and the pharmaceutically acceptable addition salts, and the solvates thereof.

In an embodiment, the present invention concerns novel compounds of Formula (I), tautomers and stereoisomeric forms thereof, wherein $R^1$ is Ar;

$R^2$ is hydrogen, or methyl; in particular methyl;

Z is methylene;

L is a covalent bond or $C_{1-6}$alkanediyl;

Ar is indolyl optionally substituted with one or more substituents each independently selected from the group consisting of halo, $Ar^2$, $C_{1-4}$alkyl optionally substituted with one or more halo substituents, and $C_{1-4}$alkyloxy optionally substituted with one or more halo substituents each independently selected from the group consisting of halo;

$Ar^2$ is phenyl;

$R^3$ is hydrogen;

$R^4$ is methyl;

$R^5$ is hydrogen;

X is CH;

and the pharmaceutically acceptable addition salts, and the solvates thereof.

In an embodiment, the present invention concerns novel compounds of Formula (I), tautomers and stereoisomeric forms thereof, wherein $R^1$ is hydrogen, $C_{1-4}$alkyl or Ar;

provided however that R' is $C_{1-4}$alkyl or Ar when L is a covalent bond;

$R^2$ is methyl;

Z is methylene or 1,2-ethanediyl, wherein methylene or 1,2-ethanediyl is optionally substituted with one or two $C_{1-4}$alkyl substituents;

L is a covalent bond, $—(CH_2)_{m-n}—Y—(CH_2)_n—$, 1,2-cyclopropanediyl, $C_{1-6}$alkanediyl optionally substituted with one or more substituents selected from the group consisting of tetrahydro-2H-pyranyl, phenyl and $C_{1-4}$alkyloxy$C_{1-4}$alkyl, or $C_{1-6}$alkanediyl wherein two geminal hydrogen atoms are replaced by $C_{2-6}$alkanediyl;

m represents 3, 4, 5, 6 or 7;

n represents 1, 2 or 3; in particular n represents 1 or 2;

Y is O or NH;

Ar is a ring system selected from the group consisting of phenyl, indolyl, oxazolyl, benzo[b]thienyl, 1,3-benzodioxolyl, 1,4-benzodioxanyl, 3,4-dihydro-2H-1,5-benzodioxepinyl, pyridyl, indanyl, 1,2,3,4-tetrahydro-1-naphthalenyl, and naphthalenyl;

wherein said ring system is optionally substituted with one or more substituents each independently selected from the group consisting of halo, $Ar^2$, $R^0$, $C_{1-4}$alkyl optionally substituted with one or more substituents each independently selected from the group consisting of halo, $C_{1-4}$alkyloxy and cyclo$C_{3-7}$alkyl, and $C_{1-4}$alkyloxy optionally substituted with one or more substituents each independently selected from the group consisting of halo and cyclo$C_{3-7}$alkyl;

$Ar^2$ is phenyl optionally substituted with one or more substituents each independently selected from the group consisting of halo and $C_{1-4}$alkyl optionally substituted with one or more halo substituents;

$R^3$ is hydrogen, halo or $C_{1-4}$alkyl;

$R^4$ is hydrogen, halo or $C_{1-4}$alkyl;

$R^5$ is hydrogen or $C_{1-4}$alkyl;
X is $CR^6$ or N;
$R^6$ is hydrogen or $C_{1-4}$alkyl;
$R^7$ is hydrogen or $C_{1-4}$alkyl;
$R^8$ is hydrogen or $C_{1-4}$alkyl;
$R^0$ is a ring system selected from the group consisting of piperidinyl, morpholinyl, cyclo$C_{3-7}$alkyl, pyrazolyl and pyrrolidinyl; wherein said ring system is optionally substituted with one or more substituents each independently selected from the group consisting of halo or $C_{1-4}$alkyl optionally substituted with one or more halo atoms;
and the pharmaceutically acceptable addition salts, and the solvates thereof.

In an embodiment, the present invention concerns novel compounds of Formula (I), tautomers and stereoisomeric forms thereof, wherein
$R^1$ is hydrogen, $C_{1-4}$alkyl or Ar;
provided however that $R^1$ is $C_{1-4}$alkyl or Ar when L is a covalent bond;
$R^2$ is methyl;
Z is methylene or 1,2-ethanediyl, wherein methylene or 1,2-ethanediyl is optionally substituted with one or two $C_{1-4}$alkyl substituents;
L is ethylidene;
m represents 3, 4, 5, 6 or 7;
n represents 1, 2 or 3; in particular n represents 1 or 2;
Y is O or NH;
Ar is a ring system selected from the group consisting of phenyl, indolyl, oxazolyl, benzo[b]thienyl, 1,3-benzodioxolyl, 1,4-benzodioxanyl, 3,4-dihydro-2H-1,5-benzodioxepinyl, pyridyl, indanyl, 1,2,3,4-tetrahydro-1-naphthalenyl, and naphthalenyl;
wherein said ring system is optionally substituted with one or more substituents each independently selected from the group consisting of halo, $Ar^2$, $R^0$,
$C_{1-4}$alkyl optionally substituted with one or more substituents each independently selected from the group consisting of halo, $C_{1-4}$alkyloxy and cyclo$C_{3-7}$alkyl, and
$C_{1-4}$alkyloxy optionally substituted with one or more substituents each independently selected from the group consisting of halo and cyclo$C_{3-7}$alkyl;
$Ar^2$ is phenyl optionally substituted with one or more substituents each independently selected from the group consisting of halo and $C_{1-4}$alkyl optionally substituted with one or more halo substituents;
$R^3$ is hydrogen, halo or $C_{1-4}$alkyl;
$R^4$ is hydrogen, halo or $C_{1-4}$alkyl;
$R^5$ is hydrogen or $C_{1-4}$alkyl;
X is $CR^6$ or N;
$R^6$ is hydrogen or $C_{1-4}$alkyl;
$R^7$ is hydrogen or $C_{1-4}$alkyl;
$R^8$ is hydrogen or $C_{1-4}$alkyl;
$R^0$ is a ring system selected from the group consisting of piperidinyl, morpholinyl,
cyclo$C_{3-7}$alkyl, pyrazolyl and pyrrolidinyl; wherein said ring system is optionally substituted with one or more substituents each independently selected from the group consisting of halo or $C_{1-4}$alkyl optionally substituted with one or more halo atoms;
and the pharmaceutically acceptable addition salts, and the solvates thereof.

In an embodiment, the present invention concerns novel compounds of Formula (I), tautomers and stereoisomeric forms thereof, wherein
$R^1$ is hydrogen, $C_{1-4}$alkyl or Ar;
provided however that $R^1$ is $C_{1-4}$alkyl or Ar when L is a covalent bond;
$R^2$ is hydrogen, phenyl, cyclo$C_{3-7}$alkyl, tetrahydro-2H-pyranyl, tetrahydro-2H-thiopyranyl, piperidinyl, or $C_{1-4}$alkyl optionally substituted with one or more substituents each independently selected from the group consisting of halo, hydroxyl, $C_{1-4}$alkyloxy and $NR^7R^8$;
Z is methylene or 1,2-ethanediyl, wherein methylene or 1,2-ethanediyl is optionally substituted with one or two $C_{1-4}$alkyl substituents;
L is a covalent bond, $—(CH_2)_{m-n}—Y—(CH_2)_n—$, 1,2-cyclopropanediyl,
$C_{1-6}$alkanediyl optionally substituted with one or more substituents selected from the group consisting of tetrahydro-2H-pyranyl, phenyl and $C_{1-4}$alkyloxy$C_{1-4}$alkyl,
or $C_{1-6}$alkanediyl wherein two geminal hydrogen atoms are replaced by $C_{2-6}$alkanediyl;
m represents 3, 4, 5, 6 or 7;
n represents 1 or 2;
Y is O or NH;
Ar is a ring system selected from the group consisting of phenyl, indolyl, oxazolyl, benzo[b]thienyl, 1,3-benzodioxolyl, 1,4-benzodioxanyl, 3,4-dihydro-2H-1,5-benzodioxepinyl, pyridyl, indanyl, 1,2,3,4-tetrahydro-1-naphthalenyl, and naphthalenyl;
wherein said ring system is optionally substituted with one or more substituents each independently selected from the group consisting of halo, $Ar^2$, $R^0$,
$C_{1-4}$alkyl optionally substituted with one or more substituents each independently selected from the group consisting of halo, $C_{1-4}$alkyloxy and cyclo$C_{3-7}$alkyl, and
$C_{1-4}$alkyloxy optionally substituted with one or more substituents each independently selected from the group consisting of halo and cyclo$C_{3-7}$alkyl;
$Ar^2$ is phenyl optionally substituted with one or more substituents each independently selected from the group consisting of halo and $C_{1-4}$alkyl optionally substituted with one or more halo substituents;
$R^3$ is hydrogen, halo or $C_{1-4}$alkyl;
$R^4$ is hydrogen, halo or $C_{1-4}$alkyl;
$R^5$ is hydrogen or $C_{1-4}$alkyl;
X is $CR^6$ or N;
$R^6$ is hydrogen or $C_{1-4}$alkyl;
$R^7$ is hydrogen or $C_{1-4}$alkyl;
$R^8$ is hydrogen or $C_{1-4}$alkyl;
$R^0$ is a ring system selected from the group consisting of piperidinyl, morpholinyl, cyclo$C_{3-7}$alkyl, pyrazolyl and pyrrolidinyl; wherein said ring system is optionally substituted with one or more substituents each independently selected from the group consisting of halo or $C_{1-4}$alkyl optionally substituted with one or more halo atoms; and the pharmaceutically acceptable addition salts, and the solvates thereof.

In an embodiment, the present invention concerns novel compounds of Formula (I), tautomers and stereoisomeric forms thereof, wherein
$R^1$ is hydrogen, $C_{1-4}$alkyl or Ar;
provided however that R' is $C_{1-4}$alkyl or Ar when L is a covalent bond;
$R^2$ is hydrogen;
Z is methylene or 1,2-ethanediyl, wherein methylene or 1,2-ethanediyl is optionally substituted with one or two $C_{1-4}$alkyl substituents;
L is a covalent bond, $—(CH_2)_{m-n}—Y—(CH_2)_n—$, 1,2-cyclopropanediyl,
$C_{1-6}$alkanediyl optionally substituted with one or more substituents selected from the group consisting of tetrahydro-2H-pyranyl, phenyl and $C_{1-4}$alkyloxy$C_{1-4}$alkyl, or $C_{1-6}$alkanediyl wherein two geminal hydrogen atoms are replaced by $C_{2-6}$alkanediyl;

m represents 3, 4, 5, 6 or 7;

n represents 1 or 2;

Y is O or NH;

Ar is a ring system selected from the group consisting of phenyl, indolyl, oxazolyl, benzo[b]thienyl, 1,3-benzodioxolyl, 1,4-benzodioxanyl, 3,4-dihydro-2H-1,5-benzodioxepinyl, pyridyl, indanyl, 1,2,3,4-tetrahydro-1-naphthalenyl, and naphthalenyl;

wherein said ring system is optionally substituted with one or more substituents each independently selected from the group consisting of halo, $Ar^2$, $R^0$, $C_{1-4}$alkyl optionally substituted with one or more substituents each independently selected from the group consisting of halo, $C_{1-4}$alkyloxy and cyclo$C_{3-7}$alkyl, and $C_{1-4}$alkyloxy optionally substituted with one or more substituents each independently selected from the group consisting of halo and cyclo$C_{3-7}$alkyl;

$Ar^2$ is phenyl optionally substituted with one or more substituents each independently selected from the group consisting of halo and $C_{1-4}$alkyl optionally substituted with one or more halo substituents;

$R^3$ is hydrogen, halo or $C_{1-4}$alkyl;

$R^4$ is hydrogen, halo or $C_{1-4}$alkyl;

$R^5$ is hydrogen or $C_{1-4}$alkyl;

X is $CR^6$ or N;

$R^6$ is hydrogen or $C_{1-4}$alkyl;

$R^7$ is hydrogen or $C_{1-4}$alkyl;

$R^8$ is hydrogen or $C_{1-4}$alkyl;

$R^0$ is a ring system selected from the group consisting of piperidinyl, morpholinyl, cyclo$C_{3-7}$alkyl, pyrazolyl and pyrrolidinyl; wherein said ring system is optionally substituted with one or more substituents each independently selected from the group consisting of halo or $C_{1-4}$alkyl optionally substituted with one or more halo atoms; and the pharmaceutically acceptable addition salts, and the solvates thereof.

In an embodiment, the present invention concerns novel compounds of Formula (I), tautomers and stereoisomeric forms thereof, wherein $R^1$ is hydrogen, $C_{1-4}$alkyl or Ar;

provided however that R' is $C_{1-4}$alkyl or Ar when L is a covalent bond;

$R^2$ is hydrogen, phenyl, cyclo$C_{3-7}$alkyl, tetrahydro-2H-pyranyl, or $C_{1-4}$alkyl optionally substituted with one or more substituents each independently selected from the group consisting of hydroxyl, $C_{1-4}$alkyloxy and $NR^7R^8$;

Z is methylene or 1,2-ethanediyl, wherein methylene or 1,2-ethanediyl is optionally substituted with one or two $C_{1-4}$alkyl substituents;

L is a covalent bond, $-(CH_2)_{m-n}-Y-(CH_2)_n-$, 1,2-cyclopropanediyl, $C_{1-6}$alkanediyl optionally substituted with one or more substituents selected from the group consisting of tetrahydro-2H-pyranyl, phenyl and $C_{1-4}$alkyloxy$C_{1-4}$alkyl, or $C_{1-6}$alkanediyl wherein two geminal hydrogen atoms are replaced by $C_{2-6}$alkanediyl;

m represents 3;

n represents 2;

Y is O;

Ar is a ring system selected from the group consisting of phenyl, indolyl, oxazolyl, benzo[b]thienyl, 1,3-benzodioxolyl, 1,4-benzodioxanyl, 3,4-dihydro-2H-1,5-benzodioxepinyl, pyridyl, indanyl, 1,2,3,4-tetrahydro-1-naphthalenyl, and naphthalenyl;

wherein said ring system is optionally substituted with one or more substituents each independently selected from the group consisting of halo, $Ar^2$, $R^0$, $C_{1-4}$alkyl optionally substituted with one or more substituents each independently selected from the group consisting of halo, $C_{1-4}$alkyloxy and cyclo$C_{3-7}$alkyl, and $C_{1-4}$alkyloxy optionally substituted with one or more substituents each independently selected from the group consisting of halo and cyclo$C_{3-7}$alkyl;

$Ar^2$ is phenyl optionally substituted with one or more substituents each independently selected from the group consisting of halo and $C_{1-4}$alkyl optionally substituted with one or more halo substituents;

$R^3$ is hydrogen or halo;

$R^4$ is hydrogen, halo or $C_{1-4}$alkyl;

$R^5$ is hydrogen or $C_{1-4}$alkyl;

X is $CR^6$ or N;

$R^6$ is hydrogen or $C_{1-4}$alkyl;

$R^7$ is hydrogen or $C_{1-4}$alkyl;

$R^8$ is $C_{1-4}$alkyl;

$R^0$ is a ring system selected from the group consisting of piperidinyl, morpholinyl, cyclo$C_{3-7}$alkyl, pyrazolyl and pyrrolidinyl; wherein said ring system is optionally substituted with one or more $C_{1-4}$alkyl groups optionally substituted with one or more halo atoms;

and the pharmaceutically acceptable addition salts, and the solvates thereof.

In an embodiment, the present invention concerns novel compounds of Formula (I), tautomers and stereoisomeric forms thereof, wherein $R^1$ is hydrogen, tert-butyl or Ar;

provided however that $R^1$ is tert-butyl or Ar when L is a covalent bond;

$R^2$ is hydrogen, phenyl, cyclopropyl, tetrahydro-2H-pyranyl, or $C_{1-4}$alkyl optionally substituted with one or more substituents each independently selected from the group consisting of hydroxyl, $C_{1-4}$alkyloxy and $NR^7R^8$;

Z is methylene or 1,2-ethanediyl, wherein methylene or 1,2-ethanediyl is optionally substituted with one or two methyl substituents;

L is a covalent bond, $-(CH_2)_{m-n}-Y-(CH_2)_n-$, 1,2-cyclopropanediyl, $C_{1-3}$alkanediyl optionally substituted with one or more substituents selected from the group consisting of tetrahydro-2H-pyranyl, phenyl and $C_{1-4}$alkyloxy$C_{1-4}$alkyl, or $C_{1-3}$alkanediyl wherein two geminal hydrogen atoms are replaced by $C_{2-6}$alkanediyl;

m represents 3;

n represents 2;

Y is O;

Ar is a ring system selected from the group consisting of phenyl, indolyl, oxazolyl, benzo[b]thienyl, 1,3-benzodioxolyl, 1,4-benzodioxanyl, 3,4-dihydro-2H-1,5-benzodioxepinyl, pyridyl, indanyl, 1,2,3,4-tetrahydro-1-naphthalenyl, and naphthalenyl;

wherein said ring system is optionally substituted with one or more substituents each independently selected from the group consisting of Br, Cl, F, $Ar^2$, $R^0$, $C_{1-4}$alkyl optionally substituted with one or more substituents each independently selected from the group consisting of F, $C_{1-4}$alkyloxy and cyclopropyl, and $C_{1-4}$alkyloxy optionally substituted with one or more substituents each independently selected from the group consisting of F and cyclopropyl;

$Ar^2$ is phenyl optionally substituted with one or more substituents each independently selected from the group consisting of F, Cl and $C_{1-4}$alkyl optionally substituted with one or more F substituents;

$R^3$ is hydrogen or Cl;

$R^4$ is hydrogen, Cl, methyl or ethyl;

$R^5$ is hydrogen or $C_{1-4}$alkyl;

X is $CR^6$ or N;

$R^6$ is hydrogen or methyl;

$R^7$ is hydrogen or methyl;

$R^8$ is methyl;

$R^0$ is a ring system selected from the group consisting of piperidinyl, morpholinyl, cyclo$C_{3-7}$alkyl, pyrazolyl and pyrrolidinyl; wherein said ring system is optionally substituted with one or more $C_{1-4}$alkyl groups optionally substituted with one or more halo atoms;

and the pharmaceutically acceptable addition salts, and the solvates thereof.

In an embodiment, the present invention concerns novel compounds of Formula (I), wherein one or more of the following restrictions apply:

(a) $R^1$ is Ar;

(b) $R^2$ is phenyl, cyclo$C_{3-7}$alkyl, tetrahydro-2H-pyranyl, tetrahydro-2H-thiopyranyl, piperidinyl, or $C_{1-4}$alkyl optionally substituted with one or more substituents each independently selected from the group consisting of hydroxyl, $C_{1-4}$alkyloxy and $NR^7R^8$;

(c) Z is methylene or 1,2-ethanediyl;

(d) L is a $-(CH_2)_{m-n}-Y-(CH_2)_n-$, $C_{1-6}$alkanediyl optionally substituted with one or more substituents selected from the group consisting of tetrahydro-2H-pyranyl, phenyl and $C_{1-4}$alkyloxy$C_{1-4}$alkyl;

(e) m represents 3, 4, 5 or 6;

(f) n represents 1;

(g) Y is O;

(h) Ar is a ring system selected from the group consisting of phenyl optionally substituted with one or more substituents each independently selected from the group consisting of halo, $Ar^2$, $R^0$, $C_{1-4}$alkyl optionally substituted with one or more substituents each independently selected from the group consisting of halo, $C_{1-4}$alkyloxy and cyclo$C_{3-7}$alkyl, and $C_{1-4}$alkyloxy optionally substituted with one or more substituents each independently selected from the group consisting of halo and cyclo$C_{3-7}$alkyl;

(i) $Ar^2$ is phenyl optionally substituted with one or more substituents each independently selected from the group consisting of halo and $C_{1-4}$alkyl optionally substituted with one or more halo substituents;

(j) $R^3$ is hydrogen;

(k) $R^4$ is $C_{1-4}$alkyl;

(l) $R^5$ is hydrogen;

(m) X is $CR^6$;

(n) $R^6$ is hydrogen;

(o) $R^7$ is $C_{1-4}$alkyl;

(p) $R^8$ is $C_{1-4}$alkyl;

(q) $R^0$ is a ring system selected from the group consisting of piperidinyl optionally substituted with one or more substituents each independently selected from the group consisting of halo or $C_{1-4}$alkyl optionally substituted with one or more halo atoms.

In an embodiment, the present invention relates to those compounds of formula (I), or any subgroup thereof as mentioned in any of the other embodiments, wherein $R^0$ is a ring system selected from the group consisting of piperidinyl, morpholinyl, cyclo$C_{3-7}$alkyl, pyrazolyl and pyrrolidinyl; wherein said ring system is optionally substituted with one or more $C_{1-4}$alkyl groups optionally substituted with one or more halo atoms.

In an embodiment, the present invention relates to those compounds of formula (I), or any subgroup thereof as mentioned in any of the other embodiments, wherein $R^8$ is $C_{1-4}$alkyl.

In an embodiment, the present invention relates to those compounds of formula (I), or any subgroup thereof as mentioned in any of the other embodiments, wherein $R^2$ is phenyl, cyclo$C_{3-7}$alkyl, tetrahydro-2H-pyranyl, tetrahydro-2H-thiopyranyl, piperidinyl, or $C_{1-4}$alkyl optionally substituted with one or more substituents each independently selected from the group consisting of halo, hydroxyl, $C_{1-4}$alkyloxy and $NR^7R^8$.

In an embodiment, the present invention relates to those compounds of formula (I), or any subgroup thereof as mentioned in any of the other embodiments, wherein $R^2$ is $C_{1-4}$alkyl optionally substituted with one or more substituents each independently selected from the group consisting of halo, hydroxyl, $C_{1-4}$alkyloxy and $NR^7R^8$.

In an embodiment, the present invention relates to those compounds of formula (I), or any subgroup thereof as mentioned in any of the other embodiments, wherein $R^2$ is $C_{1-4}$alkyl.

In an embodiment, the present invention relates to those compounds of formula (I), or any subgroup thereof as mentioned in any of the other embodiments, wherein $R^2$ is methyl.

In an embodiment, the present invention relates to those compounds of formula (I), or any subgroup thereof as mentioned in any of the other embodiments, wherein $R^2$ is H.

In an embodiment, the present invention relates to those compounds of formula (I), or any subgroup thereof as mentioned in any of the other embodiments, wherein $R^3$ is hydrogen or halo.

In an embodiment, the present invention relates to those compounds of formula (I), or any subgroup thereof as mentioned in any of the other embodiments, wherein Z is methylene or 1,2-ethanediyl, wherein methylene is optionally substituted with one or two $C_{1-4}$alkyl substituents.

In an embodiment, the present invention relates to those compounds of formula (I), or any subgroup thereof as mentioned in any of the other embodiments, wherein m represents 3, 4, 5 or 6; in particular 3, 4 or 5; more in particular 3 or 4; even more in particular 3.

In an embodiment, the present invention relates to those compounds of formula (I), or any subgroup thereof as mentioned in any of the other embodiments, wherein n represents 1 or 2; in particular 2.

In an embodiment, the present invention relates to those compounds of formula (I), or any subgroup thereof as mentioned in any of the other embodiments, wherein $R^1$ is Ar.

In an embodiment, the present invention relates to those compounds of formula (I), or any subgroup thereof as mentioned in any of the other embodiments, wherein m represents 3 or 4 and wherein n represents 1 or 2; more in particular wherein m represents 3 and wherein n represents 2.

In an embodiment, the present invention relates to those compounds of formula (I), or any subgroup thereof as mentioned in any of the other embodiments, wherein Y represents O.

In an embodiment, the present invention relates to those compounds of formula (I), or any subgroup thereof as mentioned in any of the other embodiments, wherein L is a covalent bond, 1,2-cyclopropanediyl, $C_{1-6}$alkanediyl optionally substituted with one or more substituents selected from the group consisting of tetrahydro-2H-pyranyl, phenyl and $C_{1-4}$alkyloxy$C_{1-4}$alkyl, or $C_{1-6}$alkanediyl wherein two geminal hydrogen atoms are replaced by $C_{2-6}$alkanediyl.

In an embodiment, the present invention relates to those compounds of formula (I), or any subgroup thereof as mentioned in any of the other embodiments, wherein Ar is indolyl optionally substituted as defined in any of the other embodiments, and wherein L is a covalent bond, 1,2-cyclopropanediyl, $C_{1-6}$alkanediyl optionally substituted with one or more substituents selected from the group consisting of tetrahydro-2H-pyranyl, phenyl and $C_{1-4}$alkyloxy$C_{1-4}$alkyl, or $C_{1-6}$alkanediyl wherein two geminal hydrogen atoms are replaced by $C_{2-6}$alkanediyl.

In an embodiment, the present invention relates to those compounds of formula (I), or any subgroup thereof as mentioned in any of the other embodiments, wherein L is a covalent bond or $C_{1-6}$alkanediyl;

$R^1$ is Ar;

Ar is indolyl optionally substituted with one or more substituents each independently selected from the group consisting of halo, $Ar^2$, $R^0$, $C_{1-4}$alkyl optionally substituted with one or more substituents each independently selected from the group consisting of halo, $C_{1-4}$alkyloxy and cyclo$C_{3-7}$alkyl, and $C_{1-4}$alkyloxy optionally substituted with one or more substituents each independently selected from the group consisting of halo and cyclo$C_{3-7}$alkyl.

An interesting group of compounds relates to those compounds of formula (I) wherein the position of $R^3$ is fixed as shown in (I-x)

(I-x)

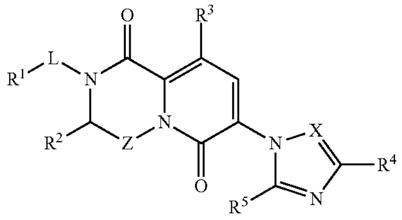

tautomers and stereoisomeric forms thereof, wherein all the substituents have the same meaning as defined in any of the embodiments hereinbefore, and the pharmaceutically acceptable addition salts and the solvates thereof.

An interesting group of compounds relates to those compounds of formula (I) wherein the position of $R^3$ is fixed as shown in (I-x)

(I-x)

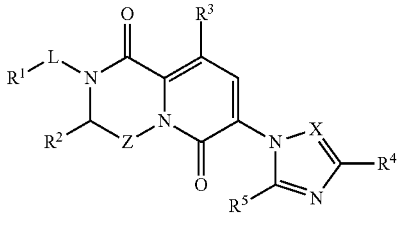

tautomers and stereoisomeric forms thereof, wherein all the substituents have the same meaning as defined in any of the embodiments hereinbefore or hereinafter, and the pharmaceutically acceptable addition salts and the solvates thereof.

An interesting group of compounds relates to those compounds of formula (I) wherein the position of $R^3$ is fixed as shown in (I-x1)

(I-x1)

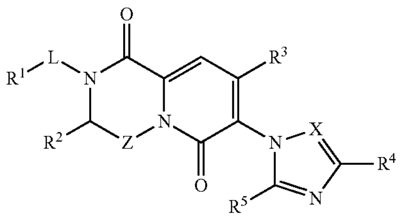

tautomers and stereoisomeric forms thereof, wherein all the substituents have the same meaning as defined in any of the embodiments hereinbefore or hereinafter, and the pharmaceutically acceptable addition salts and the solvates thereof.

In an embodiment, the present invention concerns novel compounds of Formula (I), tautomers and stereoisomeric forms thereof, wherein:

$R^1$ is Ar;

$R^2$ is hydrogen or $C_{1-4}$alkyl;

Z is methylene;

L is a $C_{1-6}$alkanediyl, in particular methylene;

Ar is a ring system selected from the group consisting of phenyl optionally substituted with one or more substituents each independently selected from the group consisting of halo, $Ar^2$, $R^0$, $C_{1-4}$alkyl optionally substituted with one or more substituents each independently selected from the group consisting of halo, $C_{1-4}$alkyloxy and cyclo$C_{3-7}$alkyl, and $C_{1-4}$alkyloxy optionally substituted with one or more substituents each independently selected from the group consisting of halo and cyclo$C_{3-7}$alkyl;

$Ar^2$ is phenyl optionally substituted with one or more substituents each independently selected from the group consisting of halo and $C_{1-4}$alkyl optionally substituted with one or more halo substituents;

$R^3$ is hydrogen;

$R^4$ is $C_{1-4}$alkyl;

$R^5$ is hydrogen;

X is CH;

$R^0$ is a ring system selected from the group consisting of piperidinyl, morpholinyl, cyclo$C_{3-7}$alkyl, pyrazolyl and pyrrolidinyl; wherein said ring system is optionally substituted with one or more substituents each independently selected from the group consisting of halo or $C_{1-4}$alkyl optionally substituted with one or more halo atoms; in particular $R^0$ is piperidinyl;

and the pharmaceutically acceptable addition salts, and the solvates thereof.

In an embodiment, the present invention concerns novel compounds of Formula (I), tautomers and stereoisomeric forms thereof, wherein:

$R^1$ is Ar;

$R^2$ is $C_{1-4}$alkyl; in particular methyl

Z is methylene;

L is a $C_{1-6}$alkanediyl, in particular methylene;

Ar is phenyl substituted with one or more substituents each independently selected from the group consisting of $C_{1-4}$alkyl optionally substituted with one, two or three substituents each independently selected from the group consisting of halo;

$R^3$ is hydrogen;

$R^4$ is $C_{1-4}$alkyl; in particular methyl;

$R^5$ is hydrogen;

X is CH;

and the pharmaceutically acceptable addition salts, and the solvates thereof.

In an embodiment, the present invention relates to those compounds of formula (I), or any subgroup thereof as mentioned in any of the other embodiments, wherein L is $C_{1-6}$alkanediyl; in particular wherein L is methylene or ethylidene; more in particular wherein L is ethylidene.

In an embodiment, the present invention relates to those compounds of formula (I), or any subgroup thereof as mentioned in any of the other embodiments, wherein L is methylene.

In an embodiment, the present invention relates to those compounds of formula (I), or any subgroup thereof as mentioned in any of the other embodiments, wherein $R^2$ is methyl and L is ethylidene or methylene; in particular wherein $R^2$ is methyl and L is ethylidene.

In an embodiment, the present invention relates to those compounds of formula (I), or any subgroup thereof as mentioned in any of the other embodiments, wherein $R^2$ is $C_{1-4}$alkyl and L is $C_{1-6}$alkanediyl.

In an embodiment, the present invention relates to those compounds of formula (I), or any subgroup thereof as mentioned in any of the other embodiments, wherein L is a covalent bond, $-(CH_2)_{m-n}-Y-(CH_2)_n-$, 1,2-cyclopropanediyl, $C_{1-6}$alkanediyl substituted with one or more substituents selected from the group consisting of tetrahydro-2H-pyranyl, phenyl and $C_{1-4}$alkyloxy$C_{1-4}$alkyl, or $C_{1-6}$alkanediyl wherein two geminal hydrogen atoms are replaced by $C_{2-6}$alkanediyl; in particular wherein L is a covalent bond, $-(CH_2)_{m-n}-Y-(CH_2)_n-$, 1,2-cyclopropanediyl, or $C_{1-6}$alkanediyl wherein two geminal hydrogen atoms are replaced by $C_{2-6}$alkanediyl; more in particular wherein L is a covalent bond, $-(CH_2)_{m-n}-Y-(CH_2)_n-$, or 1,2-cyclopropanediyl.

In an embodiment, the present invention relates to those compounds of formula (I), or any subgroup thereof as mentioned in any of the other embodiments, wherein Ar is a ring system selected from the group consisting of indolyl, oxazolyl, benzo[b]thienyl, 1,3-benzodioxolyl, 1,4-benzodioxanyl, 3,4-dihydro-2H-1,5-benzodioxepinyl, pyridyl, indanyl, 1,2,3,4-tetrahydro-1-naphthalenyl, and naphthalenyl;

wherein said ring system is optionally substituted with one or more substituents each independently selected from the group consisting of halo, $Ar^2$, $R^0$, $C_{1-4}$alkyl optionally substituted with one or more substituents each independently selected from the group consisting of halo, $C_{1-4}$alkyloxy and cyclo$C_{3-7}$alkyl, and $C_{1-4}$alkyloxy optionally substituted with one or more substituents each independently selected from the group consisting of halo and cyclo$C_{3-7}$alkyl.

In an embodiment, the present invention relates to those compounds of formula (I), or any subgroup thereof as mentioned in any of the other embodiments, wherein Ar is indolyl optionally substituted with one or more substituents each independently selected from the group consisting of halo, $Ar^2$, $R^0$, $C_{1-4}$alkyl optionally substituted with one or more substituents each independently selected from the group consisting of halo, $C_{1-4}$alkyloxy and cyclo$C_{3-7}$alkyl, and $C_{1-4}$alkyloxy optionally substituted with one or more substituents each independently selected from the group consisting of halo and cyclo$C_{3-7}$alkyl.

In an embodiment, the present invention relates to those compounds of formula (I), or any subgroup thereof as mentioned in any of the other embodiments, wherein Ar is indolyl substituted with one or more substituents each independently selected from the group consisting of halo, $Ar^2$, $R^0$, $C_{1-4}$alkyl optionally substituted with one or more substituents each independently selected from the group consisting of halo, $C_{1-4}$alkyloxy and cyclo$C_{3-7}$alkyl, and $C_{1-4}$alkyloxy optionally substituted with one or more substituents each independently selected from the group consisting of halo and cyclo$C_{3-7}$alkyl.

In an embodiment, the present invention relates to those compounds of formula (I), or any subgroup thereof as mentioned in any of the other embodiments, wherein $R^2$ is phenyl, cyclo$C_{3-7}$alkyl, tetrahydro-2H-pyranyl, tetrahydro-2H-thiopyranyl, piperidinyl, or $C_{1-4}$alkyl optionally substituted with one or more substituents each independently selected from the group consisting of halo, hydroxyl, $C_{1-4}$alkyloxy and $NR^7R^8$.

In an embodiment, the present invention relates to those compounds of formula (I), or any subgroup thereof as mentioned in any of the other embodiments, wherein $R^2$ is methyl; and wherein L is a covalent bond, 1,2-cyclopropanediyl, $C_{1-6}$alkanediyl optionally substituted with one or more substituents selected from the group consisting of tetrahydro-2H-pyranyl, phenyl and $C_{1-4}$ alkyloxy$C_{1-4}$ alkyl, or $C_{1-6}$alkanediyl wherein two geminal hydrogen atoms are replaced by $C_{2-6}$ alkanediyl.

In an embodiment, the present invention relates to those compounds of formula (I), or any subgroup thereof as mentioned in any of the other embodiments, wherein one or more of the following heterocyclic groups in the Ar definition are restricted: indolyl is restricted to indol-3-yl, oxazolyl is restricted to 2-oxazolyl, benzo[b]thienyl is restricted to benzo[b]thien-3-yl, 1,3-benzodioxolyl is restricted to 1,3-benzodioxol-5-yl, 1,4-benzodioxanyl is restricted to benzodioxan-2-yl, 3,4-dihydro-2H-1,5-benzodioxepinyl is restricted to 3,4-dihydro-2H-1,5-benzodioxepin-7-yl, pyridyl is restricted to 2-pyridinyl or 4-pyridinyl, indanyl is restricted to indan-1-yl or indan-2-yl, naphthalenyl is restricted to 2-naphthalenyl; it should be understood that any of these heterocyclic groups may be substituted as defined in any of the other embodiments.

In an embodiment, the present invention relates to those compounds of formula (I), or any subgroup thereof as mentioned in any of the other embodiments, wherein one or more of the following heterocyclic groups in the $R^2$ definition are restricted: tetrahydro-2H-pyranyl is restricted to tetrahydro-2H-pyran-4-yl, tetrahydro-2H-thiopyranyl is restricted to tetrahydro-2H-thiopyran-4-yl, piperidinyl is restricted to 1-piperidinyl or 4-piperidinyl;

it should be understood that any of these heterocyclic groups may be substituted as defined in any of the other embodiments.

In an embodiment, the present invention relates to those compounds of formula (I), or any subgroup thereof as mentioned in any of the other embodiments, wherein one or more of the following heterocyclic groups in the $R^0$ definition are restricted: piperidinyl is restricted to 1-piperidinyl, morpholinyl is restricted to 1-morpholinyl, pyrazolyl is restricted to 1-pyrazolyl, pyrrolidinyl is restricted to 1-pyrrolidinyl; it should be understood that any of these heterocyclic groups may be substituted as defined in any of the other embodiments.

In an embodiment, the present invention relates to those compounds of formula (I), or any subgroup thereof as mentioned in any of the other embodiments, wherein one or more of the heterocyclic groups in the Ar, $R^2$ and $R^0$ definitions are restricted as indicated in the 3 embodiments hereabove.

In an embodiment the compound of Formula (I) is selected from the group consisting of:

2-([1,1'-biphenyl]-3-ylmethyl)-3,4-dihydro-7-(4-methyl-1H-imidazol-1-yl)-2H-pyrido[1,2-a]pyrazine-1,6-dione,
3,4-dihydro-2-[(3-methoxyphenyl)methyl]-7-(3-methyl-1H-1,2,4-triazol-1-yl)-2H-pyrido[1,2-a]pyrazine-1,6-dione,
3,4-dihydro-7-(3-methyl-1H-1,2,4-triazol-1-yl)-2-[[3-(trifluoromethyl)phenyl]-methyl]-2H-pyrido[1,2-a]pyrazine-1,6-dione,
3,4-dihydro-2-[(3-methoxyphenyl)methyl]-7-(4-methyl-1H-imidazol-1-yl)-2H-pyrido[1,2-a]pyrazine-1,6-dione,
3,4-dihydro-7-(4-methyl-1H-imidazol-1-yl)-2-(phenylmethyl)-2H-pyrido[1,2-a]pyrazine-1,6-dione,
2-[(3,4-dichlorophenyl)methyl]-3,4-dihydro-7-(4-methyl-1H-imidazol-1-yl)-2H-pyrido[1,2-a]pyrazine-1,6-dione,
2-[[3,5-bis(trifluoromethyl)phenyl]methyl]-3,4-dihydro-7-(4-methyl-1H-imidazol-1-yl)-2H-pyrido[1,2-a]pyrazine-1,6-dione,
3,4-dihydro-7-(4-methyl-1H-imidazol-1-yl)-2-[[3-(trifluoromethoxy)phenyl]methyl]-2H-pyrido[1,2-a]pyrazine-1,6-dione,
3,4-dihydro-7-(4-methyl-1H-imidazol-1-yl)-2-[1-[3-(trifluoromethyl)phenyl]ethyl]-2H-pyrido[1,2-a]pyrazine-1,6-dione,
3,4-dihydro-7-(4-methyl-1H-imidazol-1-yl)-2-[1-[3-(trifluoromethyl)phenyl]ethyl]-2H-pyrido[1,2-a]pyrazine-1,6-dione (R or S; enantiomer A (SFC-MS)),
3,4-dihydro-7-(4-methyl-1H-imidazol-1-yl)-2-[1-[3-(trifluoromethyl)phenyl]ethyl]-2H-pyrido[1,2-a]pyrazine-1,6-dione (S or R; enantiomer B (SFC-MS)),
3,4-dihydro-7-(4-methyl-1H-imidazol-1-yl)-2-[[3-(trifluoromethyl)phenyl]methyl]-2H-pyrido[1,2-a]pyrazine-1,6-dione,
2-[[1-(4-chlorophenyl)cyclopropyl]methyl]-3,4-dihydro-7-(4-methyl-1H-imidazol-1-yl)-2H-pyrido[1,2-a]pyrazine-1,6-dione .HCl,
2-[[1-(4-chlorophenyl)cyclopropyl]methyl]-3,4-dihydro-7-(4-methyl-1H-imidazol-1-yl)-2H-pyrido[1,2-a]pyrazine-1,6-dione,
3,4-dihydro-7-(5-methyl-1H-imidazol-1-yl)-2-(phenylmethyl)-2H-pyrido[1,2-a]pyrazine-1,6-dione,
2-[(3,4-dichlorophenyl)methyl]-2,3,4,5-tetrahydro-8-(4-methyl-1H-imidazol-1-yl)-pyrido[1,2-a][1,4]diazepine-1,7-dione,
2-[(3,4-dichlorophenyl)methyl]-2,3,4,5-tetrahydro-8-(5-methyl-1H-imidazol-1-yl)-pyrido[1,2-a][1,4]diazepine-1,7-dione,
2-[2-(4-chlorophenyl)ethyl]-3,4-dihydro-7-(4-methyl-1H-imidazol-1-yl)-2H-pyrido[1,2-a]pyrazine-1,6-dione,
(3S)-2-[(3,4-dichlorophenyl)methyl]-3,4-dihydro-3-methyl-7-(4-methyl-1H-imidazol-1-yl)-2H-pyrido[1,2-a]pyrazine-1,6-dione,
(3R)-2-[(3,4-dichlorophenyl)methyl]-3,4-dihydro-3-methyl-7-(4-methyl-1H-imidazol-1-yl)-2H-pyrido[1,2-a]pyrazine-1,6-dione,
2-[[4'-fluoro-2'-(trifluoromethyl) [1,1'-biphenyl]-3-yl]methyl]-3,4-dihydro-7-(4-methyl-1H-imidazol-1-yl)-2H-pyrido[1,2-a]pyrazine-1,6-dione,
2-(2-cyclopropylethyl)-3,4-dihydro-7-(2-propyl-1H-imidazol-1-yl)-2H-pyrido[1,2-a]pyrazine-1,6-dione,
2-(cyclopropylmethyl)-3,4-dihydro-7-(2-propyl-1H-imidazol-1-yl)-2H-pyrido[1,2-a]pyrazine-1,6-dione,
3,4-dihydro-7-(4-methyl-1H-imidazol-1-yl)-2-[(2-methylphenyl)methyl]-2H-pyrido[1,2-a]pyrazine-1,6-dione,
2-[(4-fluoro-2-methylphenyl)methyl]-3,4-dihydro-7-(4-methyl-1H-imidazol-1-yl)-2H-pyrido[1,2-a]pyrazine-1,6-dione,
2-[[2-fluoro-3-(trifluoromethyl)phenyl]methyl]-3,4-dihydro-7-(4-methyl-1H-imidazol-1-yl)-2H-pyrido[1,2-a]pyrazine-1,6-dione,
3,4-dihydro-7-(4-methyl-1H-imidazol-1-yl)-2-(2-methylphenyl)-2H-pyrido[1,2-a]pyrazine-1,6-dione,
3,4-dihydro-7-(4-methyl-1H-imidazol-1-yl)-2-[[2-methyl-3-(trifluoromethyl)phenyl]-methyl]-2H-pyrido[1,2-a]pyrazine-1,6-dione,
2-[(3-cyclopropylphenyl)methyl]-3,4-dihydro-7-(4-methyl-1H-imidazol-1-yl)-2H-pyrido[1,2-a]pyrazine-1,6-dione,
3,4-dihydro-7-(4-methyl-1H-imidazol-1-yl)-2-[[3-(4-morpholinyl)phenyl]methyl]-2H-pyrido[1,2-a]pyrazine-1,6-dione,
2-(4-fluoro-2-methylphenyl)-3,4-dihydro-7-(4-methyl-1H-imidazol-1-yl)-2H-pyrido[1,2-a]pyrazine-1,6-dione,
3,4-dihydro-7-(4-methyl-1H-imidazol-1-yl)-2-[[3-(1-piperidinyl)phenyl]methyl]-2H-pyrido[1,2-a]pyrazine-1,6-dione,
2H-pyrido[1,2-a]pyrazine-1,6-dione, 3,4-dihydro-7-(4-methyl-1H-imidazol-1-yl)-2-[[2-(1-piperidinyl)phenyl]methyl]-
2H-pyrido[1,2-a]pyrazine-1,6-dione, 2-[2-fluoro-3-(trifluoromethyl)phenyl]-3,4-dihydro-7-(4-methyl-1H-imidazol-1-yl)-
2H-pyrido[1,2-a]pyrazine-1,6-dione, 3,4-dihydro-7-(4-methyl-1H-imidazol-1-yl)-2-[2-methyl-3-(trifluoromethyl)phenyl]-
3,4-dihydro-7-(4-methyl-1H-imidazol-1-yl)-2-[[2-methyl-3-(1-piperidinyl)phenyl]-methyl]-2H-pyrido[1,2-a]pyrazine-1,6-dione,
3,4-dihydro-7-(4-methyl-1H-imidazol-1-yl)-2-[[4-methyl-3-(1-piperidinyl)phenyl]-methyl]-2H-pyrido[1,2-a]pyrazine-1,6-dione,
(3R)-3,4-dihydro-3-methyl-7-(4-methyl-1H-imidazol-1-yl)-2-[(2-methylphenyl)-methyl]-2H-pyrido[1,2-a]pyrazine-1,6-dione,
(3R)-2-[(3,4-dichlorophenyl)methyl]-3,4-dihydro-3-(1-methylethyl)-7-(4-methyl-1H-imidazol-1-yl)-2H-pyrido[1,2-a]pyrazine-1,6-dione,
2-[2-(4-chlorophenyl)cyclopropyl]-3,4-dihydro-7-(4-methyl-1H-imidazol-1-yl)-2H-pyrido[1,2-a]pyrazine-1,6-dione (TRANS),
(3R)-3,4-dihydro-3-methyl-7-(4-methyl-1H-imidazol-1-yl)-2-[[3-(1-piperidinyl)-phenyl]methyl]-2H-pyrido[1,2-a]pyrazine-1,6-dione,
(3R)-2-[[1-(4-chlorophenyl)cyclopropyl]methyl]-3,4-dihydro-3-methyl-7-(4-methyl-1H-imidazol-1-yl)-2H-pyrido[1,2-a]pyrazine-1,6-dione,
(3R)-3,4-dihydro-3-methyl-7-(4-methyl-1H-imidazol-1-yl)-2-[[4-methyl-3-(1-piperidinyl)phenyl]methyl]-2H-pyrido[1,2-a]pyrazine-1,6-dione .HCl,
(3R)-3,4-dihydro-3-methyl-7-(4-methyl-1H-imidazol-1-yl)-2-[[4-methyl-3-(1-piperidinyl)phenyl]methyl]-2H-pyrido[1,2-a]pyrazine-1,6-dione,
2-([1,1'-biphenyl]-3-ylmethyl)-3,4-dihydro-7-(1H-imidazol-1-yl)-2H-pyrido[1,2-a]pyrazine-1,6-dione,
2-([1,1'-biphenyl]-3-ylmethyl)-3,4-dihydro-7-(2-methyl-1H-imidazol-1-yl)-2H-pyrido[1,2-a]pyrazine-1,6-dione,
(3R)-2-[[3,5-bis(trifluoromethyl)phenyl]methyl]-3,4-dihydro-3-methyl-7-(4-methyl-1H-imidazol-1-yl)-2H-pyrido[1,2-a]pyrazine-1,6-dione, 2-([1,1'-biphenyl]-3-ylmethyl)-7-(2,4-dimethyl-1H-imidazol-1-yl)-3,4-dihydro-2H-pyrido[1,2-a]pyrazine-1,6-dione, 2-([1,1'-biphenyl]-3-ylmethyl)-9-chloro-3,4-dihydro-7-(4-methyl-1H-imidazol-1-yl)-2H-pyrido[1,2-a]pyrazine-1,6-dione, (3R)-2-[(3-chlorophenyl)methyl]-3,4-dihydro-3-methyl-7-(4-methyl-1H-imidazol-1-yl)-2H-pyrido[1,2-a]pyrazine-1,6-dione, (3R)-2-[(3-chlorophenyl)methyl]-3,4-dihydro-3-methyl-7-(4-methyl-1H-imidazol-1-yl)-2H-pyrido[1,2-a]pyrazine-1,6-dione .HCl, 2-[2-[(4-chlorophenyl)methoxy]ethyl]-3,4-dihydro-7-(4-methyl-1H-imidazol-1-yl)-2H-pyrido[1,2-a]pyrazine-1,6-dione, 2-(2-cyclohexylethyl)-3,4-dihydro-7-(4-methyl-1H-imidazol-1-yl)-2H-pyrido[1,2-a]pyrazine-1,6-dione, 2-[(3-chlorophenyl)methyl]-3,4-dihydro-7-(4-methyl-1H-imidazol-1-yl)-2H-pyrido[1,2-a]pyrazine-1,6-dione, (3R)-3,4-dihydro-3-methyl-7-(4-methyl-1H-imidazol-1-yl)-2-[[1-(2-methylphenyl)-cyclopropyl]methyl]-2H-pyrido[1,2-a]pyrazine-1,6-dione, 3,4-dihydro-7-(4-methyl-1H-imidazol-1-yl)-2-[[2-methyl-4-(trifluoromethoxy)-phenyl]methyl]-2H-pyrido[1,2-a]pyrazine-1,6-dione, 2-[(3,4-dihydro-2H-1,5-benzodioxepin-7-yl)methyl]-3,4-dihydro-7-(4-methyl-1H-imidazol-1-yl)-2H-pyrido[1,2-a]pyrazine-1,6-dione, 2-[(3-chloro-2-fluorophenyl)methyl]-3,4-dihydro-7-(4-methyl-1H-imidazol-1-yl)-2H-pyrido[1,2-a]pyrazine-1,6-dione, (3R)-3,4-dihydro-3-methyl-7-(4-methyl-1H-imidazol-1-yl)-2-[[2-methyl-3-(trifluoromethyl)phenyl]methyl]-2H-pyrido[1,2-a]pyrazine-1,6-dione, 2-[[2-chloro-3-(trifluoromethyl)phenyl]methyl]-3,4-dihydro-7-(4-methyl-1H-imidazol-1-yl)-2H-pyrido[1,2-a]pyrazine-1,6-dione, (3R)-3,4-dihydro-3-methyl-7-(4-methyl-1H-imidazol-1-yl)-2-[[3-(trifluoromethoxy)-phenyl]methyl]-2H-pyrido[1,2-a]pyrazine-1,6-dione, 3,4-dihydro-7-(4-methyl-1H-imidazol-1-yl)-2-[(6-methyl-2-naphthalenyl)methyl]-2H-pyrido[1,2-a]pyrazine-1,6-dione, (3R)-2-[(3-chloro-2-fluorophenyl)methyl]-3,4-dihydro-3-methyl-7-(4-methyl-1H-imidazol-1-yl)-2H-pyrido[1,2-a]pyrazine-1,6-dione, 2-[[4-chloro-3-(trifluoromethyl)phenyl]methyl]-3,4-dihydro-7-(4-methyl-1H-imidazol-1-yl)-2H-pyrido[1,2-a]pyrazine-1,6-dione, (3R)-2-[[3-(1,1-dimethylethyl)phenyl]methyl]-3,4-dihydro-3-methyl-7-(4-methyl-1H-imidazol-1-yl)-2H-pyrido[1,2-a]pyrazine-1,6-dione, (3R)-2-[(3-chloro-2-methylphenyl)methyl]-3,4-dihydro-3-methyl-7-(4-methyl-1H-imidazol-1-yl)-2H-pyrido[1,2-a]pyrazine-1,6-dione, 3,4-dihydro-2-[[4-methoxy-3-(trifluoromethyl)phenyl]methyl]-7-(4-methyl-1H-imidazol-1-yl)-2H-pyrido[1,2-a]pyrazine-1,6-dione, 2-[2-(2,3-dihydro-1,4-benzodioxin-2-yl)ethyl]-3,4-dihydro-7-(4-methyl-1H-imidazol-1-yl)-2H-pyrido[1,2-a]pyrazine-1,6-dione, 2-[[5-(4-chlorophenyl)-2-oxazolyl]methyl]-3,4-dihydro-7-(4-methyl-1H-imidazol-1-yl)-2H-pyrido[1,2-a]pyrazine-1,6-dione, 2-(4,4-dimethylpentyl)-3,4-dihydro-7-(4-methyl-1H-imidazol-1-yl)-2H-pyrido[1,2-a]pyrazine-1,6-dione, 3,4-dihydro-2-[2-(1H-indol-3-yl)ethyl]-7-(4-methyl-1H-imidazol-1-yl)-2H-pyrido[1,2-a]pyrazine-1,6-dione, 3,4-dihydro-7-(4-methyl-1H-imidazol-1-yl)-2-[[3-methyl-4-(2,2,2-trifluoroethoxy)-2-pyridinyl]methyl]-2H-pyrido[1,2-a]pyrazine-1,6-dione, 2-[1-(2,3-dichlorophenyl)ethyl]-3,4-dihydro-7-(4-methyl-1H-imidazol-1-yl)-2H-pyrido[1,2-a]pyrazine-1,6-dione, 2-[1-(3,4-dichlorophenyl)ethyl]-3,4-dihydro-7-(4-methyl-1H-imidazol-1-yl)-2H-pyrido[1,2-a]pyrazine-1,6-dione, (3R)-2-[(3,4-dichlorophenyl)methyl]-3,4-dihydro-7-(4-methyl-1H-imidazol-1-yl)-3-phenyl-2H-pyrido[1,2-a]pyrazine-1,6-dione, (3R)-3,4-dihydro-3-methyl-7-(4-methyl-1H-imidazol-1-yl)-2-[[4-(trifluoromethyl)-phenyl]methyl]-2H-pyrido[1,2-a]pyrazine-1,6-dione, (3R)-3-cyclopropyl-2-[(3,4-dichlorophenyl)methyl]-3,4-dihydro-7-(4-methyl-1H-imidazol-1-yl)-2H-pyrido[1,2-a]pyrazine-1,6-dione, (3R)-3,4-dihydro-3-methyl-7-(4-methyl-1H-imidazol-1-yl)-2-[[3-methyl-5-(trifluoromethyl)phenyl]methyl]-2H-pyrido[1,2-a]pyrazine-1,6-dione, 2-[2,3-dihydro-4-(trifluoromethyl)-1H-inden-1-yl]-3,4-dihydro-7-(4-methyl-1H-imidazol-1-yl)-2H-pyrido[1,2-a]pyrazine-1,6-dione, (3R)-3,4-dihydro-2-[[3-methoxy-5-(trifluoromethyl)phenyl]methyl]-3-methyl-7-(4-methyl-1H-imidazol-1-yl)-2H-pyrido[1,2-a]pyrazine-1,6-dione, (3S)-2-[[3,5-bis(trifluoromethyl)phenyl]methyl]-3,4-dihydro-3-(methoxymethyl)-7-(4-methyl-1H-imidazol-1-yl)-2H-pyrido[1,2-a]pyrazine-1,6-dione, (3R)-2-[[3-chloro-5-(trifluoromethyl)phenyl]methyl]-3,4-dihydro-3-methyl-7-(4-methyl-1H-imidazol-1-yl)-2H-pyrido[1,2-a]pyrazine-1,6-dione, (3R)-3,4-dihydro-2-[[4-methoxy-3-(trifluoromethyl)phenyl]methyl]-3-methyl-7-(4-methyl-1H-imidazol-1-yl)-2H-pyrido[1,2-a]pyrazine-1,6-dione, 2-[1-(2,3-dichlorophenyl)ethyl]-3,4-dihydro-7-(4-methyl-1H-imidazol-1-yl)-2H-pyrido[1,2-a]pyrazine-1,6-dione (R or S), 2-[1-(2,3-dichlorophenyl)ethyl]-3,4-dihydro-7-(4-methyl-1H-imidazol-1-yl)-2H-pyrido[1,2-a]pyrazine-1,6-dione (S or R), 2-[1-(3,4-dichlorophenyl)ethyl]-3,4-dihydro-7-(4-methyl-1H-imidazol-1-yl)-2H-pyrido[1,2-a]pyrazine-1,6-dione (R or S), 2-[1-(3,4-dichlorophenyl)ethyl]-3,4-dihydro-7-(4-methyl-1H-imidazol-1-yl)-2H-pyrido[1,2-a]pyrazine-1,6-dione (S or R), (3R)-2-[[3,5-bis(trifluoromethyl)phenyl]methyl]-3-ethyl-3,4-dihydro-7-(4-methyl-1H-imidazol-1-yl)-2H-pyrido[1,2-a]pyrazine-1,6-dione, (3R)-2-[[3,5-bis(trifluoromethyl)phenyl]methyl]-3-ethyl-3,4-dihydro-7-(4-methyl-1H-imidazol-1-yl)-2H-pyrido[1,2-a]pyrazine-1,6-dione .HCl, (3R)-2-[[4-chloro-3-(trifluoromethyl)phenyl]methyl]-3,4-dihydro-3-methyl-7-(4-methyl-1H-imidazol-1-yl)-2H-pyrido[1,2-a]pyrazine-1,6-dione, 3,4-dihydro-7-(4-methyl-1H-imidazol-1-yl)-2-[[3-methyl-5-(trifluoromethyl)phenyl]-methyl]-2H-pyrido[1,2-a]pyrazine-1,6-dione, 2-[(3,4-dichlorophenyl)methyl]-3,4-dihydro-7-(4-methyl-1H-imidazol-1-yl)-3-(tetrahydro-2H-pyran-4-yl)-2H-pyrido[1,2-a]pyrazine-1,6-dione, 3,4-dihydro-7-(4-methyl-1H-imidazol-1-yl)-2-[1,2,3,4-tetrahydro-7-(trifluoromethyl)-1-naphthalenyl]-2H-pyrido[1,2-a]pyrazine-1,6-dione, 3,4-dihydro-7-(4-methyl-1H-imidazol-1-yl)-2-[1,2,3,4-tetrahydro-5-(trifluoromethyl)-1-naphthalenyl]-2H-pyrido[1,2-a]pyrazine-1,6-dione, 2-[[3,5-bis(trifluoromethyl)phenyl]phenylmethyl]-3,4-dihydro-7-(4-methyl-1H-imidazol-1-yl)-2H-pyrido[1,2-a]pyrazine-1,6-dione, (3R)-2-[[3,4-bis(trifluoromethyl)phenyl]methyl]-3,4-dihydro-3-methyl-7-(4-methyl-1H-imidazol-1-yl)-2H-pyrido[1,2-a]pyrazine-1,6-dione, (3R)-2-[[3,5-bis(trifluoromethyl)phenyl]methyl]-7-(4-ethyl-1H-imidazol-1-yl)-3,4-dihydro-3-methyl-2H-pyrido[1,2-a]pyrazine-1,6-dione, (3R)-2-[[3,5-bis(trifluoromethyl)phenyl]methyl]-7-(4-ethyl-1H-imidazol-1-yl)-3,4-dihydro-3-methyl-2H-pyrido[1,2-a]pyrazine-1,6-dione .HCl, 2-[[3,5-bis(trifluoromethyl)phenyl]methyl]-2,3,4,5-tetrahydro-3-methyl-8-(4-methyl-1H-imidazol-1-yl)-pyrido[1,2-a][1,4]diazepine-1,7-dione, (3S)-2-[[3,5-bis(trifluoromethyl)phenyl]methyl]-3,4-dihydro-3-methyl-7-(4-methyl-1H-imidazol-1-yl)-2H-pyrido[1,2-a]pyrazine-1,6-dione, (3S)-2-[[3,5-bis(trifluoromethyl)phenyl]methyl]-7-(4-ethyl-1H-imidazol-1-yl)-3,4-dihydro-3-(methoxymethyl)-2H-pyrido[1,2-a]pyrazine-1,6-dione, (3S)-2-[[3,5-bis(trifluoromethyl)phenyl]methyl]-7-(4-ethyl-1H-imidazol-1-yl)-3,4-dihydro-3-(hydroxymethyl)-2H-pyrido[1,2-a]pyrazine-1,6-dione, (3R)-2-[[3,5-bis(trifluoromethyl)phenyl]methyl]-3-[(dimethylamino)methyl]-7-(4-ethyl-1H-imidazol-1-yl)-3,4-dihydro-2H-pyrido[1,2-a]pyrazine-1,6-dione, (3S)-2-[[3,5-bis(trifluoromethyl)phenyl]methyl]-3,4-dihydro-3-(hydroxymethyl)-7-(4-methyl-1H-imidazol-1-yl)-2H-pyrido[1,2-a]pyrazine-1,6-dione, 2-[2-[3,5-bis(trifluoromethyl)phenyl]ethyl]-3,4-dihydro-7-(4-methyl-1H-imidazol-1-yl)-2H-pyrido[1,2-a]pyrazine-1,6-dione, 2-[[3,5-bis(trifluoromethyl)phenyl](tetrahydro-2H-pyran-4-yl)methyl]-3,4-dihydro-7-(4-methyl-1H-imidazol-1-yl)-2H-pyrido[1,2-a]pyrazine-1,6-dione, 2-[[3,5-bis(trifluoromethyl)phenyl]methyl]-3,4-dihydro-3,4-dimethyl-7-(4-methyl-1H-imidazol-1-yl)-2H-pyrido[1,2-a]pyrazine-1,6-dione (CIS), 2-[(2,3-dichlorophenyl)methyl]-3,4-dihydro-7-(4-methyl-1H-imidazol-1-yl)-2H-pyrido[1,2-a]pyrazine-1,6-dione, (3R)-2-[[3,5-bis(trifluoromethyl)phenyl]methyl]-3-[(dimethylamino)methyl]-3,4-dihydro-7-(4-methyl-1H-imidazol-1-yl)-2H-pyrido[1,2-a]pyrazine-1,6-dione, (3R)-2-[[3,5-bis(trifluoromethyl)phenyl]methyl]-3,4-dihydro-3-[(methylamino)-methyl]-7-(4-methyl-1H-imidazol-1-yl)-2H-pyrido[1,2-a]pyrazine-1,6-dione, (3R)-2-[[3-(cyclopropylmethoxy)-5-(trifluoromethyl)phenyl]methyl]-3,4-dihydro-3-methyl-7-(4-methyl-1H-imidazol-1-yl)-2H-pyrido[1,2-a]pyrazine-1,6-dione, (3R)-2-[[3-(cyclopropylmethoxy)-5-(trifluoromethyl)phenyl]methyl]-3,4-dihydro-3-methyl-7-(4-methyl-1H-imidazol-1-yl)-2H-pyrido[1,2-a]pyrazine-1,6-dione .HCl, (3R)-3,4-dihydro-3-methyl-2-[[3-(1-methylethoxy)-5-(trifluoromethyl)phenyl]methyl]-7-(4-methyl-1H-imidazol-1-yl)-2H-pyrido[1,2-a]pyrazine-1,6-dione, (3R)-3,4-dihydro-3-methyl-2-[[3-(1-methylethoxy)-5-(trifluoromethyl)phenyl]-methyl]-7-(4-methyl-1H-imidazol-1-yl)-2H-pyrido[1,2-a]pyrazine-1,6-dione .HCl, (3R)-2-[[2-fluoro-5-(trifluoromethyl)phenyl]methyl]-3,4-dihydro-3-methyl-7-(4-methyl-1H-imidazol-1-yl)-2H-pyrido[1,2-a]pyrazine-1,6-dione, (3R)-2-[[2-chloro-5-(trifluoromethyl)phenyl]methyl]-3,4-dihydro-3-methyl-7-(4-methyl-1H-imidazol-1-yl)-2H-pyrido[1,2-a]pyrazine-1,6-dione, (3R)-3,4-dihydro-3-methyl-7-(4-methyl-1H-imidazol-1-yl)-2-[[2-methyl-5-(trifluoromethyl)phenyl]methyl]-2H-pyrido[1,2-a]pyrazine-1,6-dione, (3R)-3,4-dihydro-3-methyl-7-(4-methyl-1H-imidazol-1-yl)-2-[[2-methyl-5-(trifluoromethyl)phenyl]methyl]-2H-pyrido[1,2-a]pyrazine-1,6-dione .HCl, (3R)-2-[2-[3,5-bis(trifluoromethyl)phenyl]ethyl]-3,4-dihydro-3-methyl-7-(4-methyl-1H-imidazol-1-yl)-2H-pyrido[1,2-a]pyrazine-1,6-dione, (3R)-2-[[4-chloro-3-(1-piperidinyl)phenyl]methyl]-3,4-dihydro-3-methyl-7-(4-methyl-1H-imidazol-1-yl)-2H-pyrido[1,2-a]pyrazine-1,6-dione, (3R)-2-[[3-(ethoxymethyl)-5-(trifluoromethyl)phenyl]methyl]-3,4-dihydro-3-methyl-7-(4-methyl-1H-imidazol-1-yl)-2H-pyrido[1,2-a]pyrazine-1,6-dione;

(3R)-2-[[3-(ethoxymethyl)-5-(trifluoromethyl)phenyl]methyl]-3,4-dihydro-3-methyl-7-(4-methyl-1H-imidazol-1-yl)-2H-pyrido[1,2-a]pyrazine-1,6-dione .HCl, (3R)-3,4-dihydro-3-methyl-7-(4-methyl-1H-imidazol-1-yl)-2-[[3-(1-piperidinyl)-5-(trifluoromethyl)phenyl]methyl]-2H-pyrido[1,2-a]pyrazine-1,6-dione, (3R)-3,4-dihydro-3-methyl-7-(4-methyl-1H-imidazol-1-yl)-2-[[3-(1-piperidinyl)-5-(trifluoromethyl)phenyl]methyl]-2H-pyrido[1,2-a]pyrazine-1,6-dione .HCl, (3R)-3,4-dihydro-2-[[4-methoxy-2-methyl-5-(1-methylethyl)phenyl]methyl]-3-methyl-7-(4-methyl-1H-imidazol-1-yl)-2H-pyrido[1,2-a]pyrazine-1,6-dione, (3R)-3,4-dihydro-2-[[4-methoxy-2-methyl-5-(1-methylethyl)phenyl]methyl]-3-methyl-7-(4-methyl-1H-imidazol-1-yl)-2H-pyrido[1,2-a]pyrazine-1,6-dione .HCl, 2-[1-[3,5-bis(trifluoromethyl)phenyl]-2-methoxyethyl]-3,4-dihydro-7-(4-methyl-1H-imidazol-1-yl)-2H-pyrido[1,2-a]pyrazine-1,6-dione, 2-[[3,5-bis(trifluoromethyl)phenyl]methyl]-3,4-dihydro-3,4-dimethyl-7-(4-methyl-1H-imidazol-1-yl)-2H-pyrido[1,2-a]pyrazine-1,6-dione (CIS A (SFC-MS)), 2-[[3,5-bis(trifluoromethyl)phenyl]methyl]-3,4-dihydro-3,4-dimethyl-7-(4-methyl-1H-imidazol-1-yl)-2H-pyrido[1,2-a]pyrazine-1,6-dione (CIS B (SFC-MS)), (3R)-2-[[2-chloro-5-(4-methyl-1-piperidinyl)phenyl]methyl]-3,4-dihydro-3-methyl-7-(4-methyl-1H-imidazol-1-yl)-2H-pyrido[1,2-a]pyrazine-1,6-dione, (3R)-2-[[2-chloro-5-(4-methyl-1-piperidinyl)phenyl]methyl]-3,4-dihydro-3-methyl-7-(4-methyl-1H-imidazol-1-yl)-2H-pyrido[1,2-a]pyrazine-1,6-dione .HCl, (3R)-2-[[2-chloro-5-[4-(trifluoromethyl)-1-piperidinyl]phenyl]methyl]-3,4-dihydro-3-methyl-7-(4-methyl-1H-imidazol-1-yl)-2H-pyrido[1,2-a]pyrazine-1,6-dione, (3R)-2-[[2-chloro-5-[4-(trifluoromethyl)-1-piperidinyl]phenyl]methyl]-3,4-dihydro-3-methyl-7-(4-methyl-1H-imidazol-1-yl)-2H-pyrido[1,2-a]pyrazine-1,6-dione .HCl, (3R)-2-[[2-chloro-5-(1-pyrrolidinyl)phenyl]methyl]-3,4-dihydro-3-methyl-7-(4-methyl-1H-imidazol-1-yl)-2H-pyrido[1,2-a]pyrazine-1,6-dione, (3R)-2-[[2-chloro-5-(1-pyrrolidinyl)phenyl]methyl]-3,4-dihydro-3-methyl-7-(4-methyl-1H-imidazol-1-yl)-2H-pyrido[1,2-a]pyrazine-1,6-dione .HCl, (3R)-2-[[3-(3,5-dimethyl-1H-pyrazol-1-yl)phenyl]methyl]-3,4-dihydro-3-methyl-7-(4-methyl-1H-imidazol-1-yl)-2H-pyrido[1,2-a]pyrazine-1,6-dione, (3R)-2-[[3-(cyclopropylmethyl)-5-(trifluoromethyl)phenyl]methyl]-3,4-dihydro-3-methyl-7-(4-methyl-1H-imidazol-1-yl)-2H-pyrido[1,2-a]pyrazine-1,6-dione (3R)-2-[[3-(cyclopropylmethyl)-5-(trifluoromethyl)phenyl]methyl]-3,4-dihydro-3-methyl-7-(4-methyl-1H-imidazol-1-yl)-2H-pyrido[1,2-a]pyrazine-1,6-dione .HCl, 2-[1-[3,5-bis(trifluoromethyl)phenyl]ethyl]-3,4-dihydro-3-methyl-7-(4-methyl-1H-imidazol-1-yl)-2H-pyrido[1,2-a]pyrazine-1,6-dione (1R or 1S, 3R) (diastereomer A (SFC-MS)), 2-[1-[3,5-bis(trifluoromethyl)phenyl]ethyl]-3,4-dihydro-3-methyl-7-(4-methyl-1H-imidazol-1-yl)-2H-pyrido[1,2-a]pyrazine-1,6-dione (1S or 1R, 3R) (diastereomer B (SFC-MS)), (3R)-2-[(2,2-difluoro-1,3-benzodioxol-5-yl)methyl]-3,4-dihydro-3-methyl-7-(4-methyl-1H-imidazol-1-yl)-2H-pyrido[1,2-a]pyrazine-1,6-dione, (3R)-3,4-dihydro-3-methyl-7-(4-methyl-1H-imidazol-1-yl)-2-[[4-methyl-3-(1-pyrazol-1-yl)phenyl]methyl]-2H-pyrido[1,2-a]pyrazine-1,6-dione, (3R)-3,4-dihydro-3-methyl-7-(4-methyl-1H-imidazol-1-yl)-2-[[4-methyl-3-(1-pyrazol-1-yl)phenyl]methyl]-2H-pyrido[1,2-a]pyrazine-1,6-dione .HCl, (3R)-2-[(3-bromobenzo[b]thien-5-yl)methyl]-3,4-dihydro-3-methyl-7-(4-methyl-1H-imidazol-1-yl)-2H-pyrido[1,2-a]pyrazine-1,6-dione, (3R)-2-[[3-cyclopropyl-5-(trifluoromethyl)phenyl]methyl]-3,4-dihydro-3-methyl-7-(4-methyl-1H-imidazol-1-yl)-2H-pyrido[1,2-a]pyrazine-1,6-dione, (3R)-2-[[3-cyclopropyl-5-(trifluoromethyl)phenyl]methyl]-3,4-dihydro-3-methyl-7-(4-methyl-1H-imidazol-1-yl)-2H-pyrido[1,2-a]pyrazine-1,6-dione .HCl, 2-[[1-[3,5-bis(trifluoromethyl)phenyl]cyclopropyl]methyl]-3,4-dihydro-7-(4-methyl-1H-imidazol-1-yl)-2H-pyrido[1,2-a]pyrazine-1,6-dione, and (3R)-2-[[3,5-bis(trifluoromethyl)phenyl]methyl]-7-(4-chloro-1H-imidazol-1-yl)-3,4-dihydro-3-methyl-2H-pyrido[1,2-a]pyrazine-1,6-dione, 2-[2-[3,5-bis(trifluoromethyl)phenyl]-1-methylethyl]-3,4-dihydro-7-(4-methyl-1H-imidazol-1-yl)-2H-pyrido[1,2-a]pyrazine-1,6-dione, (3R)-3,4-dihydro-3-methyl-7-(4-methyl-1H-imidazol-1-yl)-2-[[3-(1-piperidinyl)-4-(trifluoromethyl)phenyl]methyl]-2H-pyrido[1,2-a]pyrazine-1,6-dione HCl salt, 2-[[1-[2-chloro-3-(trifluoromethyl)phenyl]cyclopropyl]methyl]-3,4-dihydro-7-(4-methyl-1H-imidazol-1-yl)-2H-pyrido[1,2-a]pyrazine-1,6-dione, 2-[2-[3,5-bis(trifluoromethyl)phenyl]propyl]-3,4-dihydro-7-(4-methyl-1H-imidazol-1-yl)-2H-pyrido[1,2-a]pyrazine-1,6-dione, 2-[1-[2-fluoro-5-(trifluoromethyl)phenyl]ethyl]-3,4-dihydro-7-(4-methyl-1H-imidazol-1-yl)-2H-pyrido[1,2-a]pyrazine-1,6-dione, 2-[[3,5-bis(trifluoromethyl)phenyl]methyl]-3,4-dihydro-3-(1-hydroxyethyl)-7-(4-methyl-1H-imidazol-1-yl)-2H-pyrido[1,2-a]pyrazine-1,6-dione, (3R)-3,4-dihydro-3-methyl-7-(4-methyl-1H-imidazol-1-yl)-2-[[3-(2,2,2-trifluoroethoxy)-5-(trifluoromethyl)phenyl]methyl]-2H-pyrido[1,2-a]pyrazine-1,6-dione .HCl, (3R)-2-[(5-chlorobenzo[b]thien-3-yl)methyl]-3,4-dihydro-3-methyl-7-(4-methyl-1H-imidazol-1-yl)-2H-pyrido[1,2-a]pyrazine-1,6-dione, 2-[[1-[3,5-bis(trifluoromethyl)phenyl]cyclobutyl]methyl]-3,4-dihydro-7-(4-methyl-1H-imidazol-1-yl)-2H-pyrido[1,2-a]pyrazine-1,6-dione, (3R)-2-[[4-chloro-2-fluoro-5-(1-methylethoxy)phenyl]methyl]-3,4-dihydro-3-methyl-7-(4-methyl-1H-imidazol-1-yl)-2H-pyrido[1,2-a]pyrazine-1,6-dione .HCl, (3R)-2-[[3,5-bis(trifluoromethyl)phenyl]methyl]-3,4-dihydro-3,8-dimethyl-7-(4-methyl-1H-imidazol-1-yl)-2H-pyrido[1,2-a]pyrazine-1,6-dione, 3,4-dihydro-2-[[3-(1-methylethoxy)-5-(trifluoromethyl)phenyl]methyl]-7-(4-methyl-1H-imidazol-1-yl)-2H-pyrido[1,2-a]pyrazine-1,6-dione, (3R)-2-[[3,5-bis(trifluoromethyl)phenyl]methyl]-9-chloro-3,4-dihydro-3-methyl-7-(4-methyl-1H-imidazol-1-yl)-2H-pyrido[1,2-a]pyrazine-1,6-dione, (3R)-2-[[3,5-bis(trifluoromethyl)phenyl]methyl]-9-fluoro-3,4-dihydro-3-methyl-7-(4-methyl-1H-imidazol-1-yl)-2H-pyrido[1,2-a]pyrazine-1,6-dione, (3R)-2-[[3,5-bis(trifluoromethyl)phenyl]methyl]-8-bromo-3,4-dihydro-3-methyl-7-(4-methyl-1H-imidazol-1-yl)-2H-pyrido[1,2-a]pyrazine-1,6-dione, (3R)-3,4-dihydro-3-methyl-2-[2-[3-(1-methylethoxy)-5-(trifluoromethyl)phenyl]ethyl]-7-(4-methyl-1H-imidazol-1-yl)-2H-pyrido[1,2-a]pyrazine-1,6-dione .HCl, (3R)-2-[[3,5-bis(trifluoromethyl)phenyl]methyl]-3,4-dihydro-3-methyl-7-(3-methyl-1H-1,2,4-triazol-1-yl)-2H-pyrido[1,2-a]pyrazine-1,6-dione, 2-[1-[3,5-bis(trifluoromethyl)phenyl]ethyl]-3,4-dihydro-3-methyl-7-(4-methyl-1H-imidazol-1-yl)-2H-pyrido[1,2-a]pyrazine-1,6-dione (1RS, 3R), (3R)-3,4-dihydro-3-methyl-7-(4-methyl-1H-imidazol-1-yl)-2-[[3-(trifluoromethyl)-5-[2-(trifluoromethyl)-4-morpholinyl]phenyl]methyl]-2H-pyrido[1,2-a]pyrazine-1,6-dione HCl salt, (3R)-2-[[3-bromo-5-(trifluoromethoxy)phenyl]methyl]-3,4-dihydro-3-methyl-7-(4-methyl-1H-imidazol-1-yl)-2H-pyrido[1,2-a]pyrazine-1,6-dione .HCl, (3R)-2-[[1-[3,5-bis(trifluoromethyl)phenyl]cyclopropyl]methyl]-3,4-dihydro-3-methyl-7-(4-methyl-1H-imidazol-1-yl)-2H-pyrido[1,2-a]pyrazine-1,6-dione .HCl, (3R)-2-[[3,5-bis(trifluoromethyl)phenyl]methyl]-8-chloro-3,4-dihydro-3-methyl-7-(4-methyl-1H-imidazol-1-yl)-2H-pyrido[1,2-a]pyrazine-1,6-dione, 3,4-dihydro-2-[1-[3-methoxy-5-(trifluoromethyl)phenyl]ethyl]-3-methyl-7-(4-methyl-1H-imidazol-1-yl)-2H-pyrido[1,2-a]pyrazine-1,6-dione (1S or 1R, 3R) .HCl, 3,4-dihydro-2-[1-[3-methoxy-5-(trifluoromethyl)phenyl]ethyl]-3-methyl-7-(4-methyl-1H-imidazol-1-yl)-2H-pyrido[1,2-a]pyrazine-1,6-dione (1R or 1S, 3R) .HCl, 3,4-dihydro-3-methyl-7-(4-methyl-1H-imidazol-1-yl)-2-[1-[3-(trifluoromethoxy)phenyl]ethyl]-2H-pyrido[1,2-a]pyrazine-1,6-dione (1S or 1R, 3R) .HCl, 3,4-dihydro-3-methyl-7-(4-methyl-1H-imidazol-1-yl)-2-[1-[3-(trifluoromethoxy)phenyl]ethyl]-2H-pyrido[1,2-a]pyrazine-1,6-dione (1R or 1S, 3R) .HCl, (3R)-2-[[3-bromo-5-(trifluoromethyl)phenyl]methyl]-3,4-dihydro-3-methyl-7-(4-methyl-1H-imidazol-1-yl)-2H-pyrido[1,2-a]pyrazine-1,6-dione .HCl, 2-[1-[3-ethoxy-5-(trifluoromethyl)phenyl]ethyl]-3,4-dihydro-3-methyl-7-(4-methyl-1H-imidazol-1-yl)-2H-pyrido[1,2-a]pyrazine-1,6-dione (1S or 1R, 3R) .HCl, 2-[1-[3-ethoxy-5-(trifluoromethyl)phenyl]ethyl]-3,4-dihydro-3-methyl-7-(4-methyl-1H-imidazol-1-yl)-2H-pyrido[1,2-a]pyrazine-1,6-dione (1R or 1S, 3R) .HCl, 3,4-dihydro-2-[1-[3-methoxy-5-(trifluoromethyl)phenyl]propyl]-3-methyl-7-(4-methyl-1H-imidazol-1-yl)-2H-pyrido[1,2-a]pyrazine-1,6-dione (1S or 1R, 3R) .HCl, 3,4-dihydro-2-[1-[3-methoxy-5-(trifluoromethyl)phenyl]propyl]-3-methyl-7-(4-methyl-1H-imidazol-1-yl)-2H-pyrido[1,2-a]pyrazine-1,6-dione (1R or 1S, 3R) .HCl, (3R)-3,4-dihydro-3-methyl-7-(4-methyl-1H-imidazol-1-yl)-2-[[3-(trifluoromethoxy)-5-(trifluoromethyl)phenyl]methyl]-2H-pyrido[1,2-a]pyrazine-1,6-dione .HCl, (3R)-2-[[3-fluoro-5-(trifluoromethoxy)phenyl]methyl]-3,4-dihydro-3-methyl-7-(4-methyl-1H-imidazol-1-yl)-2H-pyrido[1,2-a]pyrazine-1,6-dione .HCl, (3R)-2-[(5-chloro-1H-indol-3-yl)methyl]-3,4-dihydro-3-methyl-7-(4-methyl-1H-imidazol-1-yl)-2H-pyrido[1,2-a]pyrazine-1,6-dione, (3R)-2-[(5-chloro-1-methyl-1H-indol-3-yl)methyl]-3,4-dihydro-3-methyl-7-(4-methyl-1H-imidazol-1-yl)-2H-pyrido[1,2-a]pyrazine-1,6-dione, 2-[1-[3-(cyclopropylmethyl)-5-(trifluoromethyl)phenyl]ethyl]-3,4-dihydro-3-methyl-7-(4-methyl-1H-imidazol-1-yl)-2H-pyrido[1,2-a]pyrazine-1,6-dione (1S or 1R, 3R) .HCl, 2-[1-[3-(cyclopropylmethyl)-5-(trifluoromethyl)phenyl]ethyl]-3,4-dihydro-3-methyl-7-(4-methyl-1H-imidazol-1-yl)-2H-pyrido[1,2-a]pyrazine-1,6-dione (1R or 1S, 3R) .HCl, (3R)-3,4-dihydro-3-methyl-7-(4-methyl-1H-imidazol-1-yl)-2-[[3-(2,2,2-trifluoroethyl)-5-(trifluoromethyl)phenyl]methyl]-2H-pyrido[1,2-a]pyrazine-1,6-dione .HCl, (3R)-2-[(3,4-difluorophenyl)methyl]-3,4-dihydro-3-methyl-7-(4-methyl-1H-imidazol-1-yl)-2H-pyrido[1,2-a]pyrazine-1,6-dione, (3R)-3,4-dihydro-2-[(3-methoxyphenyl)methyl]-3-methyl-7-(4-methyl-1H-imidazol-1-yl)-2H-pyrido[1,2-a]pyrazine-1,6-dione, (3R)-2-[(3,5-dichlorophenyl)methyl]-3,4-dihydro-3-methyl-7-(4-methyl-1H-imidazol-1-yl)-2H-pyrido[1,2-a]pyrazine-1,6-dione, 2-[1-[3-chloro-5-(trifluoromethyl)phenyl]ethyl]-3,4-dihydro-3-methyl-7-(4-methyl-1H-imidazol-1-yl)-2H-pyrido[1,2-a]pyrazine-1,6-dione (1S or 1R, 3R; diasteromer A (SFC-MS)), 2-[1-[3-chloro-5-(trifluoromethyl)phenyl]ethyl]-3,4-dihydro-3-methyl-7-(4-methyl-1H-imidazol-1-yl)-2H-pyrido[1,2-a]pyrazine-1,6-dione (1R or 1S, 3R; diasteromer B (SFC-MS));

(3R)-3,4-dihydro-3-methyl-2-[[2-(1-methylethoxy)-6-(trifluoromethyl)-4-pyridinyl]methyl]-7-(4-methyl-1H-imidazol-1-yl)-2H-pyrido[1,2-a]pyrazine-1,6-dione .HCl, 2-[1-[3-fluoro-5-(trifluoromethoxy)phenyl]ethyl]-3,4-dihydro-3-methyl-7-(4-methyl-1H-imidazol-1-yl)-2H-pyrido[1,2-a]pyrazine-1,6-dione (1S or 1R, 3R) .HCl, 2-[1-[3-fluoro-5-(trifluoromethoxy)phenyl]ethyl]-3,4-dihydro-3-methyl-7-(4-methyl-1H-imidazol-1-yl)-2H-pyrido[1,2-a]pyrazine-1,6-dione (1R or 1S, 3R) .HCl, (3R)-2-[(6-bromo-1H-indol-3-yl)methyl]-3,4-dihydro-3-methyl-7-(4-methyl-1H-imidazol-1-yl)-2H-pyrido[1,2-a]pyrazine-1,6-dione, (3R)-3,4-dihydro-3-methyl-7-(4-methyl-1H-imidazol-1-yl)-2-(phenylmethyl)-2H-pyrido[1,2-a]pyrazine-1,6-dione, (3R)-2-[(6-chloro-1H-indol-3-yl)methyl]-3,4-dihydro-3-methyl-7-(4-methyl-1H-imidazol-1-yl)-2H-pyrido[1,2-a]pyrazine-1,6-dione, (3R)-2-[(6-chloro-1-methyl-1H-indol-3-yl)methyl]-3,4-dihydro-3-methyl-7-(4-methyl-1H-imidazol-1-yl)-2H-pyrido[1,2-a]pyrazine-1,6-dione, (3R)-2-[(6-bromo-1-methyl-1H-indol-3-yl)methyl]-3,4-dihydro-3-methyl-7-(4-methyl-1H-imidazol-1-yl)-2H-pyrido[1,2-a]pyrazine-1,6-dione, (3R)-3,4-dihydro-3-methyl-7-(4-methyl-1H-imidazol-1-yl)-2-(2-phenylethyl)-2H-pyrido[1,2-a]pyrazine-1,6-dione, 2-[1-[3-fluoro-5-(trifluoromethoxy)phenyl]ethyl]-3,4-dihydro-3-methyl-7-(4-methyl-1H-imidazol-1-yl)-2H-pyrido[1,2-a]pyrazine-1,6-dione (1RS, 3R) .HCl, 2-(2,3-dihydro-1H-inden-2-yl)-3,4-dihydro-3-methyl-7-(4-methyl-1H-imidazol-1-yl)-2H-pyrido[1,2-a]pyrazine-1,6-dione (R or S; enantiomer A (SFC-MS)), 2-(2,3-dihydro-1H-inden-2-yl)-3,4-dihydro-3-methyl-7-(4-methyl-1H-imidazol-1-yl)-2H-pyrido[1,2-a]pyrazine-1,6-dione (S or R; enantiomer B (SFC-MS)), 2-[2,3-dihydro-6-(trifluoromethyl)-1H-inden-1-yl]-3,4-dihydro-3-methyl-7-(4-methyl-1H-imidazol-1-yl)-2H-pyrido[1,2-a]pyrazine-1,6-dione (1S or 1R, 3R), 2-[2,3-dihydro-6-(trifluoromethyl)-1H-inden-1-yl]-3,4-dihydro-3-methyl-7-(4-methyl-1H-imidazol-1-yl)-2H-pyrido[1,2-a]pyrazine-1,6-dione (1R or 1S, 3R), 2-[1-(5-chloro-6-fluoro-1H-indol-3-yl)ethyl]-3,4-dihydro-3-methyl-7-(4-methyl-1H-imidazol-1-yl)-2H-pyrido[1,2-a]pyrazine-1,6-dione (1R or 1S, 3R), 2-[1-(5-chloro-6-fluoro-1H-indol-3-yl)ethyl]-3,4-dihydro-3-methyl-7-(4-methyl-1H-imidazol-1-yl)-2H-pyrido[1,2-a]pyrazine-1,6-dione (1S or 1R, 3R), 2-[1-(5-chloro-6-fluoro-1-methyl-1H-indol-3-yl)ethyl]-3,4-dihydro-3-methyl-7-(4-methyl-1H-imidazol-1-yl)-2H-pyrido[1,2-a]pyrazine-1,6-dione (1R or 1S, 3R), 2-[1-(5-chloro-6-fluoro-1-methyl-1H-indol-3-yl)ethyl]-3,4-dihydro-3-methyl-7-(4-methyl-1H-imidazol-1-yl)-2H-pyrido[1,2-a]pyrazine-1,6-dione (1S or 1R, 3R), 2-[1-(5-chloro-1-ethyl-6-fluoro-1H-indol-3-yl)ethyl]-3,4-dihydro-3-methyl-7-(4-methyl-1H-imidazol-1-yl)-2H-pyrido[1,2-a]pyrazine-1,6-dione (1R or 1S, 3R), (3R)-2-[[6-bromo-1-(1-methylethyl)-1H-indol-3-yl]methyl]-3,4-dihydro-3-methyl-7-(4-methyl-1H-imidazol-1-yl)-2H-pyrido[1,2-a]pyrazine-1,6-dione, (3R)-3,4-dihydro-2-[(7-iodo-1H-indol-3-yl)methyl]-3-methyl-7-(4-methyl-1H-imidazol-1-yl)-2H-pyrido[1,2-a]pyrazine-1,6-dione, 2-[1-(5-chloro-1-ethyl-6-fluoro-1H-indol-3-yl)ethyl]-3,4-dihydro-3-methyl-7-(4-methyl-1H-imidazol-1-yl)-2H-pyrido[1,2-a]pyrazine-1,6-dione (1S or 1R, 3R), 2-[1-[5-chloro-6-fluoro-1-(1-methylethyl)-1H-indol-3-yl]ethyl]-3,4-dihydro-3-methyl-7-(4-methyl-1H-imidazol-1-yl)-2H-pyrido[1,2-a]pyrazine-1,6-dione (1R or 1S, 3R), 2-[1-[5-chloro-6-fluoro-1-(1-methylethyl)-1H-indol-3-yl]ethyl]-3,4-dihydro-3-methyl-7-(4-methyl-1H-imidazol-1-yl)-2H-pyrido[1,2-a]pyrazine-1,6-dione (1S or 1R, 3R), (3R)-2-[(5-chloro-6-fluoro-1H-indol-3-yl)methyl]-3,4-dihydro-3-methyl-7-(4-methyl-1H-imidazol-1-yl)-2H-pyrido[1,2-a]pyrazine-1,6-dione, (3R)-2-[(5-chloro-6-fluoro-1-methyl-1H-indol-3-yl)methyl]-3,4-dihydro-3-methyl-7-(4-methyl-1H-imidazol-1-yl)-2H-pyrido[1,2-a]pyrazine-1,6-dione, (3R)-2-[(6-bromo-1-phenyl-1H-indol-3-yl)methyl]-3,4-dihydro-3-methyl-7-(4-methyl-1H-imidazol-1-yl)-2H-pyrido[1,2-a]pyrazine-1,6-dione, 2-[1-(5-chloro-6-fluoro-1H-indol-3-yl)ethyl]-3,4-dihydro-7-(4-methyl-1H-imidazol-1-yl)-2H-pyrido[1,2-a]pyrazine-1,6-dione (R or S; enantiomer A (SFC-MS)), 2-[1-(5-chloro-6-fluoro-1H-indol-3-yl)ethyl]-3,4-dihydro-7-(4-methyl-1H-imidazol-1-yl)-2H-pyrido[1,2-a]pyrazine-1,6-dione (S or R; enantiomer B (SFC-MS)), 2-[1-(5-chloro-6-fluoro-1-methyl-1H-indol-3-yl)ethyl]-3,4-dihydro-7-(4-methyl-1H-imidazol-1-yl)-2H-pyrido[1,2-a]pyrazine-1,6-dione (R or S; enantiomer A (SFC-MS)), 2-[1-(5-chloro-6-fluoro-1-methyl-1H-indol-3-yl)ethyl]-3,4-dihydro-7-(4-methyl-1H-imidazol-1-yl)-2H-pyrido[1,2-a]pyrazine-1,6-dione (S or R; enantiomer B (SFC-MS)), (3R)-3,4-dihydro-3-methyl-7-(4-methyl-1H-imidazol-1-yl)-2-[[2-methyl-5-(trifluoromethyl)-1H-indol-3-yl]methyl]-2H-pyrido[1,2-a]pyrazine-1,6-dione, (3R)-2-[[1,2-dimethyl-5-(trifluoromethyl)-1H-indol-3-yl]methyl]-3,4-dihydro-3-methyl-7-(4-methyl-1H-imidazol-1-yl)-2H-pyrido[1,2-a]pyrazine-1,6-dione, (3R)-2-[[1-ethyl-2-methyl-5-(trifluoromethyl)-1H-indol-3-yl]methyl]-3,4-dihydro-3-methyl-7-(4-methyl-1H-imidazol-1-yl)-2H-pyrido[1,2-a]pyrazine-1,6-dione, (3R)-3,4-dihydro-2-[(5-methoxy-1H-indol-3-yl)methyl]-3-methyl-7-(4-methyl-1H-imidazol-1-yl)-2H-pyrido[1,2-a]pyrazine-1,6-dione, (3R)-3,4-dihydro-3-methyl-7-(4-methyl-1H-imidazol-1-yl)-2-[[5-(trifluoromethyl)-1H-indol-3-yl]methyl]-2H-pyrido[1,2-a]pyrazine-1,6-dione, (3R)-3,4-dihydro-2-[(6-methoxy-1H-indol-3-yl)methyl]-3-methyl-7-(4-methyl-1H-imidazol-1-yl)-2H-pyrido[1,2-a]pyrazine-1,6-dione, (3R)-3,4-dihydro-3-methyl-7-(4-methyl-1H-imidazol-1-yl)-2-[[6-(trifluoromethyl)-1H-indol-3-yl]methyl]-2H-pyrido[1,2-a]pyrazine-1,6-dione, 2-[1-(3,5-dichlorophenyl)ethyl]-3,4-dihydro-3-methyl-7-(4-methyl-1H-imidazol-1-yl)-2H-pyrido[1,2-a]pyrazine-1,6-dione (1R or 1S, 3R), 2-[1-(3,5-dichlorophenyl)ethyl]-3,4-dihydro-3-methyl-7-(4-methyl-1H-imidazol-1-yl)-2H-pyrido[1,2-a]pyrazine-1,6-dione (1S or 1R, 3R), (3R)-2-[2-(5-chloro-2-methoxyphenyl)ethyl]-3,4-dihydro-3-methyl-7-(4-methyl-1H-imidazol-1-yl)-2H-pyrido[1,2-a]pyrazine-1,6-dione, (3R)-2-[2-[2-fluoro-5-(trifluoromethyl)phenyl]ethyl]-3,4-dihydro-3-methyl-7-(4-methyl-1H-imidazol-1-yl)-2H-pyrido[1,2-a]pyrazine-1,6-dione, (3R)-2-[2-(2,3-dichlorophenyl)ethyl]-3,4-dihydro-3-methyl-7-(4-methyl-1H-imidazol-1-yl)-2H-pyrido[1,2-a]pyrazine-1,6-dione .HCl, (3R)-2-[2-(2,5-dichlorophenyl)ethyl]-3,4-dihydro-3-methyl-7-(4-methyl-1H-imidazol-1-yl)-2H-pyrido[1,2-a]pyrazine-1,6-dione, (3R)-3,4-dihydro-3-methyl-7-(4-methyl-1H-imidazol-1-yl)-2-[2-[2-methyl-3-(trifluoromethyl)phenyl]ethyl]-2H-pyrido[1,2-a]pyrazine-1,6-dione, (3R)-3,4-dihydro-3-methyl-7-(4-methyl-1H-imidazol-1-yl)-2-[[1-methyl-6-(trifluoromethyl)-1H-indol-3-yl]methyl]-2H-pyrido[1,2-a]pyrazine-1,6-dione, (3R)-2-[[1-ethyl-5-(trifluoromethyl)-1H-indol-3-yl]methyl]-3,4-dihydro-3-methyl-7-(4-methyl-1H-imidazol-1-yl)-2H-pyrido[1,2-a]pyrazine-1,6-dione, (3R)-3,4-dihydro-3-methyl-7-(4-methyl-1H-imidazol-1-yl)-2-[[1-methyl-5-(trifluoromethyl)-1H-indol-3-yl]methyl]-2H-pyrido[1,2-a]pyrazine-1,6-dione, (3R)-3,4-dihydro-2-[[5-methoxy-1-(1-methylethyl)-1H-indol-3-yl]methyl]-3-methyl-7-(4-methyl-1H-imidazol-1-yl)-2H-pyrido[1,2-a]pyrazine-1,6-dione, 2-[1-(5-chloro-7-fluoro-1H-indol-3-yl)ethyl]-3,4-dihydro-3-methyl-7-(4-methyl-1H-imidazol-1-yl)-2H-pyrido[1,2-a]pyrazine-1,6-dione (1R or 1S, 3R), 2-[1-(5-chloro-7-fluoro-1H-indol-3-yl)ethyl]-3,4-dihydro-3-methyl-7-(4-methyl-1H-imidazol-1-yl)-2H-pyrido[1,2-a]pyrazine-1,6-dione (1S or 1R, 3R), 2-[1-(5-chloro-7-fluoro-1-methyl-1H-indol-3-yl)ethyl]-3,4-dihydro-3-methyl-7-(4-methyl-1H-imidazol-1-yl)-2H-pyrido[1,2-a]pyrazine-1,6-dione (1S or 1R, 3R), (3R)-2-[[1-ethyl-6-(trifluoromethyl)-1H-indol-3-yl]methyl]-3,4-dihydro-3-methyl-7-(4-methyl-1H-imidazol-1-yl)-2H-pyrido[1,2-a]pyrazine-1,6-dione, 2-[1-(5-chloro-7-fluoro-1-methyl-1H-indol-3-yl)ethyl]-3,4-dihydro-3-methyl-7-(4-methyl-1H-imidazol-1-yl)-2H-pyrido[1,2-a]pyrazine-1,6-dione (1R or 1S, 3R), 2-[1-(3,5-dichlorophenyl)ethyl]-3,4-dihydro-7-(4-methyl-1H-imidazol-1-yl)-2H-pyrido[1,2-a]pyrazine-1,6-dione (S or R; enantiomer A (SFC-MS)), 2-[1-(3,5-dichlorophenyl)ethyl]-3,4-dihydro-7-(4-methyl-1H-imidazol-1-yl)-2H-pyrido[1,2-a]pyrazine-1,6-dione (R or S; enantiomer B (SFC-MS)), 2-[1-(5-chloro-1-ethyl-7-fluoro-1H-indol-3-yl)ethyl]-3,4-dihydro-3-methyl-7-(4-methyl-1H-imidazol-1-yl)-2H-pyrido[1,2-a]pyrazine-1,6-dione (1R or 1S, 3R), 2-[1-(5-chloro-1-ethyl-7-fluoro-1H-indol-3-yl)ethyl]-3,4-dihydro-3-methyl-7-(4-methyl-1H-imidazol-1-yl)-2H-pyrido[1,2-a]pyrazine-1,6-dione (1S or 1R, 3R), 2-[1-[1-ethyl-5-(trifluoromethyl)-1H-indol-3-yl]ethyl]-3,4-dihydro-3-methyl-7-(4-methyl-1H-imidazol-1-yl)-2H-pyrido[1,2-a]pyrazine-1,6-dione (1R or 1S, 3R), 2-[1-[1-ethyl-5-(trifluoromethyl)-1H-indol-3-yl]ethyl]-3,4-dihydro-3-methyl-7-(4-methyl-1H-imidazol-1-yl)-2H-pyrido[1,2-a]pyrazine-1,6-dione (1S or 1R, 3R), 3,4-dihydro-3-methyl-7-(4-methyl-1H-imidazol-1-yl)-2-[1-[1-methyl-5-(trifluoromethyl)-1H-indol-3-yl]ethyl]-2H-pyrido[1,2-a]pyrazine-1,6-dione (1R or 1S, 3R), 3,4-dihydro-3-methyl-7-(4-methyl-1H-imidazol-1-yl)-2-[1-[1-methyl-5-(trifluoromethyl)-1H-indol-3-yl]ethyl]-2H-pyrido[1,2-a]pyrazine-1,6-dione (1S or 1R, 3R), 3,4-dihydro-3-methyl-7-(4-methyl-1H-imidazol-1-yl)-2-[1-[5-(trifluoromethyl)-1H-indol-3-yl]ethyl]-2H-pyrido[1,2-a]pyrazine-1,6-dione (1R or 1S, 3R), 3,4-dihydro-3-methyl-7-(4-methyl-1H-imidazol-1-yl)-2-[1-[5-(trifluoromethyl)-1H-indol-3-yl]ethyl]-2H-pyrido[1,2-a]pyrazine-1,6-dione (1S or 1R, 3R), (3R)-2-[[7-fluoro-1-methyl-5-(trifluoromethyl)-1H-indol-3-yl]methyl]-3,4-dihydro-3-methyl-7-(4-methyl-1H-imidazol-1-yl)-2H-pyrido[1,2-a]pyrazine-1,6-dione, (3R)-2-[[7-fluoro-5-(trifluoromethyl)-1H-indol-3-yl]methyl]-3,4-dihydro-3-methyl-7-(4-methyl-1H-imidazol-1-yl)-2H-pyrido[1,2-a]pyrazine-1,6-dione, (3R)-2-[[6-fluoro-5-(trifluoromethyl)-1H-indol-3-yl]methyl]-3,4-dihydro-3-methyl-7-(4-methyl-1H-imidazol-1-yl)-2H-pyrido[1,2-a]pyrazine-1,6-dione, (3R)-2-[(5-bromo-6-fluoro-1H-indol-3-yl)methyl]-3,4-dihydro-3-methyl-7-(4-methyl-1H-imidazol-1-yl)-2H-pyrido[1,2-a]pyrazine-1,6-dione, (3R)-2-[[6-fluoro-1-methyl-5-(trifluoromethyl)-1H-indol-3-yl]methyl]-3,4-dihydro-3-methyl-7-(4-methyl-1H-imidazol-1-yl)-2H-pyrido[1,2-a]pyrazine-1,6-dione, (3R)-2-[(5-bromo-6-fluoro-1-methyl-1H-indol-3-yl)methyl]-3,4-dihydro-3-methyl-7-(4-methyl-1H-imidazol-1-yl)-2H-pyrido[1,2-a]pyrazine-1,6-dione, 3,4-dihydro-3-methyl-7-(4-methyl-1H-imidazol-1-yl)-2-[1-[6-(trifluoromethyl)-1H-indol-3-yl]ethyl]-2H-pyrido[1,2-a]pyrazine-1,6-dione (1R or 1S, 3R), 2-[1-[1-ethyl-6-(trifluoromethyl)-1H-indol-3-yl]ethyl]-3,4-dihydro-3-methyl-7-(4-methyl-1H-imidazol-1-yl)-2H-pyrido[1,2-a]pyrazine-1,6-dione (1S or 1R, 3R), (3R)-2-[3-(Cyclopropylmethoxy)-4-methylbenzyl]-3-methyl-7-(4-methyl-1H-imidazol-1-yl)-3,4-dihydro-2H-pyrido[1,2-a]pyrazine-1,6-dione .HCl, (3R)-2-[3-(Cyclopropylmethoxy)-4-methylbenzyl]-3-methyl-7-(4-methyl-1H-imidazol-1-yl)-3,4-dihydro-2H-pyrido[1,2-a]pyrazine-1,6-dione, (3R)-2-[3,5-Bis(trifluoromethyl)benzyl]-7-(1H-imidazol-1-yl)-3-methyl-3,4-dihydro-2H-pyrido[1,2-a]pyrazine-1,6-dione, (3R)-2-[(5-Cyclopropyl-6-fluoro-1-methyl-1H-indol-3-yl)methyl]-3-methyl-7-(4-methyl-1H-imidazol-1-yl)-3,4-dihydro-2H-pyrido[1,2-a]pyrazine-1,6-dione, (3R)-2-[(6-fluoro-1-methyl-1H-indol-3-yl)methyl]-3-methyl-7-(4-methyl-1H-imidazol-1-yl)-3,4-dihydro-2H-pyrido[1,2-a]pyrazine-1,6-dione, 2-[1-(5-Chloro-1-ethyl-1H-indol-3-yl)ethyl]-3-methyl-7-(4-methyl-1H-imidazol-1-yl)-3,4-dihydro-2H-pyrido[1,2-a]pyrazine-1,6-dione (1S or 1R, 3R), 2-[1-(5-Chloro-1H-indol-3-yl)ethyl]-3-methyl-7-(4-methyl-1H-imidazol-1-yl)-3,4-dihydro-2H-pyrido[1,2-a]pyrazine-1,6-dione (1R or 1S, 3R), 2-[1-(5-Chloro-1H-indol-3-yl)ethyl]-3-methyl-7-(4-methyl-1H-imidazol-1-yl)-3,4-dihydro-2H-pyrido[1,2-a]pyrazine-1,6-dione (1S or 1R, 3R), 2-{1-[1-Ethyl-6-(trifluoromethyl)-1H-indol-3-yl]ethyl}-3-methyl-7-(4-methyl-1H-imidazol-1-yl)-3,4-dihydro-2H-pyrido[1,2-a]pyrazine-1,6-dione (1R or 1S, 3R), (3R)-2-[(5-Cyclopropyl-1-methyl-1H-indol-3-yl)methyl]-3-methyl-7-(4-methyl-1H-imidazol-1-yl)-3,4-dihydro-2H-pyrido[1,2-a]pyrazine-1,6-dione, (3R)-2-[(5-Cyclopropyl-1-ethyl-1H-indol-3-yl)methyl]-3-methyl-7-(4-methyl-1H-imidazol-1-yl)-3,4-dihydro-2H-pyrido[1,2-a]pyrazine-1,6-dione, 2-[1-(5-Chloro-1-cyclopropyl-6-fluoro-1H-indol-3-yl)ethyl]-3-methyl-7-(4-methyl-1H-imidazol-1-yl)-3,4-dihydro-2H-pyrido[1,2-a]pyrazine-1,6-dione (1S or 1R, 3R), 2-[1-(5-Chloro-1-ethyl-1H-indol-3-yl)ethyl]-3-methyl-7-(4-methyl-1H-imidazol-1-yl)-3,4-dihydro-2H-pyrido[1,2-a]pyrazine-1,6-dione (1R or 1S, 3R), (3R)-2-[(1-Ethyl-5-methyl-1H-indol-3-yl)methyl]-3-methyl-7-(4-methyl-1H-imidazol-1-yl)-3,4-dihydro-2H-pyrido[1,2-a]pyrazine-1,6-dione, (3R)-2-[(6-Chloro-1-ethyl-5-methoxy-1H-indol-3-yl)methyl]-3-methyl-7-(4-methyl-1H-imidazol-1-yl)-3,4-dihydro-2H-pyrido[1,2-a]pyrazine-1,6-dione, (3R)-3-Methyl-7-(4-methyl-1H-imidazol-1-yl)-2-{[5-(trifluoromethoxy)-1H-indol-3-yl]methyl}-3,4-dihydro-2H-pyrido[1,2-a]pyrazine-1,6-dione, (3R)-3-Methyl-7-(4-methyl-1H-imidazol-1-yl)-2-{[1-methyl-5-(trifluoromethoxy)-1H-indol-3-yl]methyl}-3,4-dihydro-2H-pyrido[1,2-a]pyrazine-1,6-dione. HCl, (3R)-3-Methyl-7-(4-methyl-1H-imidazol-1-yl)-2-{[1-methyl-5-(trifluoromethoxy)-1H-indol-3-yl]methyl}-3,4-dihydro-2H-pyrido[1,2-a]pyrazine-1,6-dione, 2-[(5,6-Dichloro-1-methyl-1H-indol-3-yl)methyl]-7-(4-methyl-1H-imidazol-1-yl)-3,4-dihydro-2H-pyrido[1,2-a]pyrazine-1,6-dione, (3R)-2-[(5,6-Dichloro-1-methyl-1H-indol-3-yl)methyl]-3-methyl-7-(4-methyl-1H-imidazol-1-yl)-3,4-dihydro-2H-pyrido[1,2-a]pyrazine-1,6-dione, 2-[1-(5-Chloro-6-methoxy-1-methyl-1H-indol-3-yl)ethyl]-3-methyl-7-(4-methyl-1H-imidazol-1-yl)-3,4-dihydro-2H-pyrido[1,2-a]pyrazine-1,6-dione (1S or 1R, 3R), (3R)-2-{[5-Fluoro-7-(trifluoromethyl)-1H-indol-3-yl]methyl}-3-methyl-7-(4-methyl-1H-imidazol-1-yl)-3,4-dihydro-2H-pyrido[1,2-a]pyrazine-1,6-dione, (3R)-2-{[5-Fluoro-1-methyl-6-(trifluoromethyl)-1H-indol-3-yl]methyl}-3-methyl-7-(4-methyl-1H-imidazol-1-yl)-3,4-dihydro-2H-pyrido[1,2-a]pyrazine-1,6-dione, 2-[(5,7-Dichloro-1-methyl-1H-indol-3-yl)methyl]-7-(4-methyl-1H-imidazol-1-yl)-3,4-dihydro-2H-pyrido[1,2-a]pyrazine-1,6-dione, 2-[(5,7-Dichloro-1H-indol-3-yl)methyl]-7-(4-methyl-1H-imidazol-1-yl)-3,4-dihydro-2H-pyrido[1,2-a]pyrazine-1,6-dione, (3R)-2-{[5-Fluoro-1-methyl-7-(trifluoromethyl)-1H-indol-3-yl]methyl}-3-methyl-7-(4-methyl-1H-imidazol-1-yl)-3,4-dihydro-2H-pyrido[1,2-a]pyrazine-1,6-dione, (3R)-3-Methyl-7-(4-methyl-1H-imidazol-1-yl)-2-{[5-methyl-1-(2,2,2-trifluoroethyl)-1H-indol-3-yl]methyl}-3,4-dihydro-2H-pyrido[1,2-a]pyrazine-1,6-dione, 2-{[6-fluoro-1-methyl-5-(trifluoromethyl)-1H-indol-3-yl]methyl}-7-(4-methyl-1H-imidazol-1-yl)-3,4-dihydro-2H-pyrido[1,2-a]pyrazine-1,6-dione, 2-{[1-ethyl-6-fluoro-5-(trifluoromethyl)-1H-indol-3-yl]methyl}-7-(4-methyl-1H-imidazol-1-yl)-3,4-dihydro-2H-pyrido[1,2-a]pyrazine-1,6-dione, 2-{1-[6-fluoro-1-methyl-5-(trifluoromethyl)-1H-indol-3-yl]ethyl}-7-(4-methyl-1H-imidazol-1-yl)-3,4-dihydro-2H-pyrido[1,2-a]pyrazine-1,6-dione (1R or 1S; enantiomer A (SFC-MS)), 2-{1-[6-fluoro-1-methyl-5-(trifluoromethyl)-1H-indol-3-yl]ethyl}-7-(4-methyl-1H-imidazol-1-yl)-3,4-dihydro-2H-pyrido[1,2-a]pyrazine-1,6-dione (1S or 1R; enantiomer B (SFC-MS)), 2-{1-[6-fluoro-5-(trifluoromethyl)-1H-indol-3-yl]ethyl}-7-(4-methyl-1H-imidazol-1-yl)-3,4-dihydro-2H-pyrido[1,2-a]pyrazine-1,6-dione (1R or 1S; enantiomer A (SFC-MS)), 2-{1-[6-fluoro-5-(trifluoromethyl)-1H-indol-3-yl]ethyl}-7-(4-methyl-1H-imidazol-1-yl)-3,4-dihydro-2H-pyrido[1,2-a]pyrazine-1,6-dione (1S or 1R; enantiomer B (SFC-MS)), (3R)-2-[(6-Chloro-5-methoxy-1H-indol-3-yl)methyl]-3-methyl-7-(4-methyl-1H-imidazol-1-yl)-3,4-dihydro-2H-pyrido[1,2-a]pyrazine-1,6-dione, (3R)-3-Methyl-7-(4-methyl-1H-imidazol-1-yl)-2-[(5-methyl-1H-indol-3-yl)methyl]-3,4-dihydro-2H-pyrido[1,2-a]pyrazine-1,6-dione, (3R)-2-[(5,6-Dichloro-1H-indol-3-yl)methyl]-3-methyl-7-(4-methyl-1H-imidazol-1-yl)-3,4-dihydro-2H-pyrido[1,2-a]pyrazine-1,6-dione, (3R)-2-[(5-Cyclopropyl-1H-indol-3-yl)methyl]-3-methyl-7-(4-methyl-1H-imidazol-1-yl)-3,4-dihydro-2H-pyrido[1,2-a]pyrazine-1,6-dione, (3R)-2-[(5-chloro-4-fluoro-1-methyl-1H-indol-3-yl)methyl]-3-methyl-7-(4-methyl-1H-imidazol-1-yl)-3,4-dihydro-2H-pyrido[1,2-a]pyrazine-1,6-dione, (3R)-2-{[4-fluoro-1-methyl-5-(trifluoromethyl)-1H-indol-3-yl]methyl}-3-methyl-7-(4-methyl-1H-imidazol-1-yl)-3,4-dihydro-2H-pyrido[1,2-a]pyrazine-1,6-dione, 7-(4-methyl-1H-imidazol-1-yl)-2-{1-[1-methyl-5-(trifluoromethyl)-1H-indol-3-yl]ethyl}-3,4-dihydro-2H-pyrido[1,2-a]pyrazine-1,6-dione (1R or 1S; enantiomer A (SFC-MS)), 7-(4-methyl-1H-imidazol-1-yl)-2-{1-[1-methyl-5-(trifluoromethyl)-1H-indol-3-yl]ethyl}-3,4-dihydro-2H-pyrido[1,2-a]pyrazine-1,6-dione (1S or 1R; enantiomer B (SFC-MS)), 2-{1-[1-ethyl-6-(trifluoromethyl)-1H-indol-3-yl]ethyl}-7-(4-methyl-1H-imidazol-1-yl)-3,4-dihydro-2H-pyrido[1,2-a]pyrazine-1,6-dione (1R or 1S; enantiomer A (SFC-MS)), 2-{1-[1-ethyl-6-(trifluoromethyl)-1H-indol-3-yl]ethyl}-7-(4-methyl-1H-imidazol-1-yl)-3,4-dihydro-2H-pyrido[1,2-a]pyrazine-1,6-dione (1S or 1R; enantiomer B (SFC-MS)), 2-[1-(5-Chloro-6-methoxy-1H-indol-3-yl)ethyl]-3-methyl-7-(4-methyl-1H-imidazol-1-yl)-3,4-dihydro-2H-pyrido[1,2-a]pyrazine-1,6-dione (1S or 1R, 3R), 7-(4-Methyl-1H-imidazol-1-yl)-2-{1-[5-(trifluoromethyl)-1H-indol-3-yl]ethyl}-3,4-dihydro-2H-pyrido[1,2-a]pyrazine-1,6-dione, 7-(4-methyl-1H-imidazol-1-yl)-2-{1-[6-(trifluoromethyl)-1H-indol-3-yl]ethyl}-3,4-dihydro-2H-pyrido[1,2-a]pyrazine-1,6-dione, 2-[(5,6-dichloro-1H-indol-3-yl)methyl]-7-(4-methyl-1H-imidazol-1-yl)-3,4-dihydro-2H-pyrido[1,2-a]pyrazine-1,6-dione, 2-{[6-fluoro-5-(trifluoromethyl)-1H-indol-3-yl]methyl}-7-(4-methyl-1H-imidazol-1-yl)-3,4-dihydro-2H-pyrido[1,2-a]pyrazine-1,6-dione, 2-{1-[6-fluoro-5-(trifluoromethyl)-1H-indol-3-yl]ethyl}-7-(4-methyl-1H-imidazol-1-yl)-3,4-dihydro-2H-pyrido[1,2-a]pyrazine-1,6-dione, 2-{1-[6-fluoro-1-methyl-5-(trifluoromethyl)-1H-indol-3-yl]ethyl}-7-(4-methyl-1H-imidazol-1-yl)-3,4-dihydro-2H-pyrido[1,2-a]pyrazine-1,6-dione, 7-(4-methyl-1H-imidazol-1-yl)-2-{1-[1-methyl-5-(trifluoromethyl)-1H-indol-3-yl]ethyl}-3,4-dihydro-2H-pyrido[1,2-c]pyrazine-1,6-dione, 2-{1-[1-ethyl-6-(trifluoromethyl)-1H-indol-3-yl]ethyl}-7-(4-methyl-1H-imidazol-1-yl)-3,4-dihydro-2H-pyrido[1,2-c]pyrazine-1,6-dione, (3R)-2-{[5-fluoro-6-(trifluoromethyl)-1H-indol-3-yl]methyl}-3-methyl-7-(4-methyl-1H-imidazol-1-yl)-3,4-dihydro-2H-pyrido[1,2-c]pyrazine-1,6-dione, (3R)-2-{[4-fluoro-5-(trifluoromethyl)-1H-indol-3-yl]methyl}-3-methyl-7-(4-methyl-1H-imidazol-1-yl)-3,4-dihydro-2H-pyrido[1,2-c]pyrazine-1,6-dione, (3R)-2-[(5-chloro-4-fluoro-1H-indol-3-yl)methyl]-3-methyl-7-(4-methyl-1H-imidazol-1-yl)-3,4-dihydro-2H-pyrido[1,2-c]pyrazine-1,6-dione, 2-[1-(5-chloro-1-ethyl-1H-indol-3-yl)ethyl]-7-(4-methyl-1H-imidazol-1-yl)-3,4-dihydro-2H-pyrido[1,2-c]pyrazine-1,6-dione (1R or 1S; enantiomer A (SFC-MS)), 2-[1-(5-chloro-1-ethyl-1H-indol-3-yl)ethyl]-7-(4-methyl-1H-imidazol-1-yl)-3,4-dihydro-2H-pyrido[1,2-c]pyrazine-1,6-dione (1S or 1R; enantiomer B (SFC-MS)), tautomers and stereoisomeric forms thereof, and the free bases, the pharmaceutically acceptable addition salts, and the solvates thereof.

In an embodiment the compound of Formula (I) is selected from the group consisting of:

(3R)-2-[(3,4-dichlorophenyl)methyl]-3,4-dihydro-3-methyl-7-(4-methyl-1H-imidazol-1-yl)-2H-pyrido[1,2-a]pyrazine-1,6-dione, (3R)-2-[[3,5-bis(trifluoromethyl)phenyl]methyl]-3-ethyl-3,4-dihydro-7-(4-methyl-1H-imidazol-1-yl)-2H-pyrido[1,2-a]pyrazine-1,6-dione .HCl, (3R)-2-[[3,5-bis(trifluoromethyl)phenyl]methyl]-3,4-dihydro-3-methyl-7-(4-methyl-1H-imidazol-1-yl)-2H-pyrido[1,2-a]pyrazine-1,6-dione, (3R)-3,4-dihydro-3-methyl-7-(4-methyl-1H-imidazol-1-yl)-2-[[4-methyl-3-(1-piperidinyl)phenyl]methyl]-2H-pyrido[1,2-a]pyrazine-1,6-dione .HCl, (3R)-3,4-dihydro-3-methyl-7-(4-methyl-1H-imidazol-1-yl)-2-[[4-methyl-3-(1-piperidinyl)phenyl]methyl]-2H-pyrido[1,2-a]pyrazine-1,6-dione, 2-([1,1'-biphenyl]-3-ylmethyl)-3,4-dihydro-7-(4-methyl-1H-imidazol-1-yl)-2H-pyrido[1,2-a]pyrazine-1,6-dione, and (3R)-2-[[3-(cyclopropylmethoxy)-5-(trifluoromethyl)phenyl]methyl]-3,4-dihydro-3-methyl-7-(4-methyl-1H-imidazol-1-yl)-2H-pyrido[1,2-a]pyrazine-1,6-dione .HCl, tautomers and stereoisomeric forms thereof, and the free bases, the pharmaceutically acceptable addition salts, and the solvates thereof.

In an embodiment the compound of Formula (I) is (3R)-2-[[3,5-bis(trifluoromethyl)-phenyl]methyl]-3,4-dihydro-3-methyl-7-(4-methyl-1H-imidazol-1-yl)-2H-pyrido[1,2-a]pyrazine-1,6-dione.

In an embodiment the compound of Formula (I) is selected from the group consisting of:

2-[1-[1-ethyl-5-(trifluoromethyl)-1H-indol-3-yl]ethyl]-3,4-dihydro-3-methyl-7-(4-methyl-1H-imidazol-1-yl)-2H-pyrido[1,2-a]pyrazine-1,6-dione (1S or 1R, 3R), 2-[1-(5-chloro-1-ethyl-7-fluoro-1H-indol-3-yl)ethyl]-3,4-dihydro-3-methyl-7-(4-methyl-1H-imidazol-1-yl)-2H-pyrido[1,2-a]pyrazine-1,6-dione (1S or 1R, 3R), tautomers and stereoisomeric forms thereof, and the free bases, the pharmaceutically acceptable addition salts, and the solvates thereof.

In an embodiment the compound of Formula (I) is selected from the group consisting of:

2-[1-(5-chloro-1-ethyl-6-fluoro-1H-indol-3-yl)ethyl]-3,4-dihydro-3-methyl-7-(4-methyl-1H-imidazol-1-yl)-2H-pyrido[1,2-a]pyrazine-1,6-dione (1S or 1R, 3R)

(3R)-3,4-dihydro-3-methyl-7-(4-methyl-1H-imidazol-1-yl)-2-[[1-methyl-5-(trifluoromethyl)-1H-indol-3-yl]methyl]-2H-pyrido[1,2-a]pyrazine-1,6-dione tautomers and stereoisomeric forms thereof, and the free bases, the pharmaceutically acceptable addition salts, and the solvates thereof.

All possible combinations of the above-indicated interesting embodiments are considered to be embraced within the scope of this invention.

Preparation of the Compounds

The present invention also encompasses processes for the preparation of compounds of Formula (I), intermediates and subgroups thereof. In the reactions described, it can be necessary to protect reactive functional groups, for example hydroxy, amino, or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1999.

The compounds of Formula (I) and the subgroups thereof can be prepared by a succession of steps as described hereunder and as described in the specific examples. They are generally prepared from starting materials which are either commercially available or prepared by standard means obvious to those skilled in the art. The compounds of the present invention can be also prepared using standard synthetic processes commonly used by those skilled in the art of organic chemistry.

The skilled person will realize that in some reactions microwave heating may be used instead of conventional heating to shorten the overall reaction time.

The general preparation of some typical examples is shown below. All variables are defined as mentioned hereabove unless otherwise is indicated.

Experimental Procedures—Scheme 1

Scheme 1

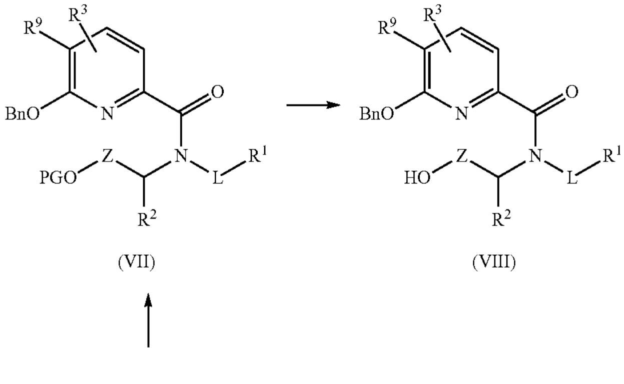

(VII) (VIII)

-continued

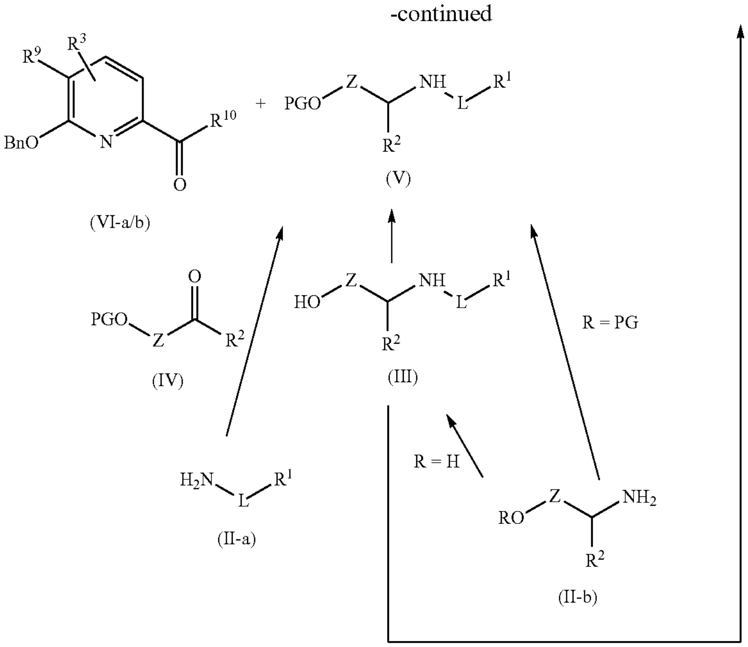

Experimental Procedure 1

An intermediate of formula (III), wherein all the variables are defined as described in the scope of the invention, can be prepared via nucleophilic substitution by an intermediate of formula (II-a) on an appropriate electrophile, such as for example an alkyl halide, such as for example an alkyl iodide, with methods known to the person skilled in the art, such as for example refluxing the mixture of nucleophile and electrophile in the presence or absence of solvent. Inert atmosphere may enhance the reaction outcome.

Alternatively, intermediate (III) can be obtained by reductive amination, starting from the appropriate aminoalcohol (II-b), in the presence of the desired carbonyl compound, such as for example a ketone or an aldehyde. The reaction can be typically performed in the presence of a suitable solvent, such as MeOH (methanol) and a reducing agent, such as $NaBH_4$ (sodium borohydride) or $NaCNBH_3$ (sodium cyanoborohydride). Pre-stirring of the mixture in the absence of the reducing agent under heating, and subsequent addition of the reducing agent at lower temperature, can enhance the reaction outcome.

Alternatively, intermediate (III) can be obtained by manipulation of any suitable precursor by methods known to the person skilled in the art, such as reduction of the corresponding α-aminoacid, for example by using borane-methyl sulphide in the presence of a suitable solvent, such as THF (tetrahydrofuran). Precooling of the reaction mixture, followed by heating after the addition of all the reagents, may enhance the reaction outcome.

Experimental Procedure 2

An intermediate of formula (V), wherein all the variables are defined as described in the scope of the invention, can be obtained via protection of the alcohol functionality of intermediate (III). The protection can be for example a silylation, that can be performed in the presence of a suitable solvent, such as DCM (dichloromethane), an additive, such as imidazole, and a silylating agent, such as TBSCl (tert-butyldimethylsilyl chloride) or TMSCl (trimethylsilyl chloride), following standard conditions known to the person skilled in the art.

Alternatively, intermediate (V) can be obtained by reductive amination of an appropriate amine (II-a) with a carbonyl intermediate such as (IV), where for example PG (the protecting group) can be tert-butyldimethylsilyl. Typical conditions involve stirring of the reagents in a suitable solvent, such as DCE (1,2-dichloroethane), in the presence of a reducing agent, such as $NaBH(OAc)_3$ (sodium triacetoxyborohydride). The person skilled in the art will notice that intermediate (V) can also be obtained via standard reductive amination conditions, starting from an intermediate of structure (II-b), where R is the desired protecting group (PG).

Experimental Procedure 3

An intermediate of formula (VII), wherein

PG is a protecting group;

and all the other variables are defined as described in the scope of the invention, can be obtained via acylation of intermediate (V) with an intermediate of structure (VI), where $R^9$ is hydrogen or bromine;

$R^{10}$ is hydroxyl or chlorine.

Structure (VI) is hereby named (VI-a) when $R^{10}$ is hydroxyl, and (VI-b) when $R^{10}$ is a chlorine. Acylation using intermediate (VI-a) can be performed for example under classical peptide synthesis conditions. Typically, the reaction requests stirring of the starting materials (V) and (VI-a) in the presence of a base, such as DIPEA (diisopropylethyl amine) and a peptide coupling reagent, such as HBTU (O-benzotriazole-N,N,N',N'-tetramethyl-uronium-hexafluoro-phosphate), in a suitable solvent, such as DMF (N,N-dimethyl formamide).

Alternatively, acylation can be achieved by reacting intermediate (V) with an intermediate of formula (VI-b). The reaction can be performed for example by stirring the starting materials in the presence of a base, such as DIPEA, in a suitable solvent, such as DMF.

Experimental Procedure 4

An intermediate of formula (VIII), wherein $R^9$ is hydrogen or bromine;

and all the other variables are defined as described in the scope of the invention, can be obtained by deprotection of intermediate (VII), by methods known to the person skilled in the art. In the case of a silyl protecting group, for example, one standard method would be treating intermediate (VII), dissolved in a suitable solvent, such as THF, with a fluoride source, such as TBAF (tetrabutylammonium fluoride).

Alternatively, an intermediate of formula (VIII) can be obtained by direct acylation of a suitable aminoalcohol of structure (III) with an acid of structure (VI-a). The reaction can be performed for example under peptide coupling conditions, in the presence of a base, such as DIPEA, and a peptide coupling reagent, such as HBTU, in a suitable solvent, such as DMF.

Experimental Procedures—Scheme 2

Experimental Procedure 5

An intermediate of formula (IX), wherein $R^9$ is hydrogen or bromine;

and all the other variables are defined as described in the scope of the invention, can be obtained by debenzylation of intermediate (VIII), using standard methods known to the person skilled in the art. For example, the benzylation can be achieved by stirring a solution of intermediate (VIII) in a suitable solvent, such as MeOH or MeOH/THF, and in the presence of a hydrogenation catalyst, such as 10% Pd/C (palladium on carbon), under hydrogen atmosphere.

Scheme 2

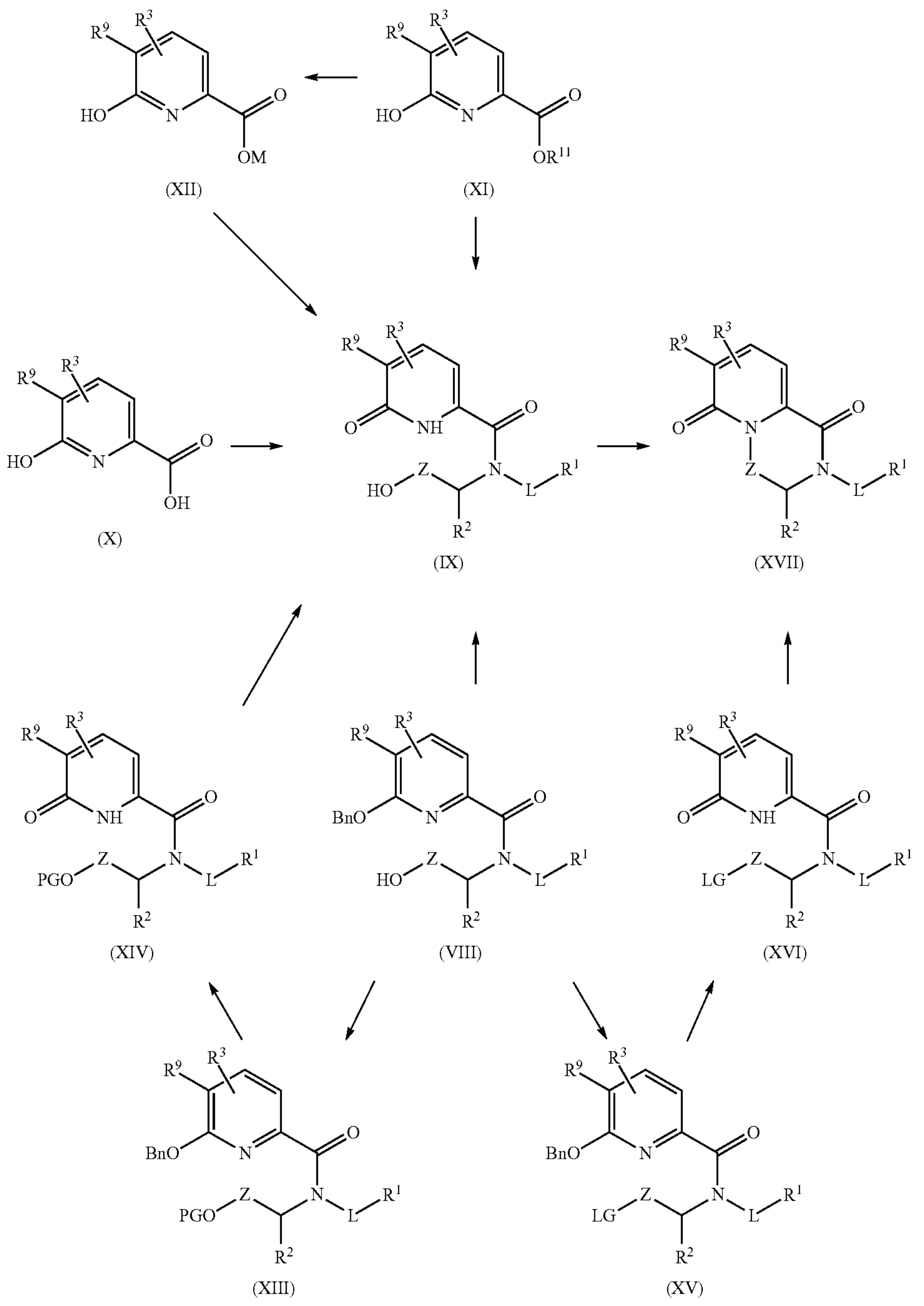

Alternatively, intermediate (IX) can be obtained by amide synthesis starting from a suitable ester, such as intermediate (XI), where $R^{11}$ is for example a methyl group. Typical conditions involve stirring a solution of the ester in a suitable solvent, such as MeOH, in the presence of a desired aminoalcohol of structure (III) under reflux. Alternatively, starting as well from intermediate (XI), intermediate (IX) can be obtained by using a 2-step method. First, ester (XI) can be saponified to give intermediate (XII), where M is a metal. The reaction can be performed for example by adding an hydroxide, such as LiOH (lithium hydroxide), to a solution of ester (XI) in a suitable polar solvent or in a mixture of miscible solvents of which one is highly polar, such as THF and water. Heating the reaction mixture can enhance the reaction outcome. In the second step, intermediate (XII) can be reacted with an aminoalcohol of structure (III), to afford intermediate (IX). Typically, peptide coupling conditions can be applied, such as stirring the starting material, dissolved in a suitable solvent, such as DMF, in the presence of a peptide coupling agent, such as HBTU. The skilled in the art will appreciate that when a base, such as DIPEA, is present in the mixture, the reaction affords directly the cyclised intermediate (XVII). Heating the reaction mixture can enhance the reaction outcome.

Alternatively, intermediate (IX) can be obtained starting from acid (X), using for example standard peptide coupling conditions, such as stirring intermediate (X) and the desired aminoalcohol (III), dissolved in a suitable solvent, such as DMF, in the presence of a peptide coupling reagent, such as HBTU.

Alternatively, intermediate (IX) can be obtained by using a 3-step synthesis starting from intermediate (VIII). First, the free alcohol functionality can be protected using standard protection methods, such as for example acylation to the ester. Typical conditions would be for example treating intermediate (VIII) with a suitable acylating agent, such as a combination of acetic anhydride and DMAP (dimethylaminopyridine), in the presence of a base, such as $Et_3N$ (triethylamine) in a suitable inert solvent, such as DCM. The so obtained intermediate (XIII) can subsequently undergo debenzylation using standard deprotection methods, such as stirring in a suitable solvent, such as MeOH, under hydrogen atmosphere in the presence of a hydrogenation catalyst, such as 10% Pd/C. Pyridone intermediate (XIV) can be finally converted into intermediate (IX) by using one of the available deprotection methods for the chosen protecting group. In the case of protection of the alcohol as an ester, saponification using a base, such as NaOH (sodium hydroxide) in a suitable solvent, such as MeOH, can afford the desired free alcohol (IX). The skilled in the art will recognize that this method is valuable when the alcohol functionality present in intermediate (VIII) could be liable under debenzylation conditions.

Experimental Procedure 6

An intermediate of formula (XVII), wherein $R^9$ is hydrogen or bromine;

and all the other variables are defined as described in the scope of the invention, can be obtained via intramolecular cyclization, for example by applying Mitsunobu conditions to intermediate (IX). The reaction can be performed by treating a solution of intermediate (IX) in a suitable inert and dry solvent, such as THF, with an azadicarboxylate species, such as DIAD (diisopropyl azodicarboxylate), in the presence of a phosphine, such as triphenylphosphine, under inert atmosphere. Precooling of the solution may be used.

Alternatively, starting from intermediate (VIII) a 3-step method can be used. First, the free hydroxyl function in intermediate (VIII) can be converted into a suitable leaving group. For example, intermediate (XV-a), where LG=chlorine, can be obtained under mild conditions by dissolving intermediate (VIII) in a suitable solvent, such as DCM, and treating it with a chlorinating agent, such as thionyl chloride. Precooling of the solution before addition of the chlorinating agent can enhance the outcome of the reaction. Intermediate (XV) can then undergo debenzylation to give intermediate (XVI), using standard methods compatible with the presence of the leaving group. In the case of intermediate (XV-a), for example, debenzylation can be achieved by treating the intermediate, dissolved in a suitable and inert solvent, such as DCM, with a Lewis acid such as $BBr_3$ (boron tribromide). Precooling of the reaction mixture before addition of the Lewis acid can enhance the reaction outcome. The person skilled in the art will notice that for some cases where $R^2$ is $C_{1-4}$alkyl substituted with $C_{1-4}$alkyloxy and/or Y is O, alternative methods to the one suggested should be considered, to avoid side reactions. Finally, intermediate (XVI) can be processed to intermediate (XVII) by using standard substitution conditions. For example, starting from intermediate (XVI-a), where LG=chlorine, the ring closure can be achieved by treating the substrate, dissolved in a suitable solvent, such as DMF, with a base, such as NaH (sodium hydride). Precooling of the reaction and a level of dilution high enough to avoid intermolecular reactions can enhance the reaction outcome.

Experimental Procedures—Scheme 3

Scheme 3

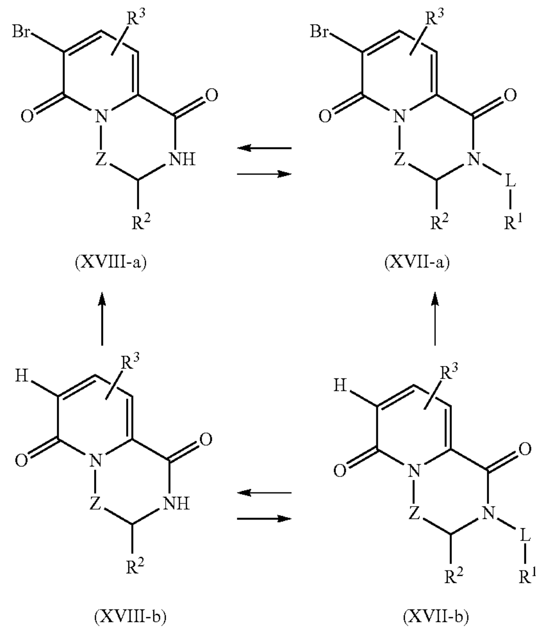

(XVIII-a) (XVII-a) (XVIII-b) (XVII-b)

Experimental Procedure 7

An intermediate of formula (XVIII-b), wherein all the variables are defined as described in the scope of the invention, can be obtained from an intermediate of structure (XVII-b), where all the variables are defined as mentioned hereabove, with the exception of the residual -L-$R^1$, defined for structure (XVII-b) as any kind of protecting group suitable for an amidic nitrogen, such as, but not restricted to, a benzyl group (L=$CH_2$, $R^1$=phenyl) or a PMB group (p-methoxybenzyl, L=$CH_2$, $R^1$=p-methoxyphenyl). Intermediate (XVII-b) can be converted into intermediate (XVIII-b) by means of deprotection methods known to the person skilled in the art. For example, when L=$CH_2$, $R^1$=phenyl, deprotection can be achieved by treating intermediate (XVII-b), dissolved in a suitable solvent, such as dry toluene, with a strong acid, such as TfOH (trifluoromethansulfonic acid). Heating the reaction mixture under stirring can enhance the reaction outcome.

Experimental Procedure 8

An intermediate of formula (XVII-b), wherein all the variables are defined as described in the scope of the invention, can be obtained from intermediate (XVIII-b) by means of any manipulation known to the person skilled in the art for the functionalization of an amidic nitrogen. Two general examples are reported:

EXAMPLE 1

When $R^1$ is Ar;

L is a covalent bond;

functionalization can be achieved for example by means of a copper catalyzed C—N coupling. Standard conditions, such as stirring a mixture of intermediate (XVIII-b), dissolved in a suitable solvent, such as DMF, in the presence of a base, such as $K_3PO_4$ (potassium phosphate), a ligand, such as N,N'-dimethyl-1,2-cyclohexanediamine, an aryl halide and a copper catalyst, such as CuI, could be used. Degassing the reaction mixture with an inert gas, such as $N_2$ or argon, and heating the reaction mixture to high temperatures, such as reflux temperature, may enhance the reaction outcome.

EXAMPLE 2

When

L is one of the variables described in the scope of the invention, with the exception of L being a covalent bond if $R^1$ is Ar;

and with the exception of m and n simultaneously having value 3;

functionalization can be achieved for example by treating intermediate (XVIII-b), dissolved in a suitable and inert solvent, such as DMF, with a base, such as NaH, followed by addition of an electrophile. Precooling of the reaction mixture can enhance the reaction outcome.

Experimental Procedure 9

An intermediate of formula (XVIII-a), wherein all the variables are defined as described in the scope of the invention, can be obtained from an intermediate of structure (XVII-a), where all the variables are defined as mentioned hereabove, with the exception of the residual -L-$R^1$, defined for structure (XVII-a) as any kind of protecting group suitable for an amidic nitrogen, such as, but not restricted to, a benzyl group (L=$CH_2$, $R^1$=phenyl) or a PMB group (p-methoxybenzyl, L=$CH_2$, $R^1$=p-methoxyphenyl).

Intermediate (XVII-a) can be converted into intermediate (XVIII-a) by means of deprotection methods known to the person skilled in the art. For example, when L=$CH_2$, $R^1$=phenyl, deprotection can be achieved by treating intermediate (XVII-a), dissolved in a suitable solvent, such as dry toluene, with a strong acid, such as TfOH. Heating the reaction mixture under stirring can enhance the reaction outcome. Alternatively, an intermediate of formula (XVIII-a) can be obtained starting from an intermediate of formula (XVIII-b) by means of direct bromination. Different brominating agents can be used. For example, the reaction can be performed by dissolving intermediate (XVIII-b) in a mixture of solvents such as DCM/AcOH (acetic acid) and adding bromine to the mixture, or by adding NBS (N-bromosuccinimide) to a solution of intermediate (XVIII-b) in an appropriate solvent, such as acetonitrile. The reaction mixture may be stirred under heating and inert atmosphere.

Experimental Procedure 10

An intermediate of formula (XVII-a), wherein all the variables are defined as described in the scope of the invention, can be obtained from intermediate (XVIII-a) by means of any manipulation known to the person skilled in the art for the functionalization of an amidic nitrogen. One general example is reported:

EXAMPLE 1

When

L is one of the variables described in the scope of the invention, with the exception of L being a covalent bond if $R^1$ is Ar;

and with the exception of m and n simultaneously having value 3;

functionalization can be achieved for example by treating intermediate (XVIII-a), dissolved in a suitable and inert solvent, such as DMF, with a base, such as NaH, followed by an electrophile. Precooling of the reaction mixture can enhance the reaction outcome.

Alternatively, intermediate (XVII-a) can be obtained by direct bromination of intermediate (XVII-b), for example by adding bromine to a solution of intermediate (XVII-b), dissolved in a mixture of solvents such as DCM/AcOH.

Experimental Procedures—Scheme 4

Scheme 4

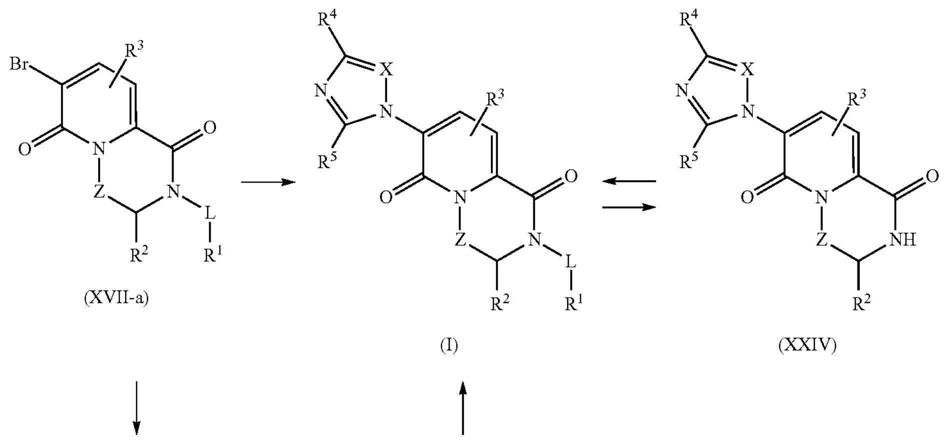

(XVII-a) (I) (XXIV)

-continued

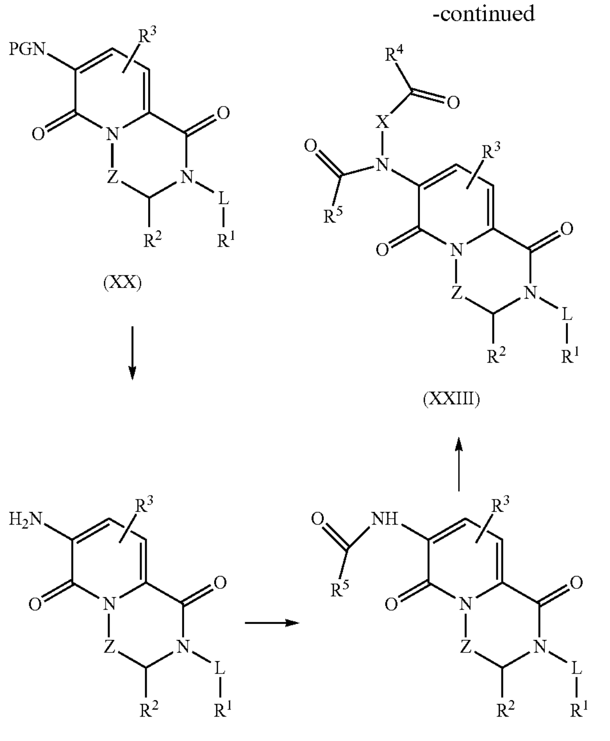

(XX)

(XXIII)

(XXI)

(XXII)

Experimental Procedure 11

A compound of formula (I), wherein all the variables are defined as described in the scope of the invention, can be obtained for example by copper catalyzed C—N coupling. Standard conditions involve stirring of intermediate (XVII-a) in the presence of a copper catalyst, such as CuI, a base, such as $Cs_2CO_3$ (cesium carbonate), the coupling partner, such as for example 4-methylimidazole, and a ligand, such as N,N'-dimethyl-1,2-cyclohexanediamine, in a suitable solvent, such as DMF. Degassing the reaction mixture with an inert gas, such as $N_2$ or argon, and heating the reaction mixture to high temperatures, such as reflux temperature, may enhance the reaction outcome.

Alternatively, a compound of formula (I), where $R^5$ is restricted to hydrogen, can be obtained by palladium catalyzed C—N coupling. Typically, an intermediate of formula (XVII-a) is stirred and heated in the presence of a base, such as $K_3PO_4$, a palladium source, such as $Pd_2(dba)_3$ (tris(dibenzylideneacetone)dipalladium(0)), a ligand, such as 2-di-tert-butylphosphino-3,4,5,6-tetramethyl-2',4',6'-triisopropyl-1,1'-biphenyl and the desired imidazole, in the presence of a solvent or a mixture of solvents, such as toluene/dioxane. Premixing of the catalyst and the ligand followed by heating before addition of the remaining reagents, degassing of the solution and heating can enhance the reaction outcome.

Alternatively, a compound of formula (I) can be obtained via a 5-step synthesis. In the first step, intermediate (XVII-a) can be converted into intermediate (XX), where PG is a mono or divalent nitrogen protecting group. For example, when PG=acetyl, the reaction can be performed using known amide coupling methodologies. For example, acetamide can be reacted with intermediate (XVII-a) in the presence of a base, such as $K_3PO_4$, a palladium source, such as $Pd_2(dba)_3$, a ligand, such as (9,9-dimethyl-9H-xanthene-4,5-diyl)bis[diphenylphosphine] (Xantphos), in a suitable solvent, such as dry THF. Degassing of the reaction mixture during the set-up with an inert gas, such as $N_2$ or argon, anhydrous conditions, and the use of high temperatures, such as reflux temperature, can enhance the reaction outcome. In the second step, intermediate (XX) can be converted into the free amine intermediate (XXI) by using any deprotection method tolerated by the other functionalities present in the molecule. For example, when PG in intermediate (XX)=acetyl, an acidic hydrolysis, using for example HCl (hydrochloric acid), in a suitable solvent, such as MeOH, can be used. In the third step, the amino group in intermediate (XXI) can be acylated to give intermediate (XXII). For example, if $R^5$ in compound (XVII) represents hydrogen, formylation of intermediate (XXI) can be obtained by adding to intermediate (XXI), dissolved in a suitable inert solvent, such as THF, a formylating agent, such as a mixture of acetic anhydride and formic acid. Stirring of the reaction under heating can enhance the reaction outcome. In the fourth step, intermediate (XXII) can be converted to the cyclization precursor (XXIII) with methodologies known to the person skilled in the art and depending on the desired functionalities X and $R^4$. For example, if in compound (XVII) X=CH and $R^4$=alkyl, the reaction can be performed by adding the desired α-haloketone, such as for example 1-bromo-2-butanone, to a mixture of intermediate (XXII), and a base, such as $K_2CO_3$, in a suitable solvent, such as DMF. If the halogen of the α-haloketone is different from iodine, the reaction can be improved by means of an in-situ Filkenstein reaction, performed by adding an iodine salt, such as KI, to the reaction mixture. Finally, intermediate (XXIII) can be converted into compound (I) by means of a classical imidazole synthesis. Diketo precursor (XXIII) can be cyclized into desired compound (I) in the presence of a nitrogen source, such as ammonium acetate, and an acid, such as AcOH. Heating the reaction to reflux temperature can enhance the reaction outcome.

Alternatively, when the residual -L-$R^1$ in compound (I) corresponds to any kind of protecting group suitable for an amidic nitrogen, such as, but not restricted to, a benzyl group ($L=CH_2$, $R^1$=phenyl) or a PMB group (p-methoxybenzyl, $L=CH_2$, $R^1$=p-methoxyphenyl), the compound can be further converted via a two-step method to generate other structures that can be described as well with the general formula (I). In the first step, compound (I) can be converted into intermediate (XXIV) by means of deprotection methods known to the person skilled in the art. For example, when $L=CH_2$, $R^1$=p-methoxyphenyl, deprotection can be achieved by treating compound (I), dissolved in a suitable solvent, such as dry toluene, with a strong acid, such as TfOH. Heating the reaction mixture under stirring can enhance the reaction outcome. In the second step, intermediate (XXIV) can be converted to a compound of general formula (I), by means of known N-functionalization methods.

For example, when L is one of the variables described above;

with the exception of L being a covalent bond if $R^1$ is Ar;

and with the exception of m and n simultaneously having value 3;

one possibility would be treating intermediate (XXIV), dissolved in a suitable and inert solvent, such as DMF, with a base, such as NaH, followed by an electrophile. Precooling of the reaction mixture and anhydrous conditions can enhance the reaction outcome.

Alternatively, intermediate (XVII-a) wherein $R^3$ is restricted to halo (halo=Cl, Br, I), hereby called intermediate (XVII-b), may be obtained starting from intermediate (XVII-a) wherein $R^3$ is restricted to hydrogen, hereby called (XVII-a1), via a halogenation reaction. For example, if halo is Cl in intermediate (XVII-b), the reaction can be performed by treating intermediate (XVII-a1), dissolved in a suitable solvent, such as DMF, with a chlorine source, such as NCS (N-chlorosuccinimide).

Scheme 4a

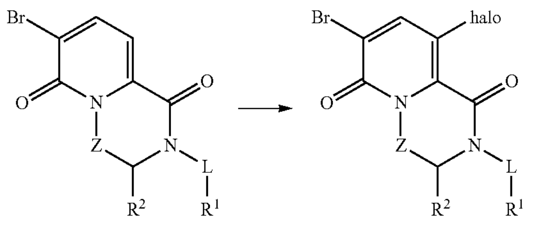

(XVII-a1) (XVII-b)

Alternatively, a compound of formula (I) bearing an $R^1$ group which can undergo further manipulation, could be converted into other compounds described as well with the general formula (I), by mean of one or several subsequent chemical transformations known to the person skilled in the art. For example, when $R^1$=indole, the indolic nitrogen could undergo methylation, for example by treating the compound, dissolved in a suitable and inert solvent, such as DMF, with a base, such as NaH, followed by a methylating agent, such as iodomethane. Precooling of the reaction mixture and anhydrous conditions can enhance the reaction outcome.

Experimental Procedures—Scheme 5

Scheme 5

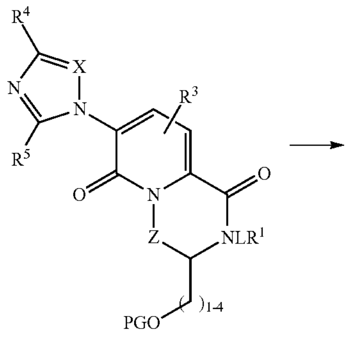

(I-a)

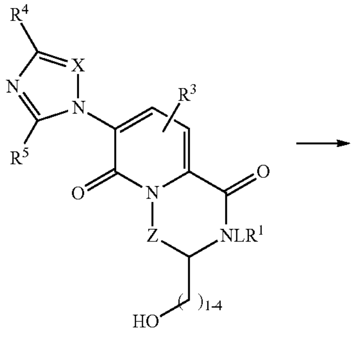

(XXV)

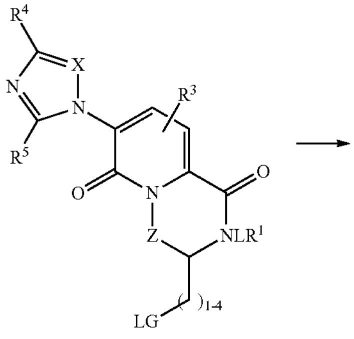

(XXVI)

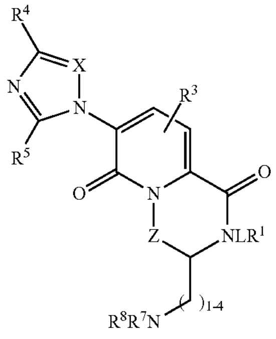

(I-b)

Experimental Procedure 12

A compound of formula (I), wherein $R^2$ is $C_{1-4}$alkyl substituted with hydroxyl;

and all the other variables are defined as described in the scope of the invention, hereby named a compound of formula (XXV), can be obtained from a compound of structure (I), where $R^2$ is restricted to $C_{1-4}$alkyl substituted with a protected hydroxyl group, such as for example a methoxy group (PG=methyl), hereby named compound (I-a). The conversion of the ether to the alcohol can be achieved for example by treating compound (I-a), dissolved in a suitable solvent, such as DCM, with a Lewis acid, such as $BBr_3$.

reaction can be performed by adding dimethylamine to a solution of intermediate (XXVI), dissolved in a suitable solvent, such as DMF. Precooling of the reaction mixture before addition, followed by heating after the addition is complete, can enhance the reaction outcome.

Experimental Procedures—Scheme 6

Scheme 6

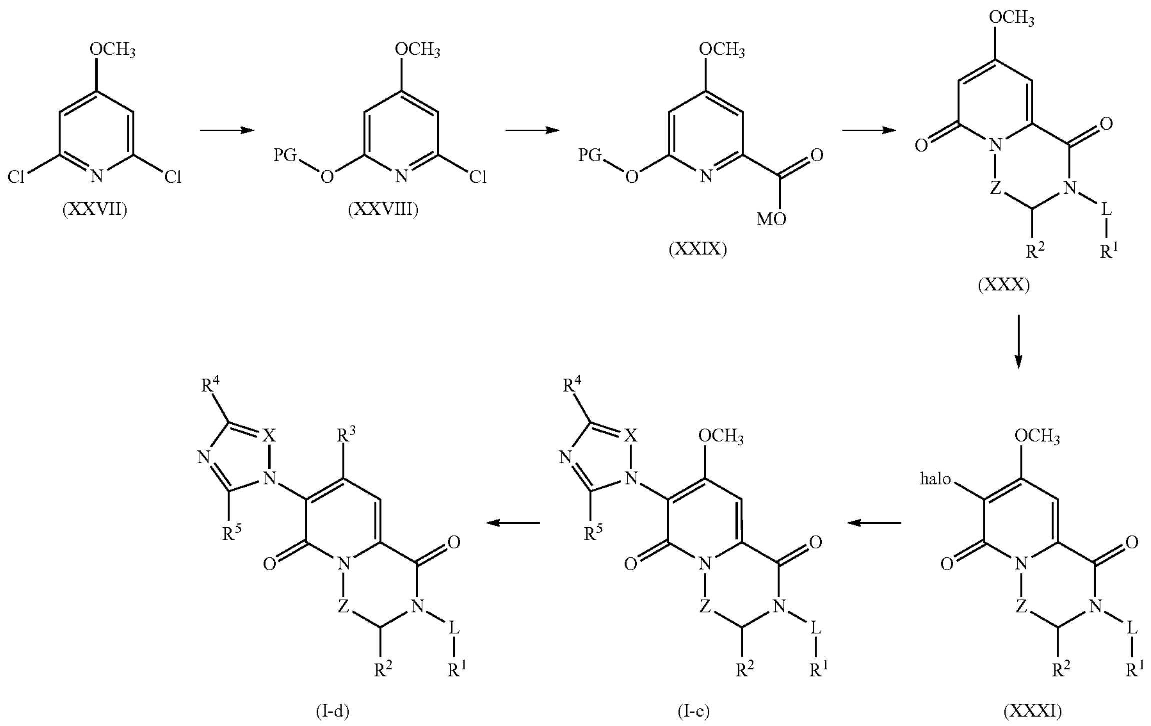

The person skilled in the art will notice that for some cases where $R^2$ is $C_{1-4}$alkyl substituted with $C_{1-4}$alkyloxy and/or Y is O, PG=alkyl should be avoided, because of possible side reactions during the deprotection.

Experimental Procedure 13

An intermediate of structure (XXVI), wherein $R^2$ is $C_{1-4}$alkyl substituted with a leaving group;

and all the other variables are defined as described in the scope of the invention, can be obtained starting from compound (XXV) by means of conversion of the hydroxyl group into a leaving group, for which different methodologies, known to the person skilled in the art, are available. For example, if LG=Ms (mesylate), intermediate (XXVI) can be obtained by treating compound (XXV), dissolved in a suitable solvent, such as DCM, with a base, such as DIPEA, and a suitable mesylating agent, such as methansulphonyl chloride. Precooling of the solution of compound (XXV) before addition of the other reagents can enhance the reaction outcome.

Experimental Procedure 14

A compound of formula (I), wherein $R^2$ is $C_{1-4}$alkyl substituted with $NR^7R^8$;

and all the other variables are defined as described in the scope of the invention, hereby named compound (I-b), can be obtained starting from intermediate (XXVI), by nucleophilic substitution using a mono or disubstituted amine. For example, if $R^7$=$R^8$=methyl in compound (I-b), the Experimental Procedure 15

A compound of formula (I-d), wherein $R^3$ is fluorine, chlorine or bromine;

and all the other variables are defined as described in the scope of the invention, can be obtained via a multi-step synthesis, starting from the commercially available 2,6-dichloro-4-methoxypyridine (XXVII).

In the first step, one of the chlorine atoms can undergo substitution with an alkoxy group, following conditions known to the person skilled in the art, such as treating the substituted pyridine (XXVII), dissolved in a suitable inert solvent, such as THF, in the presence of a base, such as NaH, with a suitable electrophile. PG has to be a moiety which can be further removed with simple manipulations, such as, for example, a benzyl or a p-methoxybenzyl group. The so-obtained intermediate (XXVIII) can then be converted into intermediate (XXIX), where M is a metal, by mean for example of a cross-coupling reaction to give the corresponding 2-vinyl pyridine: the newly installed double bond can then be oxidized, for example by using potassium permanganate, to obtain the carboxyl functionality. Salt (XXIX) can then undergo a series of reactions, under conditions similar to the ones described in Scheme 2, to afford the bicyclic scaffold (XXX), which can undergo selective halogenation, by using for example NIS (N-iodosuccinimide), to give intermediate (XXXI), where halo is a halogen, preferably iodine. Under the conditions described in Scheme 4, intermediate (XXXI)

can then be converted to compound (I-c). The methoxy moiety of compound (I-c) can then finally be displaced to afford compound (I-d), using a suitable halogen oxychloride, such as $POCl_3$ (phosphorus oxychloride) in the presence of a suitable inert solvent, such as acetonitrile.
Experimental Procedures—Scheme 7
Scheme 6
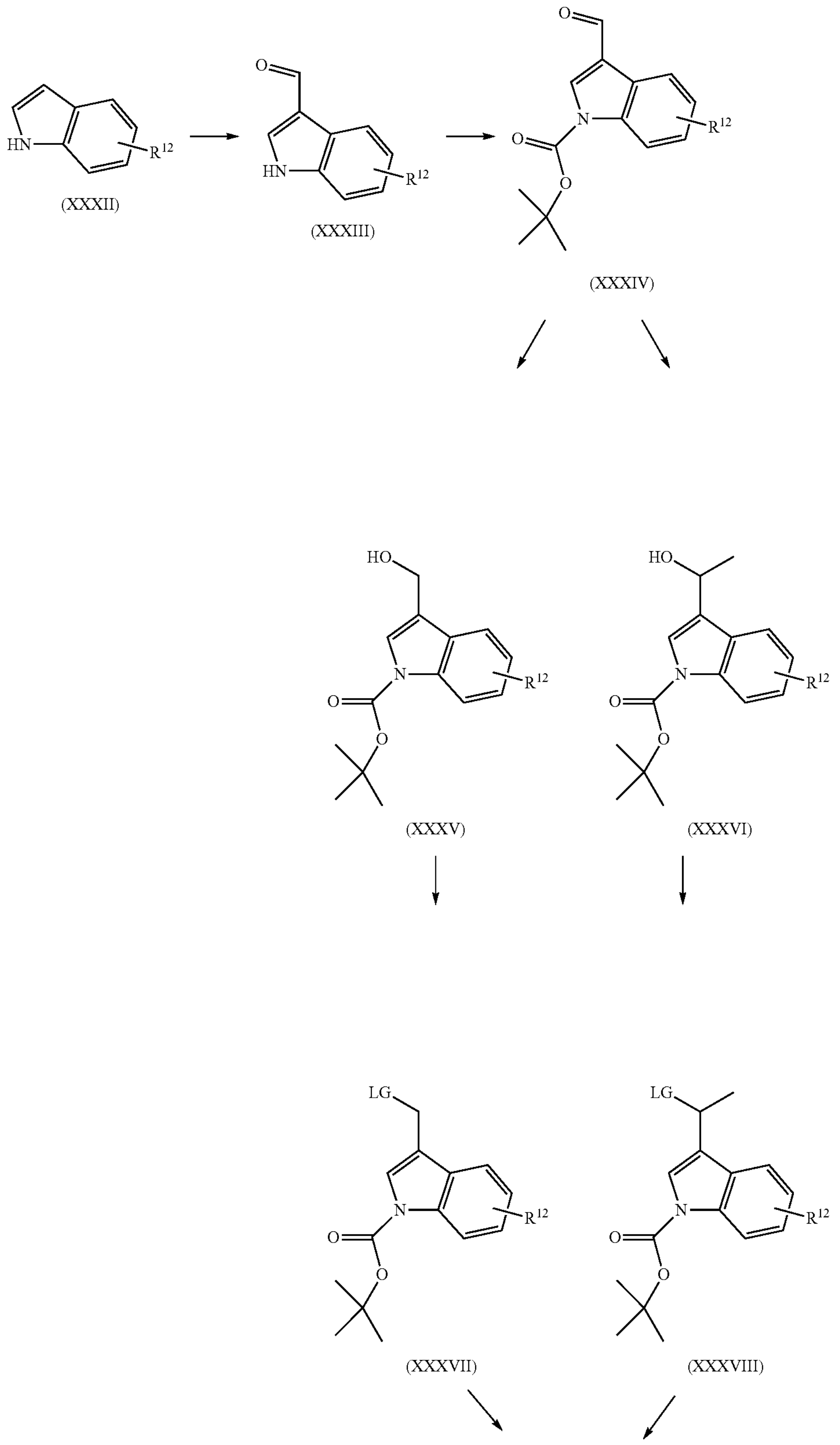
(XXXII) (XXXIII) (XXXIV) (XXXV) (XXXVI) (XXXVII) (XXXVIII)

-continued

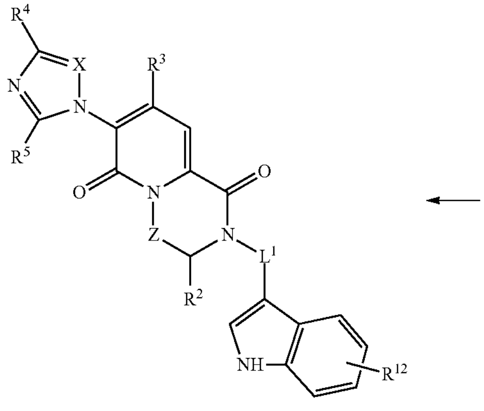

(I-e)

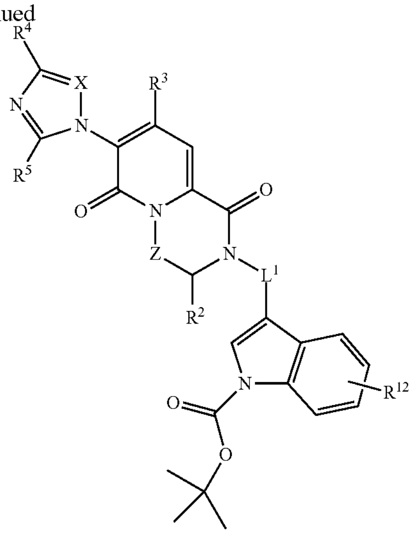

(XXXIX)

Experimental Procedure 16

A compound of formula (I-e), wherein $R^{12}$ describes the pattern of substituents allowed on the indolyl ring, as defined in the scope of the invention, or groups from which the allowed substituents can be obtained by mean of simple manipulations, such as for example cross-coupling reactions or dehalogenation reactions;

$L^1$ is $CH_2$ or $CH(CH_3)$;

and all the other variables are defined as described in the scope of the invention, can be obtained via a multi-step synthesis, starting from indole (XXXII), which can be commercially available or obtained by methods known to the person skilled in the art.

In the first step, indole (XXXII) can be functionalized on position 3 with a carbonyl group by mean of methods reported in the literature, such as for example a Vilsmeier-Haack reaction, to give intermediate (XXXIII). The indol nitrogen of intermediate (XXXIII) can then be protected with a protecting group, such as a tert-butoxycarbonyl, under conditions known to the person skilled in the art, to give intermediate (XXXIV).

The carbonyl group in intermediate (XXXIV) can be subsequently reduced to the corresponding alcohol by treating it with a reducing agent, such as for example $NaBH_4$, in the presence of a suitable solvent, such as for example MeOH, to give intermediate (XXXV). The alcohol group in intermediate (XXXV) can then be converted into a leaving group, via a reaction for which different methodologies, known to the person skilled in the art, are available. For example, if LG=Ms (mesylate), intermediate (XXXVII) can be obtained by treating intermediate (XXXV), dissolved in a suitable solvent, such as DCM, with a base, such as DIPEA, and a suitable mesylating agent, such as methanesulphonyl chloride. Alternatively, if LG=Cl, intermediate (XXXVII) can be obtained by treating intermediate (XXXV), dissolved in a suitable solvent, such as DCM, in the present of a chlorinating agent, such as thionyl chloride. Precooling of the reaction mixture can enhance the reaction outcome.

Alternatively, intermediate (XXXIV) can be treated with a organometallic species such as for example methylmagnesium chloride, in the presence of a suitable solvent, such as THF, to convert the carbonyl compound into intermediate (XXXVI). Precooling of the reaction mixture can enhance the reaction outcome. The alcohol group in intermediate (XXXVI) can then be converted into a leaving group, via a reaction for which different methodologies, known to the person skilled in the art, are available. For example, if LG=Ms (mesylate), intermediate (XXXVIII) can be obtained by treating intermediate (XXXVI), dissolved in a suitable solvent, such as DCM, with a base, such as DIPEA, and a suitable mesylating agent, such as methanesulphonyl chloride. Alternatively, if LG=Cl, intermediate (XXXVIII) can be obtained by treating intermediate (XXXVI), dissolved in a suitable solvent, such as DCM, in the present of a chlorinating agent, such as thionyl chloride. Precooling of the reaction mixture can enhance the reaction outcome.

Intermediate (XXXIX) can be obtained by reacting intermediate (XXIV) where $R^3$ is H, with the suitable intermediate (XXXVII) or (XXXVIII), depending on which L' is desired in the final compound. Standard reaction conditions would involve the use of a base, such as NaH, in the presence of a suitable inert solvent, such as DMF. Precooling of the reaction mixture can enhance the reaction outcome.

The protected intermediate (XXXIX) can be finally converted into final compound (I-e) by mean of standard deprotection conditions. The person skilled in the art will appreciate that intermediate (XXXIX), when $R^{12}$ describes groups from which the substituents on the indolyl ring defined in the scope can be obtained by mean of simple manipulations, is normally the intermediate of choice to perform the requested manipulations.

Starting materials can be obtained commercially or can be prepared by those skilled in the art.

In order to obtain the HCl salt forms of the compounds, several procedures known to those skilled in the art can be used. In a typical procedure, for example, the free base can be dissolved in DIPE or $Et_2O$ and subsequently, a 6 N HCl solution in 2-propanol or a 1 N HCl solution in $Et_2O$ can be added dropwise. The mixture typically is stirred for 10 minutes after which the product can be filtered off. The HCl salt usually is dried in vacuo.

Where necessary or desired, any one or more of the following further steps in any order may be performed:

Compounds of Formula (I) and any subgroup thereof may be converted into further compounds of Formula (I) and any subgroup thereof, using procedures known in the art.

It will be appreciated by those skilled in the art that in the processes described above the functional groups of intermediate compounds may need to be blocked by protecting groups. In case the functional groups of intermediate compounds were blocked by protecting groups, they can be deprotected after a reaction step.

In all these preparations, the reaction products may be isolated from the reaction medium and, if necessary, further purified according to methodologies generally known in the art such as, for example, extraction, crystallization, trituration and chromatography. In particular, stereoisomers can be isolated chromatographically using a chiral stationary phase such as, for example, Chiralpak® AD (amylose 3,5 dimethylphenyl carbamate) or Chiralpak® AS, both purchased from Daicel Chemical Industries, Ltd, in Japan, or by Supercritical Fluid Chromatography (SFC).

The chirally pure forms of the compounds of Formula (I) form a preferred group of compounds. It is therefore that the chirally pure forms of the intermediates and their salt forms are particularly useful in the preparation of chirally pure compounds of Formula (I). Also enantiomeric mixtures of the intermediates are useful in the preparation of compounds of Formula (I) with the corresponding configuration.

Pharmacology

It has been found that the compounds of the present invention modulate the γ-secretase activity. The compounds according to the invention and the pharmaceutically acceptable compositions thereof therefore may be useful in the treatment or prevention of AD, TBI, dementia pugilistica, MCI, senility, dementia, dementia with Lewy bodies, cerebral amyloid angiopathy, multi-infarct dementia, Down's syndrome, dementia associated with Parkinson's disease and dementia associated with beta-amyloid; preferably AD.

The compounds according to the present invention and the pharmaceutically acceptable compositions thereof may be useful in the treatment or prevention of a disease or condition selected from the group consisting of AD, TBI, dementia pugilistica, MCI, senility, dementia, dementia with Lewy bodies, cerebral amyloid angiopathy, multi-infarct dementia, Down's syndrome, dementia associated with Parkinson's disease and dementia associated with beta-amyloid.

As used herein, the term "modulation of γ-secretase activity" refers to an effect on the processing of APP by the γ-secretase-complex. Preferably it refers to an effect in which the overall rate of processing of APP remains essentially as without the application of said compounds, but in which the relative quantities of the processed products are changed, more preferably in such a way that the amount of the Aβ42-peptide produced is reduced. For example a different Abeta species can be produced (e.g. Abeta-38 or other Abeta peptide species of shorter amino acid sequence instead of Abeta-42) or the relative quantities of the products are different (e.g. the ratio of Abeta-40 to Abeta-42 is changed, preferably increased).

It has been previously shown that the γ-secretase complex is also involved in the processing of the Notch-protein. Notch is a signaling protein which plays a crucial role in developmental processes (e.g. reviewed in Schweisguth F (2004) Curr. Biol. 14, R129). With respect to the use of γ-secretase modulators in therapy, it seems particularly advantageous not to interfere with the Notch-processing activity of the γ-secretase activity in order to avoid putative undesired side-effects. While γ-secretase inhibitors show side effects due to concomitant inhibition of Notch processing, γ-secretase modulators may have the advantage of selectively decreasing the production of highly aggregatable and neurotoxic forms of Aβ, i.e. Aβ42, without decreasing the production of smaller, less aggregatable forms of Aβ, i.e. Aβ38 and without concomitant inhibition of Notch processing. Thus, compounds are preferred which do not show an effect on the Notch-processing activity of the γ-secretase-complex.

As used herein, the term "treatment" is intended to refer to all processes, wherein there may be a slowing, interrupting, arresting, or stopping of the progression of a disease, but does not necessarily indicate a total elimination of all symptoms.

The invention relates to compounds according to the general Formula (I), the tautomers and the stereoisomeric forms thereof, and the pharmaceutically acceptable acid or base addition salts and the solvates thereof, for use as a medicament.

The invention also relates to compounds according to the general Formula (I), the tautomers and the stereoisomeric forms thereof and the pharmaceutically acceptable acid or base addition salts and the solvates thereof, for use in the modulation of γ-secretase activity.

The invention also relates to compounds according to the general Formula (I), the tautomers and the stereoisomeric forms thereof, and the pharmaceutically acceptable acid or base addition salts and the solvates thereof, for use in the treatment or prevention of diseases or conditions selected from the group consisting of AD, TBI, dementia pugilistica, MCI, senility, dementia, dementia with Lewy bodies, cerebral amyloid angiopathy, multi-infarct dementia, Down's syndrome, dementia associated with Parkinson's disease and dementia associated with beta-amyloid.

In an embodiment, said disease or condition is preferably AD.

The invention also relates to compounds according to the general Formula (I), the tautomers and the stereoisomeric forms thereof, and the pharmaceutically acceptable acid or base addition salts and the solvates thereof, for use in the treatment of said diseases.

The invention also relates to compounds according to the general Formula (I), the tautomers and the stereoisomeric forms thereof, and the pharmaceutically acceptable acid or base addition salts and the solvates thereof, for the treatment or prevention of said diseases.

The invention also relates to compounds according to the general formula (I), the tautomers and the stereoisomeric forms thereof, and the pharmaceutically acceptable acid or base addition salts and the solvates thereof, for the treatment or prevention, in particular treatment, of γ-secretase mediated diseases or conditions.

The invention also relates to the use of compounds according to the general Formula (I), the tautomers and the stereoisomeric forms thereof, and the pharmaceutically acceptable acid or base addition salts and the solvates thereof, for the manufacture of a medicament.

The invention also relates to the use of compounds according to the general Formula (I), the tautomers and the stereoisomeric forms thereof and the pharmaceutically acceptable acid or base addition salts and the solvates thereof, for the manufacture of a medicament for the modulation of γ-secretase activity.

The invention also relates to the use of compounds according to the general Formula (I), the tautomers and the stereoisomeric forms thereof and the pharmaceutically acceptable acid or base addition salts and the solvates thereof, for the manufacture of a medicament for the treatment or prevention of any one of the disease conditions mentioned hereinbefore.

The invention also relates to the use of compounds according to the general Formula (I), the tautomers and the stereoisomeric forms thereof and the pharmaceutically acceptable acid or base addition salts and the solvates thereof, for the manufacture of a medicament for the treatment of any one of the disease conditions mentioned hereinbefore.

In the invention, particular preference is given to compounds of Formula (I), or any subgroup thereof with a $IC_{50}$ value for the inhibition of the production of Aβ42-peptide of less than 1000 nM, preferably less than 100 nM, more preferably less than 50 nM, even more preferably less than 20 nM as determined by a suitable assay, such as the assay used in the Examples below.

The compounds of Formula (I) can be administered to mammals, preferably humans for the treatment or prevention of any one of the diseases mentioned hereinbefore.

In view of the utility of the compounds of Formula (I), there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I), the tautomers and the stereoisomeric forms thereof and the pharmaceutically acceptable acid or base addition salts and the solvates thereof, to warm-blooded animals, including humans.

The present invention also concerns to the use of compounds of Formula (I) for the modulation of γ-secretase activity resulting in a decrease in the relative amount of Aβ42-peptides produced.

An advantage of the compounds or a part of the compounds of the present invention may be their enhanced CNS-penetration.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent Alzheimer's disease or the symptoms thereof, may be administered alone or in combination with one or more additional therapeutic agents. Combination therapy includes administration of a single pharmaceutical dosage formulation which contains a compound of Formula (I) and one or more additional therapeutic agents, as well as administration of the compound of Formula (I) and each additional therapeutic agents in its own separate pharmaceutical dosage formulation. For example, a compound of Formula (I) and a therapeutic agent may be administered to the patient together in a single oral dosage composition such as a tablet or capsule, or each agent may be administered in separate oral dosage formulations.

While it is possible for the active ingredient to be administered alone, it is preferable to present it as a pharmaceutical composition.

Accordingly, the present invention further provides a pharmaceutical composition comprising a pharmaceutically acceptable carrier and, as active ingredient, a therapeutically effective amount of a compound according to Formula (I).

The carrier or diluent must be "acceptable" in the sense of being compatible with the other ingredients of the composition and not deleterious to the recipients thereof.

For ease of administration, the subject compounds may be formulated into various pharmaceutical forms for administration purposes. The compounds according to the invention, in particular the compounds according to Formula (I), the tautomers and the stereoisomeric forms thereof and the pharmaceutically acceptable acid or base addition salts and the solvates thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing compounds of Formula (I) may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally administrable compounds, pharmaceutical compositions comprising said compounds for administration orally are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of Formula (I), and, from 1 to 99.95% by weight, more preferably from 30 to 99.9% by weight, even more preferably from 50 to 99.9% by weight of a pharmaceutically acceptable carrier, all percentages being based on the total weight of the composition.

The following examples illustrate the present invention.

EXAMPLES

Hereinafter, the term "DCM" means dichloromethane; "MeOH" means methanol; "LCMS" means Liquid Chromatography/Mass spectrometry; "HPLC" means high-performance liquid chromatography; "sol." means solution; "sat." means saturated; "aq." means aqueous; "r.t." means room temperature; "CO" means carbon monoxide; "AcOH" means acetic acid; "TFA" means trifluoroacetic acid; "m.p." means melting point; "$N_2$" means nitrogen; "RP" means reversed phase; "min" means minute(s); "h" means hour(s); "EtOAc" means ethyl acetate; "$Et_3N$" means triethylamine; "EtOH" means ethanol; "eq." means equivalent; "r.m." means reaction mixture(s); "DIPE" means diisopropyl ether; "THF" means tetrahydrofuran; "DMF" means N,N-dimethyl formamide; 'iPrOH" means 2-propanol; "$NH_3$" means ammonia; "SFC" means Supercritical Fluid Chromatography; "TBAF" means tetrabutylammonium fluoride; "OR" means optical rotation; "DIPEA" means diisopropylethylamine; "TfOH" means trifluoromethanesulfonic acid; "v/v" means volume/volume %; "$Et_2O$" means diethyl ether; "$Cs_2CO_3$" means cesium carbonate; "DIAD" means diisopropyl azodicarboxylate; "DMAP" means 4-dimethylamino-pyridine; "HBTU" means 0-Benzotriazole-N,N,N',N'-tetramethyl-uronium-hexafluoro-phosphate; "$CO_2$" means carbon dioxide; "$iPrNH_2$" means isopropylamine; "EDTA" means ethylenediaminetetraacetic acid; "HCl" means hydrochloric acid; "$K_2CO_3$" means potassium carbonate; "$K_3PO_4$" means potassium phosphate; "KOH" means potassium hydroxide; "$MgSO_4$" means magnesium sulphate; "$Na_2SO_4$" means sodium sulphate; "$NaBH_4$" means sodium borohydride; "$LiAlH_4$" means lithium aluminium hydride; "$NaHCO_3$" means sodium hydrogencarbonate; "NaOH" means sodium hydroxide; "$MgCO_3$" means magnesium carbonate; "NCS" means N-chlorosuccinimide; "NIS" means N-iodosuccinimide; "$NH_4Cl$" means ammonium chloride; "$NaCNBH_3$" means sodium cyanoborohydride; "Pd/C" means palladium on carbon; "$Pd_2(dba)_3$" means tris(dibenzylideneacetone)dipalladium(0); "$PdCl_2(dppf)$" means [1,1-bis(diphenylphosphino)ferrocene]dichloropalladium(II); "Xantphos" means 4,5-Bis(diphenylphosphino)-9,9-dimethylxanthene; "RuPhos" means 2-dicyclohexylphosphino-2',6'-diisopropoxybiphenyl; "$Pd(OAc)_2$" means palladium (II) acetate; "X-Phos" means 2-dicyclohexyl-phosphino-2',4',6'-triisopropylbiphenyl; "dppf" means 1,1-bis(diphenylphosphino) ferrocene; "EDTA" means ethylenediaminetetraacetic acid; "TBSCl" means tert-butyldimethylsilyl chloride; "tBuOH" means tert-butanol; "w/v %" means percent weight to volume; "MsCl" means methansulphonyl chloride; "TLC" means thin layer chromatography and "TPP" means triphenylphospine.

A. Preparation of the Intermediates

Example A1 a) Preparation of Intermediate 1

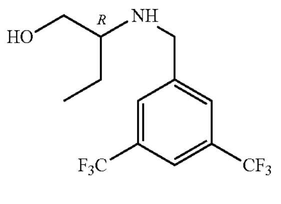

3,5-Bis(trifluoromethyl)benzaldehyde (1.7 mL, 10.2 mmol) was dissolved in MeOH (51 mL), then (R)-(−)-2-amino-1-butanol (1.05 mL, 11.22 mmol) and $NaHCO_3$ (0.7 g, 20.4 mmol) were added. The r.m. was stirred at 80° C. for 2 h, and was then cooled to 25° C. $NaBH_4$ (0.386 g, 10.2 mmol) was added portionwise by keeping the temperature at 25° C. The mixture was stirred at 25° C. for 1 h, then quenched with HCl 2N (pH=1) and $NaHCO_3$ (pH=7-8). MeOH was evaporated in vacuo, then EtOAc was added. The organic layer was separated, dried over $MgSO_4$, filtered and the solvents evaporated in vacuo to yield a white solid. The crude intermediate 1 (R-enantiomer) was used as such in the next step (quantitative yield).

b) Preparation of Intermediate 2

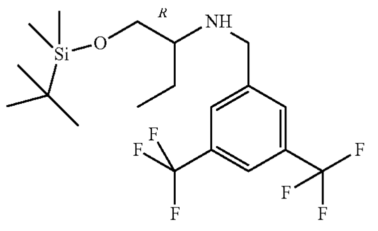

To a suspension of intermediate 1 (crude material, 10.2 mmol) and imidazole (2.1 g, 30.6 mmol) in DCM (30 mL) was added TBSCl (1.6 g, 10.71 mmol), and the r.m. was stirred at r.t. for 4 h. DCM was added and the organic layer was washed with aq. sat. $NaHCO_3$, then collected, dried over $MgSO_4$, filtered and evaporated under reduced pressure. The crude product was purified by flash column chromatography (silica; EtOAc/hexane 0/100 to 20/80). The desired fractions were collected and concentrated in vacuo to yield intermediate 2 (R-enantiomer) as a colorless oil (3.7 g, 84%).

c) Preparation of Intermediate 3

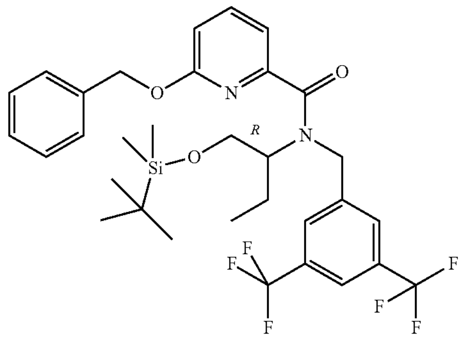

HBTU (4.2 g, 11.2 mmol) was added to a stirred solution of 6-(benzyloxy)pyridine-2-carboxylic acid (1.97 g, 8.61 mmol), DIPEA (1.93 mL, 11.2 mmol) and intermediate 2 (3.7 g, 8.61 mmol) in DMF (40 mL). The r.m. was stirred at r.t. overnight, then aq. sat. $NaHCO_3$ was added and the mixture was extracted with EtOAc. The combined extracts were dried over $MgSO_4$ and concentrated in vacuo. The crude product was purified by flash column chromatography (silica; EtOAc/hexane 0/100 to 20/80). The desired fractions were collected and concentrated in vacuo to yield intermediate 3 as an oil (4.42 g, 80%; R-enantiomer).

d) Preparation of Intermediate 4

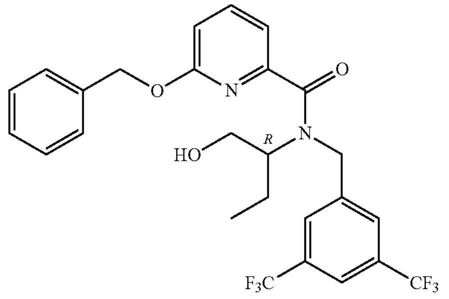

TBAF (3.3 g, 10.34 mmol) was added to a solution of intermediate 3 (4.42 g, 6.9 mmol) in THF (21 mL). The r.m. was stirred at r.t. for 1 h, then diluted with water and extracted with EtOAc. The organic layer was separated, dried over $MgSO_4$, filtered and the solvents were evaporated in vacuo. The crude product was purified by flash column chromatography (silica; EtOAc/hexane 0/100 to 50/50). The desired fractions were collected and concentrated in vacuo to yield intermediate 4 as a colourless oil (2.4 g, 66%; R-enantiomer).

e) Preparation of Intermediate 5

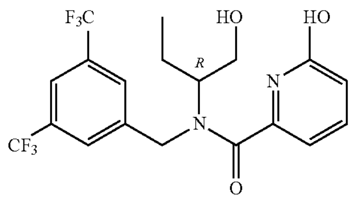

10% Pd/C (0.240 g) was added to a solution of intermediate 4 (2.4 g, 4.56 mmol) in MeOH (14 mL) at 0° C. The mixture was hydrogenated (atmospheric pressure) at r.t. for 2 h. The catalyst was filtered through diatomaceous earth and the solvent evaporated in vacuo to yield a colorless oil. The crude was used such in the next reaction step (quantitative yield; R-enantiomer).

f) Preparation of Intermediate 6

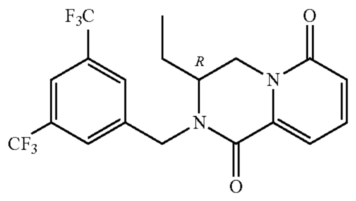

DIAD (1.3 mL, 6.84 mmol) was added to a stirred solution of intermediate 5 (crude material, 4.56 mmol) and TPP (1.8 g, 6.84 mmol) in dry THF (14 mL) under $N_2$ at 0° C. The mixture was stirred at r.t. for 4 h. The solvents were then evaporated in vacuo. The crude product was purified by flash column chromatography (silica; EtOAc/hexane 0/100 to 50/50). The desired fractions were collected and concentrated in vacuo to afford intermediate 6 (quantitative yield; R-enantiomer).

g) Preparation of Intermediate 7

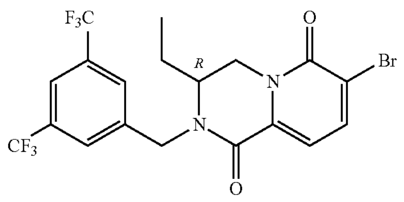

Bromine (0.280 mL, 5.47 mmol) was added dropwise slowly to a stirred solution of intermediate 6 (4.56 mmol) in DCM/AcOH 4:1 (40 mL) under $N_2$. The mixture was stirred at r.t. overnight, then diluted with aq. sat. $NaHCO_3$ and extracted with DCM. The organic layer was separated, dried over $MgSO_4$, filtered and the solvents evaporated in vacuo. The crude product was purified by flash column chromatography (silica; EtOAc/hexane 0/100 to 50/50). The desired fractions were collected and concentrated in vacuo to yield intermediate 7 as an oil (1.26 g, 55%; R-enantiomer).

Example A2 a) Preparation of Intermediate 8

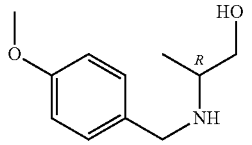

p-Anisaldehyde (7.4 mL, 61 mmol) was dissolved in MeOH (300 mL), then D-alaninol (5.0 g, 66 mmol) and $NaHCO_3$ (10.2 g, 121 mmol) were added and the reaction stirred at 80° C. for 2 h. The r.m. was then cooled to 25° C. $NaBH_4$ (2.3 g, 61 mmol) was added portionwise while keeping the temperature below 25° C. The mixture was stirred at 25° C. for 1 additional h, then quenched with HCl 2N (pH=1) and $NaHCO_3$ (pH=7-8). MeOH was evaporated in vacuo, then EtOAc was added. The organic layer was separated, dried over $MgSO_4$, filtered and the solvents evaporated in vacuo to yield intermediate 8 as a white solid (quantitative yield; R-enantiomer).

b) Preparation of Intermediate 9

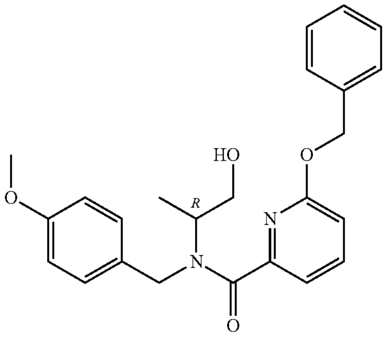

HBTU (2.15 g, 5.67 mmol) was added to a stirred solution of 6-(benzyloxy)pyridine-2-carboxylic acid (1 g, 4.36 mmol), DIPEA (0.98 mL, 5.68 mmol) and intermediate 8 (0.852 g, 4.36 mmol) in DMF (12 mL). The mixture was stirred at r.t. overnight. Sat. aq. $NaHCO_3$ was added and the mixture was extracted with EtOAc. The combined extracts were dried over $MgSO_4$ and concentrated in vacuo. The crude product was purified by flash column chromatography (silica; EtOAc/hexane 0/100 to 50/50). The desired fractions were collected and concentrated in vacuo to yield intermediate 9 as an oil (1.51 g, 85%; R-enantiomer).

c) Preparation of Intermediate 10

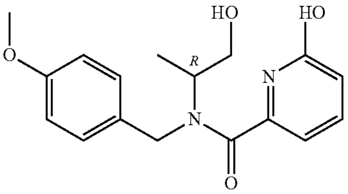

10% Pd/C (0.187 g) was added to a solution of intermediate 9 (1.87 g, 4.60 mmol) in MeOH (20 mL) at 0° C. The mixture was hydrogenated (atmospheric pressure) at r.t. for 6 h. The catalyst was filtered through diatomaceous earth and the solvent evaporated in vacuo to yield a colorless oil. The crude intermediate 10 was used as such in the next reaction step (quantitative yield; R-enantiomer).

d) Preparation of Intermediate 11

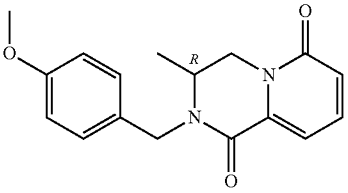

DIAD (1.36 mL, 6.90 mmol) was added to a stirred solution of intermediate 10 (crude material, 4.60 mmol) and TPP (1.8 g, 6.86 mmol) in dry THF (20 mL) under $N_2$. The mixture was stirred at r.t. overnight. The solvents were then evaporated in vacuo. The crude product was purified by flash column chromatography (silica; EtOAc/hexane 0/100 to 100/0). The desired fractions were collected and concentrated in vacuo to afford intermediate 11 as a white solid (927 mg, 68% over two steps; R-enantiomer).

e) Preparation of Intermediate 12

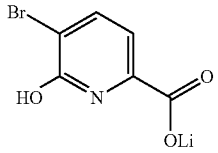

Lithium hydroxide monohydrate (0.766 g, 18.25 mmol) was added portionwise to a stirred solution of methyl 3-bromo-2-hydroxy-6-pyridinecarboxylate (3.85 g, 16.6 mmol) in a mixture of THF (66 mL) and water (17 mL). The mixture was stirred at 60° C. for 24 h, then the solvent was evaporated in vacuo. The crude intermediate 12 was dried in vacuo and used as such in the next reaction step (quantitative yield; R-enantiomer).

f) Preparation of Intermediate 13

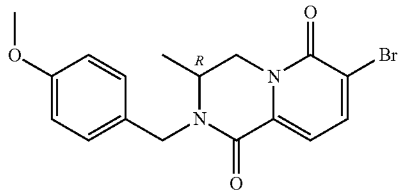

Bromine (0.17 mL, 3.32 mmol) was added dropwise slowly to a stirred solution of intermediate 11 (0.825 g, 2.76 mmol) in DCM/AcOH 4:1 (15 mL) under $N_2$. The mixture was stirred at r.t. overnight, then diluted with aq. sat. $NaHCO_3$ and extracted with DCM. The organic layer was separated, dried over $MgSO_4$, filtered and the solvents evaporated in vacuo. The crude product was purified by flash column chromatography (silica; EtOAc/hexane 0/100 to 50/50). The desired fractions were collected and concentrated in vacuo to yield intermediate 13 as an oil (530 mg, 51%; R-enantiomer).

f1) Alternative Preparation of Intermediate 13

HBTU (16.2 g, 42.66 mmol) was added portionwise to a stirred solution of intermediate 12 (crude material, 28.44 mmol), intermediate 8 (5.55 g, 28.44 mmol) and DIPEA (7.3 mL, 42 mmol) in DMF (24 mL). The mixture was stirred at r.t. for 14 h, then 0.5 additional eq. of HBTU and DIPEA were added. The mixture was stirred at r.t. for 4 h, then poured into aq. sat. $NaHCO_3$ and extracted with EtOAc. The organic layer was separated, dried over $MgSO_4$, filtered and the solvents evaporated in vacuo. The crude product was purified by flash column chromatography (silica; EtOAc/hexane 0/100 to 50/50). The desired fractions were collected and concentrated in vacuo to yield intermediate 13 as an oil (7.03 g, 65% over two steps; R-enantiomer).

g) Preparation of Intermediate 14

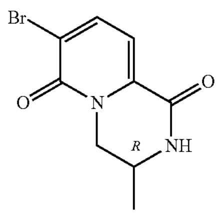

Trifluoromethanesulfonic acid (0.5 mL, 5.62 mmol) was added to a stirred solution of intermediate 13 (0.53 g, 1.4 mmol) in toluene (5 mL). The mixture was stirred at reflux for 2 h, then diluted with NaOH 1M to pH=8 and the solvents evaporated in vacuo. The crude product was purified by flash column chromatography (silica; EtOAc/DCM 0/100 to 100/0). The desired fractions were collected and concentrated in vacuo to yield intermediate 14 as a solid in quantitative yield (R-enantiomer).

h) Preparation of Intermediate 15

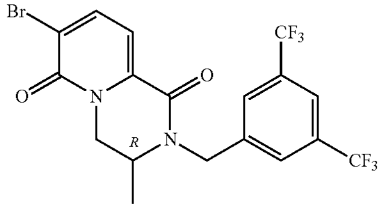

Intermediate 14 (1.58 g, 6.14 mmol) and sodium hydride (60% in mineral oil, 0.270 g, 6.76 mmol) were dissolved in DMF (18 mL) at 0° C., then 3,5-bis(trifluoromethyl)benzyl bromide (1.24 mL, 6.76 mmol) was added. The mixture was stirred at r.t. for 4 h. EtOAc and water were added. The organic phase was separated and dried over $MgSO_4$, filtered and concentrated to dryness. The crude product was purified by flash column chromatography (silica; EtOAc/hexane 0/100 to 70/30). The desired fractions were collected and concentrated in vacuo to yield intermediate 15 as an oil (2.8 g, 94%; R-enantiomer).

i) Preparation of Intermediate 16

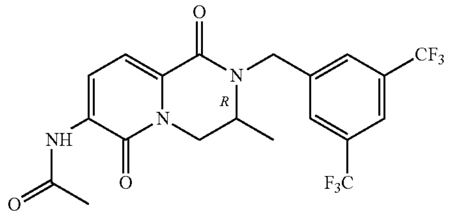

$K_3PO_4$ (0.721 g, 3.40 mmol), $Pd_2(dba)_3$ (0.062 g, 0.07 mmol) and Xantphos (0.068 g, 0.12 mmol) were added to a stirred solution of intermediate 15 (0.821 g, 1.70 mmol) in dry THF (5 mL) at r.t., while $N_2$ was bubbled through the solution. After 10 min, acetamide (0.11 g, 1.86 mmol) was added and the mixture was stirred at r.t. for another 10 min, then heated for 3 h at 90° C. The reaction was then cooled to r.t., sat. aq. $NaHCO_3$ and EtOAc added, the phases were separated and the aq. phase was extracted once more with EtOAc. The combined organic layers were dried over $MgSO_4$, filtered and evaporated. The crude was purified by flash column chromatography (silica; EtOAc/heptane 0/100 to 70/30). The desired fractions were collected and concentrated in vacuo to yield intermediate 16 as a pale brown solid (0.708 g, 90%; R-enantiomer).

l) Preparation of Intermediate 17

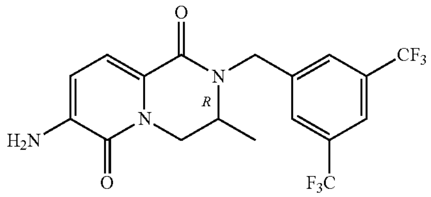

HCl (6N in iPrOH, 0.853 mL, 5.12 mmol) was added to a solution of intermediate 16 (0.787 g, 1.71 mmol) in MeOH (10 mL) at r.t. The r.m. was stirred overnight at r.t. The solvent was evaporated, and sat. aq. $NaHCO_3$ and EtOAc were added. The phases were separated and the aq. phase extracted once more with EtOAc. The combined organic phases were dried over $MgSO_4$, filtered and evaporated. The crude intermediate 17 was used as such in the subsequent reaction step (quantitative yield; R-enantiomer).

m) Preparation of Intermediate 18

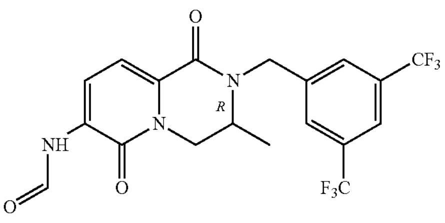

Acetic anhydride (0.614 mL, 6.50 mmol) was added dropwise to formic acid (0.967 mL, 25.65 mmol) at r.t. and stirred for 30 min at the same temperature. To this solution was added dropwise intermediate 17 (1.71 mmol, crude material) in THF (10 mL). The r.m. was then stirred 16 h at 60° C. After this time the reaction was partitioned between water and EtOAc, the phases were separated, the aq. phase extracted once more with EtOAc, and the combined organic phases were dried ($MgSO_4$), filtered and evaporated. The crude intermediate 18 was used as such in the next reaction step (quantitative yield; R-enantiomer).

n) Preparation of Intermediate 19

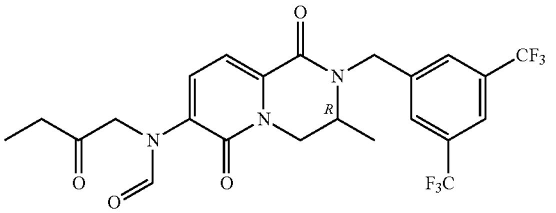

1-Bromo-2-butanone (0.436 mL, 4.27 mmol) was added dropwise to a stirred suspension of intermediate 18 (1.71 mmol, crude material), $K_2CO_3$ (0.827 g, 5.99 mmol) and potassium iodide (28 mg, 0.17 mmol) in DMF (5 mL) at r.t. The mixture was stirred for 16 h at the same temperature, then water and EtOAc were added and the phases separated. The aq. phase was extracted once more with EtOAc, the combined organic phases were dried over $MgSO_4$, filtered and evaporated. The crude intermediate 19 was used as such in the subsequent reaction step (quantitative yield; R-enantiomer).

Example A3 a) Preparation of Intermediate 20

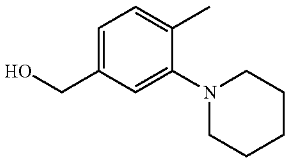

To a suspension of 4-methyl-3-piperidin-1-yl-benzoic acid (2.46 g, 11.2 mmol) in dry THF (22 mL) was added borane-methyl sulfide (2M in THF, 11.2 mL, 22.4 mmol) at 0° C. The r.m. was heated at 50° C. overnight, then cooled. Aq. sat. $NaHCO_3$ was added carefully. The r.m. was extracted with DCM. The organic layer was dried, filtered and concentrated to dryness. The crude product was purified by flash column chromatography (silica; EtOAc/hexane 0/100 to 20/80). The desired fractions were collected and concentrated in vacuo to yield intermediate 20 as an oil (2.3 g, 94%).

b) Preparation of Intermediate 21

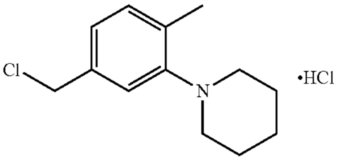

Thionyl chloride (0.497 mL, 0.81 mmol) was added to a solution of intermediate 20 (0.7 g, 3.4 mmol) in DCM (12 mL) at 0° C. The mixture was stirred at r.t. for 2 h, then concentrated in vacuo. The crude intermediate 21 was used as such in the next reaction step as a white solid (quantitative yield).

c) Preparation of Intermediate 22

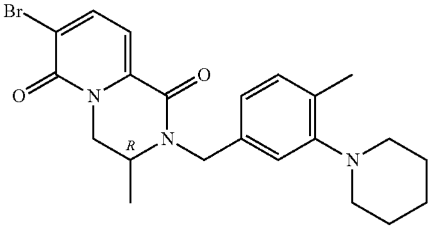

Intermediate 14 (0.3 g, 1.17 mmol) and sodium hydride (60% in mineral oil, 0.094 g, 2.34 mmol) were dissolved in DMF (5 mL) at 0° C., then intermediate 21 (crude material, 1.28 mmol) was added. The mixture was stirred at r.t. overnight. EtOAc and water were added. The organic phase was separated and dried over $MgSO_4$, filtered and concentrated to dryness. The crude product was purified by flash column chromatography (silica; EtOAc/hexane 0/100 to 20/80). The desired fractions were collected and concentrated in vacuo to yield intermediate 22 as an oil (0.219 g, 42%; R-enantiomer).

Example A4 a) Preparation of Intermediate 23

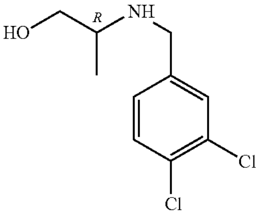

3,4-Dichlorobenzaldehyde (10 g, 57.142 mmol) was dissolved in MeOH (300 mL), then D-alaninol (4.7 g, 62.85 mmol) and $NaHCO_3$ (9.599 g, 114.28 mmol) were added and the reaction stirred at 80° C. for 2 h. The r.m. was then cooled to 25° C. $NaBH_4$ (2.171 g, 57.142 mmol) was added portion-wise while keeping the temperature below 25° C. The mixture was stirred at 25° C. for 1 h, then quenched with water (100 mL). MeOH was evaporated in vacuo, then the residual extracted with DCM (3×100 mL). The organic layers were collected, washed with water (50 mL) and evaporated in vacuo to afford intermediate 23 (13 g, 97%; R-enantiomer).

b) Preparation of Intermediate 24

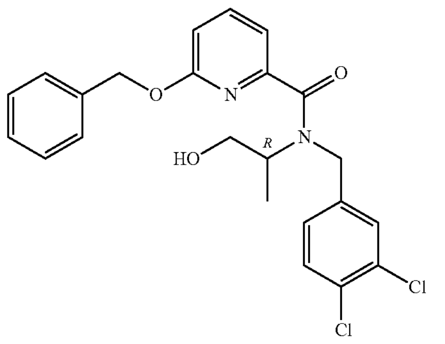

HBTU (1.07 g, 2.83 mmol) was added to a stirred solution of 6-benzyloxy-2-pyridinecarboxylic acid (0.5 g, 2.18 mmol), DIPEA (0.407 mL, 2.83 mmol) and intermediate 23 (0.511 g, 2.18 mmol) in DMF (10 mL). The mixture was stirred at r.t. 4 h. Sat. aq. $NaHCO_3$ was added, followed by extraction with EtOAc. The combined extracts were dried over $MgSO_4$ and concentrated in vacuo. The crude product was purified by flash column chromatography (silica; EtOAc/hexane 0/100 to 20/80). The desired fractions were collected and concentrated in vacuo to yield intermediate 24 as an oil (0.690 g, 71%; R-enantiomer).

c) Preparation of Intermediate 25

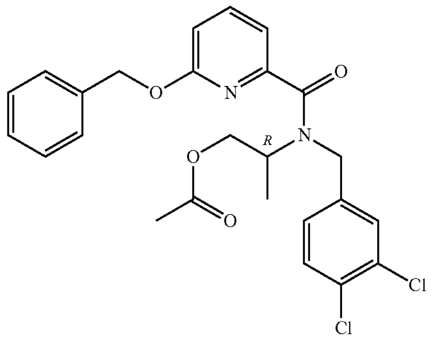

Acetic anhydride (0.176 mL, 1.86 mmol) was added to a solution of intermediate 24 (0.69 g, 1.55 mmol), $Et_3N$ (0.323 mL, 2.32 mmol) and DMAP (1 mg, 0.01 mmol) in DCM (5 mL). The mixture was stirred at r.t. overnight. Aq. sat. $NaHCO_3$ was added and the mixture was extracted with DCM. The combined extracts were dried over $MgSO_4$ and concentrated in vacuo. The crude product was purified by flash column chromatography (silica; EtOAc/hexane 0/100 to 30/70). The desired fractions were collected and concentrated in vacuo to yield intermediate 25 as a colourless oil (0.5 g, 66%; R-enantiomer).

d) Preparation of Intermediate 26

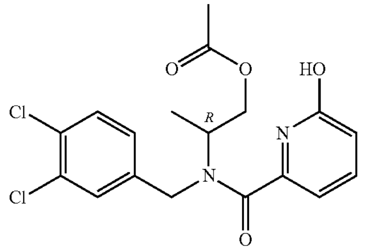

10% Pd/C (0.05 g) was added to a solution of intermediate 25 (0.5 g, 1.02 mmol) in MeOH (5 mL). The mixture was hydrogenated (atmospheric pressure) at r.t. for 6 h. The catalyst was filtered through diatomaceous earth and the solvent evaporated in vacuo to yield a colourless oil. The crude intermediate 26 was used such in the next step (quantitative yield; R-enantiomer).

e) Preparation of Intermediate 27

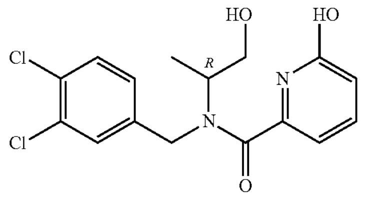

NaOH 1M (1.12 mL, 1.12 mmol) was added to a solution of intermediate 26 (crude material, 1.02 mmol) in MeOH (5 mL). The mixture was stirred for 30 min at r.t. Aq. sat. $NaHCO_3$ was added and the aq. layer was extracted with DCM. The organic layer was dried over $MgSO_4$, filtered and the solvent was removed under reduced pressure. The crude intermediate 27 was used as such in the next reaction step (quantitative yield; R-enantiomer).

f) Preparation of Intermediate 28

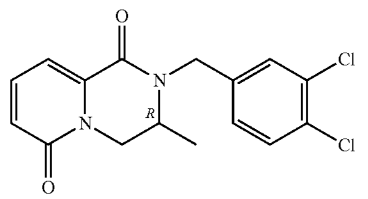

DIAD (0.303 mL, 1.53 mmol) was added to a stirred solution of intermediate 27 (crude material, 1.02 mmol) and TPP (0.401 g, 1.53 mmol) in dry THF (5 mL) under $N_2$ at 0° C. The mixture was stirred at r.t. overnight. The solvents were then evaporated in vacuo. The crude product was purified by flash column chromatography (silica; EtOAc/hexane 0/100 to 100/0). The desired fractions were collected and concentrated in vacuo to yield intermediate 28 as an oil (0.226 g, 66% over 3 steps; R-enantiomer).

2) Preparation of Intermediate 29

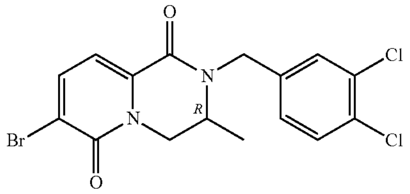

Bromine (0.041 mL, 0.8 mmol) was added dropwise slowly to a stirred solution of intermediate 28 (0.226 g, 0.67 mmol) in 5 mL of DCM/AcOH 4:1 under $N_2$. The mixture was stirred at r.t. overnight, then diluted with sat. aq. $NaHCO_3$ and extracted with DCM. The organic layer was separated, dried over $MgSO_4$, filtered and the solvents were evaporated in vacuo. The crude product was purified by flash column chromatography (silica; EtOAc/DCM 0/100 to 100/0). The desired fractions were collected and concentrated in vacuo to yield intermediate 29 as a colourless oil (0.193 g, 69%; R-enantiomer).

g1) Alternative Preparation of Intermediate 29

HBTU (8.2 g, 21.58 mmol) was added portionwise to a stirred solution of intermediate 12 (crude material, 16.6 mmol), intermediate 23 (3.89 g, 16.6 mmol) and DIPEA (4.3 mL, 24.9 mmol) in DMF (50 mL). The mixture was stirred at r.t. for 14 h, then 0.5 additional eq. of HBTU and DIPEA were added. The mixture was stirred at r.t. for 4 h, then poured into aq. sat. $NaHCO_3$ and extracted with EtOAc. The organic layer was separated, dried over $MgSO_4$, filtered and the solvents evaporated in vacuo. The crude product was purified by flash column chromatography (silica; EtOAc/DCM 0/100 to 50/50). The desired fractions were collected and concentrated in vacuo to yield the intermediate 29 as a pale yellow solid (1.89 g, 27% over two steps; R-enantiomer).

Example A5 a) Preparation of Intermediate 30

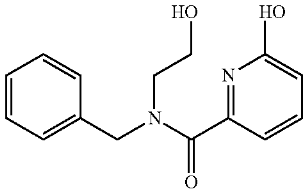 [SMILES: O=C(c1cccc(O)n1)N(CCO)Cc1ccccc1]

N-Benzylethanolamine (26.3 mL, 182.84 mmol) was added to a mixture of methyl 2-hydroxy-6-pyridinecarboxylate (14 g, 91.42 mmol) and MeOH (92 mL). The r.m. was stirred under reflux, the solvent was evaporated and the crude product purified by flash column chromatography (silica; MeOH/DCM 0/100 to 10/90). The desired fractions were collected and concentrated in vacuo to afford intermediate 30 (23.2 g, 93%).

b) Preparation of Intermediate 31

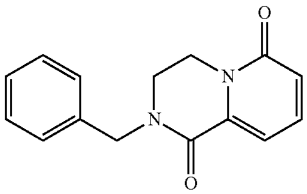 [SMILES: O=C1c2cccc(=O)n2CCN1Cc1ccccc1]

DIAD (19.05 mL, 96.117 mmol) was added to a stirred solution of intermediate 30 (17.449 g, 64.078 mmol) and TPP (25.211 g, 96.117 mmol) in dry THF (193 mL) under $N_2$. The mixture was stirred at r.t. for 2 h. The solvents evaporated in vacuo. The crude product was purified by flash column chromatography (silica; EtOAc/DCM 0/100 to 100/0). The desired fractions were collected and concentrated in vacuo to give intermediate 31 as a white solid (quantitative).

c) Preparation of Intermediate 32

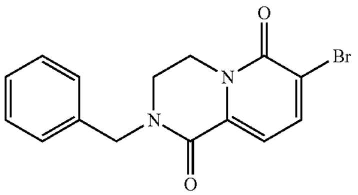 [SMILES: O=C1c2ccc(Br)c(=O)n2CCN1Cc1ccccc1]

Bromine (0.665 mL, 12.96 mmol) was added dropwise slowly to a stirred solution of intermediate 31 (2.75 g, 10.8 mmol) in DCM/AcOH 4:1 (50 mL) under $N_2$. The mixture was stirred at r.t. overnight, then diluted with aq. sat. $NaHCO_3$ and extracted with DCM. The organic layer was separated, dried over $MgSO_4$, filtered and the solvents were evaporated in vacuo. The crude product was purified by flash column chromatography (silica; EtOAc/DCM 0/100 to 20/80). The desired fractions were collected and concentrated in vacuo to yield intermediate 32 as a yellow solid (quantitative).

d) Preparation of Intermediate 33

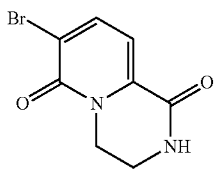 [SMILES: O=C1NCCn2c1ccc(Br)c2=O]

Trifluoromethanesulfonic acid (5.05 g, 15.15 mmol) was added to a stirred solution of intermediate 32 (5.4 mL, 60.6 mmol) in dry toluene (50 mL). The mixture was stirred at reflux for 24 h, then diluted with sat. $NH_3$ and the solvents were evaporated in vacuo. The crude product was purified by flash column chromatography (silica; MeOH/DCM 0/100 to 6/94). The desired fractions were collected and concentrated in vacuo to yield intermediate 33 as a white solid (quantitative).

e) Preparation of Intermediate 34

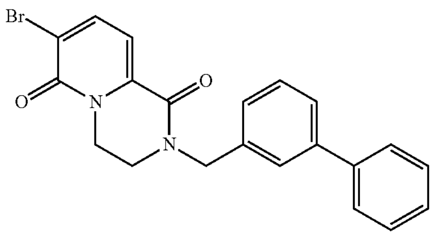 [SMILES: O=C1c2ccc(Br)c(=O)n2CCN1Cc1cccc(-c2ccccc2)c1]

Intermediate 33 (0.57 g, 2.34 mmol) and sodium hydride (60% as a dispersion in mineral oil, 0.103 g, 2.57 mmol) were dissolved in DMF (15 mL) at 0° C., then 3-phenylbenzyl bromide (0.58 g, 2.34 mmol) was added. The mixture was stirred at r.t. overnight. EtOAc and water were added. The organic phase was separated and dried over $MgSO_4$, filtered and concentrated to dryness. The crude product was purified by flash column chromatography (silica; EtOAc/hexane 0/100 to 50/50). The desired fractions were collected and concentrated in vacuo to yield intermediate 34 as a white solid (0.653 g, 98%).

Example A6 a) Preparation of Intermediate 35

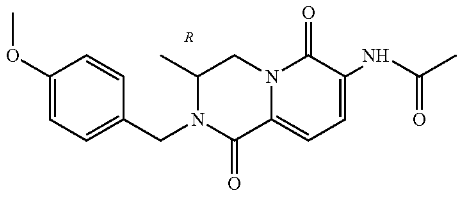

$K_3PO_4$ (0.731 g, 3.44 mmol), $Pd_2(dba)_3$ (63 mg, 0.06 mmol) and Xantphos (69 mg, 0.12 mmol) were added to a stirred solution of intermediate 13 (0.65 g, 1.72 mmol) in dry THF (5 mL) at r.t., while $N_2$ was bubbled through the mixture. After 10 min, acetamide (0.112 g, 1.89 mmol) was added and the mixture was stirred for another 10 min, then stirred for 3 h at 90° C. in a closed vessel. The reaction was then cooled to r.t. and sat. $NaHCO_3$ and EtOAc were added. The phases were separated, the aqueous phase extracted once more with EtOAc, the combined organics were dried over $MgSO_4$, filtered and evaporated. The crude was purified by flash column chromatography (silica; EtOAc/heptane 0/100 to 90/10). The desired fractions were collected and concentrated in vacuo to yield intermediate 35 as a pale yellow foam (0.335 g, 56%; R-enantiomer).

b) Preparation of Intermediate 36

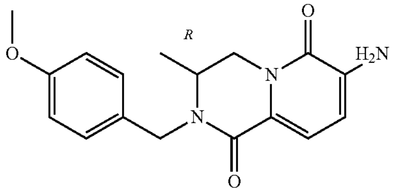

HCl (6N in 2-propanol, 0.471 mL, 2.82 mmol) was added to a solution of intermediate 35 (0.335 g, 0.94 mmol) in MeOH (5 mL) at r.t. and the mixture was stirred overnight. The solvent was then evaporated, sat. $NaHCO_3$ and EtOAc were added, the phases were separated, the aqueous phase was extracted once more and the combined organics were dried over $MgSO_4$, filtered and evaporated. The crude intermediate 36 was used as such in the next reaction step (quantitative yield; R-enantiomer).

c) Preparation of Intermediate 37

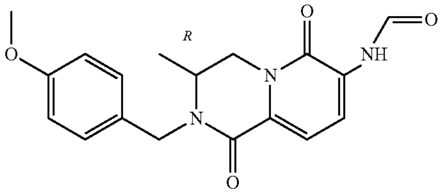

Acetic anhydride (0.339 mL, 3.58 mmol) was added dropwise to formic acid (0.533 mL, 14.13 mmol) at r.t. and stirred for 30 min at the same temperature. To this solution was added dropwise intermediate 36 (crude material, 0.94 mmol) in THF (6 mL). The r.m. was stirred 16 h at 60° C., then water and EtOAc were added. The phases were separated and the aqueous phase was extracted once more. The combined organics were dried over $MgSO_4$, filtered and evaporated. The crude intermediate 37 was used as such in the next reaction step (quantitative yield; R-enantiomer).

d) Preparation of Intermediate 38

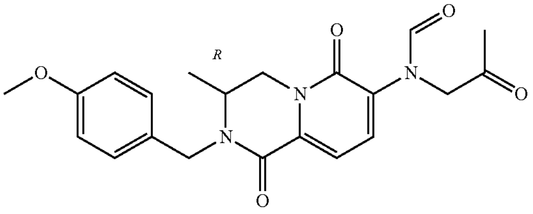

Chloroacetone (0.188 mL, 2.35 mmol) was added dropwise to a stirred suspension of intermediate 37 (crude material, 0.94 mmol), $K_2CO_3$ (0.456 g, 3.29 mmol) and KI (16 mg, 0.09 mmol) in DMF (3 mL) at r.t. The mixture was stirred for 16 h, then water and EtOAc were added. The phases were separated and the aq. phase was extracted once more. The combined organics were dried over $MgSO_4$, filtered and evaporated. The crude intermediate 38 was used as such to the next reaction step (quantitative yield; R-enantiomer).

e) Preparation of Intermediate 39

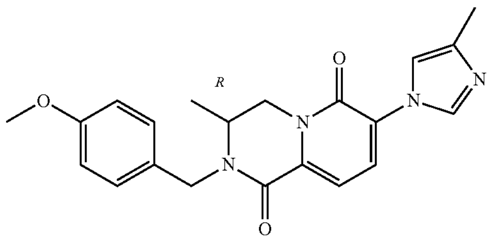

$NH_4OAc$ (0.362 g, 4.70 mmol) was added to a stirred solution of intermediate 38 (crude material, 0.94 mmol) in AcOH (2 mL) at r.t. and the mixture was stirred for 1 h at reflux. The reaction was then cooled to r.t. and poured into water at 0° C. 50% NaOH was added slowly until basic pH. The product was extracted with EtOAc (×2). The combined organics were dried over $MgSO_4$, filtered and evaporated. The crude was purified by flash column chromatography (silica; DCM-MeOH (9:1, v/v)/DCM 0/100 to 100/0). The desired fractions were collected and concentrated in vacuo to yield intermediate 39 as a sticky brown oil (0.2 g, 57% over 4 steps; R-enantiomer).

f) Preparation of Intermediate 40

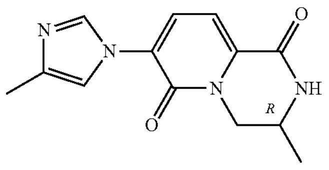

TfOH (0.186 mL, 2.11 mmol) was added to a stirred solution of intermediate 39 (0.2 g, 0.52 mmol) in dry toluene (2.5 mL) at r.t. and the mixture was stirred for 2 h at reflux. The solvent was then evaporated. NaOH 1M was added to pH=8 and the solvents were evaporated. The crude was triturated with DCM-MeOH (9:1, v/v), dried over $MgSO_4$, filtered and evaporated. The crude intermediate 40 was used as such in the next reaction step (quantitative yield; R-enantiomer).

f1) Alternative Preparation of Intermediate 40

In a first vial equipped with a magnetic stir bar and a screw cap septum, a solution of $Pd_2(dba)_3$ (55 mg, 0.06 mmol) and 2-di-tert-butylphosphino-3,4,5,6-tetramethyl-2',4',6'-triisopropy 1-1,1'-biphenyl (60 mg, 0.125 mmol) in dioxane (1.45 mL) and toluene (7.1 mL) was flushed with $N_2$ and then stirred at 120° C. for 3 min. A second vial, equipped with a magnetic stir bar and a screw cap septum, was charged with 4-methyl-imidazole (452 mg, 5.5 mmol) and $K_3PO_4$ (2.12 g, 10 mmol), then with intermediate 14 (1.312 g, 5 mmol) and also flushed with $N_2$. The premixed catalyst solution was added by syringe to the second vial. The r.m. was heated at 120° C. for 5 h. The reaction was cooled to r.t, diluted with DCM, washed with brine and neutralized with $NH_4Cl$. The solvents were evaporated until dryness, then the residue dissolved in MeOH and silica was added in order to purify the product (silica; silicaMeOH/DCM 5/95 to 20/80). The fractions were collected to give intermediate 40 (1.33 g, 98%; R-enantiomer).

Example A7 a) Preparation of Intermediate 41

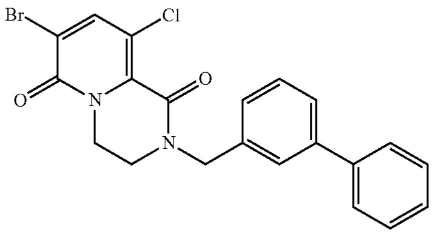 [SMILES: O=C1c2c(Cl)cc(Br)c(=O)n2CCN1Cc1cccc(-c2ccccc2)c1]

NCS (195 mg, 1.46 mmol) was added portionwise to a solution of intermediate 34 (0.5 g, 1.22 mmol) in DMF (5 mL) at r.t. The mixture was stirred overnight at 65° C. Sat. aq. $NaHCO_3$ and EtOAc were added, the phases were separated and the aq. phase was extracted once more with EtOAc. The combined organics were dried on $MgSO_4$, filtered and evaporated. The crude was purified by flash column chromatography (silica; EtOAc/heptane 0/100 to 50/50). The desired fractions were collected and concentrated in vacuo to yield intermediate 41 as a pale yellow foam (451 mg, 83%).

Example A8 a) Preparation of Intermediate 42

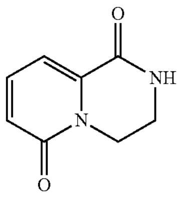 [SMILES: O=C1NCCn2c1cccc2=O]

Trifluoromethanesulfonic acid (4.2 mL, 47.19 mmol) was added to a stirred solution of intermediate 31 (3 g, 11.79 mmol) in dry toluene (33 mL). The mixture was stirred at reflux overnight, then diluted with NaOH 1M to pH=8 and the solvents were evaporated in vacuo. The crude product was purified by flash column chromatography (silica; MeOH/DCM 0/100 to 3/97). The desired fractions were collected and concentrated in vacuo to yield intermediate 42 as a yellow solid (1.58 g, 81%).

b) Preparation of Intermediate 43

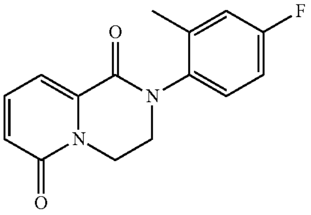 [SMILES: Cc1cc(F)ccc1N1CCn2c(cccc2=O)C1=O]

CuI (0.495 g, 2.6 mmol) was added to a solution of intermediate 42 (0.855 g, 5.2 mmol), 5-fluoro-2-iodotoluene (1.6 g, 6.77 mmol), N,N-dimethyl-1,2-ethane-diamine (0.56 mL, 5.2 mmol) and $K_3PO_4$ (2.2 g, 10.4 mmol) in DMF (15 mL), while the reaction was degassed by bubbling $N_2$ through the solution. The mixture was then heated a 100° C. for 6 h. Water was added and the aq. layer was extracted with EtOAc. The organic layer was dried over $MgSO_4$, filtered and the solvent was removed under reduced pressure. The crude product was purified by flash column chromatography (silica; EtOAc/hexane 0/100 to 100/0). The desired fractions were concentrated in vacuo to yield intermediate 43 as a brown solid (0.848 g, 60%).

Example A9 a) Preparation of Intermediate 44

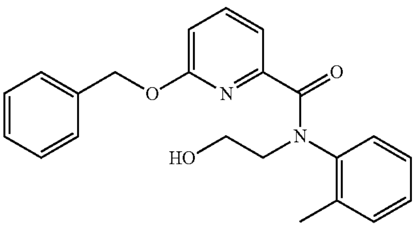 [SMILES: Cc1ccccc1N(CCO)C(=O)c1cccc(OCc2ccccc2)n1]

Starting from 2-(o-tolylamino)ethanol, intermediate 44 was prepared by analogy to the procedures reported for the synthesis of intermediate 4.

b) Preparation of Intermediate 45

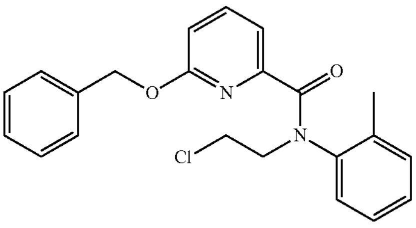 [SMILES: Cc1ccccc1N(CCCl)C(=O)c1cccc(OCc2ccccc2)n1]

Thionyl chloride (1.08 mL, 14.9 mmol) was added to a solution of intermediate 44 (2.7 g, 7.44 mmol) in DCM (15 mL) at 0° C. The mixture was stirred at r.t. overnight. DCM was added and the organic layer was washed with aq. sat. $NaHCO_3$, dried over $MgSO_4$, filtered and evaporated under reduced pressure. The crude intermediate 45 (oil) was used as such in the next reaction step (quantitative yield).

c) Preparation of Intermediate 46

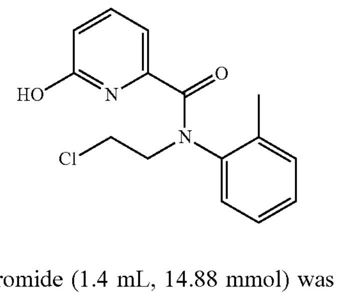

Boron tribromide (1.4 mL, 14.88 mmol) was added to a solution of intermediate 45 (crude material, 7.44 mmol) in DCM (21 mL) at 0° C. The mixture was stirred at r.t. for 2 h, then DCM and sat. aq. $NaHCO_3$ were added. The aq. layer was extracted with DCM, the organic phase was dried over $MgSO_4$, filtered and concentrated to dryness. The crude intermediate 46 was used such in the next reaction step (quantitative yield).

d) Preparation of Intermediate 47

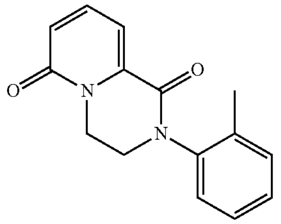 [SMILES: Cc1ccccc1N1CCn2c(cccc2=O)C1=O]

NaH (60% in mineral oil, 0.327 g, 8.2 mmol) was added portionwise to a solution of intermediate 46 (crude material, 7 44 mmol) in DMF (21 mL) at 0° C. The mixture was stirred at r.t. for 2 h. EtOAc and water were added, the organic phase was separated, dried over $MgSO_4$, filtered and concentrated to dryness. The crude product was purified by flash column chromatography (silica; EtOAc/hexane 0/100 to 100/0). The desired fractions were collected and concentrated in vacuo to yield intermediate 47 as a white solid (1.24 g, 59%).

Example A10 a) Preparation of Intermediate 48

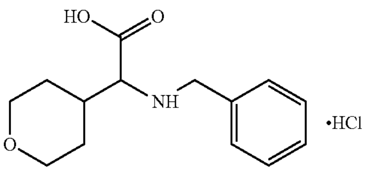 [SMILES: O=C(O)C(NCc1ccccc1)C1CCOCC1 ; Cl]

A solution of 2-(benzylamino)-2-(oxan-4-yl)acetonitrile (6.05 g, 26.28 mmol) in AcOH (5 mL) and HCl 37% (50 mL) was stirred at 95° C. for 4 days. The mixture was cooled and the solvents evaporated in vacuo. The black crude was triturated with acetone to give a white solid, that was discarded. The acetone solution was concentrated in vacuo and the residual triturated with DIPE and heptane. The sticky solid was filtered and washed with $Et_2O$, DCM and acetone. The resulting intermediate 48 (beige solid) was dried in vacuo and used as such in the next reaction step (3.77 g, 57%).

b) Preparation of Intermediate 49

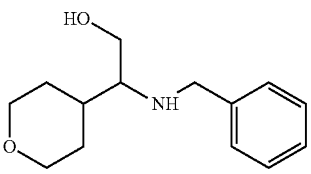 [SMILES: OCC(NCc1ccccc1)C1CCOCC1]

To a suspension of intermediate 48 (3.77 g, 13.21 mmol) in THF (21 mL) were added $Et_3N$ and borane-methyl sulfide (2M, 19.81 mL, 39.63 mmol) at 0° C. The r.m. was heated to 50° C. for 36 h, then cooled. Aq. sat. $NaHCO_3$ was added, the reaction extracted with EtOAc, the organic layer was dried, filtered and concentrated to dryness. The crude material was used as such for the next reaction step (quantitative yield).

c) Preparation of Intermediate 50

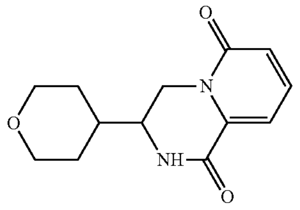 [SMILES: O=C1NC(C2CCOCC2)Cn2c1cccc2=O]

Starting from intermediate 49, intermediate 50 was prepared by analogy to the procedures reported for the synthesis of intermediate 6.

d) Preparation of Intermediate 51

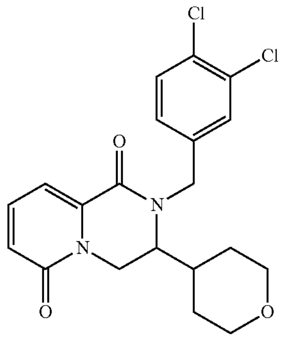 [SMILES: O=C1c2cccc(=O)n2CC(C2CCOCC2)N1Cc1ccc(Cl)c(Cl)c1]

NaH (60% in mineral oil, 0.053 g, 1.32 mmol) and intermediate 50 (0.3 g, 1.20 mmol) were dissolved in DMF (12 mL) at 0° C. 3,4-Dichlorobenzyl bromide (0.217 mL, 1.45 mmol) was then added, and the mixture was stirred at r.t. for 4 h. EtOAc and water were added, the organic phase was separated, dried over $MgSO_4$, filtered and concentrated to dryness. The crude product was purified by flash column chromatography (silica; EtOAc/hexane 0/100 to 100/0). The desired fractions were collected and concentrated in vacuo to yield intermediate 51 as an oil (0.345 g, 71%).

Example A11 a) Preparation of Intermediate 52

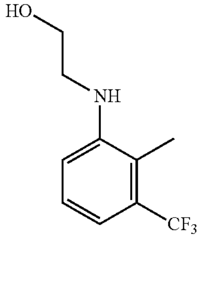

A mixture of 2-iodoethanol (0.296 mL, 3.8 mmol) and 2-methyl-3-trifluoromethyl-aniline (1 g, 5.7 mmol) was heated at 90° C. under $N_2$ atmosphere for 6 h. The resulting solid was dissolved in EtOAc and washed with 2M aq. NaOH solution. The organic layer was dried, filtered and concentrated to dryness. The crude product was purified by flash column chromatography (silica; EtOAc/hexane 0/100 to 50/50). The desired fractions were collected and concentrated in vacuo to yield intermediate 52 as an oil (0.711 g, 85%).

b) Preparation of Intermediate 53

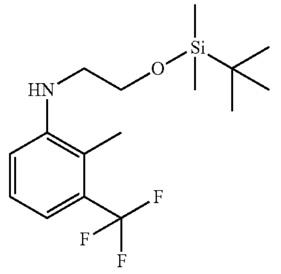 [SMILES: Cc1c(NCCO[Si](C)(C)C(C)(C)C)cccc1C(F)(F)F]

Starting from intermediate 52, intermediate 53 was prepared by analogy to the procedures reported for the synthesis of intermediate 2.

c) Preparation of Intermediate 54

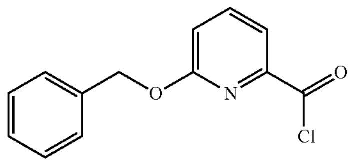 [SMILES: O=C(Cl)c1cccc(OCc2ccccc2)n1]

Thionyl chloride (0.417 mL, 4.86 mmol) was added to a solution of 6-(benzyloxy)-pyridine-2-carboxylic acid (0.724 g, 3.24 mmol) and a drop of DMF in DCM (15 mL). The mixture was stirred at r.t. for 2 h, then the solvent was removed under reduced pressure and the crude intermediate 54 used as such in the next reaction step (quantitative yield).

d) Preparation of Intermediate 55

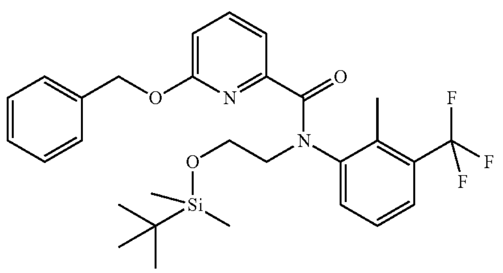 [SMILES: Cc1c(N(CCO[Si](C)(C)C(C)(C)C)C(=O)c2cccc(OCc3ccccc3)n2)cccc1C(F)(F)F]

Intermediate 53 (crude material, 3.24 mmol) was added to a solution of intermediate 54 (crude material, 3.24 mmol) and DIPEA (0.726 mL, 4.212 mmol) in DMF (12 mL). The mixture was stirred at r.t. overnight, then aq. sat. $NaHCO_3$ was added the mixture extracted with EtOAc. The combined extracts were dried over $MgSO_4$ and concentrated in vacuo. The crude was purified by flash column chromatography (silica; EtOAc/hexane 0/100 to 15/85). The desired fractions were collected and concentrated in vacuo to yield intermediate 55 as an oil (0.920 g, 52% over two steps).

Example A12 a) Preparation of Intermediate 56

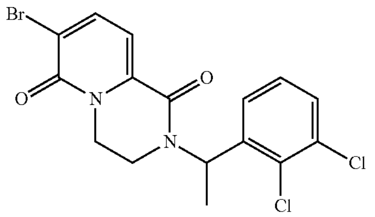 [SMILES: CC(c1cccc(Cl)c1Cl)N1CCn2c(ccc(Br)c2=O)C1=O]

Starting from 2',3'-dichloroacetophenone and ethanolamine, intermediate 56 was prepared by analogy to the procedures reported for the synthesis of intermediate 7.

Example A13 a) Preparation of Intermediate 57

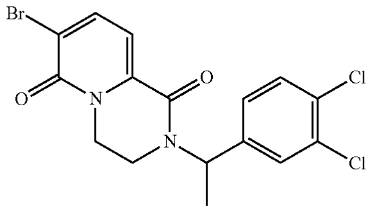 [SMILES: CC(c1ccc(Cl)c(Cl)c1)N1CCn2c(ccc(Br)c2=O)C1=O]

Starting from 3',4'-dichloroacetophenone and ethanolamine, intermediate 57 was prepared by analogy to the procedures reported for the synthesis of intermediate 7.

Example A14 a) Preparation of Intermediate 58

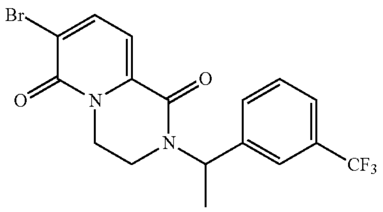 [SMILES: CC(c1cccc(C(F)(F)F)c1)N1CCn2c(ccc(Br)c2=O)C1=O]

Starting from intermediate 33, intermediate 58 was prepared by analogy to the procedures reported for the synthesis of intermediate 34. Intermediate 58 was obtained as a crude, and was used as such in the synthesis of compounds 11a and 11b.

Example A15 a) Preparation of Intermediate 59

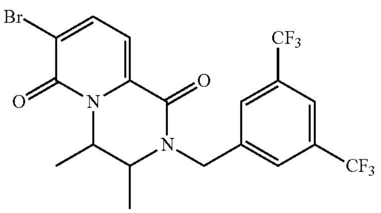

cis

Starting from 3-amino-2-butanol (mixture of R,R and S,S) and 3,5-bis(trifluoromethyl)-benzaldehyde, intermediate 59 (cis) was prepared by analogy to the procedures reported for the synthesis of intermediate 13.

Example A16 a) Preparation of Intermediate 60

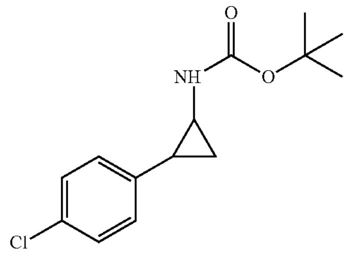

trans $Et_3N$ (4.24 mL, 30.51 mmol) was added to a solution of 2-(4-chlorophenyl)-cyclopropanecarboxylic acid (6 g, 30.51 mmol) in tBuOH (91.5 mL) at r.t. Diphenylphosphoryl azide (6.6 mL, 30.51 mmol) was added and the mixture stirred at r.t. for 30 min. The r.m. was slowly heated at 80° C. and kept at that temperature for 3 h. The solvent was evaporated in vacuo. The mixture was diluted with water and extracted with EtOAc. The organic layer was separated, dried over $MgSO_4$, filtered and the solvents evaporated in vacuo. The crude product was purified by flash column chromatography (silica; EtOAc/heptane 0/100 to 15/85). The desired fractions were collected and concentrated in vacuo to yield intermediate 60 (trans) as a white solid (2.6 g, 32%).

b) Preparation of Intermediate 61

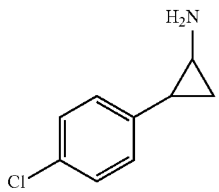

trans

Intermediate 60 (2.6 g, 9.7 mmol) and HCl (5 to 6N in 2-propanol, 9.7 mL) were dissolved in dioxane (9.7 mL). The mixture was stirred at r.t. overnight. Sat. aq. $NaHCO_3$ was added carefully. The reaction was extracted with EtOAc. The organic layer was dried, filtered and concentrated to dryness. The crude intermediate 61 (trans) was used as such in the next reaction step (quantitative yield).

c) Preparation of Intermediate 62

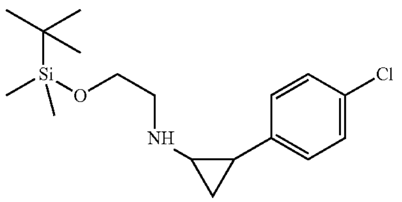

trans

Sodium triacetoxyborohydride (2.5 g, 11.64 mmol) was added to a stirred solution of intermediate 61 (crude material, 9.7 mmol) and tert-butyldimethylsilyloxy-acetaldehyde (2.03 mL, 10.67 mmol) in 1,2-dichloroethane (30 mL). The reaction was stirred at r.t. overnight. The crude product was dissolved with DCM and washed with aq. sat. $NaHCO_3$. The organic layer was separated, dried over $MgSO_4$, filtered and the solvents evaporated in vacuo. The crude product was purified by flash column chromatography (silica; EtOAc/DCM 0/100 to 20/80). The desired fractions were collected and concentrated in vacuo to yield intermediate 62 (trans) as a colorless oil (1.4 g, 44%).

Example A17 a) Preparation of Intermediate 63

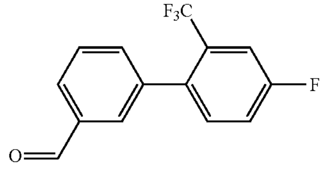 [SMILES: O=Cc1cccc(-c2ccc(F)cc2C(F)(F)F)c1]

A mixture of 5-bromo-2-fluorobenzotrifluoride (4 g, 16.46 mmol), 3-formyl-phenylboronic acid (2.96 g, 19.75 mmol), $PdCl_2(dppf)$) (0.602 g, 0.823 mmol) and $K_2CO_3$ (7.571 g, 32.92 mmol) in dioxane/water 5:1 (50 mL) was degassed for a few min with $N_2$. The r.m. was then heated at 80° C. for 5 h. The dioxane was removed under vacuum and the residual extracted with DCM. The organic layer was dried over $Na_2SO_4$, filtered and the solvent was evaporated. The residue was purified by flash chromatography (silica; EtOAc/petroleum ether 0/100 to 1/15). The desired fractions were collected and the solvent was evaporated to give intermediate 63 (3.4 g, 77%).

b) Preparation of Intermediate 64

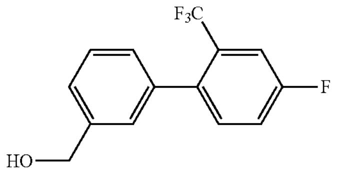 [SMILES: OCc1cccc(-c2ccc(F)cc2C(F)(F)F)c1]

A solution of intermediate 63 (3.4 g, 12.687 mmol) and MeOH (100 mL) was stirred and cooled to 0° C. $NaBH_4$ (1.04 g, 27.374 mmol) was added and the stirring was continued at 0° C. for 10 min, then the r.m. was warmed to r.t. for 2 h. After this time, 1 mL of water was added, and the mixture evaporated. 40 mL of sat. aq. $NaHCO_3$ were added, the solution washed with DCM, the organic layer collected, dried over $Na_2SO_4$, filtered and evaporated to give intermediate 64 (3.2 g, 93%).

c) Preparation of Intermediate 65

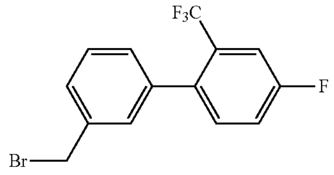 [SMILES: Fc1ccc(-c2cccc(CBr)c2)c(C(F)(F)F)c1]

A solution of intermediate 64 (2 g, 7.407 mmol) in DCM (70 mL) was cooled to 10° C. and phosphorus tribromide (4 g, 14.814 mmol) was added dropwise. The r.m. was stirred at −20° C. for 3 h. After this time, the reaction was warmed to 0° C. and stirred 1 h, then quenched with water (50 mL), and slowly brought to pH 8 with solid $K_2CO_3$. The layers were separated and the aq. layer was extracted with DCM (2×100 mL). The combined organic layers were dried over $Na_2SO_4$ and evaporated to give intermediate 65 as a clear oil (1.73 g, 70% yield).

Example A18

Following a procedure similar to the one reported for the synthesis of intermediate 21, following compounds were obtained from the commercially available corresponding acids:

| Structure | Intermediate number |
| --- | --- |
| 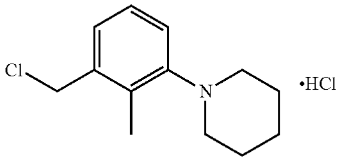 | 66 |
| 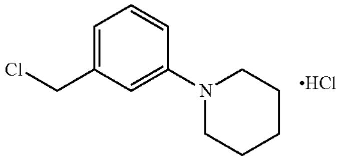 [SMILES: ClCc1cccc(N2CCCCC2)c1 ; Cl] | 67 |
| 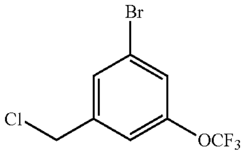 | 161 |

Example A19 a) Preparation of Intermediate 68

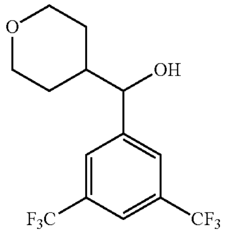 [SMILES: OC(c1cc(C(F)(F)F)cc(C(F)(F)F)c1)C1CCOCC1]

3,5-Bis(trifluoromethyl)bromobenzene (2.1 mL, 10.51 mmol) was added to a stirred solution of magnesium (0.3 g, 11.39 mmol) in THF under $N_2$ atmosphere. The mixture was stirred at reflux for 2 h, then was added to a stirred solution of 4-formyltetra-hydropyran (1 g, 8.76 mmol) in THF under $N_2$ atmosphere at r.t. The mixture was stirred at r.t. for 1 h, then aq. sat. $NH_4Cl$ was added and the mixture was extracted with EtOAc. The combined extracts were dried over $MgSO_4$ and concentrated in vacuo. The crude product was purified by flash column chromatography (silica; EtOAc/hexane 0/100 to 50/50). The desired fractions were collected and concentrated in vacuo to yield intermediate 68 as an oil (1.67 g, 58%).

b) Preparation of Intermediate 69

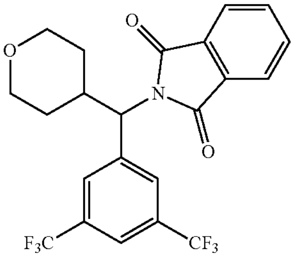 [SMILES: O=C1c2ccccc2C(=O)N1C(c1cc(C(F)(F)F)cc(C(F)(F)F)c1)C1CCOCC1]

DIAD (1.5 mL, 7.62 mmol) was added to a stirred solution of intermediate 68 (1.67 g, 5.08 mmol), phtalimide (0.812 g, 5.6 mmol) and TPP (2 g, 7.62 mmol) in dry THF and under $N_2$ at 0° C. The mixture was stirred at r.t. for 4 h, then the solvents evaporated in vacuo. The crude product was purified by flash column chromatography (silica; EtOAc/hexane 0/100 to 20/80). The desired fractions were collected and concentrated in vacuo to yield intermediate 69 as an oil (1.41 g, 61%).

c) Preparation of Intermediate 70

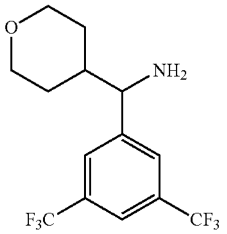 [SMILES: NC(c1cc(C(F)(F)F)cc(C(F)(F)F)c1)C1CCOCC1]

Hydrazine hydrate (64%, 0.734 mL, 15.41 mmol) was added to a stirred solution of intermediate 69 (1.41 g, 3.08 mmol) in EtOH (9 mL). The mixture was stirred at 80° C. for 4 h, then diluted with NaOH 1M and extracted with DCM. The organic layer was separated, dried over $MgSO_4$, filtered and the solvents evaporated in vacuo. The crude intermediate 70 was used as such in the reaction step (quantitative yield).

Example A20 a) Preparation of Intermediate 71

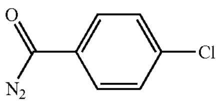

4-Chlorobenzoic acid (1.58 g, 10.09 mmol) was dissolved in DCM (10 mL). Oxalyl chloride (1.30 mL, 15.13 mmol) was added slowly at r.t. and the mixture was refluxed for 2 h. The r.m. was then concentrated in vacuo. The residue was dissolved in acetonitrile (50 mL), then trimethylsilyldiazomethane (2M in hexane, 5.55 mL, 11.10 mmol) was added at 0° C. followed by $Et_3N$. The mixture was stirred at 0° C. for 24 h. The solvent was evaporated in vacuo and the crude purified by flash column chromatography (silica; EtOAc/heptane 0/100 to 25/75) to afford intermediate 71 (0.503 g, 28%).

b1) Preparation of Intermediate 72

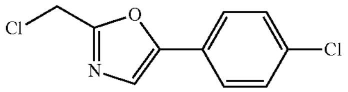

Intermediate 71 (0.503 g, 2.78 mmol) was added in small portions to a solution of chloroacetonitrile (11.2 mL, 177 mmol) and boron trifluoride etherate (0.560 mL, 9.5 mmol) at −5° C. under stirring. The reaction proceeded with vigorous evolution of $N_2$ gas and gave a grey precipitate. After the $N_2$ evolution ceased, the r.m. was cooled to −15° C. to complete the precipitation. The precipitate was separated by filtration, washed with $Et_2O$, neutralized with aq. sat. $NaHCO_3$ and extracted with $Et_2O$ (×2). The organic layer was dried over $MgSO_4$, filtered and concentrated in vacuo to afford intermediate 72 (0.602 g, 95%).

Example A21 a) Preparation of Intermediate 73

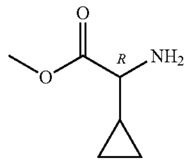

Thionyl chloride (1.394 mL. 19.109 mmol) was added to a solution of (R)-Amino-cyclopropyl-acetic acid (1 g, 8.686 mmol) in MeOH (26 mL) at 0° C. The mixture was stirred at 80° C. for 16 h. The mixture was concentrated to dryness. Toluene was added and the mixture was concentrated to dryness again to yield a colourless oil containing intermediate 73, used in the subsequent reaction step without further purification (quantitative yield; R-enantiomer).

b) Preparation of Intermediate 74

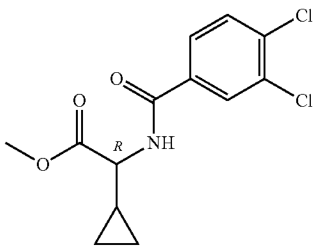

A mixture of 3,4-dichlorobenzoylchloride (2.001 g, 9.55 mmol) in DCM was added slowly dropwise to a solution of intermediate 73 (crude material, 8.686 mmol) and $Et_3N$ (3.632 mL, 26.058 mmol) in DCM (26 mL total amount). The mixture was stirred at r.t. for 15 h. The crude r.m. was diluted with aq. sat. $NaHCO_3$ and extracted with DCM. The organic layer was separated, dried over $MgSO_4$, filtered and the solvents evaporated in vacuo. The crude product was purified by flash column chromatography (silica; EtOAc/hexane 0/100 to 20/80). The desired fractions were collected and concentrated in vacuo to yield intermediate 74 as a white solid (1.136 g, 44%; R-enantiomer).

c) Preparation of Intermediate 75

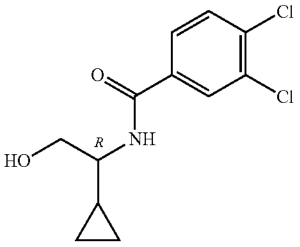

$LiAlH_4$ (0.143 g, 3.760 mmol) was added portionwise to a mixture of intermediate 74 (1.136 g, 3.760 mmol) in dry THF (11.4 mL) at 0° C. The mixture was stirred at r.t. for 16 h, then 0.5 eq of $LiAlH_4$ were added. The mixture was stirred at 0° C. and $MgSO_4$ with water were added portionwise at 0° C. The mixture was filtered and the solvents evaporated in vacuo. The crude material was used as such in the next reaction step (quantitative yield; R-enantiomer).

d) Preparation of Intermediate 76

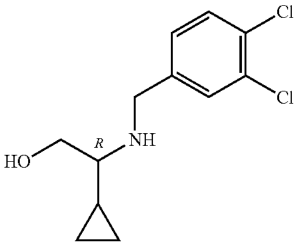

Borane dimethylsulfide (2M in THF, 4.7 mL, 9.4 mmol) was added to a suspension of intermediate 75 (crude material, 3.760 mmol) in dry THF (5.7 mL) at 0° C. The r.m. was heated at 60° C. for 16 h, then cooled down. Aq. sat. $NaHCO_3$ was added carefully. The reaction was extracted with DCM. The organic layer was dried, filtered and concentrated to dryness. The crude product was purified by flash column chromatography (silica; EtOAc/hexane 0/100 to 30/70). The desired fractions were collected and concentrated in vacuo to yield intermediate 76 as an oil (98%; R-enantiomer).

Example A22 a) Preparation of Intermediate 77

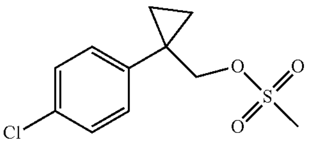 [SMILES: CS(=O)(=O)OCC1(c2ccc(Cl)cc2)CC1]

DIPEA (4.87 mL, 27.9 mmol) was added to an ice-cooled sol. of 1-(4-chlorophenyl)-1-cyclopropane methanol (1.7 g, 9.3 mmol) in DCM (23 mL). Methanesulphonyl chloride (0.72 mL, 9.3 mmol) was added and stirring was continued for 1 h, while letting the reaction reach r.t. The r.m. was quenched by aq. sat. $NaHCO_3$. The organic layer was separated, dried over $MgSO_4$, filtered and evaporated in vacuo. The crude intermediate 77 was used as such in the next reaction step (quantitative yield).

By using an analogous procedure to the one reported for the synthesis of intermediate 77, starting from the corresponding known or commercially available alcohols, following intermediates were obtained:

| Structure | Int. number |
| --- | --- |
| 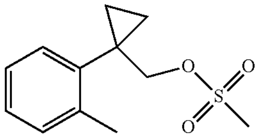 [SMILES: Cc1ccccc1C1(COS(C)(=O)=O)CC1] | 78 |
| 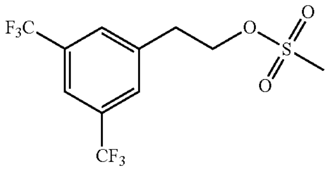 [SMILES: CS(=O)(=O)OCCc1cc(C(F)(F)F)cc(C(F)(F)F)c1] | 79 |
| 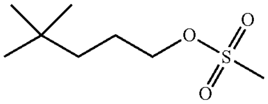 | 80 |
| 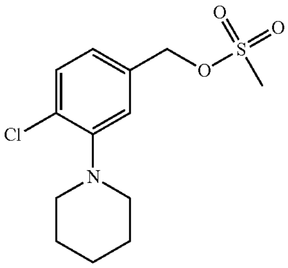 [SMILES: CS(=O)(=O)OCc1ccc(Cl)c(N2CCCCC2)c1] | 81 |
| 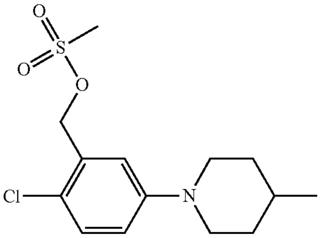 [SMILES: CC1CCN(c2ccc(Cl)c(COS(C)(=O)=O)c2)CC1] | 82 |
| 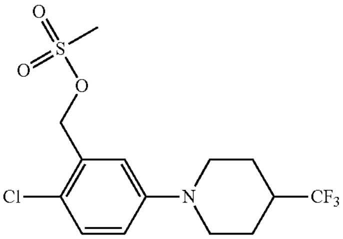 [SMILES: CS(=O)(=O)OCc1cc(N2CCC(C(F)(F)F)CC2)ccc1Cl] | 83 |

-continued

| Structure | Int. number |
| --- | --- |
| 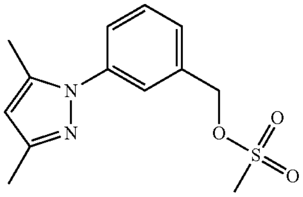 [SMILES: Cc1cc(C)n(-c2cccc(COS(C)(=O)=O)c2)n1] | 84 |
| 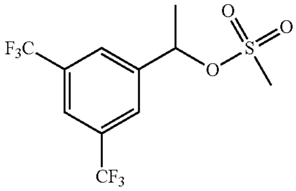 [SMILES: CC(OS(C)(=O)=O)c1cc(C(F)(F)F)cc(C(F)(F)F)c1] | 85 |
| 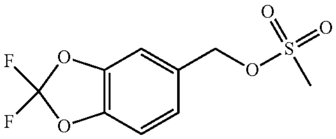 [SMILES: CS(=O)(=O)OCc1ccc2c(c1)OC(F)(F)O2] | 86 |
| 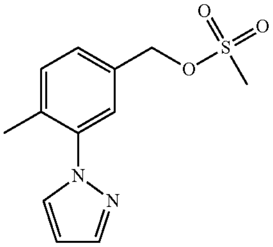 [SMILES: Cc1ccc(COS(C)(=O)=O)cc1-n1cccn1] | 87 |
| 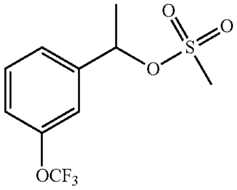 [SMILES: CC(OS(C)(=O)=O)c1cccc(OC(F)(F)F)c1] | 120 |
| 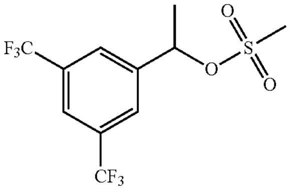 [SMILES: CC(OS(C)(=O)=O)c1cc(C(F)(F)F)cc(C(F)(F)F)c1] | 125 |
| 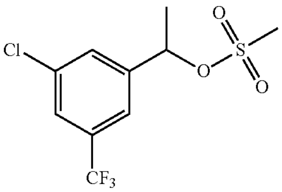 [SMILES: CC(OS(C)(=O)=O)c1cc(Cl)cc(C(F)(F)F)c1] | 143 |

-continued

| Structure | Int. number |
| --- | --- |
| 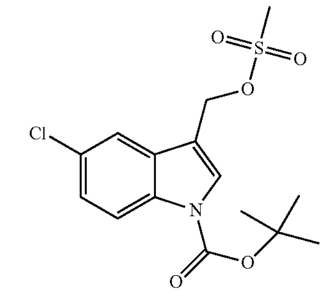 [SMILES: CC(C)(C)OC(=O)n1cc(COS(C)(=O)=O)c2cc(Cl)ccc21] | 144 |
| 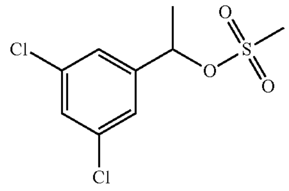 | 193 |
| 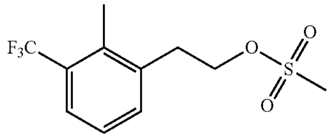 [SMILES: Cc1c(CCOS(C)(=O)=O)cccc1C(F)(F)F] | 194 |
| 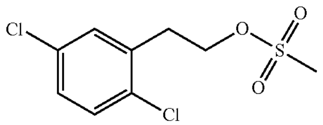 | 195 |
| 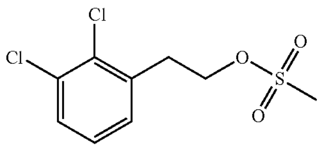 | 196 |
| 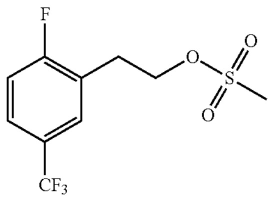 [SMILES: CS(=O)(=O)OCCc1cc(C(F)(F)F)ccc1F] | 197 |
| 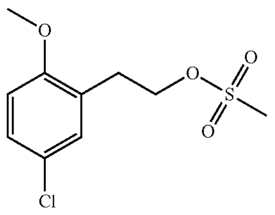 [SMILES: COc1ccc(Cl)cc1CCOS(C)(=O)=O] | 198 |

Example A23 a) Preparation of Intermediate 88

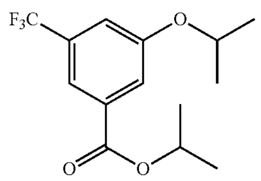 [SMILES: CC(C)OC(=O)c1cc(OC(C)C)cc(C(F)(F)F)c1]

DIAD (2.885 mL, 14.555 mmol) was added to a stirred solution of 3-hydroxy-5-(trifluoromethyl)benzoic acid (1.2 g, 5.822 mmol), iPrOH (0.981 mL, 12.808 mmol) and TPP (3.82 g, 14.555 mmol) in dry THF (25 mL) under $N_2$ at 5° C. The mixture was stirred at r.t. for 12 h, then concentrated in vacuo. The crude product was purified by flash column chromatography (silica; EtOAc/heptane 0/100 to 10/90). The desired fractions were concentrated in vacuo to yield a colourless oil (1.55 g, 91%).

b) Preparation of Intermediate 89

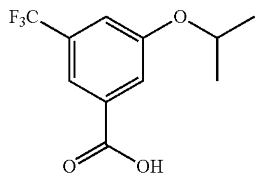 [SMILES: CC(C)Oc1cc(C(=O)O)cc(C(F)(F)F)c1]

NaOH 1M (8.01 mL, 8.01 mmol) was added to a stirred solution of intermediate 88 (1.55 g, 5.340 mmol) in MeOH (10 mL). The mixture was stirred at 55° C. for 12 h. The solvent was evaporated in vacuo. The mixture was diluted with water and acidified with HCl 2N until pH=2 and extracted with EtOAc. The organic layer was separated, dried ($MgSO_4$), filtered and the solvents evaporated in vacuo. The crude intermediate 89 was used as such for the next reaction step (1.280 g, 95%).

c) Preparation of Intermediate 90

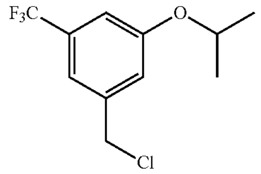 [SMILES: CC(C)Oc1cc(CCl)cc(C(F)(F)F)c1]

By following an analogous procedure as described for the synthesis of intermediate 21, intermediate 90 was obtained starting from intermediate 89.

Example A24 a) Preparation of Intermediate 91

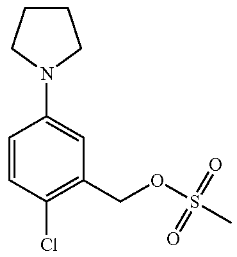 [SMILES: CS(=O)(=O)OCc1cc(N2CCCC2)ccc1Cl]

By following an analogous procedure as described for the synthesis of intermediate 20 and intermediate 77, intermediate 91 was obtained starting from the commercially available acid.

Example A25 a) Preparation of Intermediate 92

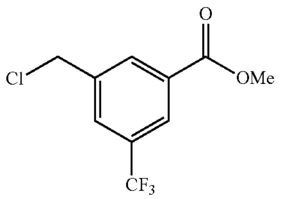 [SMILES: COC(=O)c1cc(CCl)cc(C(F)(F)F)c1]

By following an analogous procedure as described for the synthesis of intermediate 21, intermediate 92 was obtained starting from the known alcohol (69%).

b) Preparation of Intermediate 93

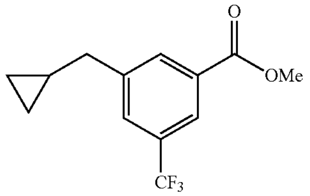

RuPhos (78 mg, 0.168 mmol), $Pd_2(dba)_3$ (77 mg, 0.084 mmol), $K_2CO_3$ (4.54 mg, 3.36 mmol) and potassium cyclopropyltrifluoroborate (297 mg, 2.01 mmol) were added to a stirred solution of intermediate 92 (424 mg, 1.678 mmol) in toluene (19 mL) and water (1 mL) at r.t. while $N_2$ was bubbled throughout the mixture. The reaction was then stirred for 15 h at 120° C. After cooling to r.t.sat. $NaHCO_3$ and EtOAc were added. The aq. phase was extracted with EtOAc. The combined organics were dried over $MgSO_4$, filtered and evaporated. The crude was purified by flash column chromatography (silica; EtOAc/heptane 0/100 to 10/90). The desired fractions were collected and concentrated in vacuo to yield intermediate 93 as an oil (110 mg, 25%, 63% purity).

c) Preparation of Intermediate 94

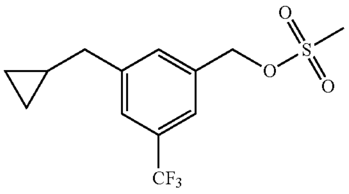 [SMILES: CS(=O)(=O)OCc1cc(CC2CC2)cc(C(F)(F)F)c1]

By following an analogous procedure as described for the synthesis of intermediate 89, 64 and 77, intermediate 94 was obtained starting from intermediate 93.

Example A26 a) Preparation of Intermediate 95

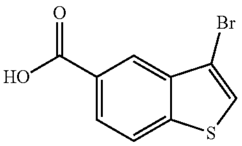 [SMILES: O=C(O)c1ccc2scc(Br)c2c1]

Bromine (0.16 mL, 3.11 mmol) was added to a solution of 1-benzothiophene-5-carboxylic acid (0.5 g, 2.8 mmol) in AcOH (15 mL). The solution was then stirred at r.t. for 4 h. Additional bromine was added and the solution stirred at r.t. for additional 16 h. The solution was then poured in water (90 mL) with vigorous stirring and the resulting solids were collected by suction filtration, washed with water and dried, to afford intermediate 95 in quantitative yield.

b) Preparation of Intermediate 96

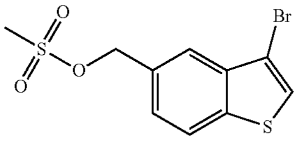 [SMILES: CS(=O)(=O)OCc1ccc2scc(Br)c2c1]

By following analogous procedures as described for the synthesis of intermediates 64 and 77, intermediate 96 was obtained starting from intermediate 95.

Example A27 a) Preparation of Intermediate 97

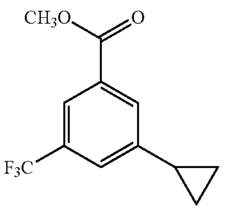

$NaHCO_3$ (0.889 g, 10.59 mmol) was added to a sol. of methyl 3-bromo-5-(trifluoro-methyl)benzoate (1 g, 3.53 mmol), cyclopropylboronic acid (0.334 g, 3.89 mmol) and $PdCl_2(dppf)_2$ (144 mg, 0.177 mmol) in dioxane (8 mL) and water (3 mL), while $N_2$ was bubbled through the mixture. The solution was stirred at 100° C. overnight, then diluted with water and extracted with DCM. The organic layer was separated, dried ($MgSO_4$), filtered and the solvents evaporated in vacuo. The crude product was purified by flash column chromatography (silica; EtOAc/heptane 0/100 to 40/60). The fractions were collected and evaporated in vacuo to yield intermediate 97 (0.35 g, 41%).

b) Preparation of Intermediate 98

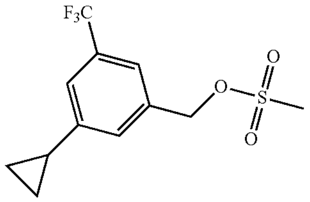 [SMILES: CS(=O)(=O)OCc1cc(C2CC2)cc(C(F)(F)F)c1]

By following analogous procedures as described for the synthesis of intermediate 94, intermediate 98 was obtained starting from intermediate 97.

Example A28 a) Preparation of Intermediate 99

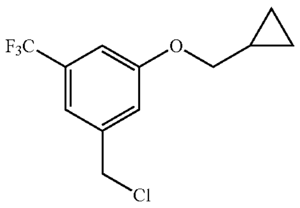 [SMILES: FC(F)(F)c1cc(CCl)cc(OCC2CC2)c1]

By following analogous procedures as described for the synthesis of intermediate 21, intermediate 99 was obtained starting from the known corresponding alcohol.

Example A29 a) Preparation of Intermediate 100

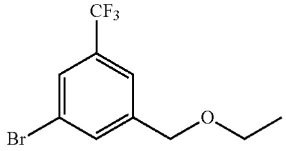

Ethyl iodide (0.5 mL, 6.12 mmol) was added to a mixture of 3-bromo-5-(trifluoro-methyl)benzyl alcohol (1.3 g, 5.10 mmol), sodium hydride (60% in mineral oil, 0.23 g, 5.61 mmol) in DMF (15 mL) at 0° C. The mixture was stirred at r.t. for 1 h, then diluted with sat. $NaHCO_3$ and extracted with EtOAc. The organic layer was washed with $NaHCO_3$ solution, dried ($MgSO_4$), filtered and the solvents were evaporated in vacuo. The crude product was purified by flash chromatography (silica; EtOAc/heptane 0/100 to 20/80). The desired fractions were collected and concentrated in vacuo, to yield intermediate 100 (1 g, 69%).

b) Preparation of Intermediate 101

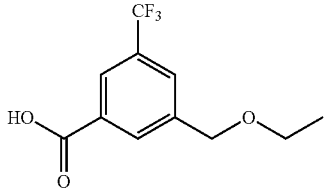 [SMILES: CCOCc1cc(C(=O)O)cc(C(F)(F)F)c1]

Buthyllithium (1.6 M in hexanes, 2.65 mL, 4.24 mmol) was added to a solution of intermediate 100 (1 g, 3.53 mmol) in dry THF (8 mL) at −78° C. The mixture was stirred at the same temperature for 1 hour, then an excess of $CO_2$ was added and the mixture was allowed to warm to rt. The mixture was stirred at r.t. overnight, then washed with 1N HCl and extracted with EtOAc. The organic layer was separated, dried ($MgSO_4$), filtered and the solvents were evaporated in vacuo. The crude product was purified by flash column chromatography (silica; EtOAc/heptane 0/100 to 30/70), to yield intermediate 101 (0.285 g, 73%).

c) Preparation of Intermediate 102

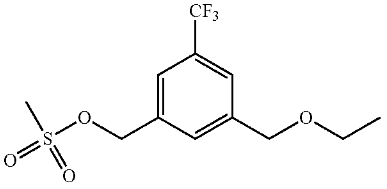 [SMILES: CCOCc1cc(COS(C)(=O)=O)cc(C(F)(F)F)c1]

By following a synthetic route similar to the one described for the synthesis of intermediate 20 and intermediate 77, intermediate 102 was obtained starting from intermediate 101.

Example A30

Preparation of Intermediate 103

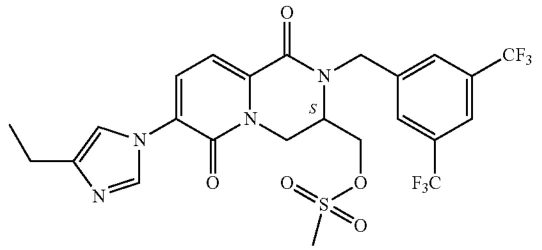

DIPEA (0.034 mL, 0.196 mmol) was added to an ice-cooled solution of compound 13 (approximately 0.098 mmol) in DCM (5 mL). Methanesulphonyl chloride (0.009 mL, 0.118 mmol) was added and stirring was continued for 2 h, while letting the reaction to come to r.t. The r.m. was then quenched with sat. aq. $NaHCO_3$. The organic layer was separated, dried over $MgSO_4$, filtered and evaporated in vacuo. The crude material was used as such in the next reaction step (quantitative yield; S-enantiomer).

Example A31

Preparation of Intermediates 104 and 105 intermediate 104

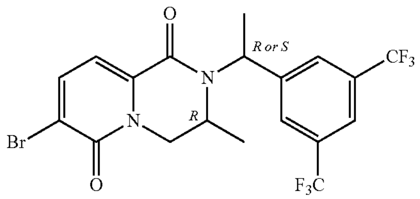

intermediate 105

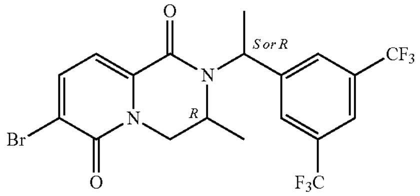

By following a synthetic route similar to the one described for the synthesis of intermediate 15, starting from intermediate 14 and intermediate 85, a crude mixture was obtained. The crude material was subsequently purified by flash column chromatography (silica; EtOAc/heptane 0/100 to 20/80), to yield intermediate 104 and intermediate 105.

Example A32

Preparation of Intermediate 106

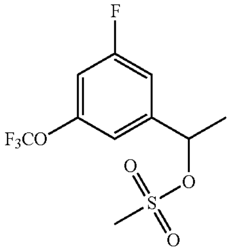 [SMILES: CC(OS(C)(=O)=O)c1cc(F)cc(OC(F)(F)F)c1]

By following a synthetic route similar to the one described for the synthesis of intermediate 64 and intermediate 77, intermediate 106 was obtained starting from the commercially available aldehyde.

Example A33 a) Preparation of Intermediate 155

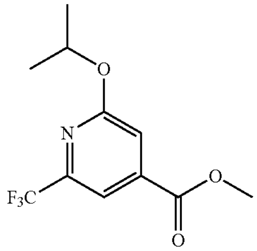 [SMILES: COC(=O)c1cc(OC(C)C)nc(C(F)(F)F)c1]

DIAD (0.86 mL, 4.34 mmol) was added dropwise to a solution of methyl 2-hydroxy-6-(trifluoromethyl)isonicotinate (640 mg, 2.894 mmol), iPrOH (191 mg, 3.183 mmol) and TPP (1.14 g, 4.341 mmol) in THF (15 mL) at 0° C. while $N_2$ was bubbled through the solution. The r.m. was stirred overnight at r.t., then the solvent was evaporated. The crude was purified by flash column chromatography (silica; heptanes/EtOAc 100/0 to 90/10). The desired fractions were collected and concentrated in vacuo to yield intermediate 155 as a yellow oil (759 mg, 99%).

b) Preparation of Intermediate 107

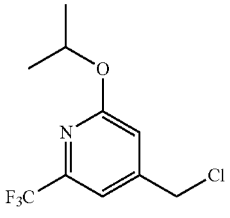 [SMILES: CC(C)Oc1cc(CCl)cc(C(F)(F)F)n1]

By following an analogous procedure as described for the synthesis of intermediate 90, intermediate 107 was obtained starting from intermediate 155.

Example A34 a) Preparation of Intermediate 108

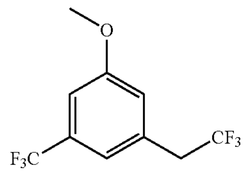

To a mixture of 3-methoxy-5-(trifluoromethyl)-phenylboronic acid (2 g, 9.09 mmol) and $Cs_2CO_3$ (11.85 g, 36.387 mmol) dissolved in dioxane (50 mL) were added $Pd_2(dba)_3$ (416 mg, 0.45 mmol) and Xantphos (894 mg, 1.546 mmol) while bubbling $N_2$ through the solution. Then, 2-iodo-1,1,1-trifluoroethane (1.792 mL, 18.19 mmol) was added. The r.m. was stirred at r.t. for 1 min, then water (3 mL) was added. The mixture was further stirred at 80° C. for 12 h. After cooling, the r.m. was extracted with EtOAc and water. The organic phase was washed with brine, dried over $MgSO_4$, filtered and the solvent was concentrated in vacuo. The crude product was purified by flash column chromatography (silica; hexane/EtOAc 100/0 to 95/5). The desired fractions were collected and concentrated in vacuo to yield intermediate 108 (1.53 g, 49%, 75% purity).

b) Preparation of Intermediate 109

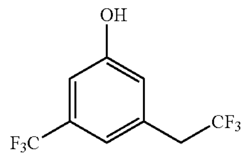

Boron tribromide (2.254 mL, 23.40 mmol) was added to a solution of intermediate 108 (1.51 g, 5.849 mmol) in DCM (10 mL) at 5° C. The mixture was stirred at r.t. for 4 h under $N_2$, then it was diluted with DCM and washed with sat. aq. $NaHCO_3$. The organic layer was separated, dried over $MgSO_4$, filtered and the solvents evaporated in vacuo. The crude product was purified by flash column chromatography (silica; heptanes/EtOAc 100/0 to 70/30). The desired fractions were collected and concentrated in vacuo to yield intermediate 109 (1.17 g, 82%, 95% purity).

c) Preparation of Intermediate 110

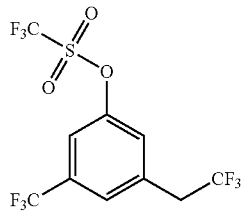 [SMILES: O=S(=O)(Oc1cc(CC(F)(F)F)cc(C(F)(F)F)c1)C(F)(F)F]

Triflic anhydride (0.958 mL, 5.77 mmol) was added to a stirred solution of intermediate 109 (1.17 g, 4.809 mmol), $Et_3N$ (0.869 mL, 6.25 mmol) and DMAP (58 mg, 0.48 mmol) in DCM (25 mL) at −15° C. The solution was stirred at −15° C. for 30 min and then warmed to r.t. over 2 h. The r.m. was then poured into a sat. sol. of $NH_4Cl$, the phases were separated and the aq. layer was extracted (×2) with DCM. The combined organic fractions were washed, dried over $MgSO_4$ and filtered. The crude material was purified by flash column chromatography (silica; hexane/EtOAc 100/0 to 90/10). The desired fractions were collected and concentrated in vacuo to yield intermediate 110 as a colourless oil (1.21 g, 66%, 95% purity).

d) Preparation of Intermediate 111

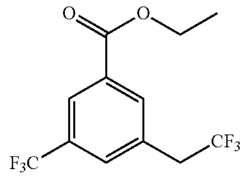

A mixture of intermediate 110 (580 mg, 1.542 mmol), $Pd(OAc)_2$ (7 mg, 0.03 mmol), dppf (34 mg, 0.06 mmol), $Et_3N$ (0.6 mL, 4.626 mmol), EtOH (10 mL) and dioxane (10 mL) was heated under CO atmosphere (6 atm) at 95° C. for 18 h. The r.m. was then diluted with aq. sat. $NaHCO_3$ and extracted with EtOAc. The organic layer was separated, dried over $MgSO_4$, filtered and the solvents evaporated in vacuo. The crude material was purified by flash column chromatography (silica; heptanes/EtOAc 100/0 to 80/20). The desired fractions were collected and concentrated in vacuo to yield intermediate 111 as a colourless oil (372 mg, 79%).

e) Preparation of Intermediate 112

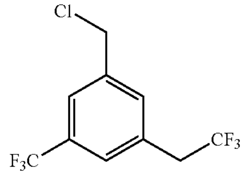 [SMILES: FC(F)(F)Cc1cc(CCl)cc(C(F)(F)F)c1]

By following a synthetic route similar to the one described for the synthesis of intermediate 89, intermediate 76 and intermediate 21, intermediate 112 was obtained starting from intermediate 111.

Example A35 a) Preparation of Intermediate 113

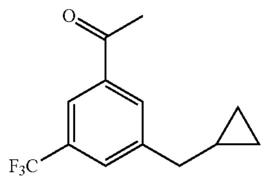

Methylmagnesium bromide (6.546 mL, 9.16 mmol) was added to a solution of 3-(cyclopropylmethyl)-5-(trifluoromethyl)benzonitrile (688 mg 3.06 mmol) in toluene (9 mL). The r.m. was stirred at 80° C. for 1 h, then treated with 10% aq. HCl and stirred at r.t. for 1 h. The phases were separated and the aq. layer was washed with EtOAc and brought to basic conditions with sat. aq. $NaHCO_3$. The resulting slurry was extracted with EtOAc and the organic phase was dried over $MgSO_4$, filtered and evaporated in vacuo. The crude product was purified by flash column chromatography (silica; hexane/EtOAc 100/0 to 85/15). The desired fractions were collected and concentrated in vacuo to yield intermediate 113 (533 mg, 72%) as a colourless oil.

b) Preparation of Intermediate 114

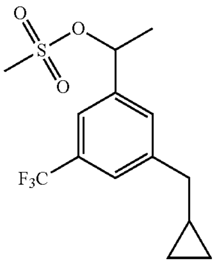 [SMILES: CC(OS(C)(=O)=O)c1cc(CC2CC2)cc(C(F)(F)F)c1]

By following a synthetic route similar to the one described for the synthesis of intermediate 64 and intermediate 77, intermediate 114 was obtained starting from intermediate 113.

Example A36

Preparation of Intermediate 115

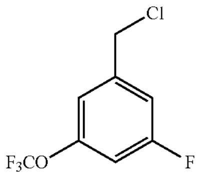

By following a synthetic route similar to the one described for the synthesis of intermediate 21, intermediate 115 was obtained starting from the commercially available alcohol.

Example A37 a) Preparation of Intermediate 116

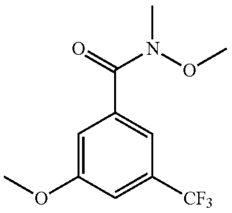

HBTU (3.411 g, 8.994 mmol) was added portionwise to a stirred solution of 3-methoxy-5-(trifluoromethyl)benzoic acid (1.32 g, 5.996 mmol), N-methoxymethylamine hydrochloride (0.702 g, 7.20 mmol) and DIPEA (3 mL, 18 mmol) in DMF (18 ml). The mixture was stirred at r.t. for 5 h, then poured into sat. aq. $NaHCO_3$ and extracted with EtOAc. The organic layer was washed with water, separated, dried over $MgSO_4$, filtered and the solvents evaporated in vacuo. The crude product was purified by flash column chromatography (silica; hexane/EtOAc 100/0 to 80/20). The desired fractions were collected and concentrated in vacuo to yield intermediate 116 as an oil (1.459 g, 92%, 92% purity).

b) Preparation of Intermediate 117

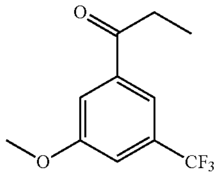 [SMILES: CCC(=O)c1cc(OC)cc(C(F)(F)F)c1]

Ethylmagnesium chloride (4.158 mL, 8.315 mmol) was added to a solution of intermediate 116 (1.459 g, 5.543 mmol) in THF (16.6 mL). The mixture was stirred at r.t. for 1 h, then diluted with water and extracted with EtOAc. The organic layer was separated, dried over $MgSO_4$, filtered and the solvents evaporated in vacuo. The crude product was purified by flash column chromatography (silica; hexane/EtOAc 100/0 to 70/30). The desired fractions were collected and concentrated in vacuo to yield intermediate 117 as a white solid (1.155 g, 89%, 94% purity).

c) Preparation of Intermediate 118

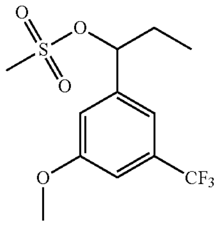 [SMILES: CCC(OS(C)(=O)=O)c1cc(OC)cc(C(F)(F)F)c1]

By following a synthetic route similar to the one described for the synthesis of intermediate 64 and intermediate 77, intermediate 118 was obtained starting from intermediate 117.

By using an analogous procedure to the one reported for the synthesis of intermediate 118, starting from the corresponding known or commercially available acids, following intermediates were obtained:

| Structure | Intermediate number |
|---|---|
| 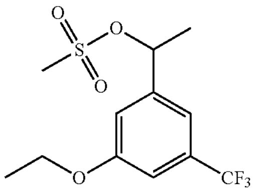 [SMILES: CCOc1cc(C(C)OS(C)(=O)=O)cc(C(F)(F)F)c1] | 119 |

-continued

| Structure | Intermediate number |
| --- | --- |
| 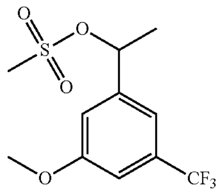 [SMILES: COc1cc(C(C)OS(C)(=O)=O)cc(C(F)(F)F)c1] | 121 |

Example A38 a) Preparation of Intermediate 123

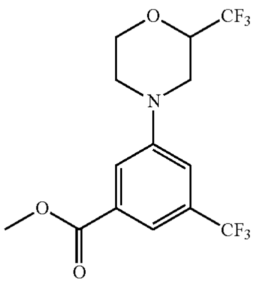 [SMILES: COC(=O)c1cc(N2CCOC(C(F)(F)F)C2)cc(C(F)(F)F)c1]

2-(Trifluoromethyl)morpholine hydrochloride (0.2 g, 1.044 mmol) was added to a stirred solution of methyl 3-bromo-5-(trifluoromethyl)benzoate (0.246 g, 0.87 mmol), X-phos (0.037 g, 0.078 mmol), $Pd_2(dba)_3$ (0.03 g, 0.035 mmol) and $Cs_2CO_3$ (0.85 g, 2.61 mmol) in toluene (10 mL) while bubbling $N_2$ through the solution. The mixture was stirred overnight at 100° C. in a sealed tube, then water and EtOAc were added. The aq. phase was extracted once more with EtOAc, then the combined organic phases were dried over $MgSO_4$, filtered and evaporated. The crude was purified by flash column chromatography (silica; heptanes/EtOAc 100/0 to 90/10). The desired fractions were collected and concentrated in vacuo to yield intermediate 123 as a sticky yellow oil (50 mg, 17%).

b) Preparation of Intermediate 124

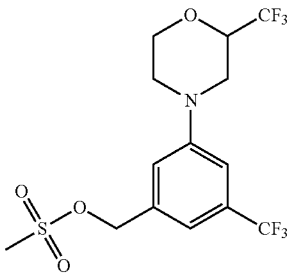 [SMILES: CS(=O)(=O)OCc1cc(N2CCOC(C(F)(F)F)C2)cc(C(F)(F)F)c1]

By following a synthetic route similar to the one described for the synthesis of intermediate 89, intermediate 76 and intermediate 77, intermediate 124 was obtained starting from intermediate 123.

Example A39 a) Preparation of Intermediate 126

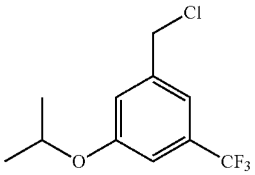 [SMILES: CC(C)Oc1cc(CCl)cc(C(F)(F)F)c1]

By following a synthetic route similar to the one described for the synthesis of intermediate 76 and intermediate 21, intermediate 126 was obtained starting from the commercially available acid.

b) Preparation of Intermediate 127

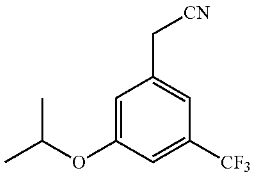

Sodium cyanide (0.417 g, 8.518 mmol) was added dropwise to a stirred solution of intermediate 126 (1.435 g, 5.679 mmol) in DMF (25 mL) at 0° C. under $N_2$ atmosphere. The r.m. was stirred for 16 h at r.t., then aq. $NaHCO_3$ sat. was added and the mixture was extracted with EtOAc. The combined extracts were dried over $MgSO_4$ and concentrated in vacuo. The crude product was purified by flash column chromatography (silica; hexane/EtOAc 100/0 to 60/40). The desired fractions were collected and concentrated in vacuo to yield intermediate 127 as a colourless oil (702 mg, 51%).

c) Preparation of Intermediate 128

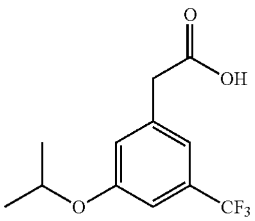 [SMILES: CC(C)Oc1cc(CC(=O)O)cc(C(F)(F)F)c1]

KOH (5 M, 17.3 mL, 86.5 mmol) was added to a stirred solution of intermediate 127 (702 mg, 2.886 mmol) in EtOH (8.6 mL). The mixture was stirred at 95° C. for 16 h, then allowed to cool to r.t., acidified with concentrated HCl under ice cooling and extracted with EtOAc. The combined extracts were dried over $MgSO_4$ and concentrated in vacuo. The crude material was used as such for the next reaction step, and the yield considered to be quantitative.

d) Preparation of Intermediate 129

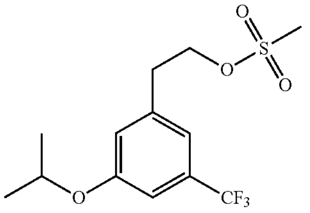 [SMILES: CC(C)Oc1cc(CCOS(C)(=O)=O)cc(C(F)(F)F)c1]

By following a synthetic route similar to the one described for the synthesis of intermediate 76 and intermediate 77, intermediate 129 was obtained starting from intermediate 128.

Example A40

Preparation of Intermediate 130

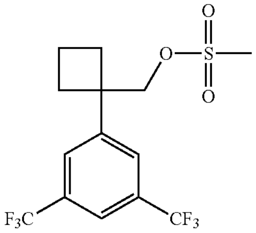 [SMILES: CS(=O)(=O)OCC1(c2cc(C(F)(F)F)cc(C(F)(F)F)c2)CCC1]

By following a synthetic route similar to the one described for the synthesis of intermediate 129, intermediate 130 was obtained starting from the commercially available nitrile.

Example A41 a) Preparation of Intermediate 131

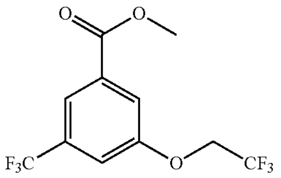 [SMILES: COC(=O)c1cc(OCC(F)(F)F)cc(C(F)(F)F)c1]

2,2,2-Trifluoroethyl perfluorobutylsulfonate (0.636 mL, 2.725 mmol) was added to a stirred solution of 3-hydroxy-5-trifluoromethyl benzoic acid methyl ester (500 mg, 2.271 mmol) and $Cs_2CO_3$ (1.48 g, 4.542 mmol) in DMF (11 mL). The mixture was stirred at r.t. for 3 h, then diluted with water and extracted with EtOAc. The organic layer was separated, dried over $MgSO_4$, filtered and the solvent evaporated in vacuo to yield an oil, which was used without further purification in the next step.

b) Preparation of Intermediate 132

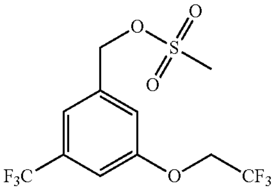 [SMILES: CS(=O)(=O)OCc1cc(OCC(F)(F)F)cc(C(F)(F)F)c1]

By following a synthetic route similar to the one described for the synthesis of intermediate 89, intermediate 76 and intermediate 77, intermediate 132 was obtained starting from intermediate 131.

Example A42 a) Preparation of Intermediate 134

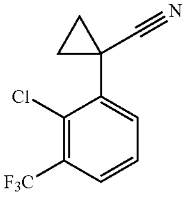 [SMILES: N#CC1(c2cccc(C(F)(F)F)c2Cl)CC1]

NaOH 50% (7.832 g, 97.0 mmol) was added dropwise to a mixture of 2-chloro-3-(trifluoromethyl)phenylacetonitrile (2 g, 9.108 mmol), 1-bromo-2-chloroethane (2.65 mL, 31.85 mmol) and benzyltriethylammonium chloride (622 mg, 2.73 mmol). The mixture was stirred at 50° C. overnight, then water was added and the mixture was extracted with EtOAc. The organic layer was washed with 5% aq. HCl, then dried over $MgSO_4$, filtered and the solvent was removed in vacuo. The product was purified by flash column chromatography (silica; hexane/EtOAc 100/0 to 80/20). The desired fractions were collected and concentrated in vacuo to yield intermediate 134 (1.52 g, 68%).

b) Preparation of Intermediate 135

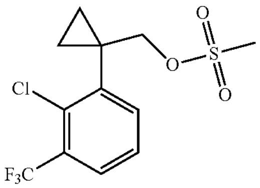 [SMILES: CS(=O)(=O)OCC1(c2cccc(C(F)(F)F)c2Cl)CC1]

By following a synthetic route similar to the one described for the synthesis of intermediate 128, intermediate 76 and intermediate 77, intermediate 135 was obtained starting from intermediate 134.

Example A43 a) Preparation of Intermediate 136

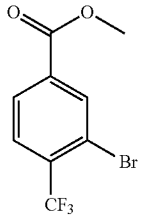

Methyl iodide (0.374 mL, 6.013 mmol) was added to a stirred solution of methyl 3-bromanyl-4-(trifluoromethyl) benzoate (1.348 g, 5.11 mmol) and $K_2CO_3$ (2.77 g, 20.043 mmol) in DMF (15 mL) at r.t., and the mixture was stirred for 5 h at the same temperature. Water and EtOAc were then added. The aq. phase was extracted once more. The combined organics were dried over $MgSO_4$, filtered and the solvent removed in vacuo. The crude was purified by flash column chromatography (silica; heptanes/EtOAc 100/0 to 95/5). The desired fractions were collected and concentrated in vacuo to yield intermediate 136 as a pale brown oil (quantitative).

b) Preparation of Intermediate 137

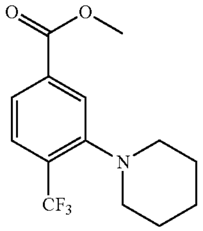 [SMILES: COC(=O)c1ccc(C(F)(F)F)c(N2CCCCC2)c1]

Piperidine (0.748 mL, 7.568 mmol) was added to a stirred solution of intermediate 136 (1.785 g, 6.306 mmol), X-Phos (0.271 g, 0.568 mmol), $Pd_2(dba)_3$ (0.231 g, 0.252 mmol) and $Cs_2CO_3$ (4.11 g, 12.613 mmol) in toluene (20 mL) while $N_2$ was bubbled through the mixture. The reaction was stirred overnight at 100° C. in a sealed tube. Water and EtOAc were then added. The aqueous phase was extracted once more, then the combined organics were dried over $MgSO_4$, filtered and evaporated. The crude was purified by flash column chromatography (silica; heptane/EtOAc 100/100 to 95/5). The desired fractions were collected and concentrated in vacuo to yield a pale yellow solid (3.623 g, 80%, 50% purity).

c) Preparation of Intermediate 138

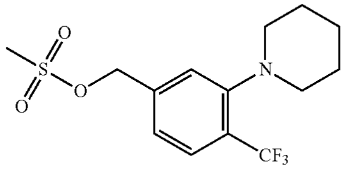 [SMILES: CS(=O)(=O)OCc1ccc(C(F)(F)F)c(N2CCCCC2)c1]

By following a synthetic route similar to the one described for the synthesis of intermediate 89, intermediate 76 and intermediate 77, intermediate 138 was obtained starting from intermediate 137.

Example A44 a) Preparation of Intermediate 139

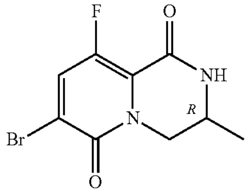

Selectfluor™ (896 mg, 2.528 mmol) was added to a solution of intermediate 14 (500 mg, 1.945 mmol) in acetonitrile (10 mL) and the mixture was stirred at 70° C. for 16 h. The solvent was then evaporated in vacuo and the crude product was purified by flash column chromatography ((silica; DCM/MeOH 100/0 to 90/10). The desired fractions were collected and concentrated in vacuo to yield intermediate 139 (295 mg, 55%).

Example A45

Following a procedure similar to the one reported for the synthesis of intermediate 21, following intermediates were obtained from the commercially available corresponding alcohols:

| Structure | Int. number |
| --- | --- |
| 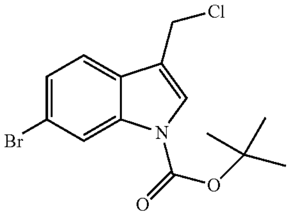 [SMILES: CC(C)(C)OC(=O)n1cc(CCl)c2ccc(Br)cc21] | 140 |

-continued

| Structure | Int. number |
|---|---|
| 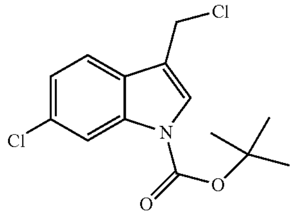 [SMILES: CC(C)(C)OC(=O)n1cc(CCl)c2ccc(Cl)cc21] | 142 |
| 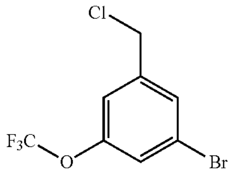 [SMILES: FC(F)(F)Oc1cc(Br)cc(CCl)c1] | 156 |

Example A46 a) Preparation of Intermediate 141

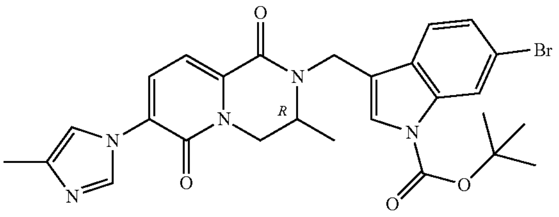

Starting from intermediate 140 and intermediate 40, intermediate 141 (R-enantiomer) was prepared by analogy to the procedure reported for the synthesis of intermediate 34. A fraction containing the corresponding BOC-deprotected compound was also recovered.

Example A47 a) Preparation of Intermediate 145

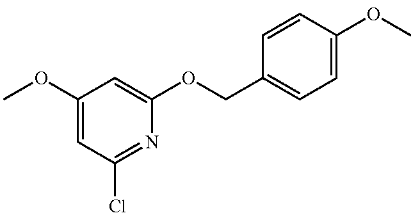

NaH (60% in mineral oil, 124 mg, 3.09 mmol) was added to a solution of 4-methoxybenzylalcohol (0.427 g, 3.09 mmol) in THF (10 mL) at 0° C. The mixture was allowed to warm to r.t. and stirred for 30 min. 2,6-Dichloro-4-methoxypyridine (0.5 g, 2.809 mmol) was added and the r.m. was heated at 100° C. in a sealed tube for 18 h, then allowed to cool down to r.t. The solvent was evaporated to dryness and the residue was dissolved in EtOAc and washed with water. The organic layer was separated, dried over $MgSO_4$, filtered and the solvents evaporated in vacuo. The crude product was purified by flash column chromatography (silica; DCM). The desired fractions were collected and concentrated in vacuo to yield intermediate 145 as a colourless oil (0.7 g, 89%).

b) Preparation of Intermediate 146

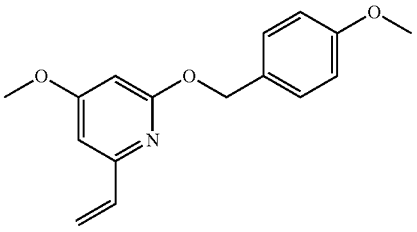

Vinylboronic acid pinacol ester (4.9 mL, 28.6 mmol) was added to a stirred suspension of intermediate 145 (4 g, 14.3 mmol), $Pd(OAc)_2$ (482 mg, 2.145 mmol), S-Phos (1.761 g, 4.29 mmol) and $K_3PO_4$ (9.106 g, 42.9 mmol) in a mixture of dioxane (40 mL) and EtOH (4 mL) under a $N_2$ atmosphere. The mixture was stirred at 100° C. for 18 h, then filtered through celite and the filtrate diluted with water and extracted with DCM. The organic layer was separated, washed with brine, dried over $MgSO_4$, filtered and the solvents evaporated in vacuo. The crude product was purified by flash column chromatography (silica; DCM). The desired fractions were collected and concentrated in vacuo to yield intermediate 146 as a colourless oil, which solidified upon standing (3.47 g, 89%).

c) Preparation of Intermediate 147

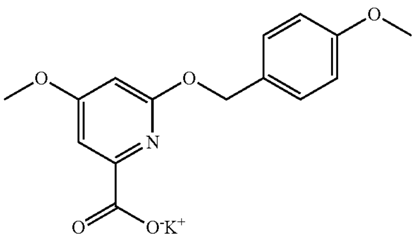

Potassium permanganate (5.659 g, 35.811 mmol) was added portionwise to a cooled solution (0° C.) of intermediate 146 (3.47 g, 12.79 mmol) in acetone (24 mL) and the mixture was stirred at 0° C. for 10 min before being allowed to warm up to r.t. Stirring was continued for 1 h, then more potassium permanganate (0.6 eq.) was added at 0° C. and the mixture stirred at r.t. for 18 h. The mixture was filtered and the solid washed with water. The filtrate was concentrated to dryness. The residue was triturated with $Et_2O$, the solid filtered and dried in vacuo to yield intermediate 147 as a white solid. The product was used in the following step without further purification (3.6 g).

d) Preparation of Intermediate 148

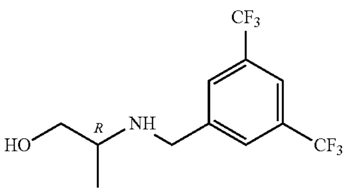

By following an analogous procedure as described for the synthesis of intermediate 1, intermediate 148 was obtained starting from the commercially available aldehyde (80%).

e) Preparation of Intermediate 149

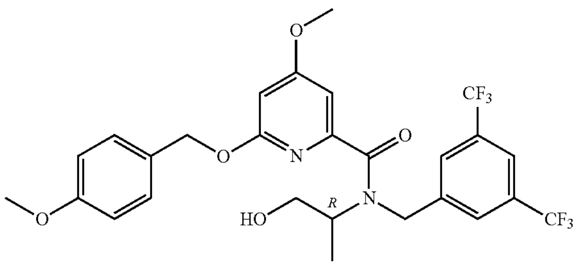

By following an analogous procedure as described for the synthesis of intermediate 3, intermediate 149 was obtained starting from intermediate 147 and intermediate 148 (74%).

f) Preparation of Intermediate 150

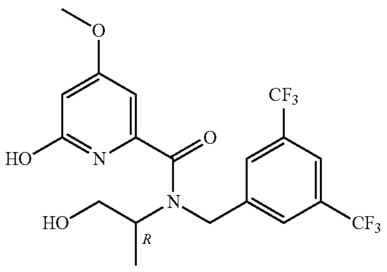

By following an analogous procedure as described for the synthesis of intermediate 5, intermediate 150 was obtained starting from intermediate 149 (94%).

g) Preparation of Intermediate 151

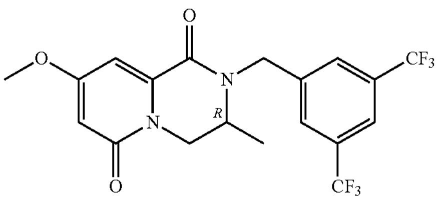

By following an analogous procedure as described for the synthesis of intermediate 6, intermediate 151 was obtained starting from intermediate 150 (82%).

h) Preparation of Intermediate 152

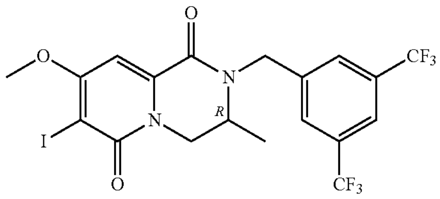

TFA (0.979 mL, 12.795 mmol) was added to a solution of intermediate 151 (975 mg, 2.245 mmol) and NIS (556 mg, 2.469 mmol) in acetonitrile (9.7 mL) and the r.m. was stirred at r.t. for 2 h. The reaction was quenched with a small amount of $Na_2SO_3$, diluted with DCM and $NaHCO_3$ sat. and extracted with DCM. The organic layer was separated, dried over $MgSO_4$, filtered and evaporated to dryness. The resulting residue was purified by flash column chromatograpy (silica; DCM/EtOAc 100/0 to 90/10). The desired fractions were collected and concentrated in vacuo to yield intermediate 152 as a white solid (1 g, 80%).

i) Preparation of Intermediate 158

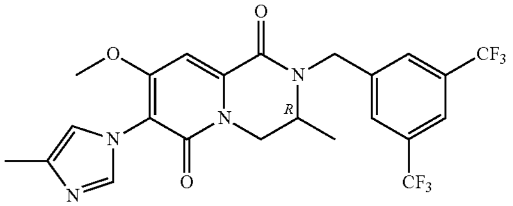

Starting from intermediate 152, intermediate 158 was prepared by analogy to the procedure B3.a1 reported for the synthesis of compound 3 (75%, R-enantiomer).

Example A48

Preparation of Intermediate 153

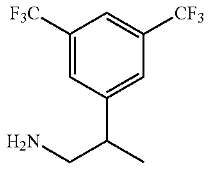 [SMILES: CC(CN)c1cc(C(F)(F)F)cc(C(F)(F)F)c1]

By following an analogous procedure as described for the synthesis of intermediate 69 and intermediate 70, intermediate 153 was obtained starting from the commercially available alcohol.

Example A49

Preparation of Intermediate 154

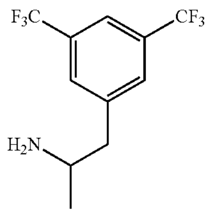 [SMILES: CC(N)Cc1cc(C(F)(F)F)cc(C(F)(F)F)c1]

By following an analogous procedure as described for the synthesis of intermediate 69 and intermediate 70, intermediate 154 was obtained starting from the commercially available alcohol.

Example A50 a) Preparation of Intermediate 157

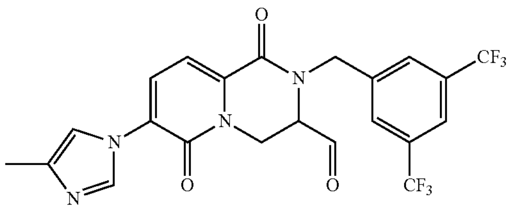 [SMILES: Cc1cn(-c2ccc3n(c2=O)CC(C=O)N(Cc2cc(C(F)(F)F)cc(C(F)(F)F)c2)C3=O)cn1]

A mixture of oxalyl chloride (0.145 mL, 1.719 mmol) in DCM (20 mL) was stirred at −78° C. DMSO (0.182 mL) was added dropwise and the mixture was stirred at −78° C. for 10 min. A solution of compound 45 (410 mg, 0.819 mmol) in DCM (10 mL) was added dropwise and the mixture was stirred for 1 h at −78° C. DIPEA (1.41 mL, 8.19 mmol) was added dropwise and the mixture was allowed to reach r.t. under stirring. The r.m. was washed with water, dried on $MgSO_4$, filtered and evaporated. The residue was purified via flash column chromatography (silica; DCM/MeOH 100/0 to 95/5). The pure fractions were evaporated, to afford an orange oil (370 mg, 91%).

Example A51 a) Preparation of Intermediate 159

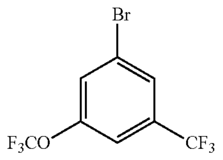

Chloro-difluoro-acetic acid methyl ester (1.38 mL, 13.082 mmol) was added to a stirred mixture of 1-bromo-3-iodo-5-trifluoromethoxybenzene (2 g, 5.451 mmol), potassium fluoride (380 mg, 6.541 mmol) and copper iodide (1.38 g, 6.541 mmol) in DMF (20 mL) in a sealed tube and under $N_2$ atmosphere. The mixture was stirred at 120° C. for 18 h, then it was diluted with water and extracted with $Et_2O$. The organic layer was separated, dried over $MgSO_4$, filtered and the solvents evaporated in vacuo. The crude product was purified by flash column chromatography (silica; pentane). The desired fractions were collected and concentrated in vacuo (200 mbar) to yield a colourless oil (1.41 g, 83%, volatile compound).

b) Preparation of Intermediate 160

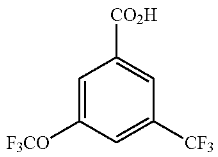

Intermediate 159 (1.41 g, 4.563 mmol) was dissolved in THF (15 mL). The solution was cooled to −78° C. under $N_2$ and butyl lithium (1.6M in hexanes, 3.1 mL, 5 mmol) was added dropwise over 15 min. Upon completion of the addition, the reaction mixture was stirred for 1 h at −78° C. Then, $CO_2$ (1.98 g, 45 mmol) was added at the same temperature. The resulting solution was allowed to warm to r.t. for 3 h. Water and HCl 1N were added, and the mixture was extracted with EtOAc. The organic phase was separated, dried over $MgSO_4$, filtered and concentrated in vacuo. The crude product was purified by flash column chromatography (silica; heptanes/EtOAc 100/0 to 50/50). The desired fractions were collected and concentrated in vacuo to yield a beige solid (1.25 g, 38%).

c) Preparation of Intermediate 161

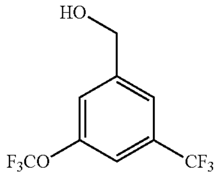

By following an analogous procedure as described for the synthesis of intermediate 20 intermediate 161 was obtained starting from intermediate 160 (65%).

Example A52 a) Preparation of Intermediate 162

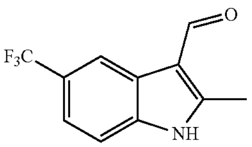 [SMILES: Cc1[nH]c2ccc(C(F)(F)F)cc2c1C=O]

Phosphorus oxychloride (144 μL, 1.55 mmol) was added dropwise at 5° C. to DMF (1.71 mL) and the mixture was further stirred for 5 min at 5° C. and then at r.t. for 45 min. The r.m. was then cooled again to 5° C. and 2-methyl-5-(trifluoromethyl)-1H-indole (220 mg, 1.11 mmol) was added portionwise. The reaction mixture was further stirred for 5 min at 5° C. and at r.t. for 45 min, then it was poured carefully onto ice and the solution was neutralized (pH=7) by the addition of a sat. $NaHCO_3$ sol. The product was extracted with EtOAc. The organic layer was washed with water, dried over $MgSO_4$ and the solvent was removed in vacuo to give a crude material, which was used in the subsequent step without further purification (320 mg).

b) Preparation of Intermediate 163

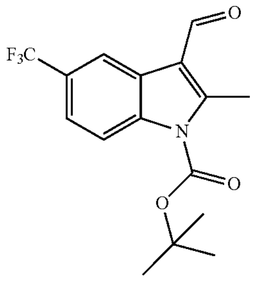 [SMILES: Cc1c(C=O)c2cc(C(F)(F)F)ccc2n1C(=O)OC(C)(C)C]

Intermediate 162 (250 mg, crude material) was dissolved in THF (20 mL). di-Tert-butyl dicarbonate (293 mg, 1.34 mmol) and DMAP (1 mg, 11 μmol) were added. The r.m. was stirred for 1 h at r.t., then $NaHCO_3$ sat. sol. was added. DCM was added and the organic layer was separated. The organic layer was dried with $MgSO_4$, filtered and the solvent was evaporated to give crude intermediate 163 as a brownish solid (225 mg). The crude was used as such in the next reaction.

c) Preparation of Intermediate 164

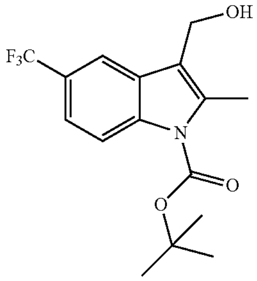 [SMILES: Cc1c(CO)c2cc(C(F)(F)F)ccc2n1C(=O)OC(C)(C)C]

Intermediate 163 (225 mg) was dissolved in MeOH (4.3 mL) and the r.m. was cooled to 0° C. by using an ice bath. $NaBH_4$ (52 mg, 1.37 mmol) was then added. The reaction mixture was stirred for 1 h at r.t., then it was added to a mixture of DCM and $NaHCO_3$ sat. sol. The organic layer was separated, washed with brine, dried over $MgSO_4$, filtered and the solvent was evaporated in vacuo to give a brownish crystalline crude (216 mg), which was used without further purification for the subsequent reaction.

d) Preparation of Intermediate 165

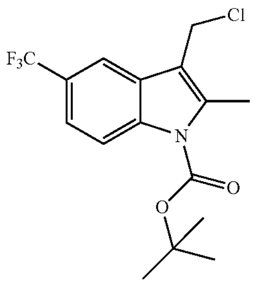 [SMILES: Cc1c(CCl)c2cc(C(F)(F)F)ccc2n1C(=O)OC(C)(C)C]

By following a synthetic procedure similar to the one reported for the synthesis of intermediate 21, intermediate 165 was obtained starting from intermediate 164.

e) Preparation of Intermediate 166

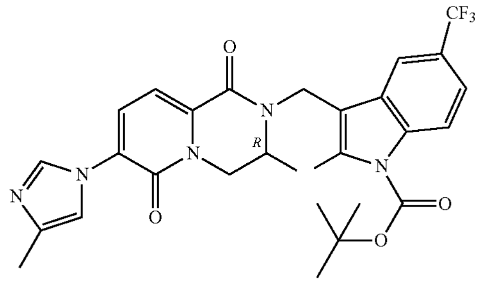

Using experimental conditions analogous to those reported for the synthesis of intermediate 47, intermediate 166 was obtained starting from intermediate 165 and intermediate 40.

Example A53

The following intermediates were synthesized by following an analogous synthetic sequence as reported in Example A52. For the preparation of some intermediates of the table below, only part of the synthetic sequence in A52 had to be followed, for example when one of the intermediates in the sequence was commercially available or in case a more efficient preparation for an intermediate in the sequence was well-known from literature.

| Structure | Intermediate number | Starting material |
|---|---|---|
| 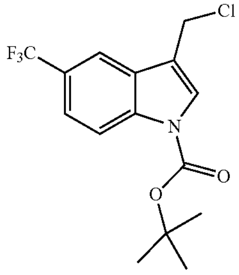 [SMILES: CC(C)(C)OC(=O)n1cc(CCl)c2cc(C(F)(F)F)ccc21] | 167 | 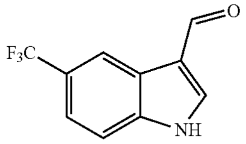 |

-continued
| Structure | Intermediate number | Starting material |
|---|---|---|
| 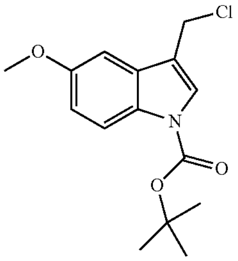 [SMILES: COc1ccc2c(c1)c(CCl)cn2C(=O)OC(C)(C)C] | 168 | 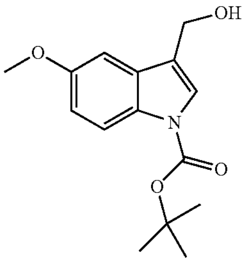 [SMILES: COc1ccc2c(c1)c(CO)cn2C(=O)OC(C)(C)C] |
| 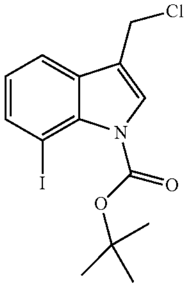 [SMILES: CC(C)(C)OC(=O)n1cc(CCl)c2cccc(I)c21] | 169 | 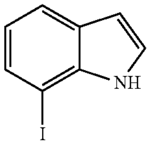 |
| 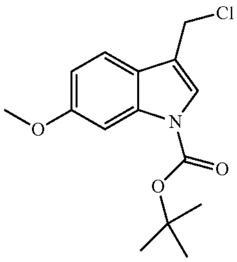 [SMILES: COc1ccc2c(CCl)cn(C(=O)OC(C)(C)C)c2c1] | 181 | 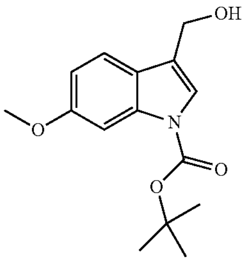 [SMILES: COc1ccc2c(CO)cn(C(=O)OC(C)(C)C)c2c1] |
| 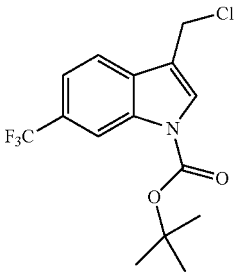 [SMILES: CC(C)(C)OC(=O)n1cc(CCl)c2ccc(C(F)(F)F)cc21] | 183 | 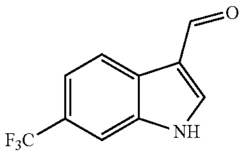 |
| 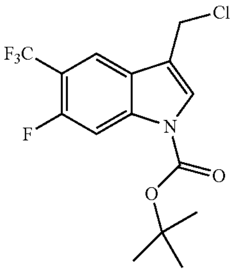 [SMILES: CC(C)(C)OC(=O)n1cc(CCl)c2cc(C(F)(F)F)c(F)cc21] | 212 | 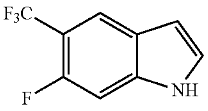 [SMILES: Fc1cc2[nH]ccc2cc1C(F)(F)F] |
-continued
| Structure | Intermediate number | Starting material |
|---|---|---|
| 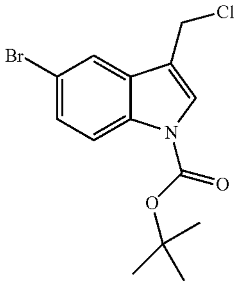 [SMILES: CC(C)(C)OC(=O)n1cc(CCl)c2cc(Br)ccc21] | 229 | 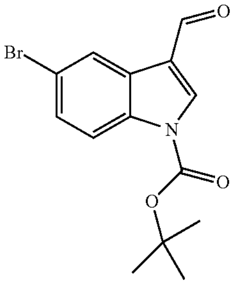 [SMILES: CC(C)(C)OC(=O)n1cc(C=O)c2cc(Br)ccc21] |
| 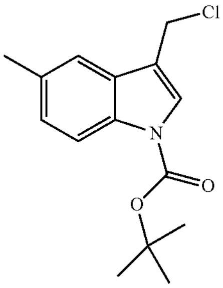 [SMILES: Cc1ccc2c(c1)c(CCl)cn2C(=O)OC(C)(C)C] | 232 | 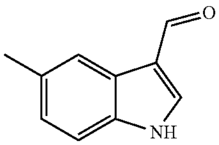 |
| 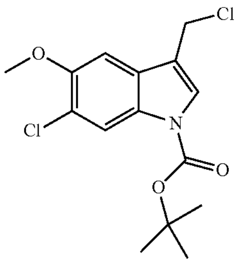 [SMILES: COc1cc2c(CCl)cn(C(=O)OC(C)(C)C)c2cc1Cl] | 234 | 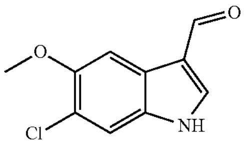 |
| 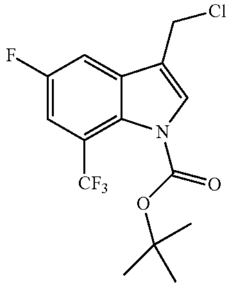 [SMILES: CC(C)(C)OC(=O)n1cc(CCl)c2cc(F)cc(C(F)(F)F)c21] | 239 | 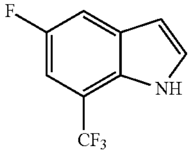 |

Example A54 a) Preparation of Intermediate 175

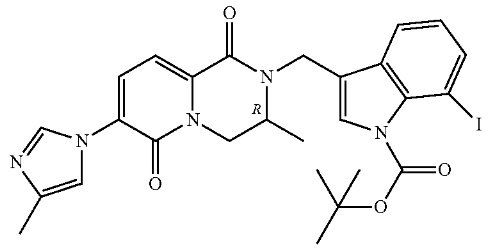

Using experimental conditions analogous to those reported for the synthesis of intermediate 47, intermediate 175 was obtained starting from intermediate 169 and intermediate 40.

Example A55 a) Preparation of Intermediate 170

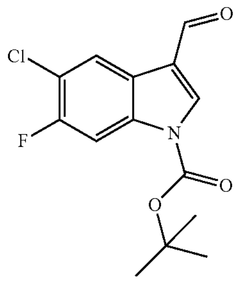 [SMILES: CC(C)(C)OC(=O)n1cc(C=O)c2cc(Cl)c(F)cc21]

By following a synthetic procedure similar to the one reported for the synthesis of intermediate 163, intermediate 170 was prepared starting from commercially available 5-chloro-6-fluoro-1H-indole-3-carbaldehyde.

b) Preparation of Intermediate 171

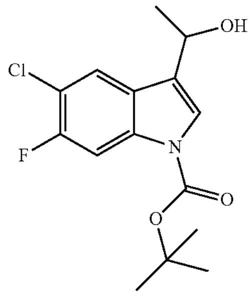 [SMILES: CC(O)c1cn(C(=O)OC(C)(C)C)c2cc(F)c(Cl)cc12]

To a stirred solution of intermediate 170 (6.34 g, 21.30 mmol) in THF (60 mL) at 0-5° C. was added methylmagnesium chloride (3 M in THF, 7.81 mL, 23.42 mmol). The reaction was stirred at 0-5° C. for 30 min and then warmed to r.t. The r.m. was then quenched with water. THF was evaporated and the product was extracted with DCM. The organic layer was dried over $MgSO_4$, filtered and evaporated. The crude was purified by flash column chromatography (silica; DCM/MeOH 100/0 to 98/2). The pure fractions were evaporated and the product was crystallized from DIPE. The crystals were filtered off and dried, yielding intermediate 171 (6.68 g, quantitative yield).

c) Preparation of Intermediate 172

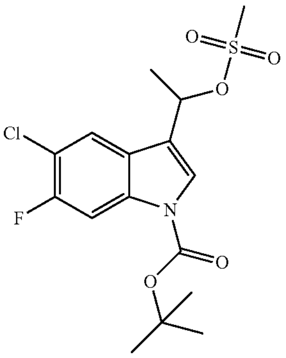 [SMILES: CC(OS(C)(=O)=O)c1cn(C(=O)OC(C)(C)C)c2cc(F)c(Cl)cc12]

Intermediate 171 (2 g, 6.38 mmol) was stirred in DCM (122 mL). MsCl (1.46 g, 12.75 mmol) was added, followed by $Et_3N$ (1.29 g, 12.75 mmol). The r.m. was stirred for 2 h at r.t. Sat. $NaHCO_3$ sol. was added and the organic layer was separated, dried over $MgSO_4$, filtered, evaporated and co-evaporated with toluene to give a crude material containing intermediate 172, which was used without further purification for the subsequent reaction (2.5 g).

d) Preparation of Intermediate 173

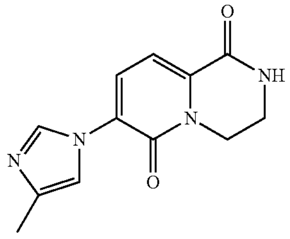 [SMILES: Cc1cn(-c2ccc3n(c2=O)CCNC3=O)cn1]

Intermediate 173 was obtained by following a synthetic procedure similar to the one reported for the synthesis of intermediate 40.

d) Preparation of Intermediate 174

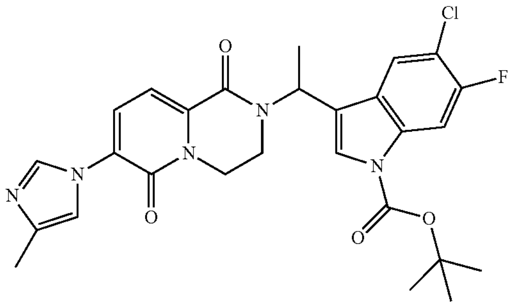 [SMILES: Cc1cn(-c2ccc3n(c2=O)CCN(C(C)c2cn(C(=O)OC(C)(C)C)c4cc(F)c(Cl)cc24)C3=O)cn1]

Using experimental conditions analogous to those reported for the synthesis of intermediate 47, intermediate 174 was obtained starting from intermediate 172 and intermediate 173.

e) Preparation of Intermediate 176

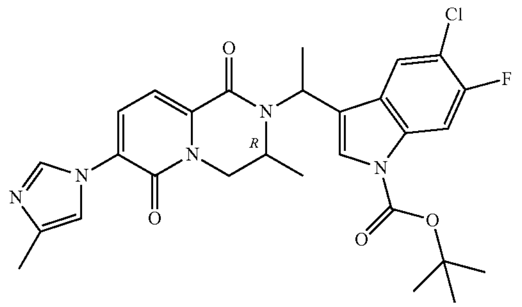

Using experimental conditions analogous to those reported for the synthesis of intermediate 47, intermediate 174 was obtained starting from intermediate 172 and intermediate 40.

Example A56 a) Preparation of Intermediate 177

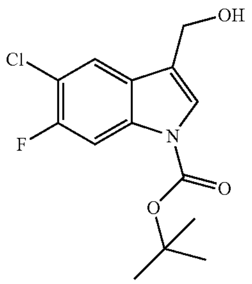 [SMILES: CC(C)(C)OC(=O)n1cc(CO)c2cc(Cl)c(F)cc21]

By following a synthetic procedure similar to the one reported for the synthesis of intermediate 164, starting from intermediate 170 intermediate 177 was obtained.

b) Preparation of Intermediate 178

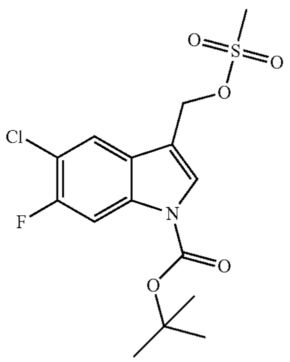 [SMILES: CC(C)(C)OC(=O)n1cc(COS(C)(=O)=O)c2cc(Cl)c(F)cc21]

By following a synthetic procedure similar to the one reported for the synthesis of intermediate 172, starting from intermediate 177 intermediate 178 was obtained.

c) Preparation of Intermediate 179

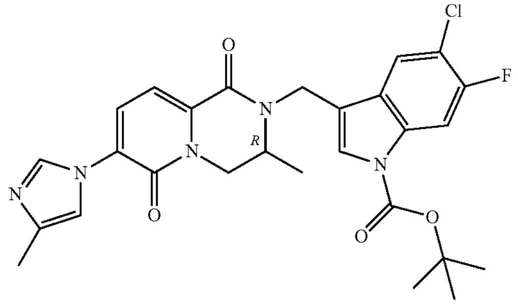

Using experimental conditions analogous to those reported for the synthesis of intermediate 47, intermediate 179 was obtained starting from intermediate 178 and intermediate 40.

Example A57 a) Preparation of Intermediate 180

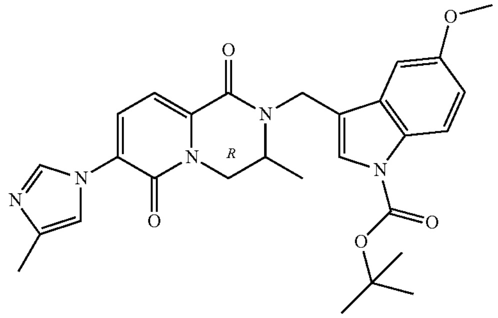

Using experimental conditions analogous to those reported for the synthesis of intermediate 47, intermediate 180 was obtained starting from intermediate 168 and intermediate 40.

Example A58 a) Preparation of Intermediate 182

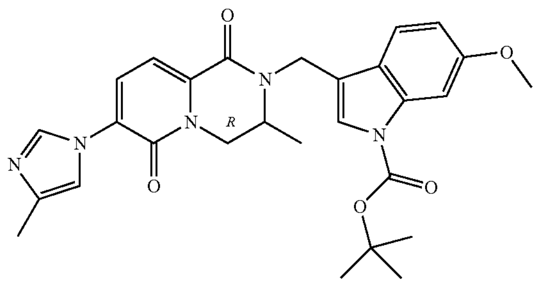

Using experimental conditions analogous to those reported for the synthesis of intermediate 47, intermediate 180 was obtained starting from intermediate 181 and intermediate 40.

Example A59 a) Preparation of Intermediate 184

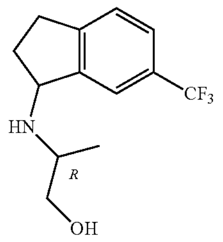

6-(Trifluoromethyl)indan-1-ol (420 mg, 2.08 mmol) was dissolved in thionyl chloride (4.2 mL), stirred at r.t. for 5 h and then evaporated unti dryness and re-dissolved in N,N-dimethylacetamide (8 mL). D-Alaninol (0.32 mL, 4.16 mmol) and DIPEA (1.03 mL) were added, and the r.m. stirred overnight at 70° C. The r.m. was then quenched with sat. aq. $NaHCO_3$ and washed with EtOAc. The organic layer was washed with brine, dried over $Na_2SO_4$ and evaporated until dryness to give a crude which was purified by flash column chromatography (silica; heptanes/EtOAc 100/0 to 0/100) to afford intermediate 184 (185 mg, 34%).

b) Preparation of Intermediate 185

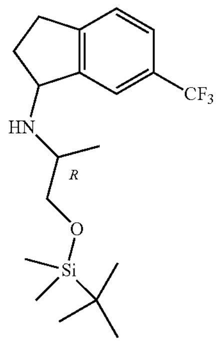

To a stirred solution of intermediate 184 (185 mg, 0.71 mmol) in DCM (9.4 mL) was added imidazole (97 mg, 1.43 mmol) and then TBSCl (161 mg, 1.07 mmol). The r.m. was stirred overnight at r.t. Water and DCM were then added and the phases separated. The water layer was again extracted with DCM. The combined organic layers were dried over $Na_2SO_4$, filtered and evaporated until dryness to give a crude which was purified by flash column chromatography (silica; heptanes/EtOAc 100/0 to 70/30) to give intermediate 185 (274 mg).

c) Preparation of Intermediate 186

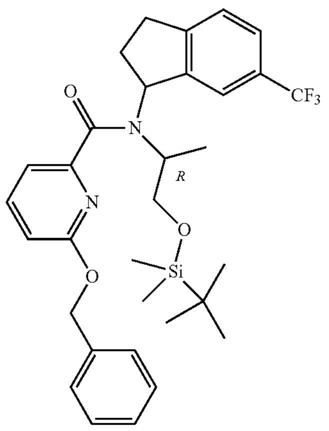

Intermediate 54 (374 mg, crude material) was dissolved in acetonitrile (5 mL) and added in portions of 1 mL to a solution of intermediate 185 (141 mg, 0.38 mmol), DIPEA (0.65 mL, 3.78 mmol) and DMAP (231 mg, 1.89 mmol) in acetonitrile (3.5 mL) at 70° C. The r.m. was stirred at reflux for 90 min, then overnight at 70° C. The reaction was then allowed to cool to r.t. and treated with aq. $NaHCO_3$. The mixture was extracted with EtOAc, the organic layer washed with water and brine, dried over $Na_2SO_4$, filtered and evaporated until dryness to give a crude, which was purified by flash column chromatography (silica; heptanes/EtOAc 100/0 to 50/50). After evaporation of the solvent, intermediate 186 was obtained (109 mg).

d) Preparation of Intermediate 187

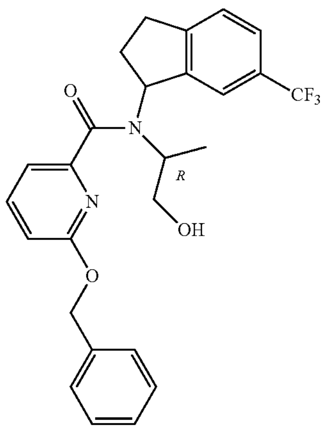

By following a synthetic procedure similar to the one reported for the synthesis of intermediate 4, intermediate 187 was obtained starting from intermediate 186.

e) Preparation of Intermediate 188

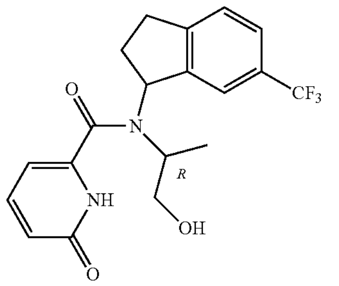

10% Pd/C (27) mg was added to a solution of intermediate 187 (115 mg, 0.24 mmol) in MeOH (8.45 mL) at r.t. and the r.m. was hydrogenated (atmospheric pressure) for 2 h at r.t. The catalyst was filtered through Dicalite® and the filtrate was evaporated until dryness to give crude intermediate 188, which was used without further purification for the subsequent reaction (90 mg).

f) Preparation of Intermediates 189 and 190

189

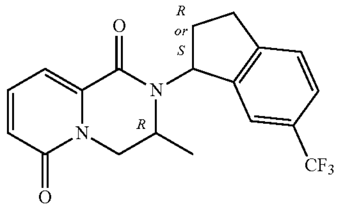

190

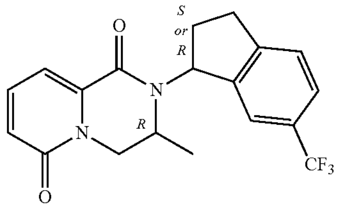

Intermediate 188 (90 mg, 0.24 mmol) and TPP (87 mg, 0.33 mmol) were stirred in THF (3 mL) at r.t. and DIAD (64 µL, 0.33 mmol) was then added dropwise via syringe. The r.m. was stirred overnight at r.t., then it was evaporated until dryness to give a crude, which was dissolved in a small amount of DCM and purified by flash column chromatography (silica; heptanes/EtOAc 95/5 to 0/100) to afford intermediate 189 (45 mg; the fraction contains also triphenylphosphine oxide) and intermediate 190 (19 mg).

Intermediates 189 and 190 were used as such in the next reaction steps, without further purificiation.

g) Preparation of Intermediate 191

191

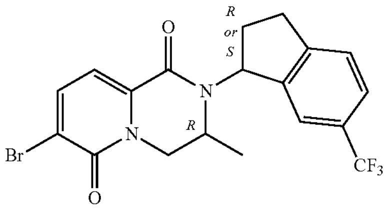

Bromine (4 µL, 0.08 mmol) was added to a stirred solution of intermediate 189 (25 mg, not pure material) in DCM (0.6 mL) and AcOH (0.14 mL). The r.m. was stirred overnight at r.t. and it was then diluted with DCM and washed with a sat. $NaHCO_3$ sol. The organic layer was washed with brine, dried over $Na_2SO_4$ and evaporated until dryness to give a crude, which was purified by flash column chromatography (silica; heptanes/EtOAc100/0 to 0/100). After collection of the fractions and evaporation of the solvent, intermediate 191 was obtained (16 mg, 79% LC-MS purity, 42%).

192

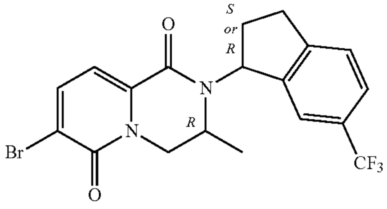

By following a synthetic procedure similar to the one reported for the synthesis of intermediate 191, intermediate 192 was obtained starting from intermediate 190.

Example A60 a) Preparation of Intermediate 199

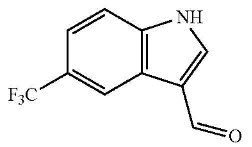 [SMILES: O=Cc1c[nH]c2ccc(C(F)(F)F)cc12]

Phosphorus oxychloride (703 µL, 7.56 mmol) was added dropwise at 5° C. to DMF (8.36 mL) and the mixture was then stirred for 5 min at 5° C. and then at r.t. for 45 min. After this time the r.m. was cooled again to 5° C. and 5-trifluoromethylindole (1 g, 5.40 mmol) was added portionwise. The r.m. was further stirred for 5 min at 5° C., at r.t. for 45 min and at 60° C. for 1 h, then it was poured carefully onto ice and the solution was neutralized (pH=7) by the addition of a sat. $NaHCO_3$ sol. A part of the product precipitated and it was filtered off to give a first batch of intermediate 199. The aqueous filtrate was extracted with EtOAc. The organic layer was dried over $MgSO_4$ and the solvent was removed in vacuo to provide an oily residue, from which the product precipitated when triturated with water. Filtration of the precipitate provided a second batch of intermediate 199. The two batches were dried in the vacuum oven and used as such in the subsequent reaction step (1 g, 87%).

b) Preparation of Intermediate 200

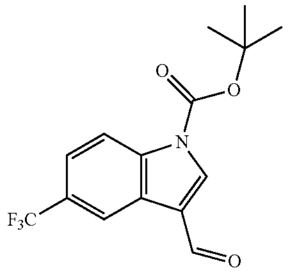 [SMILES: CC(C)(C)OC(=O)n1cc(C=O)c2cc(C(F)(F)F)ccc21]

Intermediate 199 (1 g, 4.69 mmol) was dissolved in THF (5 mL). di-Tert-butyl dicarbonate (1.251 g, 5.73 mmol) was added, followed by DMAP (5.73 mg, 0.05 mmol). The r.m. was stirred for 1 h at r.t. until LC-MS analysis showed full conversion. Sat. $NaHCO_3$ sol. was then added. Most of the product precipitated and it was filtered off and dried in the vacuum oven. DCM was added to the filtrate and the organic layer was separated, dried over $MgSO_4$, filtered and the solvent was evaporated. The residue was combined with the dried precipitate and coevaporated with toluene (×2) to afford a crude material, which was used without further purification for the subsequent reaction step (1.41 g, 96%).

c) Preparation of Intermediate 201

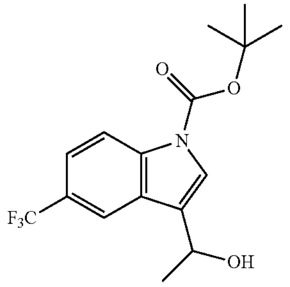 [SMILES: CC(O)c1cn(C(=O)OC(C)(C)C)c2ccc(C(F)(F)F)cc12]

Methylmagnesium bromide (3M in THF, 8.62 mL, 25.86 mmol) was added to intermediate 200 (1.62 g, 5.17 mmol) in THF (17.3 mL) at 0° C. After 30 min, 4 more eq. of methylmagnesium bromide were added at −78° C. After 30 min the r.m. was quenched at 0° C. with $NH_4Cl$, brought to r.t. and poured in EtOAc/water. The organic layer was separated, the aq. phase extracted with EtOAc, the combined organic layers dried, filtered and evaporated, to give a crude material, which was used without further purification in the subsequent reaction step (1.85 g).

d) Preparation of Intermediate 202

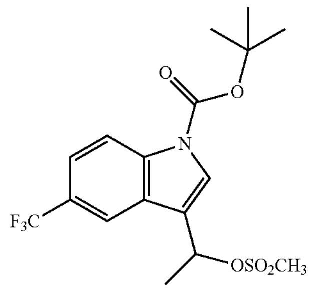

Intermediate 201 (1.12 g, 3.40 mmol) was stirred in DCM (9.5 mL) and cooled to 0° C. $Et_3N$ (0.71 mL, 5.10 mmol) was then added, followed by methanesulphonyl chloride (0.40 mL, 5.10 mmol). After 20 min LC-MS analysis showed completion of the reaction. Sat. $NaHCO_3$ sol. was added and the organic layer was separated, dried over $MgSO_4$, filtered, evaporated and co-evaporated with toluene to give a crude material, which was used without further purification in the subsequent reaction step (1.2 g).

e) Preparation of Intermediate 203

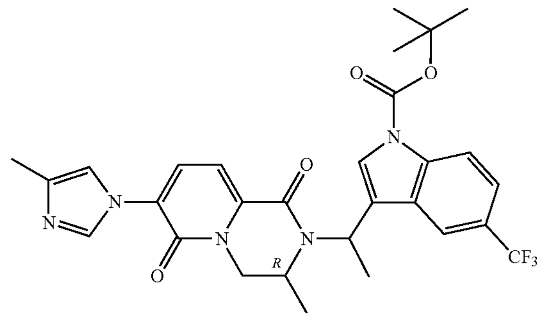

Intermediate 40 (0.659 g, 2.55 mmol) was stirred in DMF (200 mL) under $N_2$ atmosphere. NaH (60% in mineral oil, 122 mg, 3.06 mmol) was added and the mixture was stirred for 10 min. Intermediate 202 (1.2 g, crude material) was dissolved in a small amount of DMF and was added at 0° C. dropwise to the r.m. The reaction was stirred at r.t. overnight. Water was then added, the aq.layer extracted with EtOAc (×2), the organic layers collected, washed with brine, dried over $MgSO_4$, filtered and the solvent evaporated, to give a crude which was used without further purification in the subsequent reaction step.

Example A61 a) Preparation of Intermediate 204

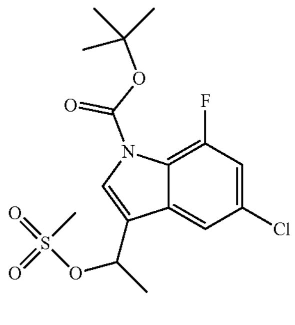 [SMILES: CC(OS(C)(=O)=O)c1cn(C(=O)OC(C)(C)C)c2c(F)cc(Cl)cc12]

By following a synthetic procedure similar to the one reported for the synthesis of intermediate 202, intermediate 204 was obtained starting from commercially available 5-chloro-7-fluoroindole.

Example A62

Using experimental conditions analogous to those reported for the synthesis of intermediate 47, starting from intermediate 14 and the corresponding mesylate, the following intermediates were obtained:

| Intermediate number | Structure | Mesylate |
|---|---|---|
| 205 | 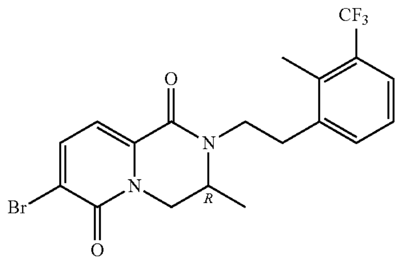 | Intermediate 194 |
| 206 | 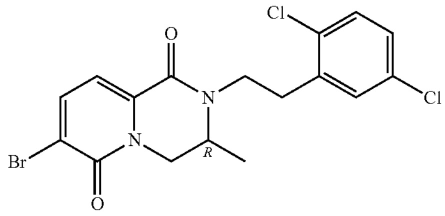 | Intermediate 195 |
| 207 | 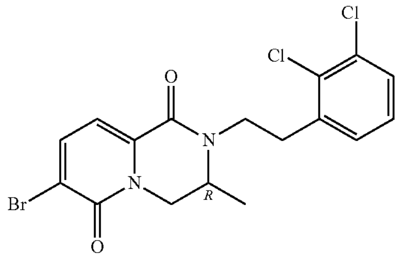 | Intermediate 196 |
| 208 | 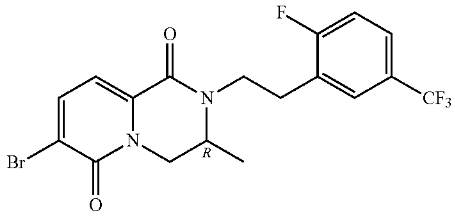 | Intermediate 197 |

-continued

| Intermediate number | Structure | Mesylate |
| --- | --- | --- |
| 209 | 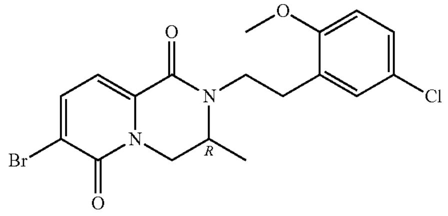 | Intermediate 198 |

Example A63 a) Preparation of Intermediate 210

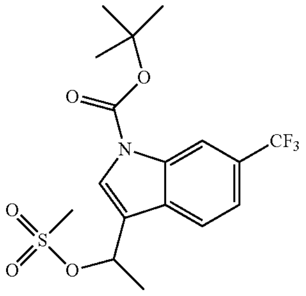 [SMILES: CC(OS(C)(=O)=O)c1cn(C(=O)OC(C)(C)C)c2cc(C(F)(F)F)ccc12]

By following a synthetic procedure similar to the one reported for the synthesis of intermediate 172, intermediate 210 was obtained starting from commercially available 6-trifluoromethyl-1H-indole-3-carboxaldehyde.

b) Preparation of Intermediate 211

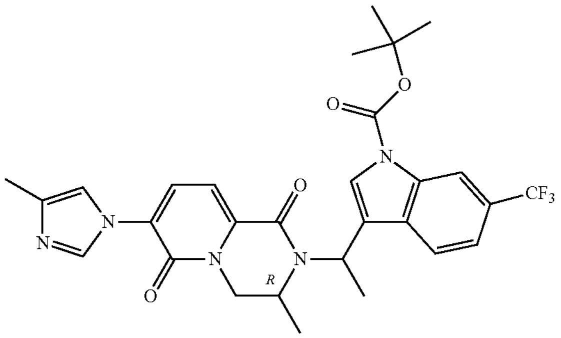

By following a synthetic procedure similar to the one reported for the synthesis of intermediate 203, intermediate 211 was obtained starting from intermediate 210.

Example A64 a) Preparation of Intermediate 213

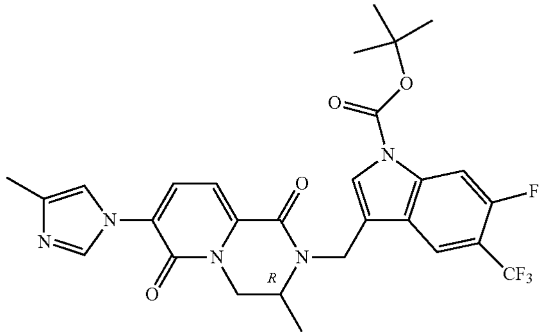

By following a synthetic procedure similar to the one reported for the synthesis of intermediate 203, intermediate 213 was obtained starting from intermediate 40 and intermediate 212. Intermediate 213 was obtained together with impurities and was used as such in the next reaction step (see B37).

Example A65 a) Preparation of Intermediate 218

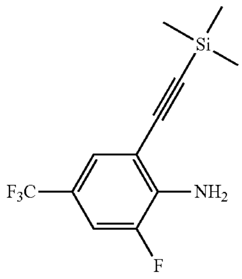 [SMILES: C[Si](C)(C)C#Cc1cc(C(F)(F)F)cc(F)c1N]

2-Fluoro-6-iodo-4-(trifluoromethyl)-benzenamine (4.1 g, 13.44 mmol) was stirred in THF (29 mL) under $N_2$. Bis (triphenylphosphine)palladium(II) dichloride (511 mg, 0.73 mmol), CuI (277 mg, 1.46 mmol), $Et_3N$ (29 mL, 210.01 mmol) and trimethylsilylacetylene (1.584 g, 16.13 mmol) were added and the mixture was stirred at r.t. for 30 min. EtOAc was added and the mixture was filtered over Dicalite®. The filtrate was evaporated and the residue was purified by flash column chromatography (silica; heptane/EtOAC 100/0 to 99/1) to afford intermediate 218 (2.77 g, 75%).

b) Preparation of Intermediate 219

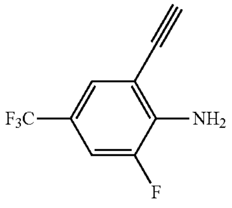

Intermediate 218 (2.75 g, 10.03 mmol), $K_2CO_3$ (1.37 g, 10.03 mmol) and MeOH (60 mL) were stirred for 30 min. The solid $K_2CO_3$ was filtered off over Dicalite® and the filtrate was evaporated to yield intermediate 219 (2.04 g, quantitative).

c) Preparation of Intermediate 220

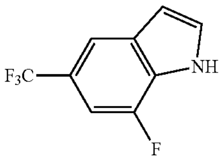 [SMILES: Fc1cc(C(F)(F)F)cc2cc[nH]c12]

Intermediate 219 (2.04 g, 10.02 mmol), potassium tert-butoxide (2.25 g, 20.04 mmol) and 1-methyl-2-pyrrolidinone (30 mL) were stirred at r.t. for 24 h under $N_2$. Water and HCl (1N) were added until acidic pH, and then the product was extracted with DIPE. The organic layer was dried over $MgSO_4$, filtered and evaporated. The residue was purified by flash column chromatography (silica; heptane/EtOAc 100/0 to 99/1) to afford intermediate 220 (1.15 g, 56%).

d) Preparation of Intermediate 221

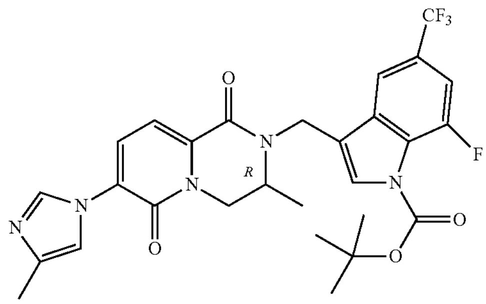

By following a synthetic procedure similar to the one described in example A52, intermediate 221 was obtained starting from intermediate 220 and intermediate 40.

Example A66 a) Preparation of Intermediate 222

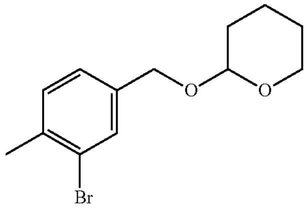 [SMILES: Cc1ccc(COC2CCCCO2)cc1Br]

Dihydropyran (0.655 mL, 7.162 mmol) and p-toluenesulphonic acid (56.7 mg, 0.298 mmol) were added to a solution of 3-bromo-4-methylbenzyl alcohol (1.2 g, 5.968 mmol) in DCM (30 mL) at r.t. The mixture was stirred overnight at r.t., then diluted with DCM, washed with sat. $NaHCO_3$ (×2), dried over $MgSO_4$, filtered and the solvent was evaporated. The crude product was purified by flash column chromatography (silica; hexane/EtOAc 100/0 to 80/20). The desired fractions were collected and concentrated in vacuo to yield a colourless oil (1.4 g, 82%).

b) Preparation of Intermediate 223

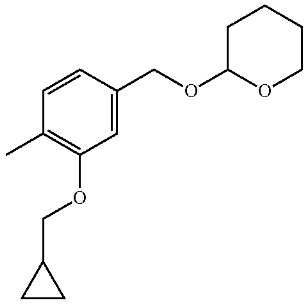 [SMILES: Cc1ccc(COC2CCCCO2)cc1OCC1CC1]

In a vial, to a solution of intermediate 222 (1.4 g, 4.909 mmol) in cyclopropanemethanol (5 mL) were added $K_3PO_4$ (2.085 g, 9.82 mmol), 8-hydroxyquinoline (71 mg, 0.491 mmol) and CuI (187 mg, 0.982 mmol), while the mixture was degassed by bubbling $N_2$. The mixture was stirred at 110° C. for 10 h, then diluted with water, extracted with EtOAc, dried over $MgSO_4$, filtered and the solvent evaporated. The crude product was purified by flash column chromatography (silica; hexane/EtOAc 100/0 to 90/10). The desired fractions were collected and concentrated in vacuo to afford intermediate 223 (1.15 g).

c) Preparation of Intermediate 224

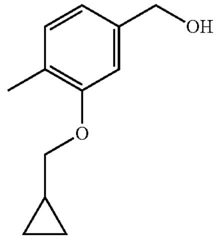

HCl (1M, 0.208 mL) was added to a solution of intermediate 223 (1.15 g) in MeOH (6 mL) at r.t. and the mixture was stirred for 2 h at the same temperature. The solvent was then evaporated, sat. $NaHCO_3$ added and the product was extracted with EtOAc (×2). The combined organic phases were dried over $MgSO_4$, filtered and evaporated. The crude was purified by flash column chromatography (silica; heptanes/EtOAc 100/0 to 30/70). The desired fractions were collected and concentrated in vacuo to yield a sticky yellow oil (200 mg).

d) Preparation of Intermediate 225

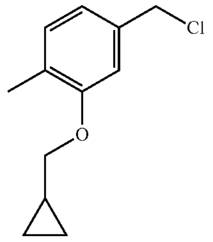

By following a synthetic procedure similar to the one reported for the synthesis of intermediate 21, intermediate 225 was obtained starting from intermediate 224.

Example A67

The following intermediates were synthesized by following an analogous synthetic sequence as reported in Example A60. For the preparation of some intermediates of the table below, only part of the synthetic sequence in A60 had to be followed, for example when one of the intermediates in the sequence was commercially available or in case a more efficient preparation for an intermediate in the sequence was well-known from literature. Separation into diastereoisomers, unless otherwise indicated, was obtained by standard flash column chromatography.

| Structure | Intermediate number | Starting materials |
|---|---|---|
| 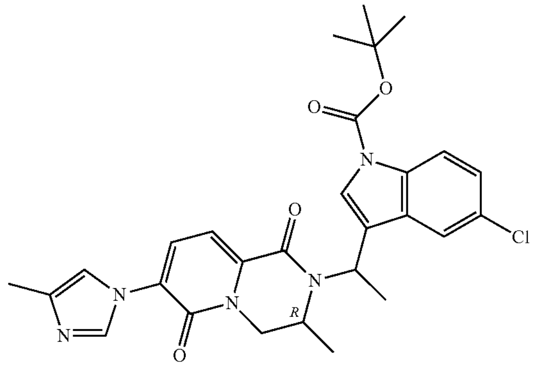 | 226 | 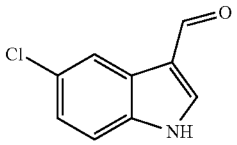 Intermediate 40 |
| 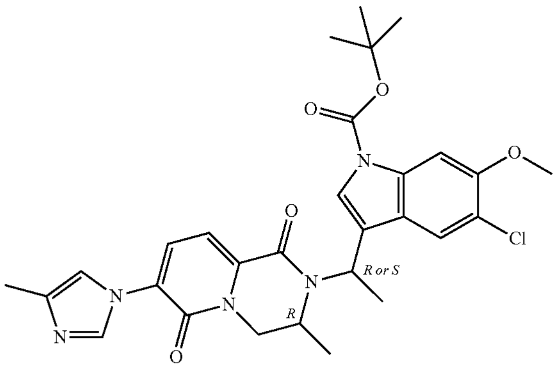 | 227 | 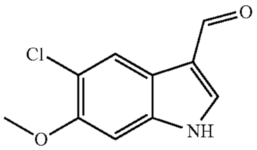 Intermediate 40 |

-continued
| Structure | Intermediate number | Starting materials |
| --- | --- | --- |
| 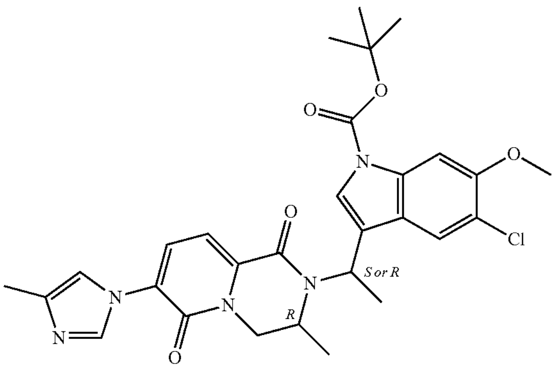 | 228 | 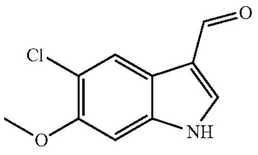 Intermediate 40 |
| 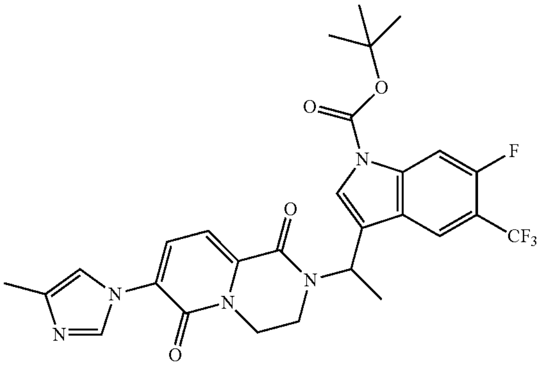 [SMILES: Cc1cn(-c2ccc3n(c2=O)CCN(C(C)c2cn(C(=O)OC(C)(C)C)c4cc(F)c(C(F)(F)F)cc24)C3=O)cn1] | 243 | 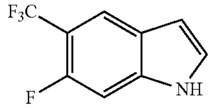 Intermediate 173 |
| 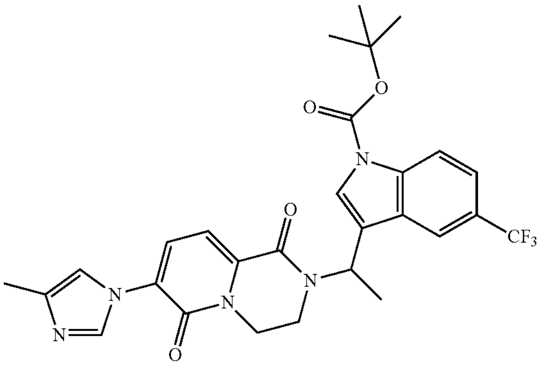 [SMILES: Cc1cn(-c2ccc3n(c2=O)CCN(C(C)c2cn(C(=O)OC(C)(C)C)c4ccc(C(F)(F)F)cc24)C3=O)cn1] | 244 | Intermediate 202<br>Intermediate 173 |
| 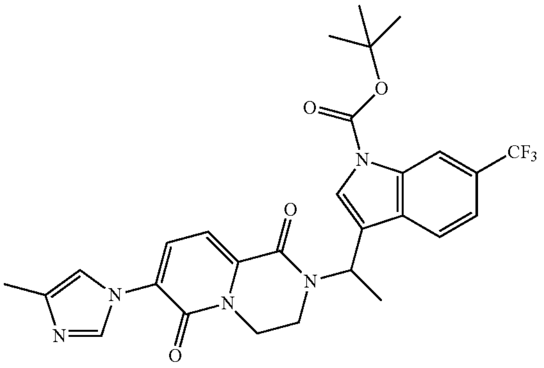 [SMILES: Cc1cn(-c2ccc3n(c2=O)CCN(C(C)c2cn(C(=O)OC(C)(C)C)c4cc(C(F)(F)F)ccc24)C3=O)cn1] | 245 | Intermediate 210<br>Intermediate 173 |

-continued

| Structure | Intermediate number | Starting materials |
|---|---|---|
| 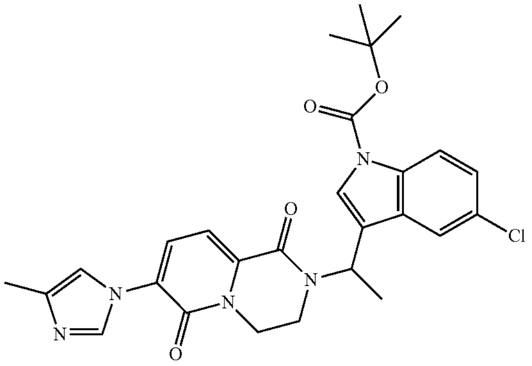 [SMILES: Cc1cn(-c2ccc3n(c2=O)CCN(C(C)c2cn(C(=O)OC(C)(C)C)c4ccc(Cl)cc24)C3=O)cn1] | 262* | 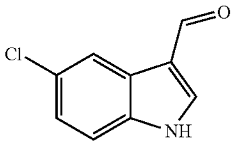 Intermediate 173 |

*the reaction was run in the presence of 0.7 equivalents of 18-crown-6

Example A68

By using experimental conditions analogous to those reported for the synthesis of intermediate 47, the following intermediates were obtained:

| Intermediate number | Structure | Starting materials |
|---|---|---|
| 230 | 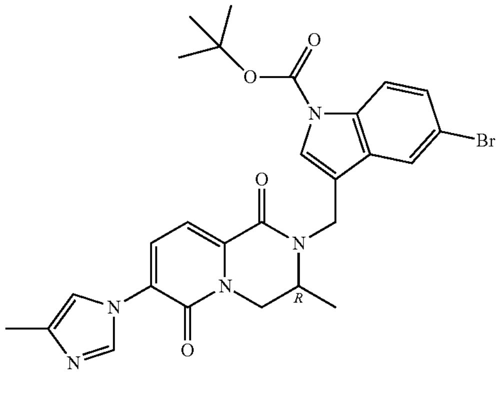 | Intermediate 229<br>Intermediate 40 |
| 233 | 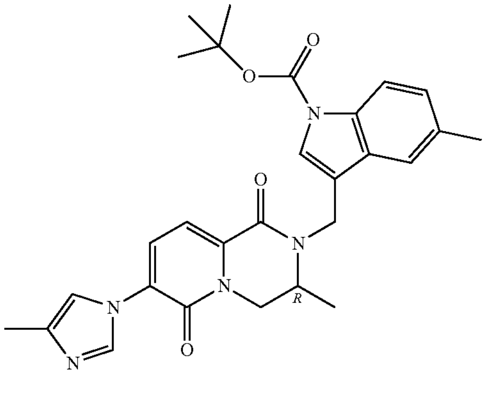 | Intermediate 232<br>Intermediate 40 |

-continued
| Intermediate number | Structure | Starting materials |
| --- | --- | --- |
| 235 | 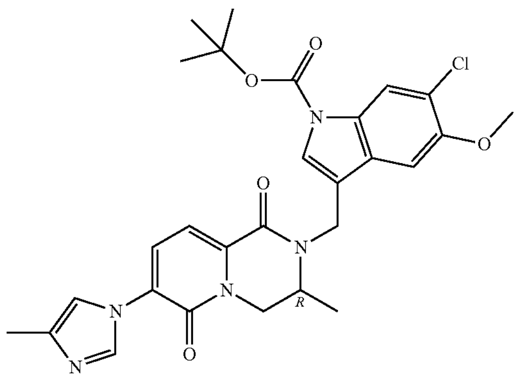 | Intermediate 234<br>Intermediate 40 |
| 240 | 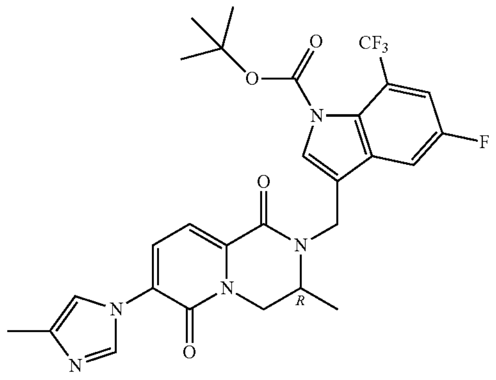 | Intermediate 239<br>Intermediate 40 |
| 241 | 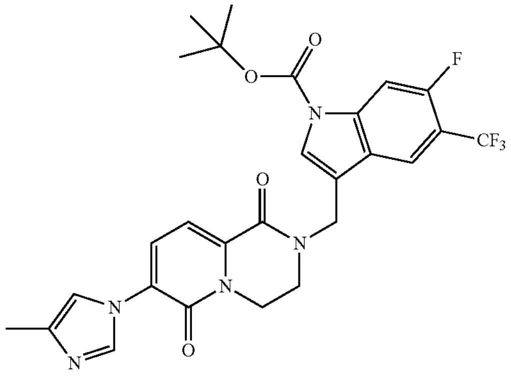 [SMILES: Cc1cn(-c2ccc3n(c2=O)CCN(Cc2cn(C(=O)OC(C)(C)C)c4cc(F)c(C(F)(F)F)cc24)C3=O)cn1] | Intermediate 212<br>Intermediate 173 |

Example A69 a) Preparation of Intermediate 231

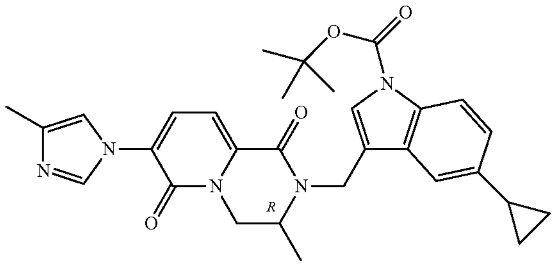

A pressure tube was charged with intermediate 230 (780 mg, 1.377 mmol), cyclopropylboronic acid (154 mg, 1.798 mmol), tricyclohexylphosphine (39 mg, 0.139 mmol) and toluene (7 mL). Then, $Pd(OAc)_2$ (32 mg, 0.07 mmol) and ground $K_3PO_4$ (1.023 g, 4.819 mmol) were added. Finally, water (0.4 mL) was added and the tube was capped and placed in a preheated oil bath of 120° C. and stirring was continued for 3 h. The r.m. was cooled and diluted with water (30 mL). The layers were separated and the aq. layer was extracted with toluene (50 mL). The combined organic layers were treated with brine (20 mL), dried over $MgSO_4$, filtered and concentrated in vacuo. The residue was purified by flash column chromatography (silica; DCM/MeOH 100/0 to 98/2) to afford intermediate 231 (410 mg, 56%).

Example A70

The following intermediates were synthesized by following an analogous synthetic sequence as reported in Example A56. For the preparation of some intermediates of the table below, only part of the synthetic sequence in A56 had to be followed, for example when one of the intermediates in the sequence was commercially available or in case a more efficient preparation for an intermediate in the sequence was well-known from literature.

| Structure | Intermediate number | Starting materials |
|---|---|---|
| 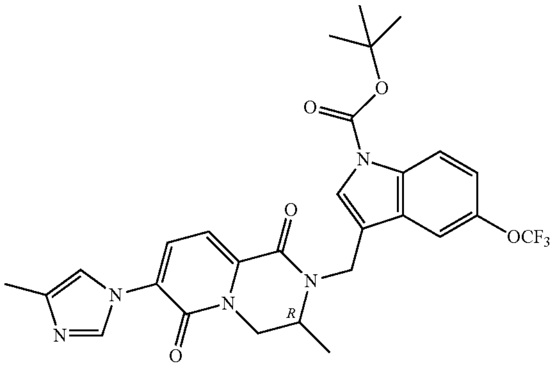 | 236 | 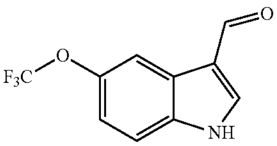 Intermediate 40 |
| 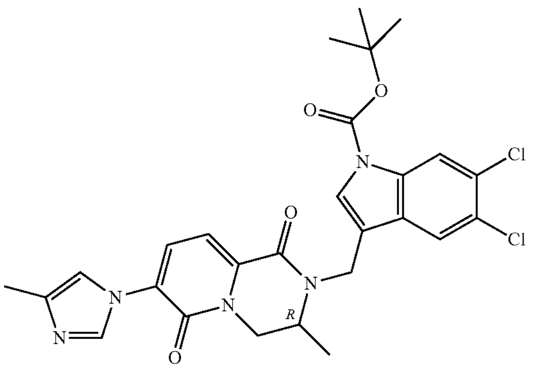 | 237 | 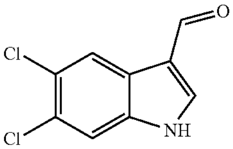 Intermediate 40 |

-continued
| Structure | Intermediate number | Starting materials |
|---|---|---|
| 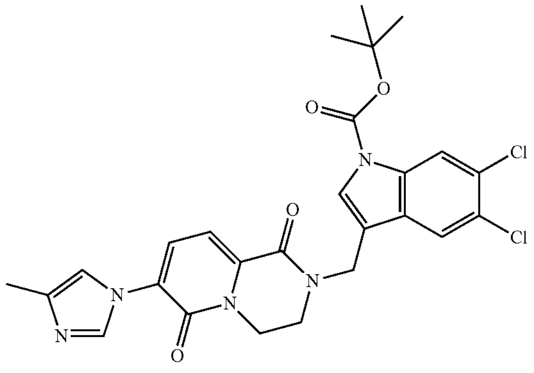 [SMILES: Cc1cn(-c2ccc3n(c2=O)CCN(Cc2cn(C(=O)OC(C)(C)C)c4cc(Cl)c(Cl)cc24)C3=O)cn1] | 238 | 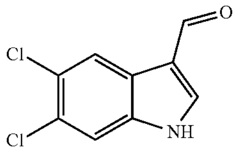 Intermediate 173 |
| 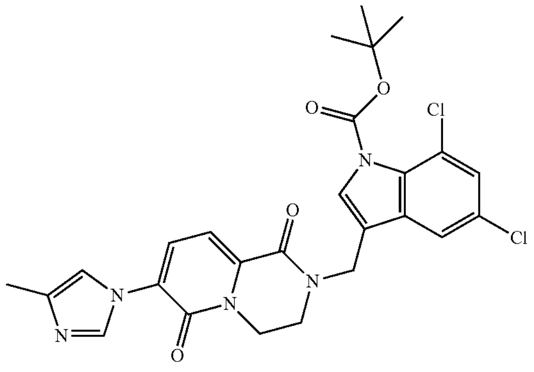 [SMILES: Cc1cn(-c2ccc3n(c2=O)CCN(Cc2cn(C(=O)OC(C)(C)C)c4c(Cl)cc(Cl)cc24)C3=O)cn1] | 242 | 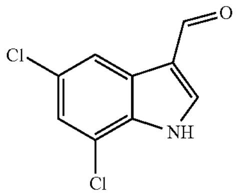 Intermediate 173 |
| 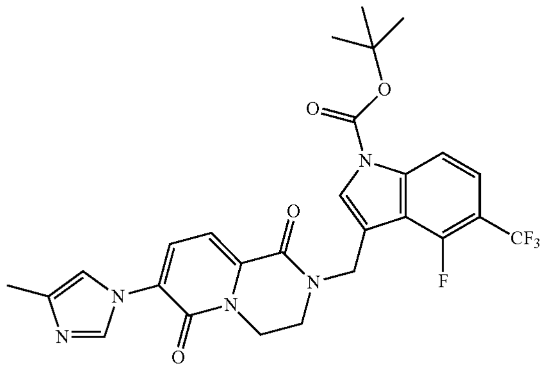 [SMILES: Cc1cn(-c2ccc3n(c2=O)CCN(Cc2cn(C(=O)OC(C)(C)C)c4ccc(C(F)(F)F)c(F)c24)C3=O)cn1] | 260 | Intermediate 259<br>Intermediate 173 |
| 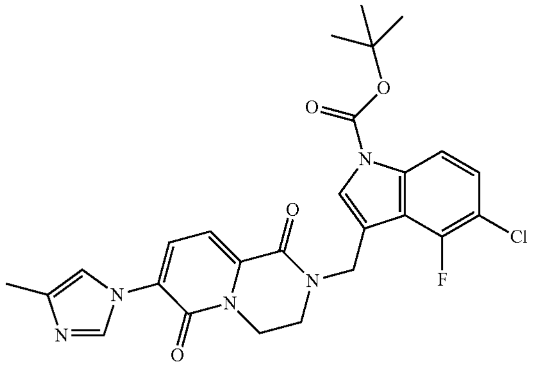 [SMILES: Cc1cn(-c2ccc3n(c2=O)CCN(Cc2cn(C(=O)OC(C)(C)C)c4ccc(Cl)c(F)c24)C3=O)cn1] | 261 | 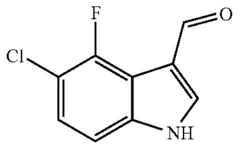 Intermediate 173 |

Example A71 a) Preparation of Intermediate 246

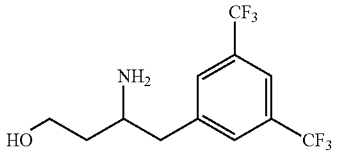 [SMILES: NC(CCO)Cc1cc(C(F)(F)F)cc(C(F)(F)F)c1]

By following a synthetic procedure similar to the one reported for the synthesis of intermediate 20, intermediate 245 was obtained starting from commercially available 3-amino-4-[3,5-bis(trifluoromethyl)phenyl]butanoic acid (661 mg).

b) Preparation of Intermediate 247

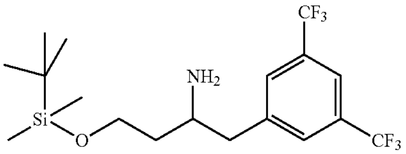 [SMILES: CC(C)(C)[Si](C)(C)OCCC(N)Cc1cc(C(F)(F)F)cc(C(F)(F)F)c1]

By following a synthetic procedure similar to the one reported for the synthesis of intermediate 2, intermediate 247 was obtained starting from intermediate 246 (0.57 g).

c) Preparation of Intermediate 248

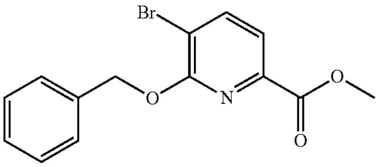 [SMILES: COC(=O)c1ccc(Br)c(OCc2ccccc2)n1]

By following a synthetic procedure similar to the one reported for the synthesis of intermediate 6, intermediate 248 was obtained starting from methyl 5-bromo-6-oxo-1,6-dihydropyridine-2-carboxylate and benzyl alcohol (6.942 g, quantitative yield).

d) Preparation of Intermediate 249

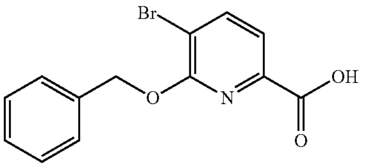 [SMILES: O=C(O)c1ccc(Br)c(OCc2ccccc2)n1]

Using experimental conditions similar to those reported for the synthesis of intermediate 128, intermediate 249 was obtained starting from intermediate 248 (2.94 g).

e) Preparation of Intermediate 250

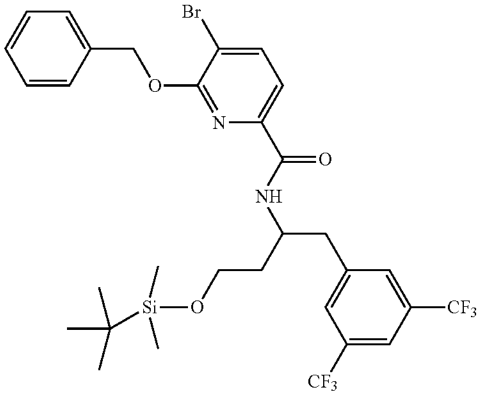 [SMILES: CC(C)(C)[Si](C)(C)OCCC(Cc1cc(C(F)(F)F)cc(C(F)(F)F)c1)NC(=O)c1ccc(Br)c(OCc2ccccc2)n1]

By following a synthetic procedure similar to the one reported for the synthesis of intermediate 3, intermediate 250 was obtained starting from intermediate 247 and intermediate 249 (571 mg).

f) Preparation of Intermediate 251

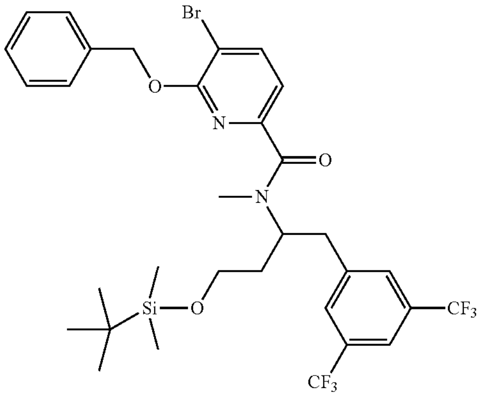 [SMILES: CN(C(=O)c1ccc(Br)c(OCc2ccccc2)n1)C(CCO[Si](C)(C)C(C)(C)C)Cc1cc(C(F)(F)F)cc(C(F)(F)F)c1]

By following a synthetic procedure similar to the one reported for the synthesis of intermediate 34, intermediate 251 was obtained starting from intermediate 250 (130 mg).

g) Preparation of Intermediate 252

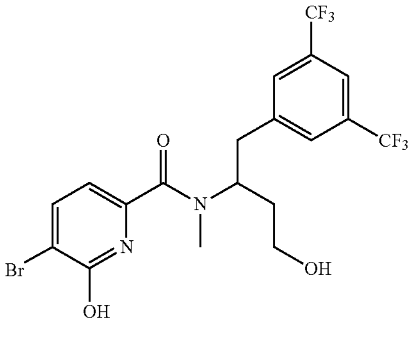 [SMILES: CN(C(=O)c1ccc(Br)c(O)n1)C(CCO)Cc1cc(C(F)(F)F)cc(C(F)(F)F)c1]

By following a synthetic procedure similar to the one reported for the synthesis of intermediate 46, intermediate 252 was obtained starting from intermediate 251 (93 mg).

h) Preparation of Intermediate 253

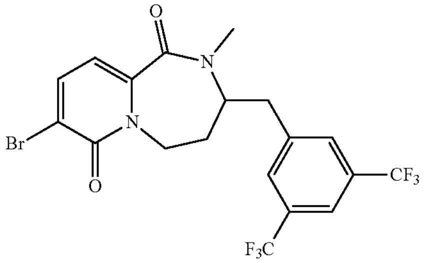 [SMILES: CN1C(=O)c2ccc(Br)c(=O)n2CCC1Cc1cc(C(F)(F)F)cc(C(F)(F)F)c1]

By following a synthetic procedure similar to the one reported for the synthesis of intermediate 6, intermediate 253 was obtained starting from intermediate 252 (45 mg).

Example A72 a) Preparation of Intermediate 254

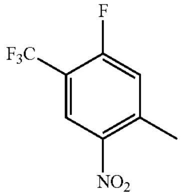

(Trifluoromethyl)trimethylsilane (5.807 mL, 39.285 mmol) was added to a stirred suspension of 1-iodo-2-fluoro-4-methyl-5-nitro-benzene (5.52 g, 19.642 mmol), copper iodide (5.611 g, 29.464 mmol) and potassium fluoride (2.282 g, 39.285 mmol) in dry DMF (75 mL). The resulting solution was stirred at 70° C. Reaction allowed to go on overnight, then cooled down, diluted with EtOAc, washed with sat. $NH_4Cl$, water and brine. The aq. phase was filtered through celite because some insoluble salts created an emulsion: some additional org. phase collected from the filtrate. The org. phase was collected, dried and the solvent was evaporated. The residue was adsorbed on silica and purified via flash column chromatography, to give an orange oil. The material was used as such in the subsequent reaction step (3.18 g, 73%).

b) Preparation of Intermediate 255

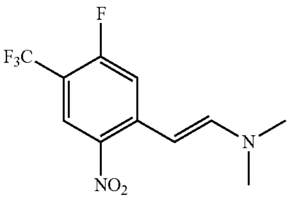 [SMILES: CN(C)/C=C/c1cc(F)c(C(F)(F)F)cc1[N+](=O)[O-]]

N,N-Dimethylformamide dimethyl acetal (9.359 mL, 70.453 mmol) was added to a solution of intermediate 254 (3.144 g, 14.091 mmol) in dry DMF (11 mL), and the r.m. was stirred at 100° C. Straight after the addition the reaction turns from red to dark green. After 1 h GC-MS shows complete conversion to the desired product. Reaction allowed to cool down, then poured into water: a dark red ppt is formed, which was dried in vacuo at 40° C. overnight and then in vacuo at r.t. over the weekend. The material was used without further purification for the subsequent reaction (3.344 g, 85%).

c) Preparation of Intermediate 256

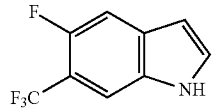 [SMILES: Fc1cc2cc[nH]c2cc1C(F)(F)F]

Intermediate 255 (3.344 g, 12.02 mmol), silica gel (1.45 g) and iron powder (3.393 g, 132.371 mmol) in toluene (49 mL) and AcOH (30 mL) were heated at 90° C. for 90 min, then the mixture was cooled to r.t., diluted with EtOAc and filtered on silica gel. The filtrate was evaporated and the resulting residue dissolved in DCM and washed with $NaHCO_3$ sat., then with water and brine. The org. layer was dried over $MgSO_4$, filtered and evaporated to give a dark oil, used without further elaboration in the subsequent reaction step (2.587 g, quantitative).

d) Preparation of Intermediate 257

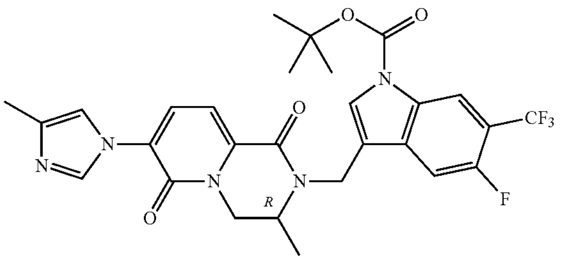

By following a synthetic procedure similar to the one reported in Example A52, intermediate 257 was obtained starting from intermediate 256 and intermediate 40.

Example A73 a) Preparation of Intermediate 258

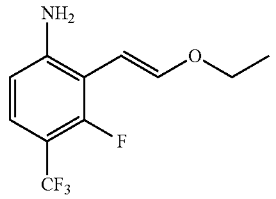

E/Z mixture

To a solution of 3-fluoro-2-iodo-4-(trifluoromethyl)-benzenamine (1.933 g, 6.337 mmol) and 2-(2-ethoxyethenyl)-4,4,5,5-tetramethyl-1,3,2-dioxaborolane (1.632 g, 8.238 mmol) in DMF (13 mL) was added lithium hydroxide monohydrate (0.798 g, 19.011 mmol) while $N_2$ was bubbled through the reaction mixture. Pd(dppf)$Cl_2$ (0.155 g, 0.190 mmol) was added and the stirring continued at 70° C. overnight. The reaction mixture was partitioned between water and EtOAc and the org. phase was dried over $MgSO_4$, filtered and concentrated in vacuo. The crude product was purified by flash column chromatography (silica; hexane/EtOAc 100/0 to 80/20). The desired fractions were collected and concentrated in vacuo to give the desired product (1.249 g, 79%).

b) Preparation of Intermediate 259

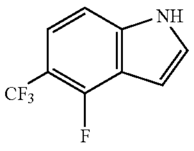 [SMILES: Fc1c(C(F)(F)F)ccc2[nH]ccc12]

Intermediate 258 (1.249 g, 5.012 mmol) was dissolved in AcOH (28.6 mL) in a sealed tube. The resulting mixture was then heated at reflux (125° C.) for 2 h. The solvent was evaporated in vacuo and the residual AcOH were removed by azeotropic evaporation with toluene. The crude product was purified by flash column chromatography (silica; hexane/EtOAc 100/0 to 70/30). The desired fractions were collected and concentrated in vacuo to give the desired product (840 mg, 83%).

B. Preparation of the Final Compounds

Example B1 a) Preparation of Compound 1

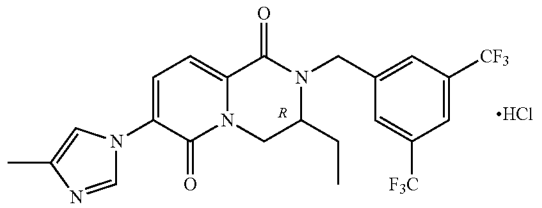

CuI (0.096 g, 0.506 mmol) was added to a suspension of intermediate 7 (1.26 g, 2.53 mmol), $Cs_2CO_3$ (2.1 g, 6.32 mmol), 4-methylimidazole (0.415 g, 5.06 mmol) and N,N-dimethyl-1,2-cyclohexanediamine (0.080 mL, 0.506 mmol) in DMF (25 mL), while the reaction was degassed by bubbling $N_2$ through the solution. The mixture was heated at 106° C. overnight. Water was then added and the aq. layer was extracted with EtOAc. The organic layer was dried over $MgSO_4$, filtered and the solvent was removed under reduced pressure. The crude product was purified by flash column chromatography (silica; MeOH/DCM 0/100 to 3/97). The desired fractions were collected and concentrated in vacuo. The residue was dissolved in EtOAc, and HCl 4N was added (1 eq). Compound 1 (R-enantiomer) was obtained pure after recrystallization from DIPE (0.177 g, 13%).

Example B2 a) Preparation of Compound 2

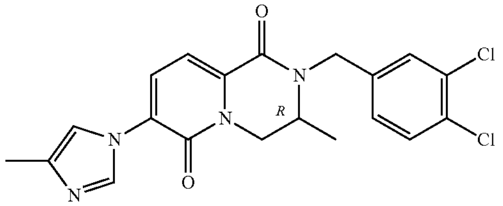

CuI (0.118 g, 0.62 mmol) was added to a solution of intermediate 29 (1.293 g, 3.1 mmol), 4-methylimidazole (0.255 g, 3.1 mmol), $Cs_2CO_3$ (2.12 g, 6.51 mmol) and N,N'-dimethyl-1,2-cyclohexanediamine (0.098 mL, 0.62 mmol) in DMF (15 mL), while the reaction was degassed by bubbling $N_2$ through the solution. The mixture was then heated at 110° C. overnight. Water was added and the aq. layer was extracted with EtOAc. The phases were separated and the organic layer was dried over $MgSO_4$, filtered and the solvent removed under reduced pressure. The crude product was purified by flash column chromatography (silica; MeOH/DCM 0/100 to 3/97). The desired fractions were collected and concentrated in vacuo to afford compound 2 (0.750 g, 58%; R-enantiomer).

Example B3 a) Preparation of Compound 3

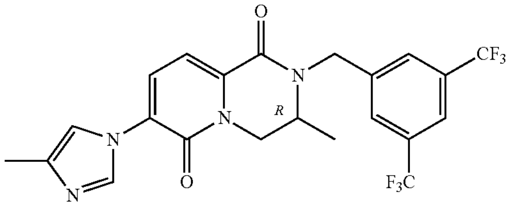

CuI (0.221 g, 1.16 mmol) was added to a suspension of intermediate 15 (2.8 g, 5.8 mmol), $Cs_2CO_3$ (4.7 g, 14.5 mmol), 4-methylimidazole (0.952 g, 11.6 mmol) and N,N-dimethyl-1,2-cyclohexanediamine (0.183 mL, 1.16 mmol) in DMF (58 mL), while the reaction was degassed by bubbling $N_2$ through the solution. The mixture was heated at 106° C. overnight. Water was then added and the aq. layer was extracted with EtOAc. The organic layer was dried over $MgSO_4$, filtered and the solvent was removed under reduced pressure. The crude product was purified by flash column chromatography (silica; MeOH/DCM 0/100 to 3/97). The desired fractions were collected and concentrated in vacuo to afford compound 3 (0.604 g, 21%; R-enantiomer).

a1) Alternative Preparation of Compound 3

In a first vial equipped with a magnetic stir bar and a screw cap septum, a solution of $Pd_2(dba)_3$ (6 mg, 0.006 mmol) and 2-di-tert-butylphosphino-3,4,5,6-tetramethyl-2',4',6'-triisopropy 1-1,1'-biphenyl (6 mg, 0.0125 mmol) in dioxane (0.17 mL) and toluene (0.83 mL) was flushed with $N_2$ and then stirred at 120° C. for 3 min. A second vial, equipped with a magnetic stir bar and a screw cap septum, was charged with 4-methylimidazole (45 mg, 0.55 mmol) and $K_3PO_4$ (213 mg, 1 mmol), then with intermediate 15 (242 mg, 0.5 mmol) and also flushed with $N_2$. The premixed catalyst solution was added by syringe to the second vial. The r.m. was heated at 120° C. for 5 h. The reaction was cooled to r.t, diluted with EtOAc, washed with brine, dried over $MgSO_4$ and concentrated in vacuo. The crude product was purified by flash column chromatography (silica MeOH/DCM 0/100 to 3/97). The fractions were collected and the solvent was evaporated to give compound 3 (170 mg, 70%; R-enantiomer).

Example B4 a) Preparation of Compound 4

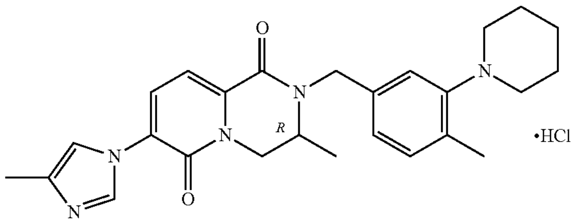

CuI (0.041 g, 0.21 mmol) was added to a solution of intermediate 22 (0.476 g, 1.07 mmol), $Cs_2CO_3$ (0.871 g, 2.68 mmol), 4-methylimidazole (0.176 g, 2.16 mmol) and N,N'-dimethyl-1,2-cyclohexanediamine (0.038 mL, 0.214 mmol) in DMF (5 mL), while the reaction was degassed by bubbling $N_2$ through the solution. The mixture was heated at 110° C. overnight. Water was then added and the aq. layer was extracted with EtOAc. The organic layer was dried ($MgSO_4$), filtered and the solvent was removed under reduced pressure. The crude product was purified by flash column chromatography (silica; MeOH/DCM 0/100 to 3/97). The desired fractions were collected and concentrated in vacuo. The product was dissolved in EtOAc (0.5 mL) and HCl 4M was added (1.0 eq). Compound 4 was obtained pure after recrystallization from DIPE (127 mg, 25%; R-enantiomer).

Example B5 a) Preparation of Compound 5

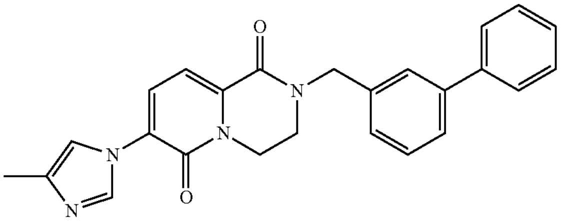 [SMILES: Cc1cn(-c2ccc3n(c2=O)CCN(Cc2cccc(-c4ccccc4)c2)C3=O)cn1]

CuI (0.102 g, 0.538 mmol) was added to a solution of intermediate 34 (1.1 g, 2.69 mmol), $Cs_2CO_3$ (1.84 g, 5.65 mmol), 4-methylimidazole (0.22 g, 2.69 mmol) and N,N-dimethyl-1,2-cyclohexanediamine (0.085 mL, 0.538 mmol) in DMF (10 mL), while the reaction was degassed by bubbling $N_2$ through the solution. The mixture was heated at 110° C. overnight. Water was then added and the aq. layer was extracted with EtOAc. The organic layer was dried over $MgSO_4$, filtered and the solvent was removed under reduced pressure. The crude product was purified by flash column chromatography (silica; MeOH/DCM 0/100 to 3/97). The desired fractions were collected and concentrated in vacuo, to afford compound 5 (0.5 g, 45%).

Example B6 a) Preparation of Compound 6

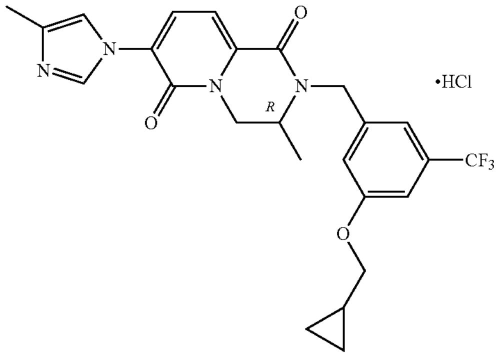

NaH (60% in mineral oil, 0.036 g, 0.91 mmol) was added to a stirred solution of intermediate 40 (crude material, 0.83 mmol) in DMF (2.5 mL) at 0° C. under $N_2$ atmosphere. The mixture was stirred for 15 min and then intermediate 99 (crude material, 0.83 mmol) was added. The r.m. was stirred for 4 h at r.t., then it was quenched with water and extracted with EtOAc. The organic layer was dried over $MgSO_4$, filtered and evaporated. The crude material was purified by flash column chromatography (silica; DCM-MeOH (9:1, v/v)/DCM, 0/100 to 35/65). The desired fractions were collected and concentrated in vacuo. The product (0.07 g) was dissolved in EtOAc (2 mL), then HCl 4M in dioxane was added to obtain the hydrochloride salt. The solvent was evaporated and the product was triturated with DIPE to yield the compound 6 as a pale brown solid (0.048 g, 69% over two steps; R-enantiomer).

Example B7 a) Preparation of Compound 7

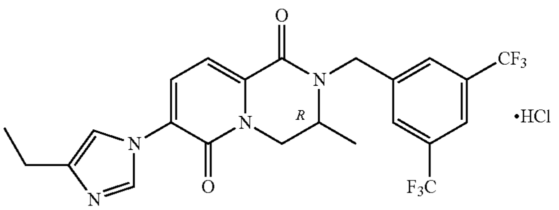

Ammonium acetate (659 mg, 8.55 mmol) was added to a stirred solution of intermediate 19 (1.71 mmol, crude material) in AcOH (3.5 mL) at r.t. The mixture was stirred for 1 h at reflux, then cooled to r.t. and poured into ice/water. NaOH 50% aq. was added slowly until basic pH. The product was extracted with EtOAc (×2). The combined organic phases were dried over $MgSO_4$, filtered and evaporated. The crude was purified by flash column chromatography (silica; EtOAc/heptane 0/100 to 90/10). The desired fractions were collected and concentrated in vacuo. The product was dissolved in EtOAc, then 4M HCl in dioxane was added to obtain the HCl salt. The solvent was evaporated and the product was triturated with DIPE to yield compound 7 as a white solid (35% over 4 steps; R-enantiomer).

Example B8 a) Preparation of Compound 8

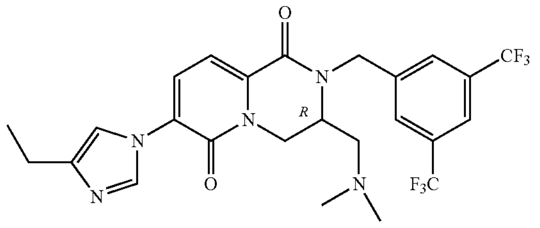

Dimethyl amine (40% solution in water, 0.062 mL, 0.49 mmol) was added to a solution of intermediate 103 (crude material, 0.098 mmol) in DMF (5 mL) at 0° C. The mixture was stirred at 80° C. overnight, then 5 additional eq. of dimethylamine were added. The mixture was stirred at 80° C. overnight. EtOAc and water were added. The organic phase was separated and dried over $MgSO_4$, filtered and concentrated to dryness. The crude product was purified by flash column chromatography (silica; MeOH/DCM 0/100 to 3/97). The desired fractions were collected and concentrated in vacuo. The solid was triturated from DIPE to afford compound 8 (0.010 g, 19% over two steps; R-enantiomer).

Example B9 a) Preparation of Compounds 9 (Racemic Mixture), 9a (R or S Enantiomer) and 9b (S or R Enantiomer)

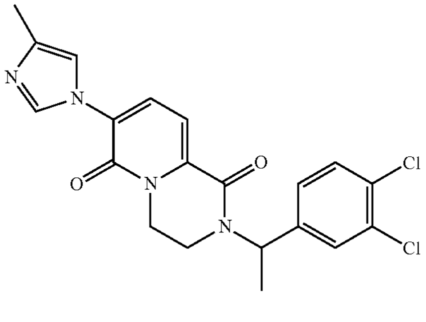 [SMILES: Cc1cn(-c2ccc3n(c2=O)CCN(C(C)c2ccc(Cl)c(Cl)c2)C3=O)cn1]

CuI (0.120 g, 0.633 mmol) was added to a solution of intermediate 57 (1.316 g, 3.163 mmol), $Cs_2CO_3$ (2.576 g, 7.907 mmol), 4-methylimidazole (0.519 g, 6.325 mmol) and N,N'-dimethyl-1,2-cyclohexanediamine (0.1 mL, 0.633 mmol) in dry DMF (30 mL), while the reaction was degassed by bubbling $N_2$ through the solution. The mixture was heated at 110° C. for 24 h. Water was then added and the aq. layer was extracted with EtOAc. The organic layer was dried over $MgSO_4$, filtered and the solvent was removed under reduced pressure. The crude product was purified by flash column chromatography (silica; MeOH in DCM 0/100 to 3/97). The desired fractions were collected and concentrated in vacuo. Compound 9 was obtained pure after recrystallization from 5% EtOAc in DIPE (435 mg, 33%, rac), and subsequently separated into its enantiomers by preparative SFC (Chiralpak Diacel OJ 20×250 mm; mobile phase ($CO_2$, MeOH with 0.2% $iPrNH_2$)). The fractions containing the separated enantiomers were collected, evaporated, dissolved again in MeOH and the solvent evaporated again, to afford the desired pure compounds. Yield: 165 mg of compound 9a (40%; R or S enantiomer) and 161 mg of compound 9b (39%; S or R enantiomer).

Example B10 a) Preparation of Compounds 10 (Racemic Mixture), 10a (R or S Enantiomer) and 10b (S or R Enantiomer)

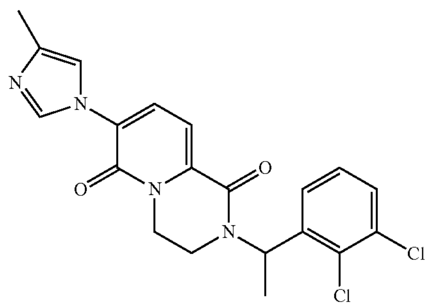 [SMILES: Cc1cn(-c2ccc3n(c2=O)CCN(C(C)c2cccc(Cl)c2Cl)C3=O)cn1]

CuI (73 mg, 0.384 mmol) was added to a solution of intermediate 56 (0.8 g, 1.92 mmol), $Cs_2CO_3$ (1.56 g, 4.8 mmol), 4-methylimidazole (0.315 g, 3.84 mmol) and N,N-dimethyl-1,2-cyclohexanediamine (0.06 mL, 0.384 mmol) in dry DMF (19 mL), while the reaction was degassed by bubbling $N_2$ through the solution. The mixture was heated at 106° C. overnight. Water was then added and the aq. layer was extracted with EtOAc. The organic layer was dried over $MgSO_4$, filtered and the solvent was removed under reduced pressure. The crude product was purified by flash column chromatography (silica; MeOH in DCM 0/100 to 3/97). The desired fractions were collected and concentrated in vacuo. Compound 10 (racemic) was obtained pure after recrystallization from DIPE (138 mg, 17%, rac), and subsequently separated into its enantiomers by preparative SFC (Chiralcel Diacel OD 20×250 mm; mobile phase ($CO_2$, MeOH with 0.2% $iPrNH_2$)). The fractions containing the separated enantiomers were collected, evaporated, dissolved again in MeOH and the solvent evaporated again, to afford the desired pure compounds. Yield: 46 mg of compound 10a (39%; R or S enantiomer) and 49 mg of compound 10b (41%; S or R enantiomer).

Example B11 a) Preparation of Compounds 11 (Racemic), 11a (R or S Enantiomer) and 11b (S or R Enantiomer)

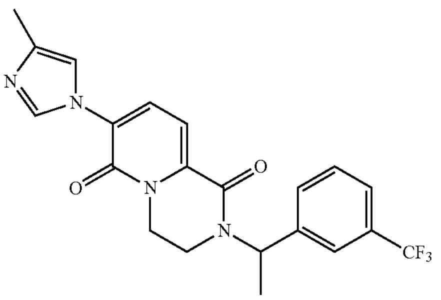 [SMILES: Cc1cn(-c2ccc3n(c2=O)CCN(C(C)c2cccc(C(F)(F)F)c2)C3=O)cn1]

4-Methylimidazole (246 mg, 3 mmol), copper iodide (38 mg, 0.2 mmol) and $Cs_2CO_3$ (977 mg, 3 mmol) were added to the crude r.m. containing intermediate 58 (crude material, 1 mmol in 20 mL of DMF). $N_2$ was bubbled through the mixture for 5 min before this was heated in a sealed flask at 110° C. under $N_2$ atmosphere for 48 h. The mixture was cooled to r.t. and partitioned between DCM (50 mL) and water (50 mL). Because the aqueous phase was cloudy, EDTA (5.6 g, 15 mmol) was added and the biphasic mixture was shaken for 5 min, until the aq. phase became clear. The organic layer was separated and the aqueous layer was extracted with DCM (2×50 mL). The combined organic layers were washed with brine, dried ($MgSO_4$), filtered and the solvent was evaporated providing the racemic compound 11 as a brown oil, that was separated into enantiomers by preparative HPLC (Chiralpak Diacel OD 20×250 mm, mobile phase (24% MeOH with 0.2% $iPrNH_2$/76% $CO_2$ hold 12.0 min, then from 24 to 50% MeOH with 0.2% $iPrNH_2$ at 15% rate and hold 2.0 min at 50%)). Yield: 112 mg of compound 11a (beige solid, 27%; R or S enantiomer; enantiomer A (SFC-MS)) and 109 mg of compound 11b (beige solid, 26%; S or R enantiomer; enantiomer B (SFC-MS)).

Example B12 a) Preparation of Compound 12

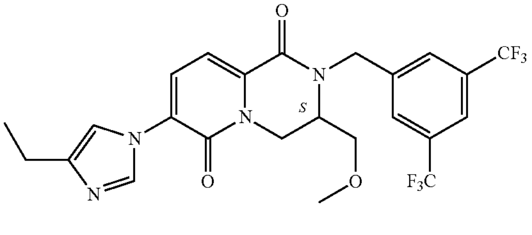

Starting from (S)-2-amino-3-methoxy-1-propanol and 3,5-bis(trifluoromethyl)benzaldehyde, compound 12 (S-enantiomer) was prepared by analogy to the procedures reported for the synthesis of compound 7.

Example B13 a) Preparation of Compound 13

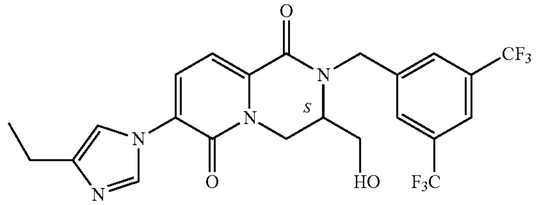

Boron tribromide (0.093 mL, 0.98 mmol) was added to a solution of compound 12 (0.052 g, 0.098 mL) in DCM (2 mL). The mixture was stirred at r.t. for 5 h, then sat. aq. $NaHCO_3$ was added. The product was extracted with DCM (×2), the combined organics were dried over $MgSO_4$, filtered and evaporated, yielding compound 13 (S-enantiomer).

Example B14 a) Preparation of Compounds 14 (Racemic), 14a (Cis A) and 14b (Cis B)

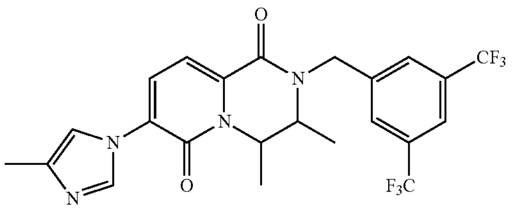 [SMILES: Cc1cn(-c2ccc3n(c2=O)C(C)C(C)N(Cc2cc(C(F)(F)F)cc(C(F)(F)F)c2)C3=O)cn1]

Starting from intermediate 59, compound 14 was obtained following an analogous synthetic route as described for compound 7. The mixture was subsequently separated into enantiomers by preparative SFC (Chiralpak Diacel OD 20×250 mm, mobile phase ($CO_2$, MeOH with 0.2% $iPrNH_2$)). Yield: 23 mg of compound 14a (49%; R,S or S,R enantiomer; cis A) and 19 mg of compound 14b (40%; S,R or R,S enantiomer; cis B).

Example B15 a) Preparation of Compound 111

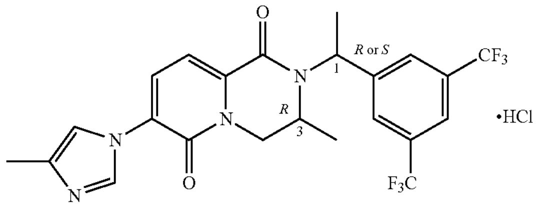

Starting from intermediate 104, compound 111 (R/R or S-diastereoisomer) was prepared by analogy to the procedure B3.a1, reported for the synthesis of compound 3. The product was subsequently dissolved in EtOAc and treated with a small excess of HCl (4M in dioxane) to obtain the hydrochloride salt (.HCl). The solvent was then evaporated and the residual triturated with DIPE to give a white solid (38%) (1R or 1S, 3R; diastereomer A (SFC-MS)).

Example B16 a) Preparation of Compound 112

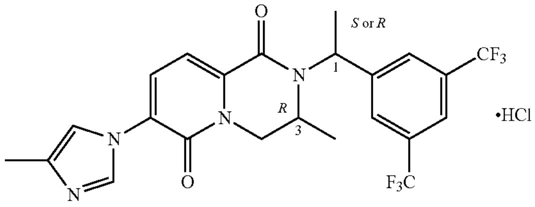

Starting from intermediate 105, compound 112 was prepared by analogy to the procedure B3.a1 reported for the synthesis of compound 3. The product was subsequently dissolved in EtOAc and treated with a small excess of HCl (4M in dioxane) to obtain the hydrochloride salt (.HCl). The solvent was then evaporated and the residual triturated with DIPE to give a white solid (43%; 15 or 1R, 3R; diastereomer B (SFC-MS)).

Example B17 a) Preparation of Compound 125

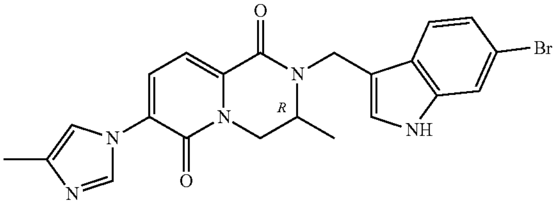

Intermediate 141 (470 mg, 0.83 mmol) was dissolved in DCM (9.4 mL) at r.t. under $N_2$ atmosphere. TFA (1 mL, 13.067 mmol) was added and the r.m. stirred overnight at r.t., then added dropwise to a mixture DCM/$NaHCO_3$ (sat. aq.) and stirred for 20 min. The organic layer was separated, washed with brine, dried over $MgSO_4$, filtered and evaporated in vacuo to give a crude, which was suspended in DIPE, under stirring. The solid so obtained was filtered and dried in vacuo at 45° C., to afford compound 125 (351 mg, 58%; R-enantiomer).

Example B18 a) Preparation of Compound 177

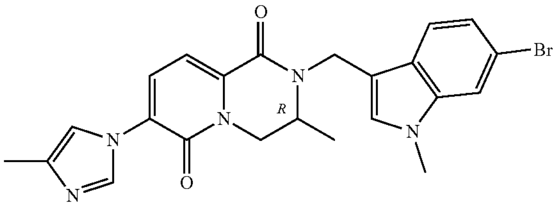

Compound 125 (170 mg, 0.365 mmol) was dissolved in DMF (13 mL) under $N_2$ atmosphere, then NaH (60% in mineral oil, 17 mg, 0.413 mmol) was added. The r.m. was stirred at r.t. for 10 min, then methyl iodide (0.025 mL, 0.402 mmol) was added. The r.m. was stirred at r.t. for 2 h. An additional amount of methyl iodide (15 μL; 0.65 eq) was added, and the reaction stirred overnight. 11 μL More methyl iodide (11 μL; 0.5 eq) was added and the r.m. stirred for 3 h. Subsequently, 14 mg of NaH was added (0.95 eq) and the reaction was allowed to stir for an additional 3 h, then the solvent was evaporated and the r.m. added dropwise to a mixture of DCM and water, and the mixture allowed to agitate for 20 min. The organic layer was then separated, dried over $MgSO_4$ and filtered. The solvent was evaporated in vacuo to give a crude which was purified via flash column chromatography (silica; MeOH/DCM 0/100 5/95): the desired fractions were collected, the solvent removed in vacuo and the residue was suspended in DIPE, the precipitate was filtered off and dried in vacuo at 40° C. overnight to afford compound 177 (69 mg, 40%; R-enantiomer).

Example B19 a) Preparation of Compound 179

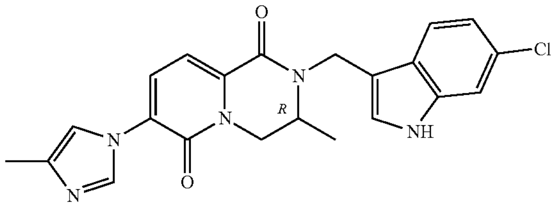

Starting from intermediate 142 and intermediate 40, compound 179 (R-enantiomer) was prepared by analogy to the procedure reported for the synthesis of intermediate 34. The deprotected form was obtained as the sole product after flash column chromatography (25%; R-enantiomer).

Example B20 a) Preparation of Compounds 175, 127 and 126

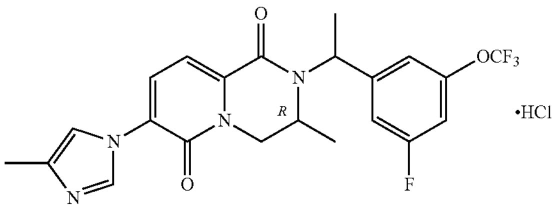

Starting from intermediate 40 and intermediate 106, compound 175 was obtained following an analogous synthetic route as described for compound 6, in the presence of 1 eq. of lithium bromide. The mixture was subsequently separated into diastereoisomers by flash column chromatography (silica; DCM/EtOAc 100/0 to 20/80). The desired fractions were collected and concentrated in vacuo. The separated diastereoisomers were dissolved in DCM and 4M HCl in dioxane was added (1 eq.) to obtain the HCl salt. The solvent was evaporated and the products triturated with $Et_2O$. Yield: 75 mg of compound 127 (8%; R,S or R,R diastereoisomer, containing 4% of compound 126) and 27 mg of compound 126 (3%; R,R or R,S diastereoisomer).

Example B21 a) Preparation of Compounds 130 and 129

129

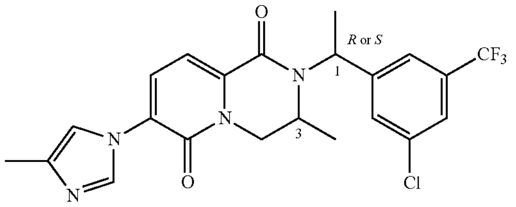

130

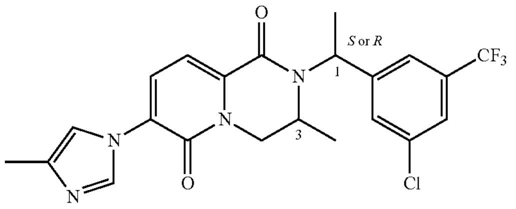

Starting from intermediate 40 and intermediate 143, a mixture of compound 130 and compound 129 was obtained as a HCl salt form following an analogous synthetic route as described for compound 6 (Example B6), in the presence of 1 eq. of lithium bromide. The mixture was subsequently separated into diastereoisomers by preparative SFC (Chiralpak Diacel AD 30×250 mm, mobile phase ($CO_2$, EtOH with 0.2% $iPrNH_2$)). Yield: 105 mg of compound 130 (23%; 1S or 1R, 3R; diastereomer A (SFC-MS)) and 182 mg of compound 129 (41%; 1R or 1S, 3R; diastereomer B (SFC-MS)).

Example B22 a) Preparation of Compound 150

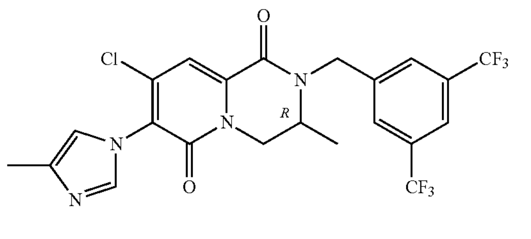

Phosphorous oxychloride (1 eq.) was added to a stirred solution of intermediate 158 (45 mg, 0.0875 mmol) in acetonitrile (0.9 mL). The mixture was heated at 90° C. in a sealed tube for 18 h, then more phosphorous oxychloride (1 eq.) was added and the mixture was heated at 90° C. for 18 h. Another eq. of phosphorous oxychloride was added and the reaction heated at 90° C. for additional 18 h, then diluted with DCM and washed with sat. $NaHCO_3$. The organic layer was separated, dried over $MgSO_4$, filtered and concentrated in vacuo. The residue was purified by flash column chromatography (silica; EtOAc). The desired fractions were collected and concentrated in vacuo. Yield: 21 mg of compound 150 (46%, R-enantiomer).

Example B23 a) Preparation of Compound 167

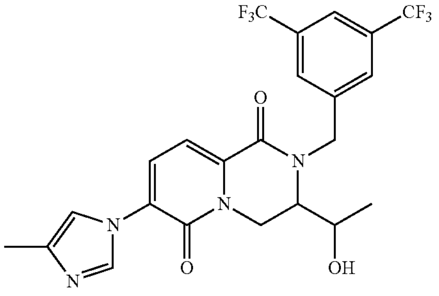 [SMILES: Cc1cn(-c2ccc3n(c2=O)CC(C(C)O)N(Cc2cc(C(F)(F)F)cc(C(F)(F)F)c2)C3=O)cn1]

Methylmagnesium bromide (1.6M in THF, 0.85 mL, 1.184 mmol) was added portionwise to a stirred solution of intermediate 157 (370 mg, 0.742 mmol) in dry THF (15 mL) under $N_2$ at 5° C. The mixture was stirred at 5° C. for 3 h, then additional methylmagnesium bromide (0.37 mL, 0.519 mmol) was added portionwise under $N_2$ at 5° C. The r.m. was stirred at r.t. overnight, then it was diluted with sat. $NH_4Cl$ and extracted with EtOAc. The organic layer was separated, dried over $MgSO_4$, filtered and the solvents evaporated in vacuo. The crude product was purified by flash column chromatography (silica; DCM/MeOH 100/0 to 95/5). The desired fractions were collected and concentrated in vacuo to yield a yellow oil. The product was purified by reversed phase chromatography twice, using (81% water with 0.1% TFA/19% MeCN-MeOH to 45% water with 0.1% TFA/55% MeCN-MeOH) and then (75% water (25 mM $NH_4HCO_3$)/25% MeCN-MeOH to 0% water (25 mM $NH_4HCO_3$)/100% MeCN-MeOH). Yield: 9 mg of compound 167 (2%).

Example B24 a) Preparation of Compound 181

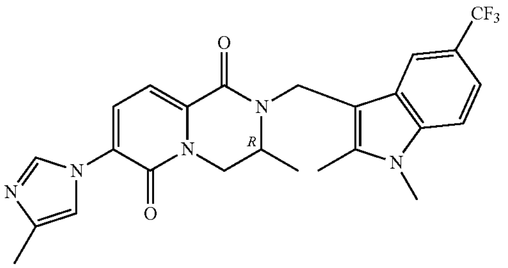

At r.t. and under $N_2$ atmosphere, NaH (60% in mineral oil, 9 mg, 0.22 mmol) was added to a solution of compound 180 (94 mg, 0.2 mmol) in DMF (3.2 mL). The r.m. was stirred at r.t. for 15 min, then methyl iodide (14 μL, 0.22 mmol) was added. The r.m. was stirred for 90 min, then 3 drops of water were added. DMF was removed in vacuo. The residue was dissolved in DCM and the organic layer was washed with water, dried over $MgSO_4$ and the solvent was removed in vacuo. The residue was crystallized from $Et_2O$. The crystals were filtered off and dried, yielding compound 181 as a white solid (60 mg, 62%).

Example B25 a) Preparation of Compounds 183 and 184

183

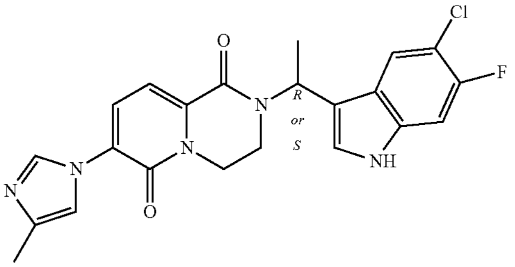

184

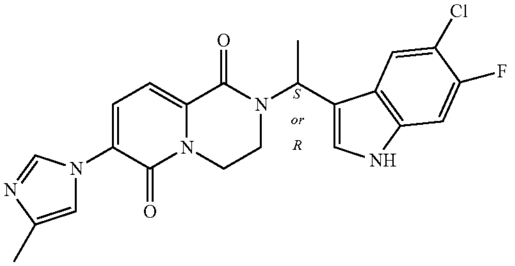

Starting from intermediate 174, a mixture of compound 183 and compound 184 was obtained following an analogous synthetic route as described for compound 125 (Example B17). The mixture was subsequently separated into enantiomers by preparative SFC (Chiralcel Diacel OD 20×250 mm, mobile phase ($CO_2$, EtOH with 0.2% $iPrNH_2$)). Yield: 93 mg of compound 183 (9%; R or S; enantiomer A (SFC-MS)) and 90 mg of compound 184 (8%; S or R; enantiomer B (SFC-MS)).

Example B26 a) Preparation of Compounds 185 and 186

185

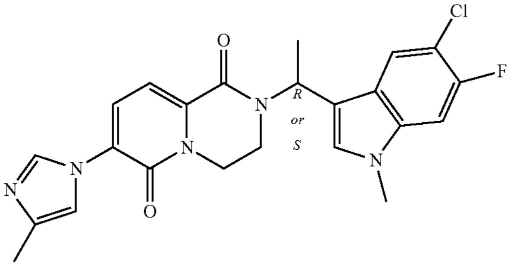

-continued

186

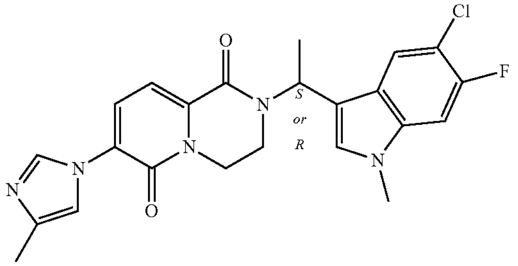

A mixture of compounds 183 and 184 (see B25.a) was processed following a synthetic route similar to the one described for the synthesis of compound 181 (Example B24) to afford a mixture of compound 185 and compound 186. The mixture was subsequently separated into enantiomers by preparative SFC (Chiralcel Diacel OD 20×250 mm, mobile phase ($CO_2$, EtOH with 0.2% $iPrNH_2$)). Yield: 139 mg of compound 185 (38%; R or S; enantiomer A (SFC-MS)) and 135 mg of compound 186 (37%; S or R; enantiomer B (SFC-MS)).

Example B27 a) Preparation of Compound 198

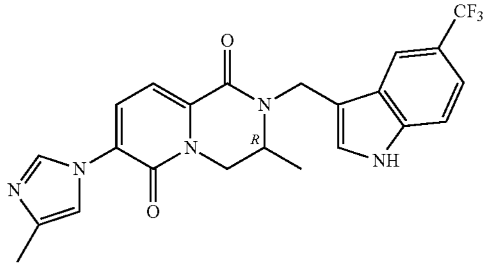

Starting from intermediate 167, compound 198 was obtained following an analogous synthetic route as described for compound 6 (Example B6).

Example B28 a) Preparation of Compound 199

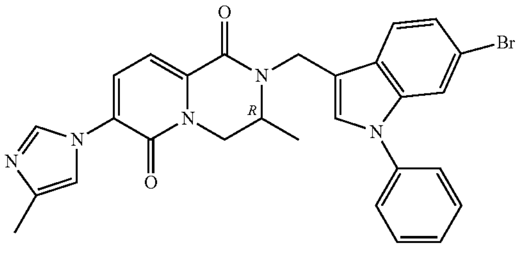

Compound 125 (125 mg, 0.27 mmol) was dissolved in DCM (6 mL). The solution was stirred for 5 min, then phenylboronic acid (66 mg, 0.54 mmol), copper acetate (97 mg, 0.54 mmol), molecular sieves, pyridine (45 μL, 0.56 mmol) and $Et_3N$ (75 μL, 0.54 mmol) were added and the r.m. was stirred overnight at r.t. After night, 2 eq. of phenylboronic acid and 2 eq. of copper acetate were added. The r.m. was stirred again overnight at rt. After this time the reaction mixture was filtered through celite. Water and brine were added to the filtrate, and all solvents were evaporated under reduced pressure. The residue was dissolved in EtOAc, filtered and the filtrate was washed with brine. The organic layer was separated, dried over $MgSO_4$, filtered off and the solvent was evaporated in vacuo to afford an intermediate (95 mg), which was purified by flash column chromatography (silica; DCM/MeOH 100/0 to 50/50). The fractions containing the product were collected and evaporated, to afford compound 199 (16 mg, 11%).

Example B29 a) Preparation of Compound 203

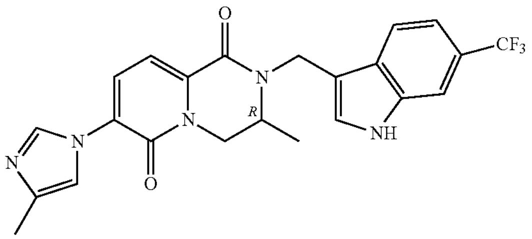

Starting from intermediate 183, compound 203 was obtained following an analogous synthetic route as described for compound 6 (Example B6).

Example B30 a) Preparation of Compound 204

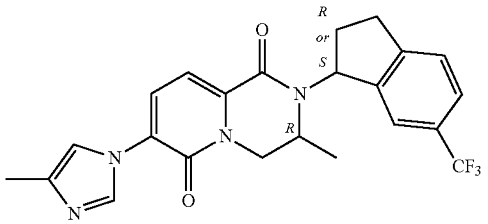

In a first vial equipped with a magnetic stir bar and a screw cap septum, a solution of $Pd_2(dba)_3$ (3 mg, 0.004 mmol) and 2-di-tert-butylphosphino-3,4,5,6-tetramethyl-2',4',6'-triisopropy 1-1,1'-biphenyl (3 mg, 0.007 mmol) in dioxane (0.1 mL) and toluene (0.45 mL) was flushed with $N_2$ and then stirred at 120° C. for 3 min. A second vial, equipped with a magnetic stir bar and a screw cap septum, was charged with 4-methylimidazole (3 mg, 0.04 mmol) and $K_3PO_4$ (8 mg, 0.04 mmol), then with intermediate 191 (8 mg, 0.02 mmol) and also flushed with $N_2$. The premixed catalyst solution was added by syringe to the second vial. The r.m. was heated at 120° C. for 5 h. The reaction was cooled to r.t., diluted with EtOAc, washed with brine, and the organic layer was filtered over an Isolute® HM-N column filter (modified form of diatomaceous earth) to remove the water. The solvent was removed under a stream of $N_2$ and the crude concentrated in vacuo before being purified by preparative HPLC (RP SunFire Prep C18 OBD-10 μm, 30×150 mm; Mobile phase: 0.25% $NH_4HCO_3$ solution in water+5% acetonitrile/acetonitrile), to yield compound 204 (6 mg, 75%).

Example B31 a) Preparation of Compounds 212 and 213

212

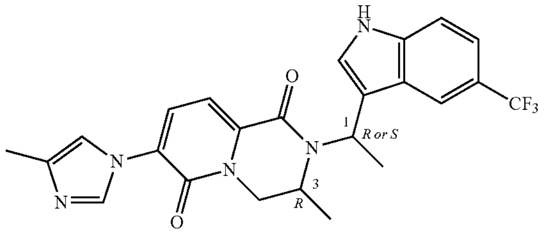

213

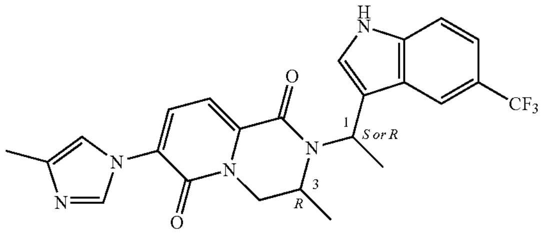

Intermediate 203 (1.2 g) was dissolved in DCM (24 mL). TFA (4.84 mL) was added and the r.m. was stirred until completion of the reaction. The solvent was then evaporated, EtOAc and sat. aq. $NaHCO_3$ sat. were added. The organic layer was separated, washed with brine and dried over $MgSO_4$. After filtration, the solvent was evaporated in vacuo to give a crude material (808 mg). 90 mg of the crude were purified by preparative SFC (Chiralpak Diacel AD 30×250 mm, mobile phase ($CO_2$, MeOH with 0.2% $iPrNH_2$)). The desired fractions were collected, evaporated, dissolved in MeOH and evaporated again. Yield: 40 mg of compound 212 (1R or 1S, 3R; diastereoisomer A (SFC-MS), white powder) and 7 mg of compound 213 (1S or 1R, 3R; diastereoisomer B (SFC-MS), white powder).

Example B32 a) Preparation of Compounds 214 and 215

214

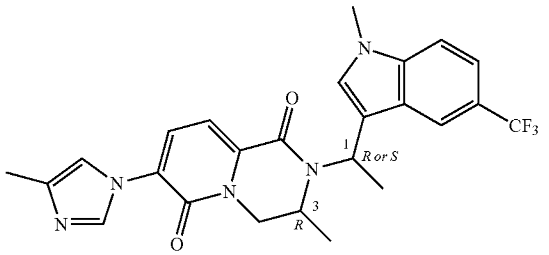

-continued

215

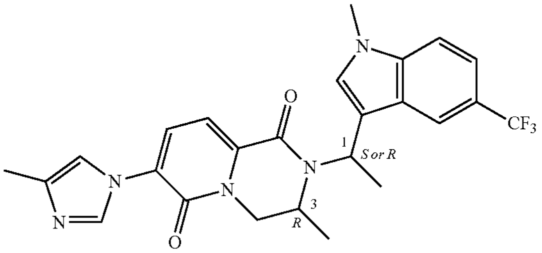

Starting from a mixture of compound 212 and compound 213, compound 214 and compound 215 were obtained as a mixture following an analogous synthetic route as described for compound 181 (Example B24). The mixture was separated into the single diastereoisomers by preparative SFC (Chiralpak Diacel AD 30×250 mm, mobile phase ($CO_2$, EtOH with 0.2% $iPrNH_2$)). The desired fractions were collected, evaporated, dissolved in MeOH and evaporated again, Yield: 86 mg of compound 214 (1R or 1S, 3R; diastereoisomer A (SFC-MS)) and 17 mg of compound 215 (1S or 1R, 3R; diastereoisomer B (SFC-MS)).

Example B33 a) Preparation of Compounds 216 and 217

216

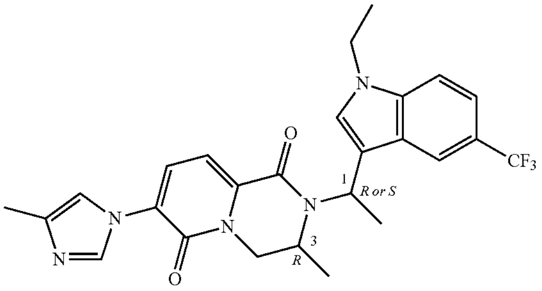

217

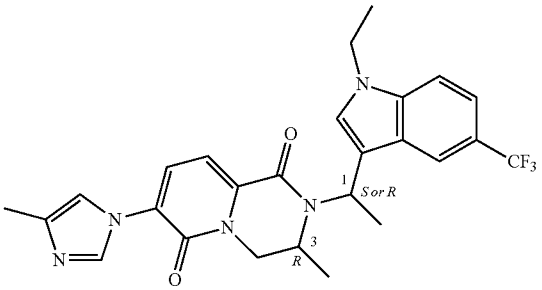

A mixture of compound 212 and compound 213 (358 mg, 0.76 mmol) was dissolved in DMF (8.7 mL) under $N_2$ flow, NaH (60% in mineral oil, 38 mg, 0.95 mmol) was added and the r.m. was stirred for 15 min. Iodoethane (69 μL, 0.86 mmol) was added and the r.m. was stirred at r.t. for 90 min, then aq. sat. $NH_4Cl$ was added. The mixture was extracted with EtOAc, the combined organic layers were dried over $MgSO_4$, filtered and the solvents were evaporated in vacuo to give a crude, which was triturated with DIPE, dried in the vacuum oven overnight and then purified by preparative SFC (Chiralpak Diacel AD 30×250 mm, mobile phase ($CO_2$, EtOH with 0.2% $iPrNH_2$)). The desired fractions were collected, evaporated, dissolved in MeOH and evaporated again. Yield: 134 mg of compound 216 (1R or 1S, 3R; diastereoisomer A (SFC-MS)) and 26 mg of compound 217 (1S or 1R, 3R; diastereoisomer B (SFC-MS)).

Example B34 a) Preparation of Compound 222

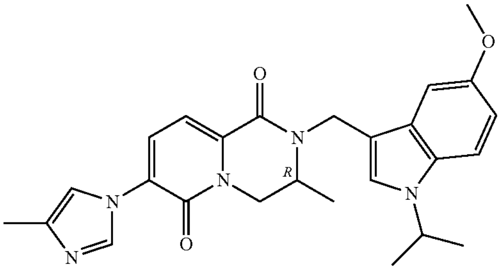

Starting from compound 201, compound 222 was obtained following an analogous synthetic route as described for compound 181 (Example B24). The crude material was purified by preparative HPLC (RP SunFire Prep C18 OBD-10 μm, 30×150 mm; Mobile phase: 0.25% $NH_4HCO_3$ solution in water, acetonitrile), to yield compound 222 (27 mg, 33%).

Example B35 a) Preparation of Compound 225

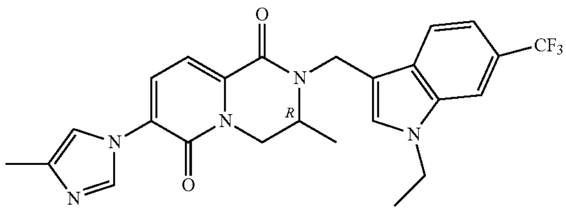

Starting from compound 203, compound 225 was obtained following an analogous synthetic route as described for compound 181 (Example B24). The crude material was purified by preparative HPLC (RP SunFire Prep C18 OBD-10 μm, 30×150 mm; Mobile phase: 0.25% $NH_4HCO_3$ solution in water, acetonitrile), to yield compound 225 (15 mg, 29%).

Example B36 a) Preparation of Compound 208 and 209

208

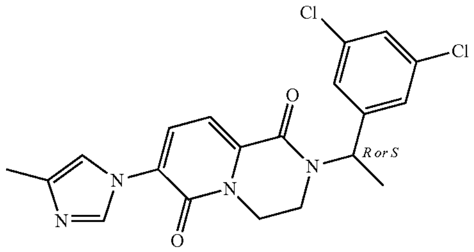

-continued

209

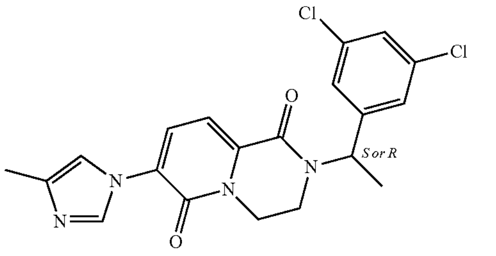

Starting from intermediate 173 and intermediate 193, a mixture of compound 208 and compound 209 was obtained following an analogous procedure as described for compound 6 (Example B6), in the presence of 1 eq. of lithium bromide. The mixture was subsequently separated into enantiomers by preparative SFC (Chiralcel Diacel OD 20×250 mm, mobile phase ($CO_2$, MeOH with 0.2% $iPrNH_2$). The desired fractions were collected, evaporated, dissolved in MeOH and evaporated again. Yield: 92 mg of compound 208 (13%; R or S; enantiomer B (SFC-MS)) and 86 mg of compound 209 (13%; S or R; enantiomer A (SFC-MS)).

Example B37 a) Preparation of Compounds 236 and 237

236

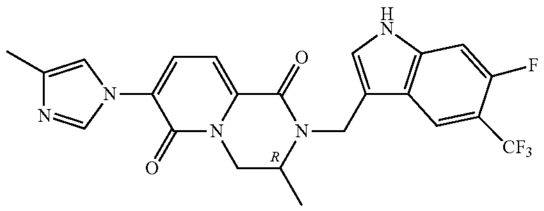

237

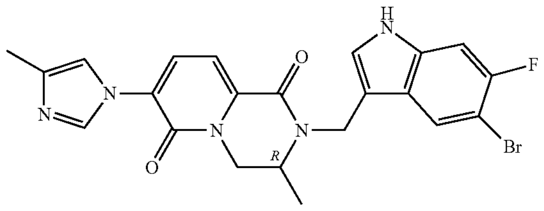

Starting from intermediate 213, a mixture of compound 236 and compound 237 (derived from an impurity present in intermediate 213) was obtained following an analogous procedure as described for compound 125 (Example B17). The mixture was subsequently separated into enantiomers by preparative SFC (Chiralcel Diacel OJ 20×250 mm, mobile phase ($CO_2$, MeOH with 0.4% $iPrNH_2$). The desired fractions were collected and evaporated. Yield: 121 mg of compound 236 (17%) and 190 mg of compound 237 (26%).

Example B38 a) Preparation of Compound 162

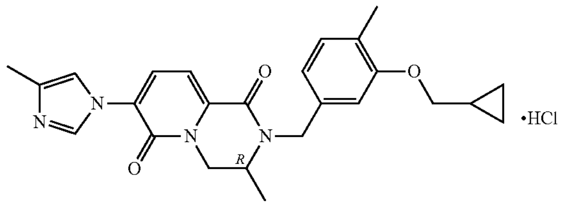

Starting from intermediate 225, compound 162 was obtained following an analogous procedure as described for compound 6 (Example B6). The crude r.m. was purified by reverse phase (90% water (0.1% acetic acid), 10% acetonitrile to 54% water (0.1% acetic acid), 46% acetonitrile). The product (0.1 g) was dissolved in EtOAc (2 mL), then HCl (4M in dioxane, 0.064 mL, 0.255 mmol) was added to obtain the hydrochloride salt. The solvent was evaporated and the product was triturated with DIPE to yield a white solid. Yield: 79 mg of compound 162 (25%).

Example B39 a) Preparation of Compound 174 and Compound 242

174

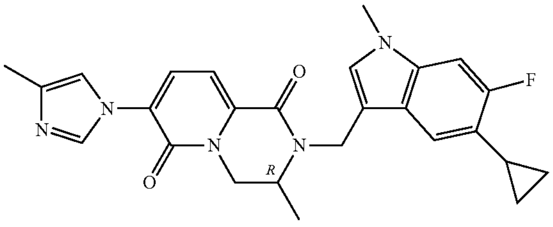

242

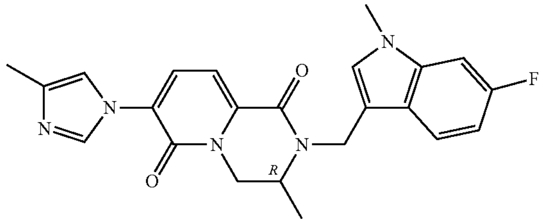

A pressure tube was charged with compound 239 (175 mg, 0.35 mmol), cyclopropylboronic acid (40 mg, 0.46 mmol), tricyclohexylphosphine (10 mg, 0.04 mmol) and toluene (1.7 mL). Then, $Pd(OAc)_2$ (8 mg, 0.02 mmol) and ground $K_3PO_4$ (261 mg, 1.23 mmol) were added. Finally, water (0.1 mL) was added and the tube was capped and placed in a preheated oil bath of 120° C. and stirring was continued for 2 h. More cyclopropylboronic acid, $Pd(OAc)_2$ and tricyclohexylphosphine were added, and the mixture was stirred overnight at 90° C. The r.m. was then cooled and diluted with water (5 mL). The layers were separated and the aqueous layer was extracted with toluene (5 mL). The combined organic layers were treated with brine (10 mL), dried over $MgSO_4$, filtered and concentrated in vacuo. The resulting residue was resubmitted to the same reaction conditions, using the same amounts of equivalents. The crude obtained was then purified by flash column chromatography (silica; DCM/MeOH 100/0 to 94/6). The product fractions were collected and purified again by Prep HPLC (RP SunFire Prep C18 OBD-10 μm 30×150 mm, mobile phase: 0.25% $NH_4HCO_3$ solution in water, MeOH), to yield compound 174 (13 mg, 8%) and compound 242 (2 mg, 1%).

Example B40 a) Preparation of Compound 244

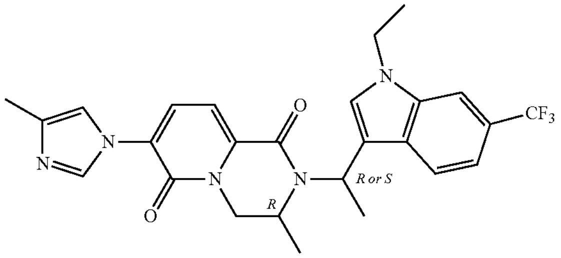

Starting from compound 234, compound 244 was obtained following an analogous procedure as described for compound 181 (Example B24). The r.m. was purified by Prep HPLC (RP SunFire Prep C18 OBD-10 μm, 30×150 mm, mobile phase: 0.25% $NH_4HCO_3$ solution in water, acetonitrile). After evaporation of the solvent, the product was dissolved in MeOH and the solvent was removed under reduced pressure (×2). The residue was dissolved in DCM/heptane and the solvents were evaporated under nitrogen flow. The residue was dried in vacuo at 50° C. 48 h. Yield: 145 mg of compound 244 (46%).

Example B41 a) Preparation of Compound 246

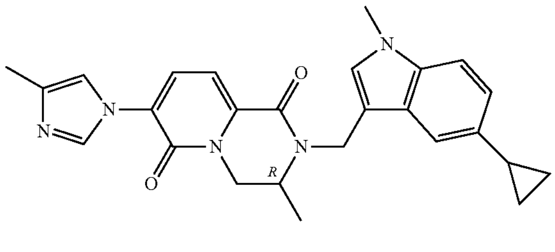

Starting from compound 277, compound 246 was obtained following an analogous procedure as described for compound 181 (Example B24). The r.m. was purified by Prep HPLC (RP SunFire Prep C18 OBD-10 μm, 30×150 mm, mobile phase: 0.25% $NH_4HCO_3$ solution in water, acetonitrile). Yield: 55 mg of compound 246 (44%).

Example B42 a) Preparation of Compound 247

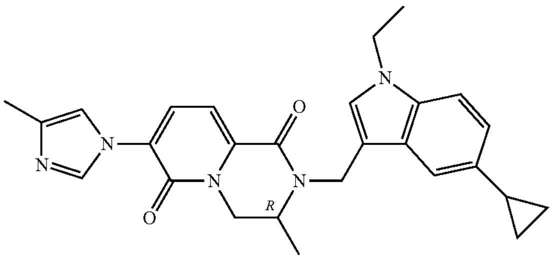

Starting from compound 277, compound 247 was obtained following an analogous procedure as described for compound 181 (Example B24). The r.m. was purified by Prep HPLC (RP SunFire Prep C18 OBD-10 μm, 30×150 mm, mobile phase: 0.25% $NH_4HCO_3$ solution in water, acetonitrile). Yield: 48 mg of compound 247 (36%).

Example B43 a) Preparation of Compound 248

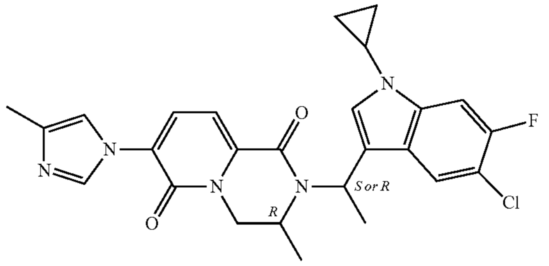

To a suspension of compound 188 (100 mg, 0.22 mmol), cyclopropylboronic acid (38 mg, 0.44 mmol) and sodium carbonate (47 mg, 0.44 mmol) in 1,2-dichloroethane (350 μL) was added a suspension of copper acetate (41 mg, 0.23 mmol) and 4,4'-di-tert-butyl-2,2'-bipyridyl (62 mg, 0.23 mmol) in hot 1,2-dichloroethane (600 μL, 50° C.). The mixture was warmed to 70° C. and stirred for 6 h and 30 min under air. The r.m. was then cooled to r.t. and sat. $NH_4Cl$ sol. was added, followed by water. The org. layer was separated and the aq. layer was extracted with DCM (×3). The combined org. layers were washed with brine, dried over $MgSO_4$, and concentrated in vacuo to afford a crude, which was purified by flash column chromatography (silica; DCM/MeOH 100/0 to 95/5). The fractions containing the product were collected and concentrated in vacuo. Yield: 58 mg of compound 248 (53%).

Example B44 a) Preparation of Compound 251

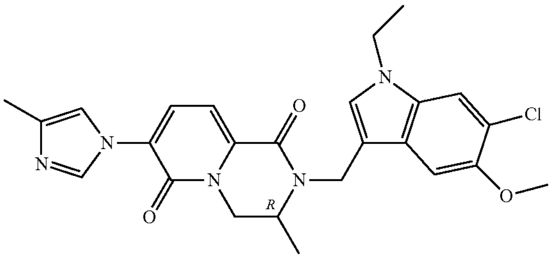

Starting from compound 279, compound 251 was obtained following an analogous procedure as described for compound 181 (Example B24). The r.m. was purified by Prep HPLC (RP Vydac Denali C18-10 μm, 200 g, 5 cm, mobile phase: 0.25% $NH_4HCO_3$ solution in water, acetonitrile). Yield: 100 mg of compound 251 (44%).

Example B45 a) Preparation of Compound 256

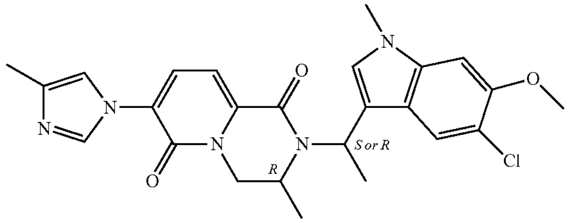

Starting from compound 282, compound 256 was obtained following an analogous procedure as described for compound 181 (Example B24). The r.m. was purified by Prep SFC (Chiralcel Diacel OJ 20×250 mm, mobile phase: $CO_2$, MeOH with 0.2% $iPrNH_2$). The desired fractions were collected, evaporated, dissolved in MeOH and evaporated again. Yield: 14 mg of compound 256 (24%).

Example B46 a) Preparation of Compounds 284 (Racemic Mixture), 267 (R or S Enantiomer) and 268 (S or R Enantiomer)

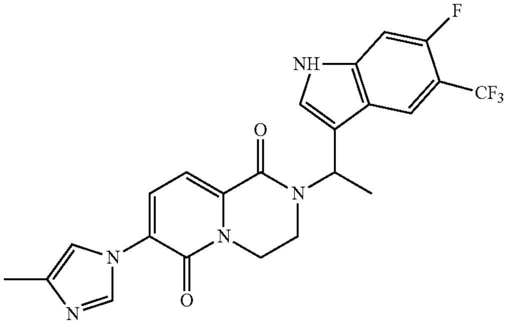 [SMILES: Cc1cn(-c2ccc3n(c2=O)CCN(C(C)c2c[nH]c4cc(F)c(C(F)(F)F)cc24)C3=O)cn1]

Starting from intermediate 243, compound 284 was obtained following an analogous procedure as described for compound 125 (Example B17). The r.m. was purified by Prep SFC (Chiralcel Diacel AD 30×250 mm, mobile phase: $CO_2$, EtOH with 0.2% $iPrNH_2$). The desired fractions were collected, evaporated, dissolved in MeOH and evaporated again. Yield: 40 mg of compound 267 and 44 mg of compound 268.

Example B47 a) Preparation of Compounds 285 (Racemic Mixture), 265 (R or S Enantiomer) and 266 (S or R Enantiomer)

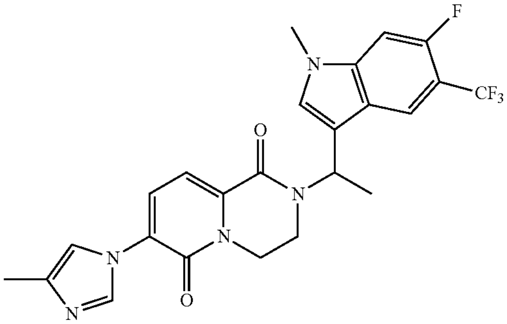 [SMILES: Cc1cn(-c2ccc3n(c2=O)CCN(C(C)c2cn(C)c4cc(F)c(C(F)(F)F)cc24)C3=O)cn1]

Starting from compound 284, compound 285 was obtained following an analogous procedure as described for compound 181 (Example B24). The r.m. was purified by Prep SFC (Chiralcel Diacel AD 30×250 mm, mobile phase: $CO_2$, EtOH with 0.2% $iPrNH_2$). The desired fractions were collected, evaporated, dissolved in MeOH and evaporated again. Yield: 135 mg of compound 265 (19%) and 130 mg of compound 266 (18%).

Example B48 a) Preparation of Compounds 287 (Racemic Mixture), 271 (R or S Enantiomer) and 272 (S or R Enantiomer)

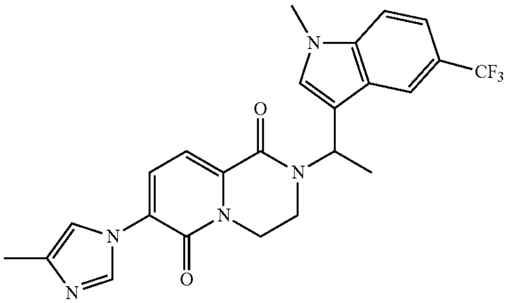 [SMILES: Cc1cn(-c2ccc3n(c2=O)CCN(C(C)c2cn(C)c4ccc(C(F)(F)F)cc24)C3=O)cn1]

Starting from compound 286, compound 287 was obtained following an analogous procedure as described for compound 181 (Example B24). The r.m. was purified by Prep SFC (Chiralcel Diacel OD 20×250 mm, mobile phase: $CO_2$, EtOH with 0.4% $iPrNH_2$). The desired fractions were collected, evaporated, dissolved in MeOH and evaporated again. Yield: 63 mg of compound 271 (25%) and 69 mg of compound 272 (27%).

Example B49 a) Preparation of Compound 262

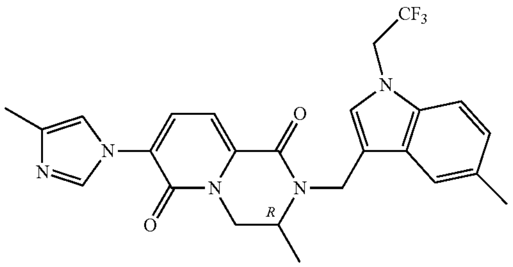

At r.t. and under $N_2$, NaH (60% in mineral oil, 21 mg, 0.523 mmol) was added to a solution of compound 278 (210 mg, 0.523 mmol) in DMF (0.49 mL). The r.m. was stirred at r.t. for 15 min and 2,2,2-trifluoroethyl perfluorobutylsulfonate (220 mg, 0.575 mmol) was added. The r.m. was stirred for 1.5 h, then DMF was removed under reduced pressure. The residue was dissolved in DCM and a few drops of MeOH and the org. solution was washed with water, dried through Extrelut® and the solvent was evaporated to afford a crude, which was purified by flash column chromatography (silica; DCM/MeOH 100/0 to 96/4). The fractions containing the product were repurified by Prep HPLC (RP Vydac Denali C18-10 μm, 200 g, 5 cm, mobile phase: 0.25% $NH_4HCO_3$ solution in water, acetonitrile) Yield: 48 mg of compound 262 (19%).

Example B50 a) Preparation of Compounds 289 (Racemic Mixture), 273 (R or S Enantiomer) and 274 (S or R Enantiomer)

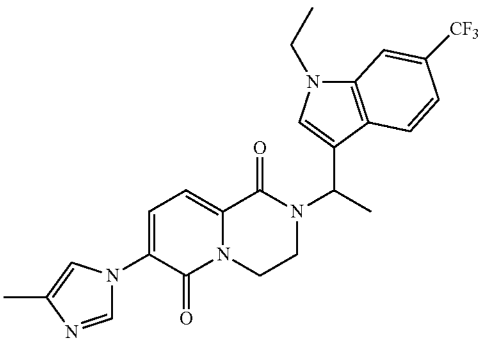 [SMILES: CCn1cc(C(C)N2CCn3c(ccc(-n4cnc(C)c4)c3=O)C2=O)c2ccc(C(F)(F)F)cc21]

Starting from compound 288, compound 289 was obtained following an analogous procedure as described for compound 181 (Example B24). The r.m. was purified by Prep SFC (Chiralcel Diacel AD 30×250 mm, mobile phase: $CO_2$, EtOH with 0.2% $iPrNH_2$). The desired fractions were collected, evaporated, dissolved in MeOH and evaporated again. Yield: 23 mg of compound 273 (27%) and 23 mg of compound 274 (27%).

Example B51 a) Preparation of Compounds 294 (Racemic Mixture), 295 (R or S Enantiomer) and 296 (S or R Enantiomer)

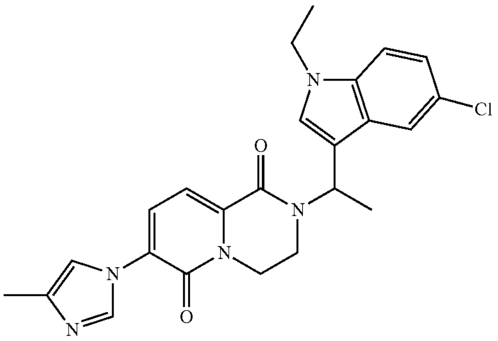 [SMILES: CCn1cc(C(C)N2CCn3c(ccc(-n4cnc(C)c4)c3=O)C2=O)c2cc(Cl)ccc21]

Starting from compound 293, compound 294 was obtained following an analogous procedure as described for compound 181 (Example B24). The r.m. was purified by Prep SFC (Chiralcel Diacel OD 20×250 mm, mobile phase: $CO_2$, EtOH with 0.2% $iPrNH_2$). The desired fractions were collected, evaporated, dissolved in MeOH and evaporated again. Yield: 96 mg of compound 295 (27%) and 100 mg of compound 296 (28%).

By using analogous reaction protocols as described in the foregoing examples, the compounds listed in Tables 1a, 1b, 1c, 1d, 1e, 1f and 1g have been prepared. 'Co. No.' means compound number. 'cb' means covalent bond. 'Pr.' refers to the Example number in analogy to which protocol the compound was synthesized.

In case no specific stereochemistry is indicated for a stereocenter of a compound, this means that the compound was obtained as a mixture of the R and the S enantiomers. In case no salt form is indicated, the compound was obtained as a free base.

B3* refers to a reaction protocol analogue to B3, but no ligand was used and the reaction was performed under microwave conditions.

TABLE 1a
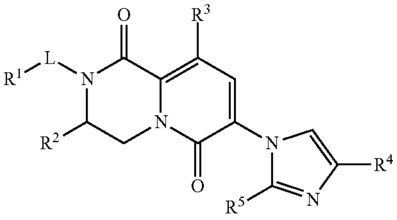
| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 15 | B3 | 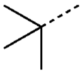 | 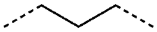 | H | H | $CH_3$ | H | |
| 16 | B3 | H | 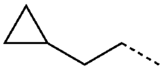 | H | H | H | $(CH_2)_2CH_3$ | |
| 17 | B3 | H | 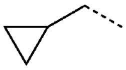 | H | H | H | $(CH_2)_2CH_3$ | |
| 18 | B3 | H | 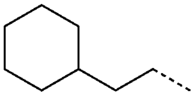 | H | H | $CH_3$ | H | |
| 19 | B3 | 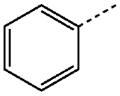 | $CH_2$ | H | H | $CH_3$ | H | |
| 20 | B3 | 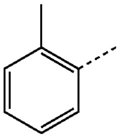 | 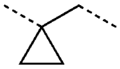 | $CH_3$ | H | $CH_3$ | H | R enantiomer |
| 21 | B3 | 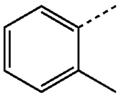 | $CH_2$ | $CH_3$ | H | $CH_3$ | H | R enantiomer |
| 22 | B3 | 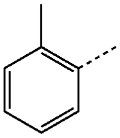 | $CH_2$ | H | H | $CH_3$ | H | |
| 23 | B3 | 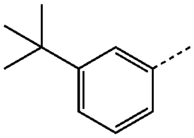 | $CH_2$ | $CH_3$ | H | $CH_3$ | H | R enantiomer |
| 24 | B3 | 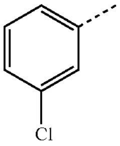 | $CH_2$ | $CH_3$ | H | $CH_3$ | H | R-enantiomer •HCl |
| 25 | B3 | 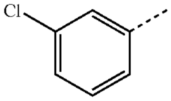 | $CH_2$ | H | H | $CH_3$ | H | |

TABLE 1a-continued
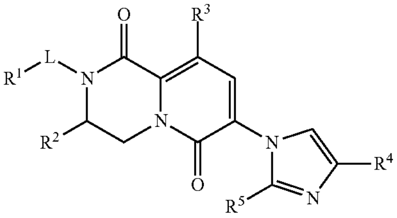
| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 26 | B3 | 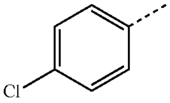 | $(CH_2)_2$ | H | H | $CH_3$ | H | |
| 27 | B3 | 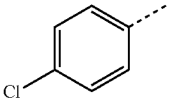 | $CH_2O(CH_2)_2$ | H | H | $CH_3$ | H | |
| 28 | B3 | 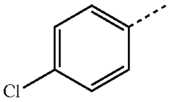 | 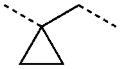 | $CH_3$ | H | $CH_3$ | H | R enantiomer |
| 29a | B3 | 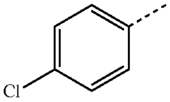 | 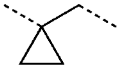 | H | H | $CH_3$ | H | •HCl |
| 29 | B3 | 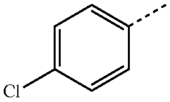 | 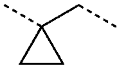 | H | H | $CH_3$ | H | |
| 30 | B1 | 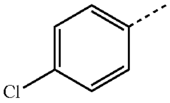 | 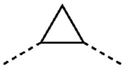 | H | H | $CH_3$ | H | TRANS |
| 2 | B2 | 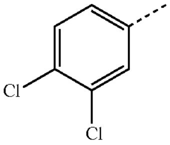 | $CH_2$ | $CH_3$ | H | $CH_3$ | H | R enantiomer |
| 31 | B1 | 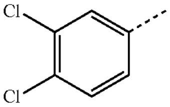 | $CH_2$ | 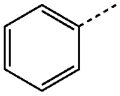 | H | $CH_3$ | H | R enantiomer |
| 32 | B1 | 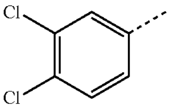 | $CH_2$ | 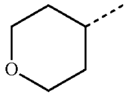 | H | $CH_3$ | H | |
| 33 | B1 | 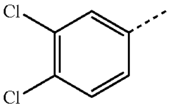 | $CH_2$ | 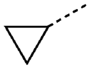 | H | $CH_3$ | H | R enantiomer |

TABLE 1a-continued

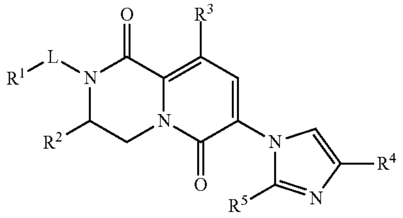

| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 34 | B2 | 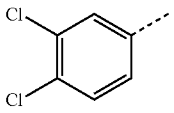 | $CH_2$ | $CH(CH_3)_2$ | H | $CH_3$ | H | R enantiomer |
| 35 | B3 | 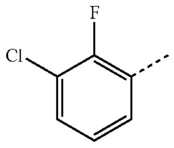 | $CH_2$ | $CH_3$ | H | $CH_3$ | H | R enantiomer |
| 36 | B3 | 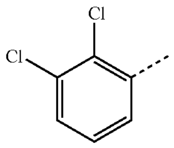 | $CH_2$ | H | H | $CH_3$ | H | |
| 37 | B3* | 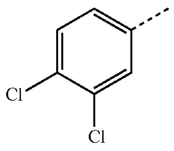 | $CH_2$ | $CH_3$ | H | $CH_3$ | H | S enantiomer |
| 9 | B9 | 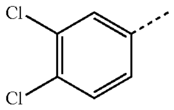 | $CH(CH_3)$ | H | H | $CH_3$ | H | racemic mixture |
| 38 | B3 | 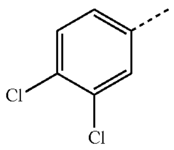 | $CH_2$ | H | H | $CH_3$ | H | |
| 9a | B9 | 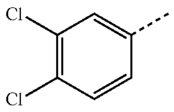 | $CH(CH_3)$ | H | H | $CH_3$ | H | R or S enantiomer OR: −121.40° (589 nm; 20° C.; 0.500 w/v %; DMF) |
| 9b | B9 | 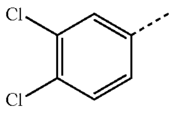 | $CH(CH_3)$ | H | H | $CH_3$ | H | S or R enantiomer |
| 10 | B10 | 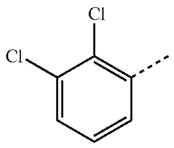 | $CH(CH_3)$ | H | H | $CH_3$ | H | racemic mixture |

TABLE 1a-continued

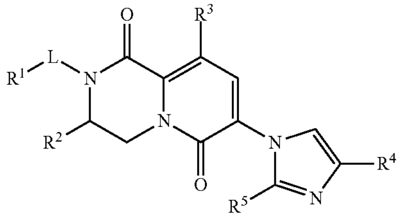

| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 10a | B10 | 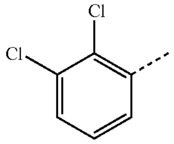 | $CH(CH_3)$ | H | H | $CH_3$ | H | R or S enantiomer OR: +193.67° (589 nm; 20° C.; 0.300 w/v %; DMF) |
| 10b | B10 | 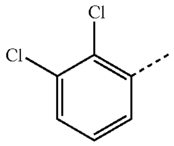 | $CH(CH_3)$ | H | H | $CH_3$ | H | S or R enantiomer OR: −168.07° (589 nm; 20° C.; 0.285 w/v %; DMF) |
| 39 | B3 | 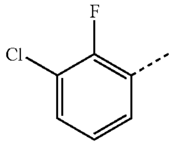 | $CH_2$ | H | H | $CH_3$ | H | |
| 40 | B3 | 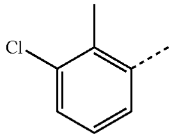 | $CH_2$ | $CH_3$ | H | $CH_3$ | H | R enantiomer |
| 41 | B3 | 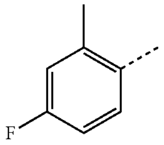 | cb | H | H | $CH_3$ | H | |
| 42 | B3 | 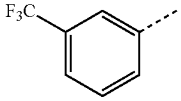 | $CH_2$ | H | H | $CH_3$ | H | |
| 11 | B11 | 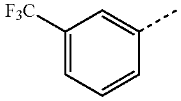 | $CH(CH_3)$ | H | H | $CH_3$ | H | racemic mixture |
| 11b | B11 | 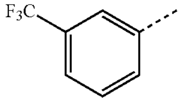 | $CH(CH_3)$ | H | H | $CH_3$ | H | S or R enantiomer; enantiomer B (SFC-MS) |
| 11a | B11 | 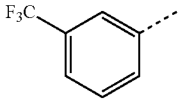 | $CH(CH_3)$ | H | H | $CH_3$ | H | R or S enantiomer; enantiomer A (SFC-MS) |

TABLE 1a-continued

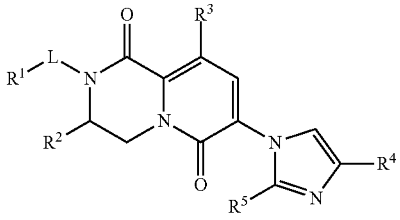

| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 43 | B3 | 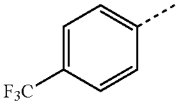 | $CH_2$ | $CH_3$ | H | $CH_3$ | H | R enantiomer |
| 8 | B8 | 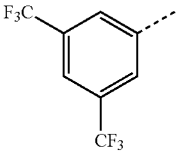 | $CH_2$ | 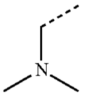 | H | $CH_2CH_3$ | H | R-enantiomer |
| 44 | B3 | 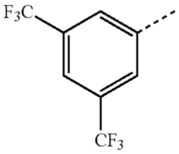 | $CH_2$ | $CH_3$ | H | $CH_3$ | H | S enantiomer |
| 13 | B13 | 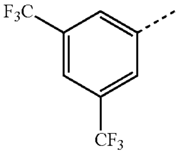 | $CH_2$ | $CH_2OH$ | H | $CH_2CH_3$ | H | S enantiomer |
| 45 | B7 | 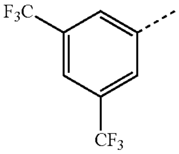 | $CH_2$ | $CH_2OH$ | H | $CH_3$ | H | S enantiomer |
| 3 | B3 | 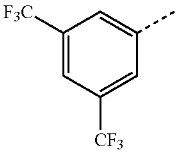 | $CH_2$ | $CH_3$ | H | $CH_3$ | H | R enantiomer OR: −25.04° (589 nm; 20° C.; 2.2405 w/v %; DMF) |
| 46 | B3 | 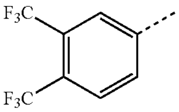 | $CH_2$ | $CH_3$ | H | $CH_3$ | H | R enantiomer |
| 47 | B1 | 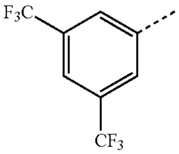 | $CH_2$ | $CH_2OCH_3$ | H | $CH_3$ | H | S enantiomer |

TABLE 1a-continued
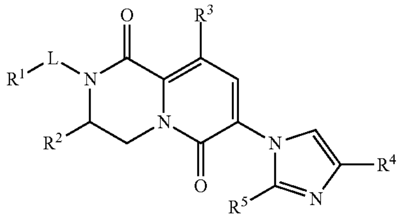
| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 48 | B8 | 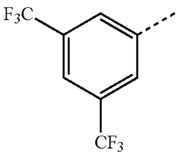 | $CH_2$ | 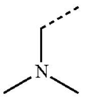 | H | $CH_3$ | H | R-enantiomer |
| 49 | B8 | 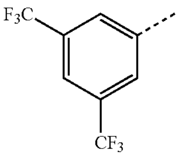 | $CH_2$ | 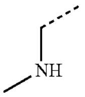 | H | $CH_3$ | H | R-enantiomer |
| 1 | B1 | 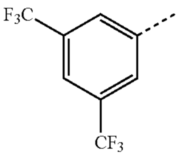 | $CH_2$ | $CH_2CH_3$ | H | $CH_3$ | H | R-enantiomer •HCl |
| 50 | B7 | 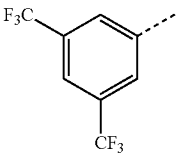 | $(CH_2)_2$ | $CH_3$ | H | $CH_3$ | H | R enantiomer |
| 7 | B7 | 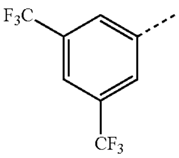 | $CH_2$ | $CH_3$ | H | $CH_2CH_3$ | H | R-enantiomer •HCl |
| 51 | B1 | 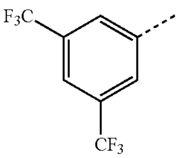 | 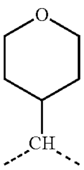 | H | H | $CH_3$ | H | |
| 52 | B3 | 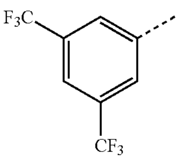 | 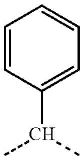 | H | H | $CH_3$ | H | racemic mixture |

TABLE 1a-continued
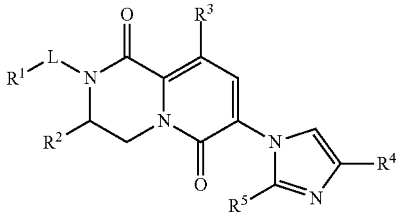
| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 53 | B3 | 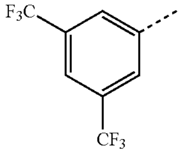 | $CH_2$ | H | H | $CH_3$ | H | |
| 54 | B7 | 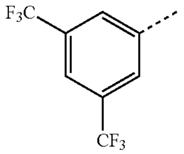 | 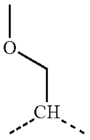 | H | H | $CH_3$ | H | |
| 55 | B3 | 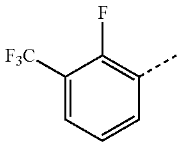 | cb | H | H | $CH_3$ | H | |
| 56 | B3 | 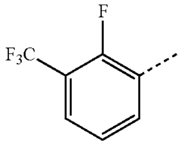 | $CH_2$ | H | H | $CH_3$ | H | |
| 57 | B1 | 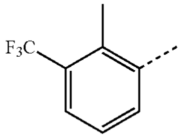 | cb | H | H | $CH_3$ | H | |
| 58 | B3 | 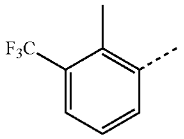 | $CH_2$ | H | H | $CH_3$ | H | |
| 59 | B3 | 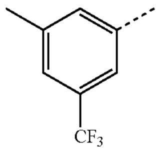 | $CH_2$ | $CH_3$ | H | $CH_3$ | H | R enantiomer |
| 60 | B3 | 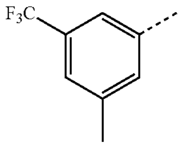 | $CH_2$ | H | H | $CH_3$ | H | |

TABLE 1a-continued
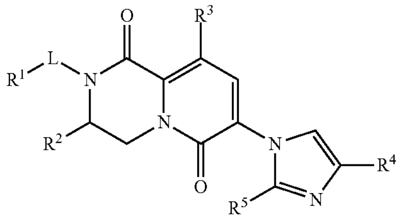
| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 61 | B1 | 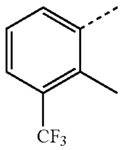 | $CH_2$ | $CH_3$ | H | $CH_3$ | H | R enantiomer |
| 62 | B1 | 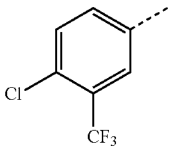 | $CH_2$ | $CH_3$ | H | $CH_3$ | H | R enantiomer |
| 63 | B3 | 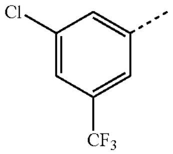 | $CH_2$ | $CH_3$ | H | $CH_3$ | H | R enantiomer |
| 64 | B3 | 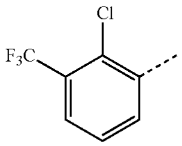 | $CH_2$ | H | H | $CH_3$ | H | |
| 65 | B3 | 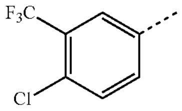 | H | H | $CH_3$ | H | | |
| 66 | B3 | 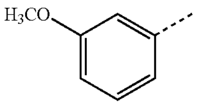 | $CH_2$ | H | H | $CH_3$ | H | |
| 67 | B3 | 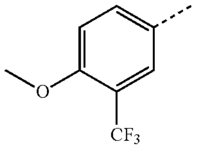 | $CH_2$ | $CH_3$ | H | $CH_3$ | H | R enantiomer |
| 68 | B3 | 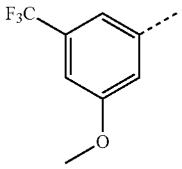 | $CH_2$ | $CH_3$ | H | $CH_3$ | H | R enantiomer |

TABLE 1a-continued
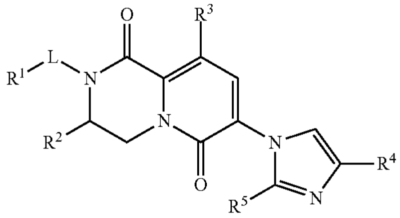
| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 69 | B3 | 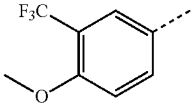 | $CH_2$ | H | H | $CH_3$ | H | |
| 70 | B7 | 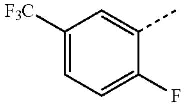 | $CH_2$ | $CH_3$ | H | $CH_3$ | H | R enantiomer |
| 71 | B7 | 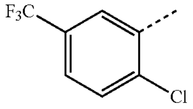 | $CH_2$ | $CH_3$ | H | $CH_3$ | H | R enantiomer |
| 72 | B7 | 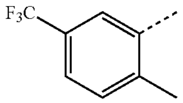 | $CH_2$ | $CH_3$ | H | $CH_3$ | H | R-enantiomer •HCl |
| 73 | B3 | 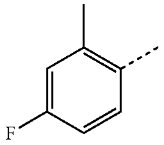 | $CH_2$ | H | H | $CH_3$ | H | |
| 74 | B3 | 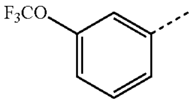 | $CH_2$ | H | H | $CH_3$ | H | |
| 75 | B3 | 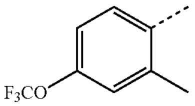 | $CH_2$ | H | H | $CH_3$ | H | |
| 76 | B6 | 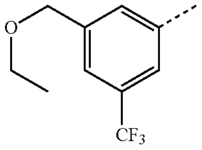 | $CH_2$ | $CH_3$ | H | $CH_3$ | H | R-enantiomer •HCl |
| 77 | B7 | 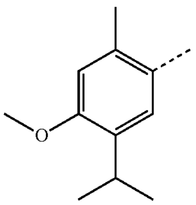 | $CH_2$ | $CH_3$ | H | $CH_3$ | H | R enantiomer •HCl |

TABLE 1a-continued
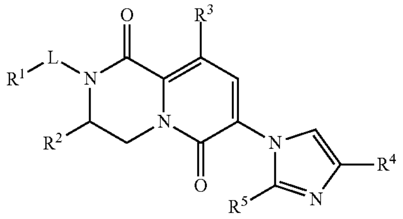
| Co. No. | Pr. | R¹ | L | R² | R³ | R⁴ | R⁵ | Salt forms/Stereo-chemistry/Optical Rotation (OR) |
|---|---|---|---|---|---|---|---|---|
| 6 | B6 | 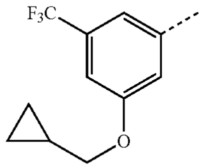 | $CH_2$ | $CH_3$ | H | $CH_3$ | H | R-enantiomer •HCl |
| 78 | B7 | 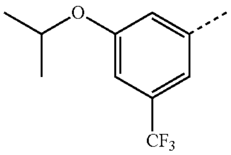 | $CH_2$ | $CH_3$ | H | $CH_3$ | H | R-enantiomer •HCl |
| 79 | B3 | 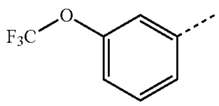 | $CH_2$ | $CH_3$ | H | $CH_3$ | H | R-enantiomer |
| 80 | B6 | 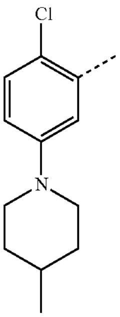 | $CH_2$ | $CH_3$ | H | $CH_3$ | H | R-enantiomer •HCl |
| 81 | B6 | 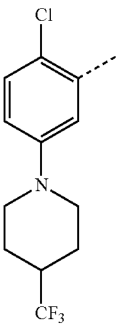 | $CH_2$ | $CH_3$ | H | $CH_3$ | H | R-enantiomer •HCl |

TABLE 1a-continued
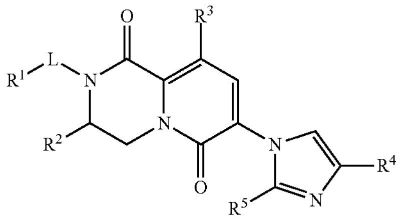
| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 82 | B6 | 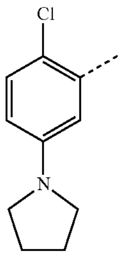 | $CH_2$ | $CH_3$ | H | $CH_3$ | H | R-enantiomer •HCl |
| 83 | B6 | 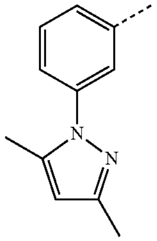 | $CH_2$ | $CH_3$ | H | $CH_3$ | H | R-enantiomer |
| 84 | B3 | 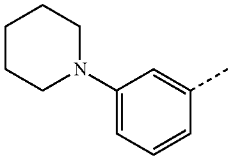 | $CH_2$ | $CH_3$ | H | $CH_3$ | H | R enantiomer |
| 4 | B4 | 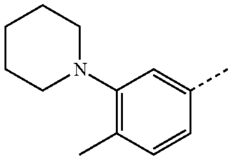 | $CH_2$ | $CH_3$ | H | $CH_3$ | H | R enantiomer •HCl |
| 4a | B4 | 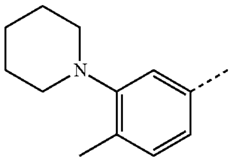 | $CH_2$ | $CH_3$ | H | $CH_3$ | H | R enantiomer |
| 85 | B6 | 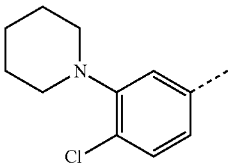 | $CH_2$ | $CH_3$ | H | $CH_3$ | H | R enantiomer |

TABLE 1a-continued
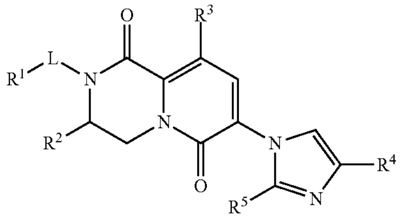
| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 86 | B6 | 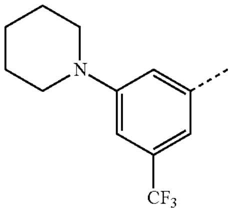 | $CH_2$ | $CH_3$ | H | $CH_3$ | H | R enantiomer •HCl |
| 87 | B3 | 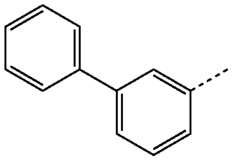 | $CH_2$ | H | H | $CH_3$ | $CH_3$ | |
| 88 | B5 | 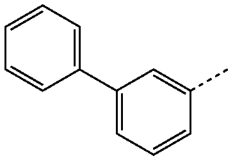 | $CH_2$ | H | Cl | $CH_3$ | H | |
| 5 | B5 | 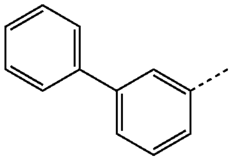 | $CH_2$ | H | H | $CH_3$ | H | |
| 90 | B3 | 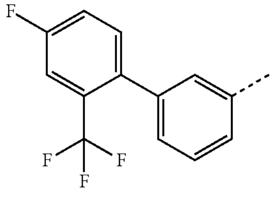 | $CH_2$ | H | H | $CH_3$ | H | |
| 91 | B3 | 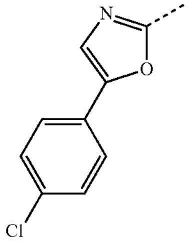 | $CH_2$ | H | H | $CH_3$ | H | |

TABLE 1a-continued
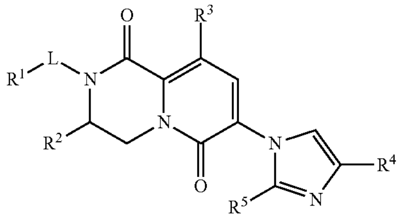
| Co. No. | Pr. | R¹ | L | $R^2$ | $R^3$ | $R^4$ | $R^5$ | Salt forms/Stereo-chemistry/Optical Rotation (OR) |
|---|---|---|---|---|---|---|---|---|
| 92 | B3 | 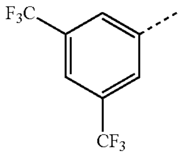 | $(CH_2)_2$ | H | H | $CH_3$ | H | |
| 93 | B3 | 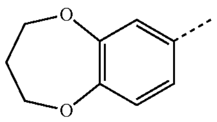 | $CH_2$ | H | H | $CH_3$ | H | |
| 94 | B3 | 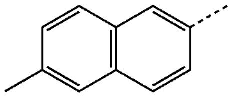 | $CH_2$ | H | H | $CH_3$ | H | |
| 95 | B3 | 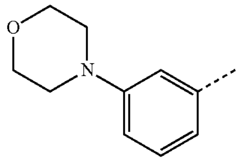 | $CH_2$ | H | H | $CH_3$ | H | |
| 96 | B3 | 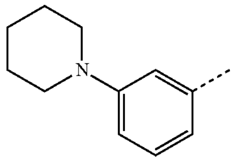 | $CH_2$ | H | H | $CH_3$ | H | |
| 97 | B3 | 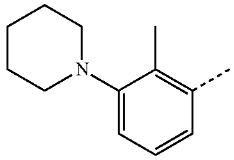 | $CH_2$ | H | H | $CH_3$ | H | |
| 98 | B1 | 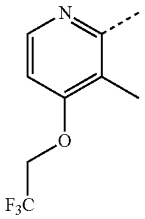 | $CH_2$ | H | H | $CH_3$ | H | |
| 99 | B3 | 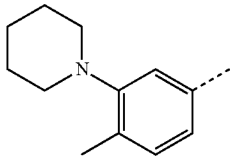 | $CH_2$ | H | H | $CH_3$ | H | |

TABLE 1a-continued
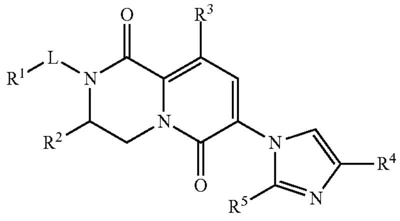
| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 100 | B3 | 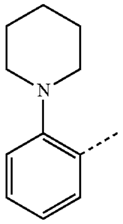 | $CH_2$ | H | H | $CH_3$ | H | |
| 101 | B3 | 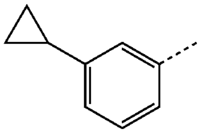 | $CH_2$ | H | H | $CH_3$ | H | |
| 102 | B1 | 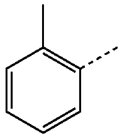 | cb | H | H | $CH_3$ | H | |
| 103 | B3 | 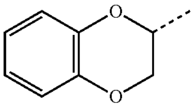 | $(CH_2)_2$ | H | H | $CH_3$ | H | |
| 104 | B1 | 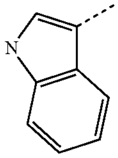 | $(CH_2)_2$ | H | H | $CH_3$ | H | |
| 105 | B1 | 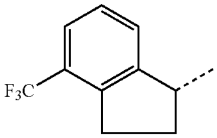 | cb | H | H | $CH_3$ | H | |
| 106 | B1 | 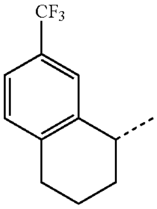 | cb | H | H | $CH_3$ | H | |

TABLE 1a-continued
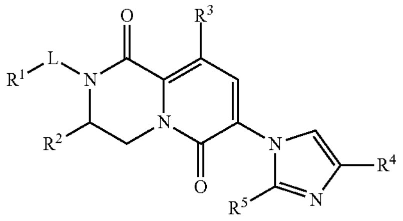
| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 107 | B1 | 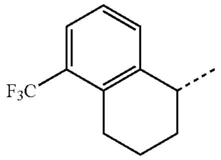 | cb | H | H | $CH_3$ | H | |
| 108 | B3 | 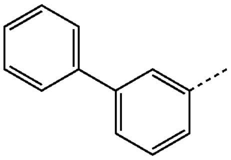 | $CH_2$ | H | H | H | $CH_3$ | |
| 109 | B3 | 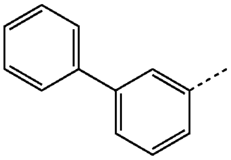 | $CH_2$ | H | H | H | H | |
| 12 | B12 | 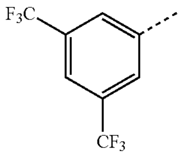 | $CH_2$ | $CH_2OCH_3$ | H | $CH_2CH_3$ | H | S enantiomer |
| 110 | B6 | 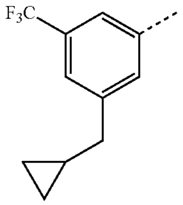 | $CH_2$ | $CH_3$ | H | $CH_3$ | H | R-enantiomer •HCl |
| 111 | B15 | 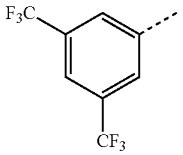 | $CH(CH_3)$ (R or S) | $CH_3$ (R) | H | $CH_3$ | H | (1R or 1S, 3R); diastereomer A (SFC-MS) •HCl |
| 112 | B16 | 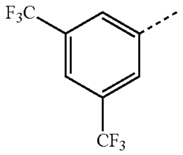 | $CH(CH_3)$ (S or R) | $CH_3$ (R) | H | $CH_3$ | H | (1S or 1R, 3R); diastereomer B (SFC-MS) •HCl |

TABLE 1a-continued
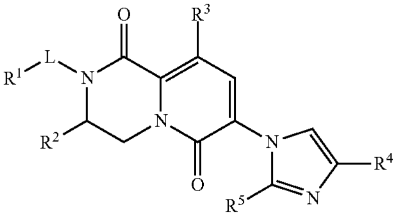
| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 113 | B3 | 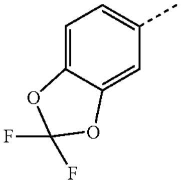 | $CH_2$ | $CH_3$ | H | $CH_3$ | H | R enantiomer |
| 114 | B6 | 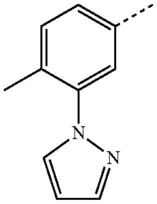 | $CH_2$ | $CH_3$ | H | $CH_3$ | H | R-enantiomer •HCl |
| 115 | B6 | 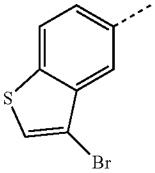 | $CH_2$ | $CH_3$ | H | $CH_3$ | H | R enantiomer |
| 116 | B6 | 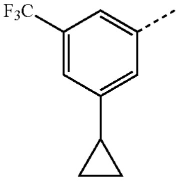 | $CH_2$ | $CH_3$ | H | $CH_3$ | H | R-enantiomer •HCl |
| 117 | B3 | 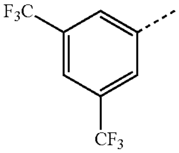 | 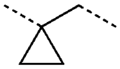 | H | H | $CH_3$ | H | |
| 118 | B3 | 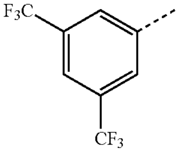 | $CH_2$ | $CH_3$ | H | Cl | H | R enantiomer |
| 175 | B20 | 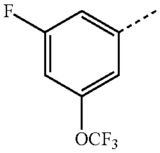 | $CH(CH_3)$ (RS) | $CH_3$ (R) | H | $CH_3$ | H | (1RS, 3R) •HCl |

TABLE 1a-continued

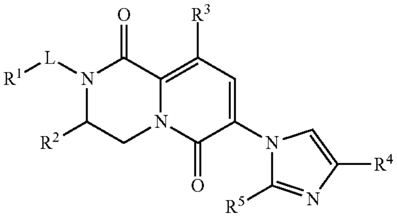

| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 176 | B6 | 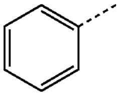 | $(CH_2)_2$ | $CH_3$ | H | $CH_3$ | H | R enantiomer |
| 177 | B18 | 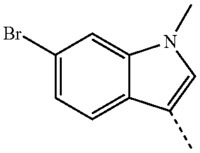 | $CH_2$ | $CH_3$ | H | $CH_3$ | H | R enantiomer |
| 178 | B18 | 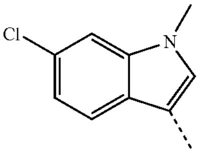 | $CH_2$ | $CH_3$ | H | $CH_3$ | H | R enantiomer |
| 179 | B19 | 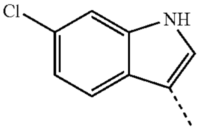 | $CH_2$ | $CH_3$ | H | $CH_3$ | H | R enantiomer |
| 124 | B6 | 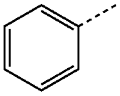 | $CH_2$ | $CH_3$ | H | $CH_3$ | H | R enantiomer |
| 125 | B17 | 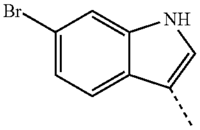 | $CH_2$ | $CH_3$ | H | $CH_3$ | H | R enantiomer |
| 126 | B20 | 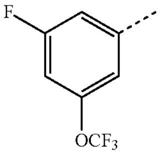 | $CH(CH_3)$ (R or S) | $CH_3$ (R) | H | $CH_3$ | H | (1R or 1S, 3R); •HCl |
| 127 | B20 | 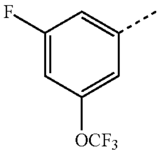 | $CH(CH_3)$ (S or R) | $CH_3$ (R) | H | $CH_3$ | H | (1S or 1R, 3R); •HCl |
| 128 | B6 | 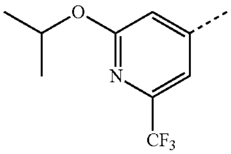 | $CH_2$ | $CH_3$ | H | $CH_3$ | H | R enantiomer •HCl |

TABLE 1a-continued

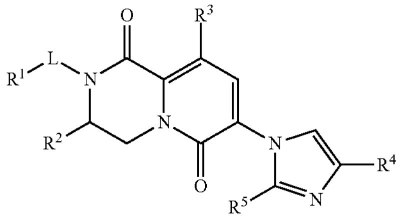

| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 129 | B21 | 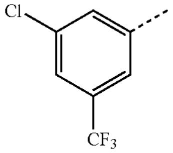 | $CH(CH_3)$ (R or S) | $CH_3$ (R) | H | $CH_3$ | H | (1R or 1S, 3R); diastereomer B (SFC-MS) |
| 130 | B21 | 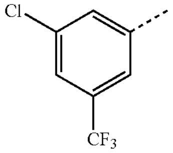 | $CH(CH_3)$ (S or R) | $CH_3$ (R) | H | $CH_3$ | H | (1S or 1R, 3R); diastereomer A (SFC-MS) |
| 131 | B6 | 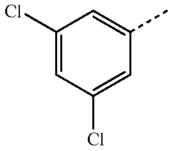 | $CH_2$ | $CH_3$ | H | $CH_3$ | H | R enantiomer |
| 132 | B3 | 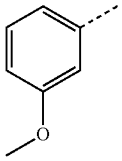 | $CH_2$ | $CH_3$ | H | $CH_3$ | H | R enantiomer OR: −15.69° (589 nm; 20°C.; 0.58 w/v %; DMF) |
| 133 | B3 | 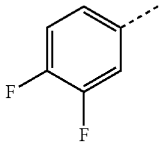 | $CH_2$ | $CH_3$ | H | $CH_3$ | H | R enantiomer |
| 134 | B6 | 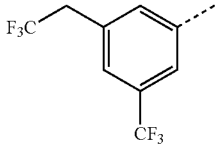 | $CH_2$ | $CH_3$ | H | $CH_3$ | H | R enantiomer; •HCl |
| 135 | B3 | 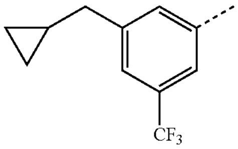 | $CH(CH_3)$ (R or S) | $CH_3$ (R) | H | $CH_3$ | H | (1R or 1S, 3R); •HCl |
| 136 | B3 | 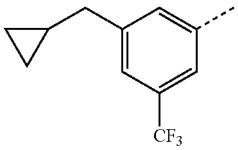 | $CH(CH_3)$ (S or R) | $CH_3$ (R) | H | $CH_3$ | H | (1S or 1R, 3R); •HCl |

TABLE 1a-continued

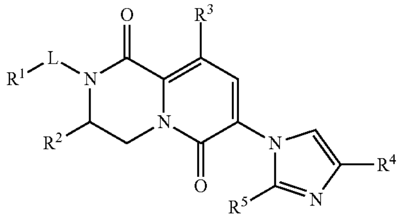

| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 137 | B18 | 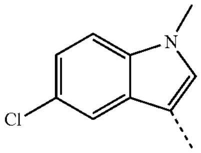 | $CH_2$ | $CH_3$ | H | $CH_3$ | H | R enantiomer OR: −13.28° (589 nm; 20° C.; 0.58 w/v %; DMF) |
| 138 | B17 | 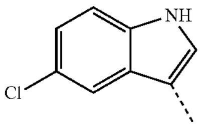 | $CH_2$ | $CH_3$ | H | $CH_3$ | H | R enantiomer |
| 139 | B6 | 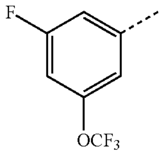 | $CH_2$ | $CH_3$ | H | $CH_3$ | H | R enantiomer; •HCl |
| 140 | B6 | 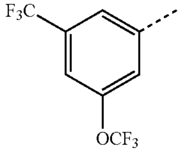 | $CH_2$ | $CH_3$ | H | $CH_3$ | H | R enantiomer; •HCl |
| 141 | B3 | 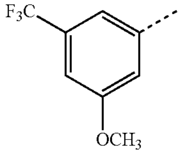 | $CH(CH_2CH_3)$ (R or S) | $CH_3$ (R) | H | $CH_3$ | H | (1R or 1S, 3R); •HCl |
| 142 | B3 | 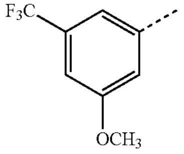 | $CH(CH_2CH_3)$ (S or R) | $CH_3$ (R) | H | $CH_3$ | H | (1S or 1R, 3R); •HCl |
| 143 | B3 | 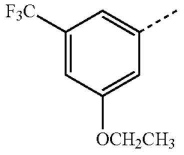 | $CH(CH_3)$ (R or S) | $CH_3$ (R) | H | $CH_3$ | H | (1R or 1S, 3R); •HCl |
| 144 | B3 | 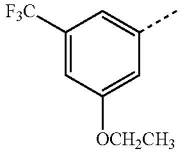 | $CH(CH_3)$ (S or R) | $CH_3$ (R) | H | $CH_3$ | H | (1S or 1R, 3R); •HCl |

TABLE 1a-continued
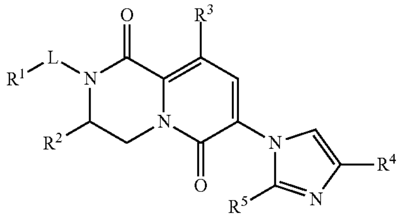
| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 145 | B6 | 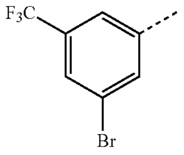 | $CH_2$ | $CH_3$ | H | $CH_3$ | H | R enantiomer; •HCl |
| 146 | B3 | 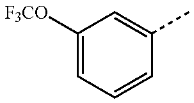 | $CH(CH_3)$ (R or S) | $CH_3$ (R) | H | $CH_3$ | H | (1R or 1S, 3R); •HCl |
| 147 | B3 | 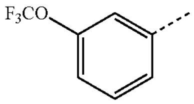 | $CH(CH_3)$ (S or R) | $CH_3$ (R) | H | $CH_3$ | H | (1S or 1R, 3R); •HCl |
| 148 | B3 | 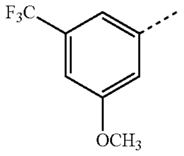 | $CH(CH_3)$ (R or S) | $CH_3$ (R) | H | $CH_3$ | H | (1R or 1S, 3R); •HCl |
| 149 | B3 | 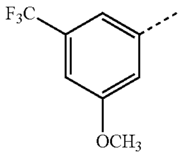 | $CH(CH_3)$ (S or R) | $CH_3$ (R) | H | $CH_3$ | H | (1S or 1R, 3R); •HCl |
| 151 | B3 | 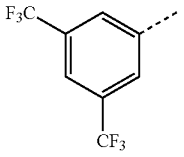 | 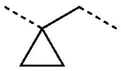 | $CH_3$ | H | $CH_3$ | H | R enantiomer •HCl |
| 152 | B6 | 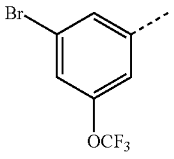 | $CH_2$ | $CH_3$ | H | $CH_3$ | H | R enantiomer; •HCl |

TABLE 1a-continued
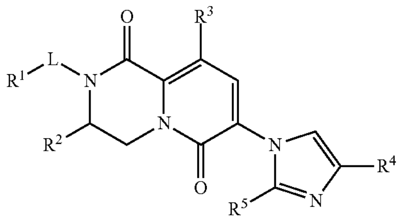
| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 153 | B3 | 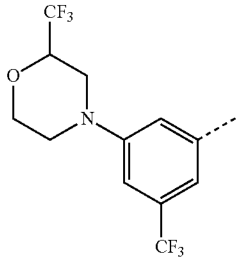 | $CH_2$ | $CH_3$ | H | $CH_3$ | H | R enantiomer; HCl salt |
| 154 | B6 | 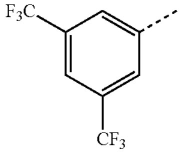 | $CH(CH_3)$ (RS) | $CH_3$ (R) | H | $CH_3$ | H | (1RS, 3R) |
| 156 | B3 | 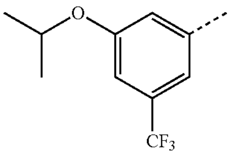 | $(CH_2)_2$ | $CH_3$ | H | $CH_3$ | H | R enantiomer; •HCl |
| 158 | B3 | 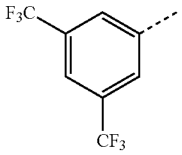 | $CH_2$ | $CH_3$ | F | $CH_3$ | H | R enantiomer OR: +10.5° (589 nm; 20° C.; 0.52 w/v %; DMF) |
| 159 | B3 | 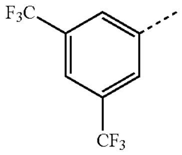 | $CH_2$ | $CH_3$ | Cl | $CH_3$ | H | R enantiomer |
| 160 | B3 | 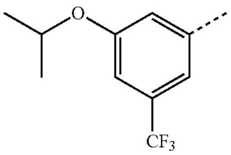 | $CH_2$ | H | H | $CH_3$ | H | |
| 163 | B3 | 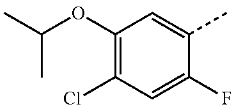 | $CH_2$ | $CH_3$ | H | $CH_3$ | H | R enantiomer; •HCl |

TABLE 1a-continued
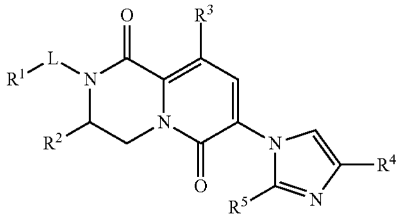
| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 164 | B3 | 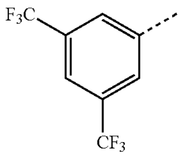 | 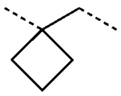 | H | H | $CH_3$ | H | |
| 165 | B6 | 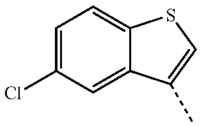 | $CH_2$ | $CH_3$ | H | $CH_3$ | H | R enantiomer |
| 166 | B3 | 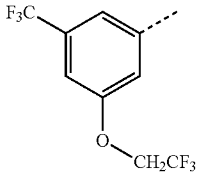 | $CH_2$ | $CH_3$ | H | $CH_3$ | H | R enantiomer; •HCl |
| 167 | B23 | 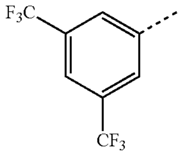 | 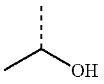 | H | $CH_3$ | H | | |
| 168 | B3 | 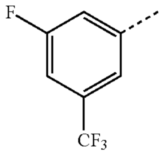 | $CH(CH_3)$ | H | H | $CH_3$ | H | |
| 169 | B3 | 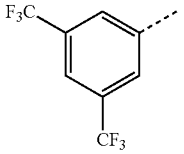 | $CH(CH_3)$ | H | H | $CH_3$ | H | |
| 170 | B3 | 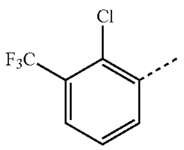 | 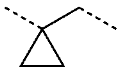 | H | H | $CH_3$ | H | |
| 171 | B6 | 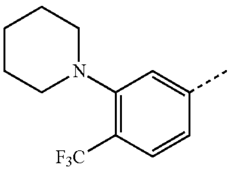 | $CH_2$ | $CH_3$ | H | $CH_3$ | H | R enantiomer; HCl salt |

TABLE 1a-continued

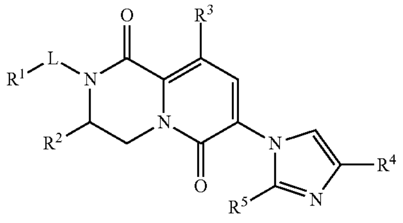

| Co. No. | Pr. | R¹ | L | R² | R³ | R⁴ | R⁵ | Salt forms/Stereo-chemistry/Optical Rotation (OR) |
|---|---|---|---|---|---|---|---|---|
| 172 | B3 | 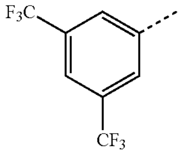 | $CH_2CH(CH_3)$ | H | H | $CH_3$ | H | |
| 180 | B17 | 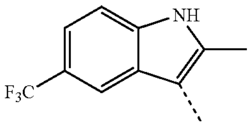 | $CH_2$ | $CH_3$ | H | $CH_3$ | H | R enantiomer |
| 181 | B24 | 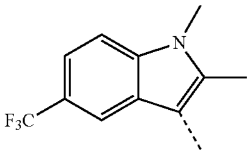 | $CH_2$ | $CH_3$ | H | $CH_3$ | H | R enantiomer |
| 182 | B24 | 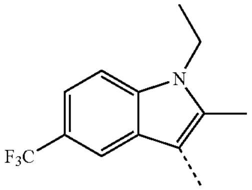 | $CH_2$ | $CH_3$ | H | $CH_3$ | H | R enantiomer |
| 183 | B25 | 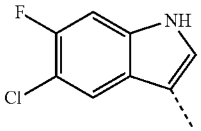 | $CH(CH_3)$ | H | H | $CH_3$ | H | R or S enantiomer; enantiomer A (SFC-MS) |
| 184 | B25 | 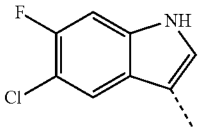 | $CH(CH_3)$ | H | H | $CH_3$ | H | S or R enantiomer; enantiomer B (SFC-MS) |
| 185 | B26 | 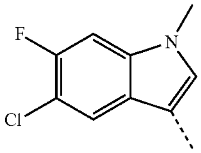 | $CH(CH_3)$ | H | H | $CH_3$ | H | R or S enantiomer; enantiomer A (SFC-MS) |
| 186 | B26 | 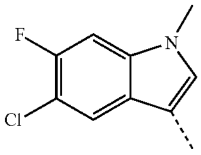 | $CH(CH_3)$ | H | H | $CH_3$ | H | S or R enantiomer; enantiomer B (SFC-MS) |

TABLE 1a-continued
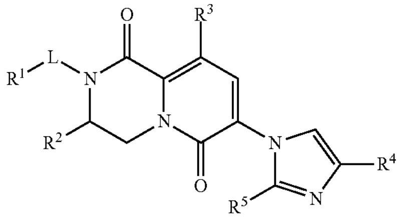
| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 187 | B17 | 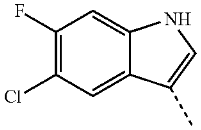 | $CH(CH_3)$ (R or S) | $CH_3$ (R) | H | $CH_3$ | H | (1R or 1S, 3R) |
| 188 | B17 | 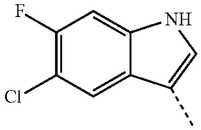 | $CH(CH_3)$ (S or R) | $CH_3$ (R) | H | $CH_3$ | H | (1S or 1R, 3R) |
| 189 | B24 | 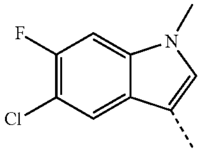 | $CH(CH_3)$ (R or S) | $CH_3$ (R) | H | $CH_3$ | H | (1R or 1S, 3R) |
| 190 | B24 | 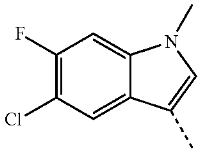 | $CH(CH_3)$ (S or R) | $CH_3$ (R) | H | $CH_3$ | H | (1S or 1R, 3R) |
| 191 | B24 | 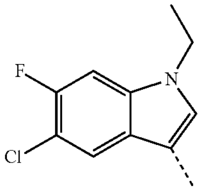 | $CH(CH_3)$ (R or S) | $CH_3$ (R) | H | $CH_3$ | H | (1R or 1S, 3R) |
| 192 | B24 | 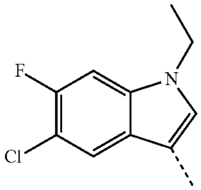 | $CH(CH_3)$ (S or R) | $CH_3$ (R) | H | $CH_3$ | H | (1S or 1R, 3R) |
| 193 | B24 | 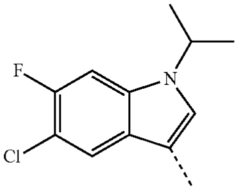 | $CH(CH_3)$ (R or S) | $CH_3$ (R) | H | $CH_3$ | H | (1R or 1S, 3R) |

TABLE 1a-continued
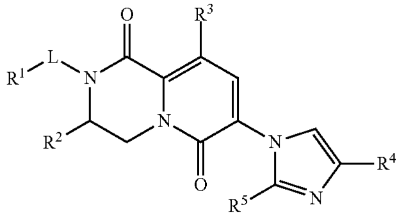
| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 194 | B24 | 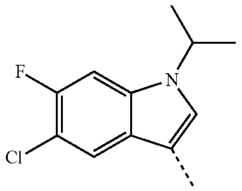 | $CH(CH_3)$ (S or R) | $CH_3$ (R) | H | $CH_3$ | H | (1S or 1R, 3R) |
| 195 | B17 | 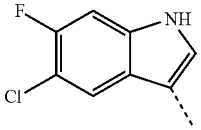 | $CH_2$ | $CH_3$ | H | $CH_3$ | H | R enantiomer |
| 196 | B24 | 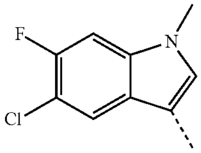 | $CH_2$ | $CH_3$ | H | $CH_3$ | H | R enantiomer |
| 197 | B17 | 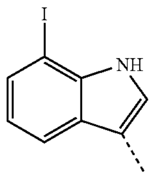 | $CH_2$ | $CH_3$ | H | $CH_3$ | H | R enantiomer |
| 198 | B27 | 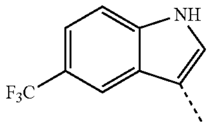 | $CH_2$ | $CH_3$ | H | $CH_3$ | H | R enantiomer |
| 199 | B28 | 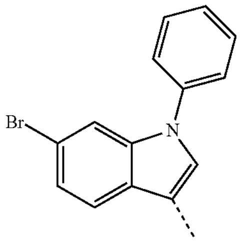 | $CH_2$ | $CH_3$ | H | $CH_3$ | H | R enantiomer |
| 200 | B24 | 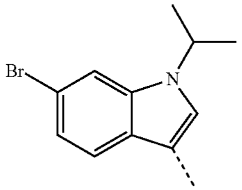 | $CH_2$ | $CH_3$ | H | $CH_3$ | H | R enantiomer |

TABLE 1a-continued

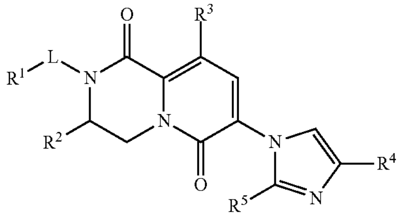

| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 201 | B17 | 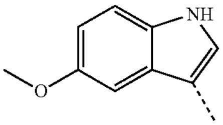 | $CH_2$ | $CH_3$ | H | $CH_3$ | H | R enantiomer |
| 202 | B17 | 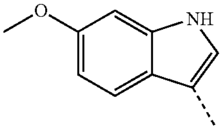 | $CH_2$ | $CH_3$ | H | $CH_3$ | H | R enantiomer |
| 203 | B29 | 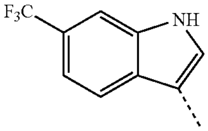 | $CH_2$ | $CH_3$ | H | $CH_3$ | H | R enantiomer |
| 206 | B30 | 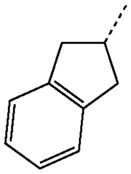 | cb | $CH_3$ | H | $CH_3$ | H | S or R enantiomer; enantiomer B (SFC-MS) |
| 207 | B30 | 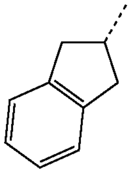 | cb | $CH_3$ | H | $CH_3$ | H | R or S enantiomer; enantiomer A (SFC-MS) |
| 208 | B21 | 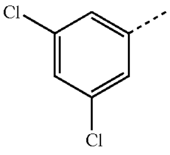 | $CH(CH_3)$ | H | H | $CH_3$ | H | R or S enantiomer; enantiomer B (SFC-MS) |
| 209 | B21 | 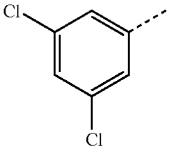 | $CH(CH_3)$ | H | H | $CH_3$ | H | S or R enantiomer; enantiomer A (SFC-MS) |
| 210 | B20 | 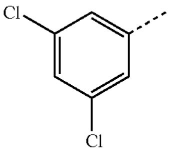 | $CH(CH_3)$ (R or S) | $CH_3$ (R) | H | $CH_3$ | H | (1R or 1S, 3R) |

TABLE 1a-continued

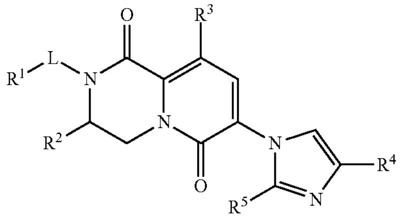

| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 211 | B20 | 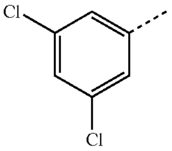 | $CH(CH_3)$ (S or R) | $CH_3$ (R) | H | $CH_3$ | H | (1S or 1R, 3R) |
| 212 | B31 | 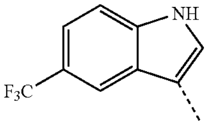 | $CH(CH_3)$ (R or S) | $CH_3$ (R) | H | $CH_3$ | H | (1R or 1S, 3R) |
| 213 | B31 | 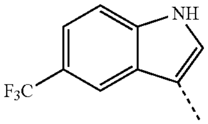 | $CH(CH_3)$ (S or R) | $CH_3$ (R) | H | $CH_3$ | H | (1S or 1R, 3R) |
| 214 | B32 | 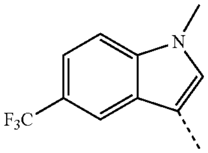 | $CH(CH_3)$ (R or S) | $CH_3$ (R) | H | $CH_3$ | H | (1R or 1S, 3R) OR: −45.62° (589 nm; 20° C.; 0.445 w/v %; DMF) |
| 215 | B32 | 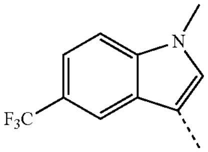 | $CH(CH_3)$ (S or R) | $CH_3$ (R) | H | $CH_3$ | H | (1S or 1R, 3R) |
| 216 | B33 | 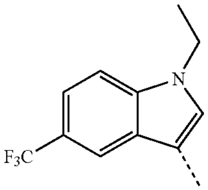 | $CH(CH_3)$ (R or S) | $CH_3$ (R) | H | $CH_3$ | H | (1R or 1S, 3R) OR: −31.67° (589 nm; 20° C.; 0.42 w/v %; DMF) |
| 217 | B33 | 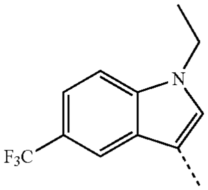 | $CH(CH_3)$ (S or R) | $CH_3$ (R) | H | $CH_3$ | H | (1S or 1R, 3R) |
| 218 | B17 | 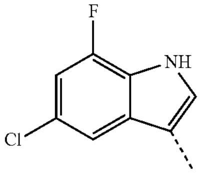 | $CH(CH_3)$ (R or S) | $CH_3$ (R) | H | $CH_3$ | H | (1R or 1S, 3R) |

TABLE 1a-continued
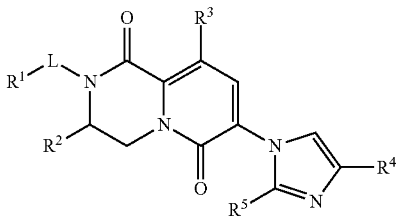
| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 219 | B17 | 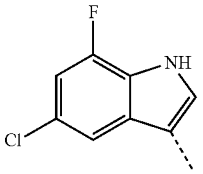 | $CH(CH_3)$ (S or R) | $CH_3$ (R) | H | $CH_3$ | H | (1S or 1R, 3R) |
| 220 | B24 | 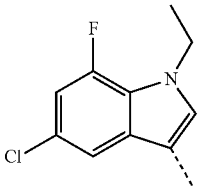 | $CH(CH_3)$ (R or S) | $CH_3$ (R) | H | $CH_3$ | H | (1R or 1S, 3R) |
| 221 | B24 | 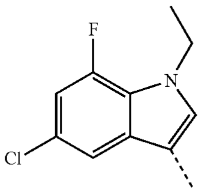 | $CH(CH_3)$ (S or R) | $CH_3$ (R) | H | $CH_3$ | H | (1S or 1R, 3R) |
| 222 | B34 | 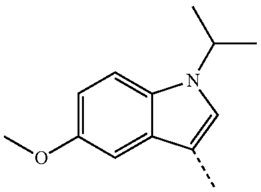 | $CH_2$ | $CH_3$ | H | $CH_3$ | H | R enantiomer |
| 223 | B24 | 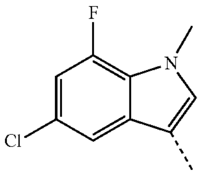 | $CH(CH_3)$ (R or S) | $CH_3$ (R) | H | $CH_3$ | H | (1R or 1S, 3R) |
| 224 | B24 | 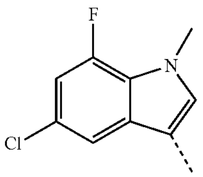 | $CH(CH_3)$ (S or R) | $CH_3$ (R) | H | $CH_3$ | H | (1S or 1R, 3R) |

TABLE 1a-continued
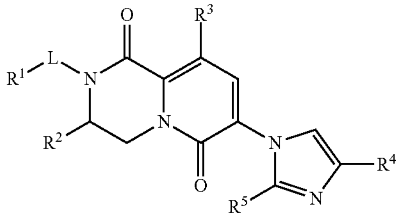
| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 225 | B35 | 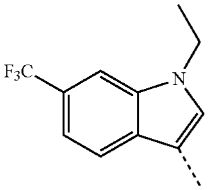 | $CH_2$ | $CH_3$ | H | $CH_3$ | H | R enantiomer |
| 226 | B24 | 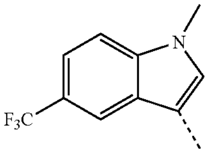 | $CH_2$ | $CH_3$ | H | $CH_3$ | H | R enantiomer |
| 227 | B24 | 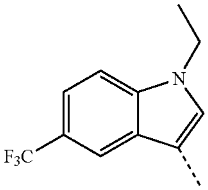 | $CH_2$ | $CH_3$ | H | $CH_3$ | H | R enantiomer |
| 228 | B24 | 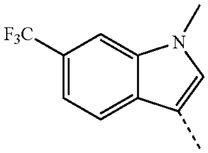 | $CH_2$ | $CH_3$ | H | $CH_3$ | H | R enantiomer |
| 229 | B3 | 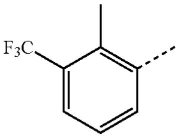 | 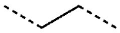 | $CH_3$ | H | $CH_3$ | H | R enantiomer |
| 230 | B3 | 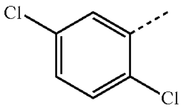 | 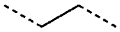 | $CH_3$ | H | $CH_3$ | H | R enantiomer |
| 231 | B3 | 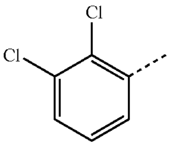 | 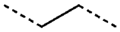 | $CH_3$ | H | $CH_3$ | H | R enantiomer •HCl |

TABLE 1a-continued
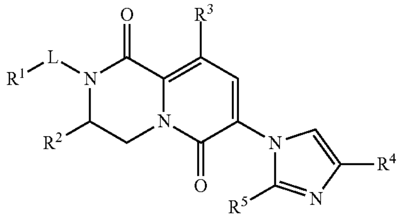
| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 232 | B3 | 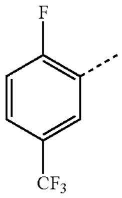 | 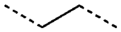 | $CH_3$ | H | $CH_3$ | H | R enantiomer |
| 233 | B3 | 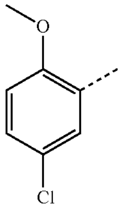 | 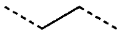 | $CH_3$ | H | $CH_3$ | H | R enantiomer |
| 234 | B17 | 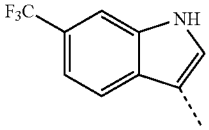 | $CH(CH_3)$ (R or S) | $CH_3$ (R) | H | $CH_3$ | H | (1R or 1S, 3R) |
| 235 | B24 | 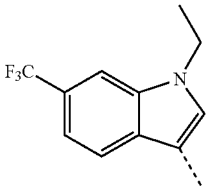 | $CH(CH_3)$ (S or R) | $CH_3$ (R) | H | $CH_3$ | H | (1S or 1R, 3R) |
| 236 | B37 | 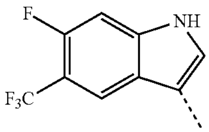 | $CH_2$ | $CH_3$ | H | $CH_3$ | H | R enantiomer |
| 237 | B37 | 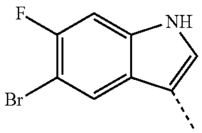 | $CH_2$ | $CH_3$ | H | $CH_3$ | H | R enantiomer |
| 238 | B24 | 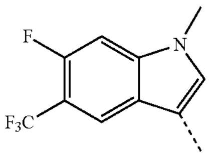 | $CH_2$ | $CH_3$ | H | $CH_3$ | H | R enantiomer |

TABLE 1a-continued
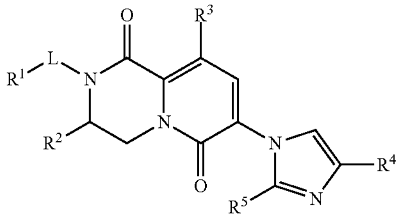
| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 239 | B24 | 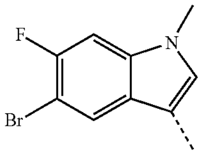 | $CH_2$ | $CH_3$ | H | $CH_3$ | H | R enantiomer |
| 240 | B17 | 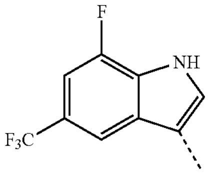 | $CH_2$ | $CH_3$ | H | $CH_3$ | H | R enantiomer |
| 241 | B24 | 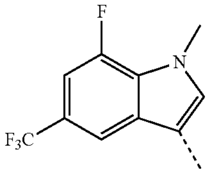 | $CH_2$ | $CH_3$ | H | $CH_3$ | H | R enantiomer |
| 162 | B38 | 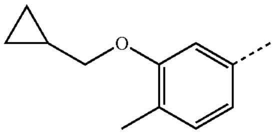 | $CH_2$ | $CH_3$ | H | $CH_3$ | H | R enantiomer; •HCl |
| 173 | B30# | 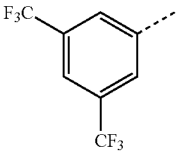 | $CH_2$ | $CH_3$ | H | H | H | R enantiomer |
| 174 | B39 | 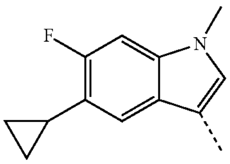 | $CH_2$ | $CH_3$ | H | $CH_3$ | H | R enantiomer |
| 242 | B39 | 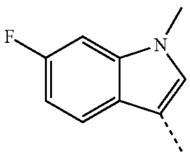 | $CH_2$ | $CH_3$ | H | $CH_3$ | H | R enantiomer |

TABLE 1a-continued

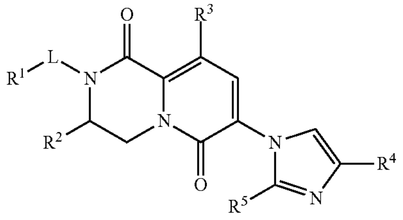

| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 243 | B24 | 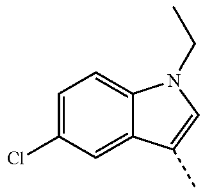 | $CH(CH_3)$ (S or R) | $CH_3$ (R) | H | $CH_3$ | H | (1S or 1R, 3R) OR: +152.25° (589 nm; 20° C.; 0.4 w/v %; DMF) |
| 244 | B40 | 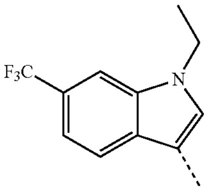 | $CH(CH_3)$ (R or S) | $CH_3$ (R) | H | $CH_3$ | H | (1R or 1S, 3R) |
| 245 | B17 | 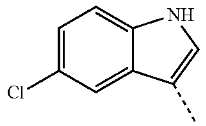 | $CH(CH_3)$ (R or S) | $CH_3$ (R) | H | $CH_3$ | H | (1R or 1S, 3R) OR: −126.29° (589 nm; 20° C.; 0.35 w/v %; DMF) |
| 276 | B17 | 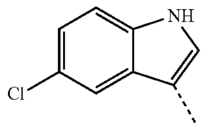 | $CH(CH_3)$ (S or R) | $CH_3$ (R) | H | $CH_3$ | H | (1S or 1R, 3R) |
| 246 | B41 | 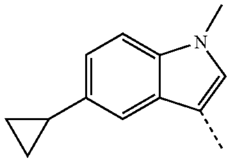 | $CH_2$ | $CH_3$ | H | $CH_3$ | H | R enantiomer |
| 247 | B42 | 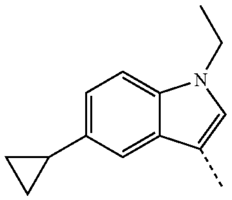 | $CH_2$ | $CH_3$ | H | $CH_3$ | H | R enantiomer |
| 248 | B43 | 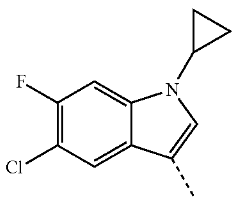 | $CH(CH_3)$ (S or R) | $CH_3$ (R) | H | $CH_3$ | H | (1S or 1R, 3R) |

TABLE 1a-continued
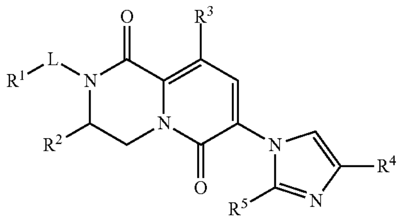
| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 249 | B24 | 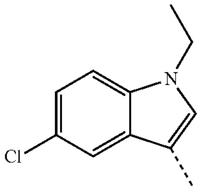 | $CH(CH_3)$ (R or S) | $CH_3$ (R) | H | $CH_3$ | H | (1R or 1S, 3R) |
| 250 | B24 | 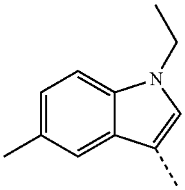 | $CH_2$ | $CH_3$ | H | $CH_3$ | H | R enantiomer |
| 251 | B44 | 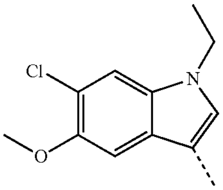 | $CH_2$ | $CH_3$ | H | $CH_3$ | H | R enantiomer |
| 252 | B17 | 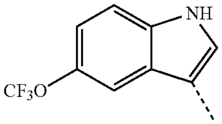 | $CH_2$ | $CH_3$ | H | $CH_3$ | H | R enantiomer |
| 253 | B24 | 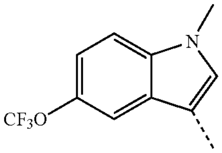 | $CH_2$ | $CH_3$ | H | $CH_3$ | H | R enantiomer; •HCl |
| 254 | B24 | 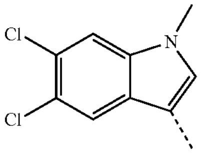 | $CH_2$ | H | H | $CH_3$ | H | |
| 255 | B24 | 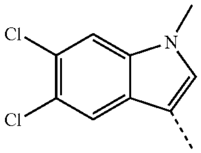 | $CH_2$ | $CH_3$ | H | $CH_3$ | H | R enantiomer |

TABLE 1a-continued
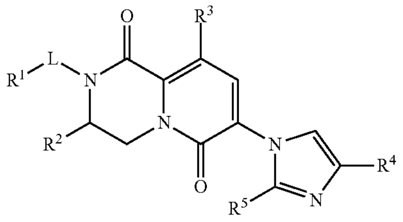
| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 256 | B45 | 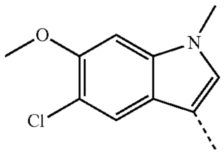 | $CH(CH_3)$ (S or R) | $CH_3$ (R) | H | $CH_3$ | H | (1S or 1R, 3R) |
| 257 | B17 | 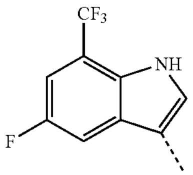 | $CH_2$ | $CH_3$ | H | $CH_3$ | H | R enantiomer |
| 258 | B24 | 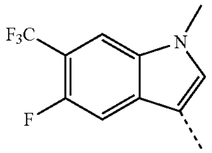 | $CH_2$ | $CH_3$ | H | $CH_3$ | H | R enantiomer |
| 259 | B24 | 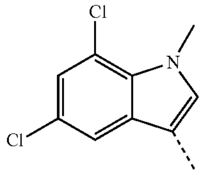 | $CH_2$ | H | H | $CH_3$ | H | |
| 260 | B17 | 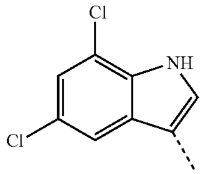 | $CH_2$ | H | H | $CH_3$ | H | |
| 261 | B24 | 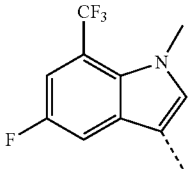 | $CH_2$ | $CH_3$ | H | $CH_3$ | H | R enantiomer |
| 262 | B49 | 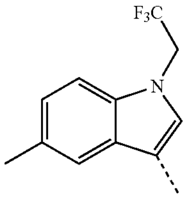 | $CH_2$ | $CH_3$ | H | $CH_3$ | H | R enantiomer |

TABLE 1a-continued

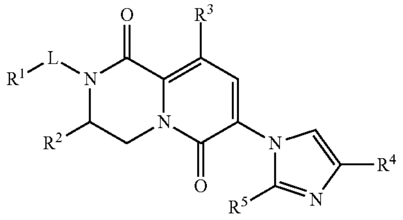

| Co. No. | Pr. | R¹ | L | $R^2$ | $R^3$ | $R^4$ | $R^5$ | Salt forms/Stereo-chemistry/Optical Rotation (OR) |
|---|---|---|---|---|---|---|---|---|
| 263 | B24 | 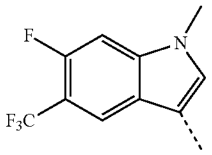 | $CH_2$ | H | H | $CH_3$ | H | |
| 264 | B24 | 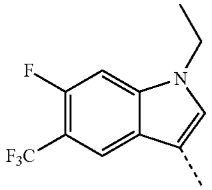 | $CH_2$ | H | H | $CH_3$ | H | |
| 265 | B47 | 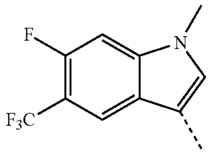 | $CH(CH_3)$ (R or S) | H | H | $CH_3$ | H | 1R or 1S enantiomer; enantiomer A (SFC-MS) |
| 266 | B47 | 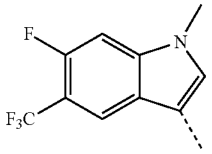 | $CH(CH_3)$ (S or R) | H | H | $CH_3$ | H | 1S or 1R enantiomer; enantiomer B (SFC-MS) |
| 267 | B46 | 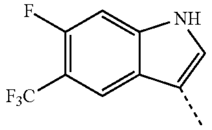 | $CH(CH_3)$ (R or S) | H | H | $CH_3$ | H | 1R or 1S enantiomer; enantiomer A (SFC-MS) |
| 268 | B46 | 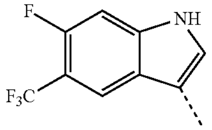 | $CH(CH_3)$ (S or R) | H | H | $CH_3$ | H | 1S or 1R enantiomer; enantiomer B (SFC-MS) |
| 269 | B24 | 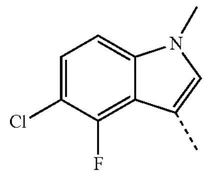 | $CH_2$ | $CH_3$ | H | $CH_3$ | H | R enantiomer |
| 270 | B24 | 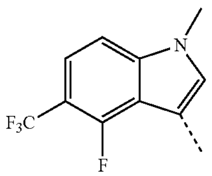 | $CH_2$ | $CH_3$ | H | $CH_3$ | H | R enantiomer |

TABLE 1a-continued

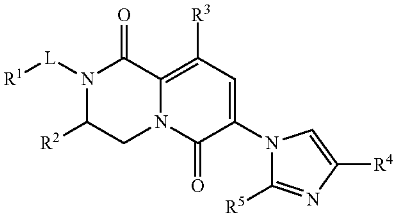

| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 271 | B48 | 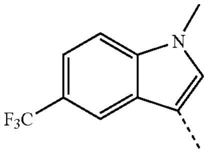 | $CH(CH_3)$ (R or S) | H | H | $CH_3$ | H | 1R or 1S enantiomer; enantiomer A (SFC-MS) |
| 272 | B48 | 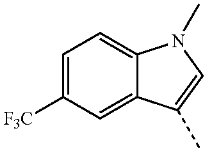 | $CH(CH_3)$ (S or R) | H | H | $CH_3$ | H | 1S or 1R enantiomer; enantiomer B (SFC-MS) |
| 273 | B50 | 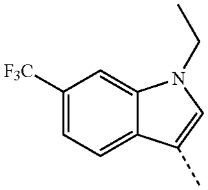 | $CH(CH_3)$ (R or S) | H | H | $CH_3$ | H | 1R or 1S enantiomer; enantiomer A (SFC-MS) |
| 274 | B50 | 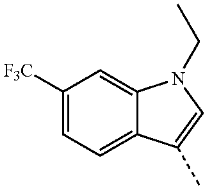 | $CH(CH_3)$ (S or R) | H | H | $CH_3$ | H | 1S or 1R enantiomer; enantiomer B (SFC-MS) |
| 277 | B17 | 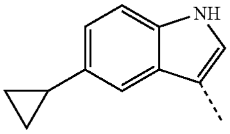 | $CH_2$ | $CH_3$ | H | $CH_3$ | H | R enantiomer |
| 278 | B17 | 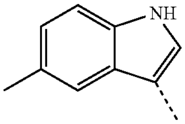 | $CH_2$ | $CH_3$ | H | $CH_3$ | H | R enantiomer |
| 279 | B17 | 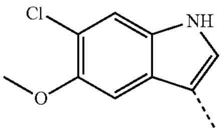 | $CH_2$ | $CH_3$ | H | $CH_3$ | H | R enantiomer |
| 280 | B17 | 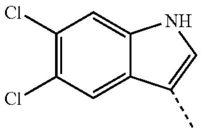 | $CH_2$ | $CH_3$ | H | $CH_3$ | H | R enantiomer |

TABLE 1a-continued
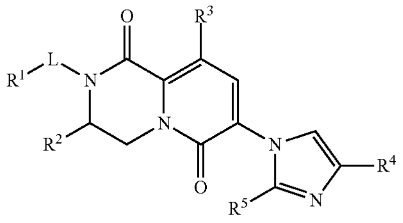
| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 281 | B17 | 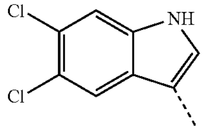 | $CH_2$ | H | H | $CH_3$ | H | |
| 282 | B17 | 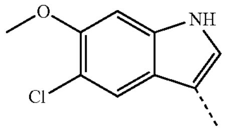 | $CH(CH_3)$ (S or R) | $CH_3$ (R) | H | $CH_3$ | H | (1S or 1R, 3R) |
| 283 | B17 | 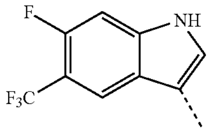 | $CH_2$ | H | H | $CH_3$ | H | |
| 284 | B46 | 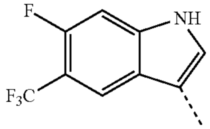 | $CH(CH_3)$ | H | H | $CH_3$ | H | |
| 285 | B47 | 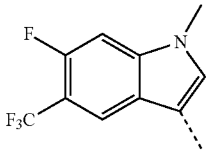 | $CH(CH_3)$ | H | H | $CH_3$ | H | |
| 286 | B17 | 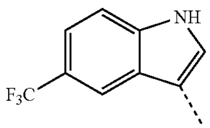 | $CH(CH_3)$ | H | H | $CH_3$ | H | |
| 287 | B48 | 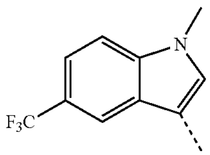 | $CH(CH_3)$ | H | H | $CH_3$ | H | |
| 288 | B17 | 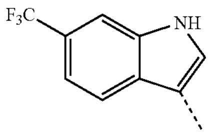 | $CH(CH_3)$ | H | H | $CH_3$ | H | |

TABLE 1a-continued

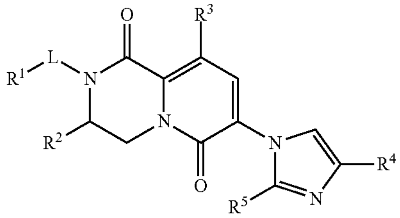

| Co. No. | Pr. | $R^1$ | L | $R^2$ | $R^3$ | $R^4$ | $R^5$ | Salt forms/Stereo-chemistry/Optical Rotation (OR) |
|---|---|---|---|---|---|---|---|---|
| 289 | B50 | 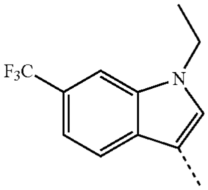 | $CH(CH_3)$ | H | H | $CH_3$ | H | |
| 290 | B17 | 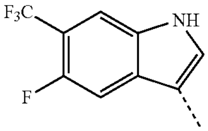 | $CH_2$ | $CH_3$ | H | $CH_3$ | H | R enantiomer |
| 291 | B17 | 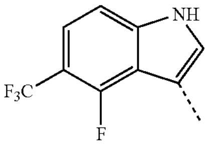 | $CH_2$ | $CH_3$ | H | $CH_3$ | H | R enantiomer |
| 292 | B24 | 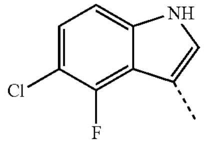 | $CH_2$ | $CH_3$ | H | $CH_3$ | H | R enantiomer |
| 293 | B51 | 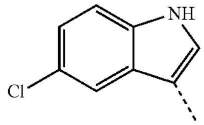 | $CH(CH_3)$ | H | H | $CH_3$ | H | $CH(CH_3)$ |
| 295 | B50 | 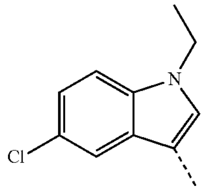 | $CH(CH_3)$ (R or S) | H | H | $CH_3$ | H | 1R or 1S enantiomer; enantiomer A (SFC-MS) |
| 296 | B50 | 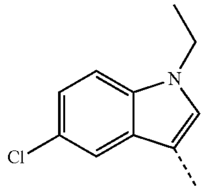 | $CH(CH_3)$ (S or R) | H | H | $CH_3$ | H | 1S or 1R enantiomer; enantiomer B (SFC-MS) |

# = imidazole was used instead of 4-methylimidazole

TABLE 1b

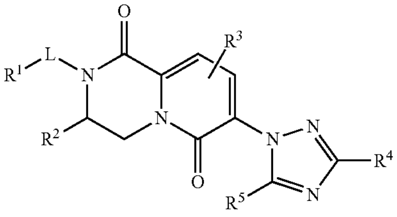

| Co. No. | Pr. | $R^1$ | L | $R^2$ | $R^3$ | $R^4$ | $R^5$ |
|---|---|---|---|---|---|---|---|
| 119 | B3 | 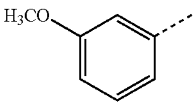 | $CH_2$ | H | H | $CH_3$ | H |
| 120 | B3 | 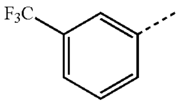 | $CH_2$ | H | H | $CH_3$ | H |
| 155 | B3 | 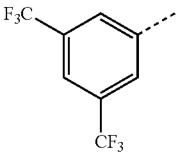 | $CH_2$ | $CH_3$ | H | $CH_3$ | H |

TABLE 1c

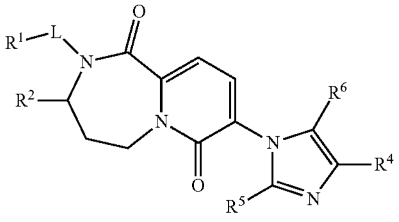

| Co. No. | Pr. | $R^1$ | L | $R^2$ | $R^4$ | $R^5$ | $R^6$ |
|---|---|---|---|---|---|---|---|
| 121 | B2 | 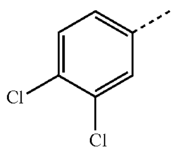 | $CH_2$ | H | $CH_3$ | H | H |
| 122 | B3 | 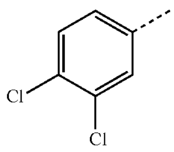 | $CH_2$ | H | H | H | $CH_3$ |
| 123 | B1 | 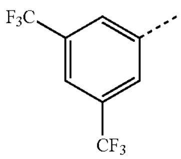 | $CH_2$ | $CH_3$ | $CH_3$ | H | H |

TABLE 1d

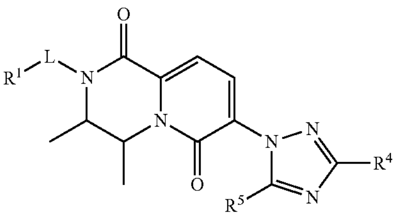

| Co. No. | Pr. | $R^1$ | L | $R^4$ | $R^5$ | Stereo-chemistry |
|---|---|---|---|---|---|---|
| 14 | B14 | 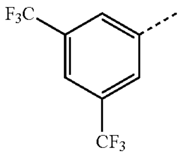 | $CH_2$ | $CH_3$ | H | cis |
| 14a | B14 | 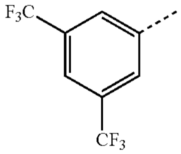 | $CH_2$ | $CH_3$ | H | cis A (SFC-MS) |
| 14b | B14 | 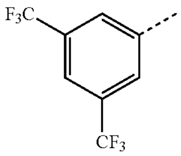 | $CH_2$ | $CH_3$ | H | cis B (SFC-MS) |

TABLE 1e

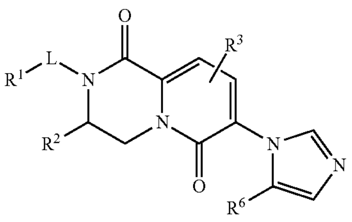

| Co. No. | Pr. | $R^1$ | L | $R^2$ | $R^3$ | $R^6$ |
|---|---|---|---|---|---|---|
| 89 | B3 | 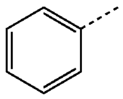 | $CH_2$ | H | H | $CH_3$ |

Compound 89 was obtained as a by-product during the synthesis of compound 19.

TABLE 1f

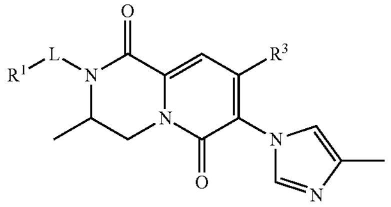

| Co. No. | Pr. | $R^1$ | $R^3$ | Salt forms/Stereo-chemistry/ Optical Rotation (OR) |
|---|---|---|---|---|
| 150 | B22 | 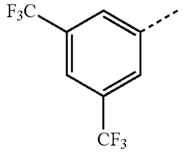 | Cl | R enantiomer |
| 157 | B22 | 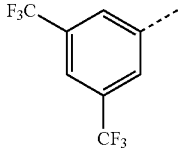 | Br | R enantiomer |
| 161 | B3 | 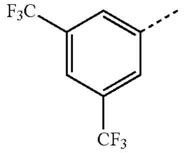 | $CH_3$ | R enantiomer OR: +5.7° (589 nm; 20° C.; 0.7 w/v %; DMF) |

TABLE 1g

| Co. No. | Pr. | Structure |
|---|---|---|
| 204 | B30 | 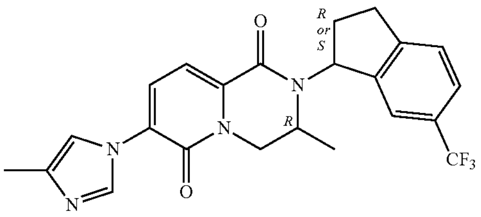 |
| 205 | B30 | 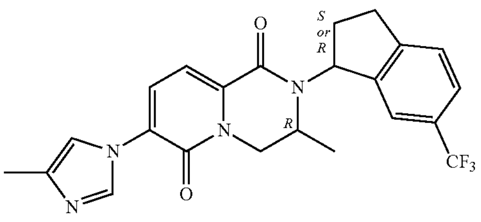 |

Analytical Part

LCMS (Liquid Chromatography/Mass spectrometry)

General Procedure A

The LC measurement was performed using an Acquity UPLC (Ultra Performance Liquid Chromatography) (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds (sec) using a dwell time of 0.02 sec. The capillary needle voltage was 3.5 kV and the source temperature was maintained at 140° C. $N_2$ was used as the nebulizer gas. Data acquisition was performed with a Waters-Micromass MassLynx-Openlynx data system.

General Procedure B

The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

General Procedure C

The HPLC measurement was performed using an Agilent G1956A LC/MSD quadrupole coupled to an Agilent 1100 series liquid chromatography system comprising a binary pump with degasser, an autosampler, a thermostated column department, a diode-array detector and a column as specified in the respective methods below. Flow from the column was split to a MS spectrometer, which was operated with an atmospheric pressure electrospray ionization source in positive ion mode. The capillary voltage was 3 kV, the fragmentor voltage was set to 70 V, and the quadrupole temperature was maintained at 100° C. The drying gas flow and temperature values were 12.0 l/min and 350° C. respectively. Nitrogen was used as the nebulizer gas. Data acquisition was performed with an Agilent Chemstation software.

General Procedure D

The HPLC measurement was performed using an Agilent 1100 module comprising a pump, a diode-array detector (DAD) (wavelength used 220 nm), a column heater and a column as specified in the respective methods below. Flow from the column was split to a Agilent MSD Series G1946C and G1956A. MS detector was configured with API-ES (atmospheric pressure electrospray ionization). Mass spectra were acquired by scanning from 100 to 1000. The capillary needle voltage was 2500 V for positive ionization mode and 3000 V for negative ionization mode. Fragmentation voltage was 50 V. Drying gas temperature was maintained at 350° C. at a flow of 10 l/min.

General Procedure E

The UPLC (Ultra Performance Liquid Chromatography) measurement was performed using an Acquity UPLC (Waters) system comprising a sampler organizer, a binary pump with degasser, a four column's oven, a diode-array detector (DAD) and a column as specified in the respective methods below. Column flow was used without split to the MS detector. The MS detector was configured with an ESCI dual ionization source (electrospray combined with atmospheric pressure chemical ionization). Nitrogen was used as the nebulizer gas. The source temperature was maintained at 140° C. Data acquisition was performed with MassLynx-Openlynx software.

General Procedure F

The LC measurement was performed using an Acquity UPLC (Waters) system comprising a binary pump, a sample organizer, a column heater (set at 55° C.), a diode-array detector (DAD) and a column as specified in the respective methods below. All the flow from the column went to a MS spectrometer. The MS detector was configured with an electrospray ionization source. Mass spectra were acquired by scanning from 120 to 1000 in 0.1 seconds. The capillary needle voltage was 3.0 kV and the source temperature was maintained at 150° C. Nitrogen was used as the nebulizer gas. Data acquisition was performed with a Waters-Micromass MassLynx-Openlynx data system.

General Procedure G

Analyses were performed using a Hitachi LaChrom Elite liquid chromatography (LC) system consisting of a pump with degasser, autosampler, thermostated column compartment and UV detector. Data acquisition was performed with Agilent EZChrom Elite software.

LCMS Method 1

In addition to general procedure A: Reversed phase UPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (mobile phase A: 25 mM ammonium acetate in $H_2O$/acetonitrile 95/5; mobile phase B: acetonitrile) were used to run a gradient condition from 95% A and 5% B to 5% A and 95% B in 1.3 minutes and hold for 0.3 minutes. An injection volume of 0.5 μl was used. Cone voltage was 30 V for positive ionization mode and 30 V for negative ionization mode.

LCMS Method 2

In addition to general procedure A: Reversed phase UPLC was carried out on a bridged ethylsiloxane/silica hybrid (BEH) C18 column (1.7 μm, 2.1×50 mm; Waters Acquity) with a flow rate of 0.8 ml/min. Two mobile phases (mobile phase A: 0.1% formic acid in $H_2O$/methanol 95/5; mobile phase B: methanol) were used to run a gradient condition from 95% A and 5% B to 5% A and 95% B in 1.3 minutes and hold for 0.2 minutes. An injection volume of 0.5 μl was used. Cone voltage was 10 V for positive ionization mode and 20 V for negative ionization mode.

LCMS Method 3

In addition to general procedure B: Reversed phase HPLC was carried out on an Xterra MS C18 column (3.5 μm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 μl was used. Cone voltage was 10 V for positive ionization mode and 20 V for negative ionization mode.

LCMS Method 4

In addition to general procedure A: Reversed phase UPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (25 mM ammonium acetate in $H_2O$/acetonitrile 95/5; mobile phase B: acetonitrile) were used to run a gradient condition from 95% A and 5% B to 5% A and 95% B in 1.3 minutes and hold for 0.3 minutes. An injection volume of 0.5 μl was used. Cone voltage was 10 V for positive ionization mode and 20 V for negative ionization mode.

LCMS Method 5

In addition to general procedure D: Reversed phase HPLC was carried out on a YMC-Pack ODS-AQ, 50×2.0 mm 5 μm column with a flow rate of 0.8 ml/min. Two mobile phases (mobile phase A: water with 0.1% TFA; mobile phase B: acetonitrile with 0.05% TFA) were used. First, 100% A was hold for 1 minute. Then a gradient was applied to 40% A and 60% B in 4 minutes and hold for 2.5 minutes. Typical injection volumes of 2 μl were used. Oven temperature was 50° C. (MS polarity: positive).

LCMS Method 6

In addition to general procedure A: Reversed phase UPLC was carried out on a BEH C18 column (1.7 μm, 2.1×50 mm; Waters Acquity) with a flow rate of 0.8 ml/min. Two mobile phases (10 mM ammonium acetate in $H_2O$/acetonitrile 95/5; mobile phase B: acetonitrile) were used to run a gradient condition from 95% A and 5% B to 5% A and 95% B in 1.3 minutes and hold for 0.3 minutes. An injection volume of 0.5 μl was used. Cone voltage was 10 V for positive ionization mode and 20 V for negative ionization mode.

LCMS Method 7

In addition to general procedure B: Column heater was set at 45° C. Reversed phase HPLC was carried out on an Atlantis C18 column (3.5 μm, 4.6×100 mm) with a flow rate of 1.6 ml/min. Two mobile phases (mobile phase A: 70% methanol+30% $H_2O$; mobile phase B: 0.1% formic acid in $H_2O$/methanol 95/5) were employed to run a gradient condition from 100% B to 5% B+95% A in 9 minutes and hold these conditions for 3 minutes. An injection volume of 10 μl was used. Cone voltage was 10 V for positive ionization mode and 20 V for negative ionization mode.

LCMS Method 8

In addition to general procedure C: Reversed phase HPLC was carried out on a YMC-Pack ODS-AQ C18 column (4.6×50 mm; 3 μm particle size) with a flow rate of 2.6 ml/min. A gradient run was used from 95% (water/0.1% formic acid) and 5% acetonitrile to 95% acetonitrile and 5% (water/0.1% formic acid) in 4.80 minutes and was hold for 1 minute. Acquisition ranges were set to 190-400 nm for the UV detector and 100 to 1400 m/z for the MS detector. Injection volume was 2 μl. Column temperature was 35° C.

LCMS Method 9

In addition to general procedure C: Reversed phase HPLC was carried out on a Phenomenex Kinetex XB-C18 column (4.6×50 mm; 2.6 μm particle size) at 35° C., with a flow rate of 3.0 ml/min. A gradient elution was performed from 95% (water+0.1% formic acid)/5% Acetonitrile to 5% (water+0.1% formic acid)/95% acetonitrile in 4.20 minutes, then the resulting composition was held for an additional 0.70 min. Acquisition ranges were set to 190-400 nm for the UV detector and 100 to 1200 m/z for the MS detector. The injection volume was 2 μl.

LCMS Method 10

In addition to general procedure D: Reversed phase HPLC was carried out on a YMC-Pack ODS-AQ, 50×2.0 mm 5 μm column with a flow rate of 0.8 ml/min. Two mobile phases (mobile phase A: water with 0.1% TFA; mobile phase B: acetonitrile with 0.05% TFA) were used. First, 90% A and 10% B was hold for 0.8 minutes. Then a gradient was applied to 20% A and 80% B in 3.7 minutes and hold for 3 minutes. Typical injection volumes of 2 μl were used. Oven temperature was 50° C.

(MS polarity: positive).

LCMS Method 11

In addition to the general procedure E: Reversed phase UPLC was carried out on a RRHD Eclipse Plus-C18 column (1.8 μm, 2.1×50 mm) from Agilent, with a flow rate of 1.0 ml/min, at 50° C. without split to the MS detector. The gradient conditions used are: 95% A (0.5 g/l ammonium acetate solution+5% acetonitrile), 5% B (acetonitrile), to 40% A, 60% B in 1.2 minutes, to 5% A, 95% B in 1.8 minutes, kept till 2.0 minutes. Injection volume 2.0 μl. Low-resolution mass spectra (single quadrupole, SQD detector) were acquired by scanning from 100 to 1000 in 0.1 seconds using an inter-channel delay of 0.08 second. The capillary needle voltage was 3 kV. The cone voltage was 25 V for positive ionization mode and 30 V for negative ionization mode.

LCMS Method 12

In addition to the general procedure E: Reversed phase UPLC was carried out on a RRHD Eclipse Plus-C18 column (1.8 μm, 2.1×50 mm) from Agilent, with a flow rate of 1.0 ml/min, at 50° C. without split to the MS detector. The gradient conditions used are: 95% A (0.5 g/1 ammonium acetate solution+5% acetonitrile), 5% B (acetonitrile), to 40% A, 60% B in 3.8 minutes, to 5% A, 95% B in 4.6 minutes, kept till 5.0 minutes. Injection volume 2.0 μl. Low-resolution mass spectra (single quadrupole, SQD detector) were acquired by scanning from 100 to 1000 in 0.1 seconds using an inter-channel delay of 0.08 second. The capillary needle voltage was 3 kV. The cone voltage was 25 V for positive ionization mode and 30 V for negative ionization mode.

LCMS Method 13

In addition to the general procedure F: Reversed phase UPLC was carried out on a HSS T3 column (1.8 μm, 2.1×100 mm; Waters) with a flow rate of 0.8 ml/min. Two mobile phases (10 mM ammonium acetate in $H_2O$/acetonitrile 95/5; mobile phase B: acetonitrile) were used to run a gradient condition from 100% A and 0% B to 5% A and 95% B in 2.1 minutes, then to 0% A and 100% B in 0.9 minutes, and finally to 5% A and 95% B in 0.5 minutes. Typical injection volumes and cone voltages which can be determined by the skilled person were used in this method.

LCMS Method 14

Identical to LCMS method 13, except that general procedure A was used.

LCMS Method 15

In addition to the general procedure G: Analyses were carried out on a Waters XTerra C18 column (100×4.6 mm I.D. 3.5 μm particles) at 40° C., with a flow rate of 1.6 mL/min. A gradient elution was performed as follows: from 100% of a solution of ammonium acetate (25 mM) in Water/Acetonitrile 90:10 to a mixture of Acetonitrile/Methanol 50:50 in 7.5 min; from the resulting composition to 100% Acetonitrile in 1.0 min; 100% Acetonitrile for 1.5 min; from 100% Acetonitrile to 100% to 100% of a solution of ammonium acetate (25 mM) in Water/Acetonitrile 90:10 (25 mM) in 3.0 minutes. The standard injection volume was 3 μL. Acquisition ranges were set to 200-400 nm for the UV.

Melting Points

For compounds 3, 5, 9a, 10a, 10b, 11a, 11b, 29, 38, 42, 53, 74, 119, 120, 121, 124, 125, 129, 130, 131, 132, 133, 155, 165, 185, 186, 189, 190, 196, 200, 208, 209, 219, 221, 223, 228, 251, 263, 264, 265, and 266 melting points (m.p.) were determined with a DSC823e or DSC1 (Mettler-Toledo). The m.p. of compounds 3, 9a, 10a, 10b, 129, 130, 131, 132, 133, 155, 165, 185, 186, 196 200, 208, 209, 219, 221, 223, 228, 251, 263, 264, 265 and 266 were measured with a temperature gradient of 10° C./min. The m.p. of compounds 5, 11a, 11b, 29, 38, 42, 53, 74, 119, 120, 121, 124, 125, 189 and 190 were measured with a temperature gradient of 30° C./min.

For compounds 1, 2, 6, 7, 14, 18, 20-22, 24, 25, 27, 28, 30, 31, 34-36, 40 43, 46, 55-59, 63, 65, 67-70, 72, 73, 75, 80-82, 84, 86, 88, 91-93, 95-97, 100-103, 105-107, 111-115, 117, 118, 128, 134, 135, 139-145, 147, 149, 151, 160, 163, 164, 166, 168-172, 162 and 253 m.p. were determined in open capillary tubes on a Mettler FP62 apparatus. M.p. were measured with a temperature ranging from 50° C. to 300° C., using a gradient of 10° C./minute. The m.p. value was read from a digital display.

For compounds 26, 37 and 90 m.p. were determined with a WRS-2A melting point apparatus that was purchased from Shanghai Precision and Scientific Instrument Co. Ltd. M.p. were measured with a linear heating up rate of 0.2-5.0° C./minute. The maximum temperature was 300° C.

For compounds 157 and 158, m.p. were determined in open capillary tubes on a FP 81HT/FP90 apparatus (Mettler-Toledo). M.p. were measured with a temperature gradient of 1, 3, 5 or 10° C./minute. Maximum temperature was 300° C. The m.p. value was read from a digital display.

For compounds 126, 127, 229, 230, 231, 232, 233, 254, 255, 259, 260, 269 and 270 m.p. were determined in open capillary tubes on a Mettler Toledo MP50 apparatus. M.p. were measured with a temperature ranging from 50° C. to 300° C., using a gradient of 10° C./minute. The m.p. value was read from a digital display.

The results of the analytical measurements are shown in table 2a.

TABLE 2a

Retention time ($R_t$) in min., $[M + H]^+$ peak (protonated molecule), LCMS method and m.p. (melting point in ° C.). (n.d. means not determined)

| Co. No. | $R_t$ | $[M + H]^+$ | LCMS Method | m.p. (° C.) |
|---|---|---|---|---|
| 1 | 2.62 | 499 | 8 | 203.6 |
| 2 | 2.20 | 418 | 8 | 185.0 |
| 3 | 1.05 | 485 | 6 | 176.6 |
| 4a | 1.55 | 446 | 8 | n.d. |
| 4 | 1.56 | 446 | 8 | n.d. |
| 5 | 0.95 | 411 | 4 | 165.6 |
| 6 | 2.65 | 487 | 8 | 175.4 |
| 7 | 2.59 | 499 | 8 | 290.0 |
| 8 | 1.93 | 542 | 8 | n.d. |
| 9 | 2.26 | 418 | 8 | n.d. |
| 9a | 0.97 | 417 | 2 | 206.8 |
| 10 | 2.11 | 418 | 8 | n.d. |
| 10a | 0.91 | 417 | 2 | 203.8 |
| 10b | 0.91 | 417 | 2 | 206.4 |
| 11a | 0.92 | 417 | 1 | 181.1 |
| 11b | 0.92 | 417 | 1 | 181.0 |
| 14 | 2.59 | 499 | 8 | 189.8 |
| 14a | 1.05 | 499 | 2 | n.d. |
| 14b | 1.05 | 499 | 2 | n.d. |
| 15 | 2.11 | 343 | 8 | n.d. |
| 18 | 2.19 | 355 | 8 | 192.6 |
| 19 | 4.39 | 335 | 3 | n.d. |
| 20 | 2.23 | 403 | 8 | 199.8 |
| 21 | 1.89 | 363 | 8 | 163.0 |
| 22 | 1.73 | 349 | 9 | 186.1 |
| 23 | 2.46 | 405 | 8 | n.d. |
| 24 | 2.00 | 383 | 8 | 184.6 |
| 25 | 1.90 | 369 | 8 | 176.7 |
| 26 | 3.23 | 383 | 10 | 184.4 |
| 27 | 1.99 | 413 | 8 | 168.0 |
| 28 | 2.30 | 423 | 8 | 157.4 |
| 29 | 2.19 | 409 | 8 | 227.1 |
| 29a | 0.98 | 409 | 2 | n.d. |
| 30 | 2.15 | 395 | 8 | 168.5 |
| 31 | 2.58 | 480 | 8 | 165.3 |
| 32 | 2.92 | 488 | 8 | n.d. |
| 33 | 2.42 | 444 | 8 | n.d. |
| 34 | 2.45 | 446 | 8 | 107.6 |
| 35 | 2.05 | 401 | 8 | 182.2 |
| 36 | 2.09 | 404 | 8 | 224.9 |
| 37 | 4.68 | 417 | 5 | 136-141 |
| 38 | 0.95 | 403 | 2 | 190.8 |
| 39 | 1.91 | 387 | 8 | n.d. |
| 40 | 2.19 | 397 | 8 | 182.1 |
| 41 | 1.54 | 353 | 8 | n.d. |
| 42 | 0.87 | 403 | 1 | 183.4 |
| 43 | 2.18 | 417 | 8 | 164.9 |
| 44 | 2.51 | 485 | 8 | n.d. |
| 45 | 2.33 | 501 | 8 | n.d. |
| 46 | 2.44 | 485 | 8 | 145.6 |
| 47 | 2.54 | 515 | 8 | n.d. |
| 48 | 1.90 | 528 | 8 | n.d. |
| 49 | 1.81 | 514 | 8 | n.d. |

TABLE 2a-continued

Retention time ($R_t$) in min., $[M + H]^+$ peak (protonated molecule), LCMS method and m.p. (melting point in ° C.). (n.d. means not determined)

| Co. No. | $R_t$ | $[M + H]^+$ | LCMS Method | m.p. (° C.) |
|---|---|---|---|---|
| 50 | 2.58 | 499 | 8 | n.d. |
| 51 | 2.51 | 555 | 8 | n.d. |
| 52 | 2.83 | 547 | 8 | n.d. |
| 53 | 1.09 | 471 | 2 | 219.0 |
| 54 | 1.90 | 515 | 9 | n.d. |
| 55 | 1.92 | 407 | 8 | 227.5 |
| 56 | 1.99 | 421 | 8 | 197.6 |
| 57 | 1.99 | 403 | 8 | 248.6 |
| 58 | 2.12 | 417 | 8 | 199.4 |
| 59 | 2.33 | 431 | 8 | 167.7 |
| 60 | 2.26 | 417 | 8 | n.d. |
| 61 | 2.32 | 431 | 8 | n.d. |
| 62 | 2.35 | 451 | 8 | n.d. |
| 63 | 2.38 | 451 | 8 | 180.4 |
| 64 | 2.20 | 437 | 8 | n.d. |
| 65 | 2.27 | 437 | 8 | 195.1 |
| 66 | 0.74 | 365 | 2 | n.d. |
| 67 | 2.20 | 447 | 8 | 140.2 |
| 68 | 2.25 | 447 | 8 | 132.4 |
| 69 | 2.08 | 433 | 8 | 177.0 |
| 70 | 2.19 | 435 | 8 | 108.5 |
| 71 | 2.34 | 451 | 8 | n.d. |
| 72 | 2.30 | 431 | 8 | 208.3 |
| 73 | 1.82 | 367 | 8 | 227.4 |
| 74 | 0.90 | 419 | 1 | 163.4 |
| 75 | 2.30 | 433 | 8 | 214.1 |
| 76 | 1.77 | 475 | 9 | n.d. |
| 77 | 2.01 | 435 | 9 | n.d. |
| 78 | 2.60 | 475 | 8 | n.d. |
| 79 | 2.24 | 433 | 8 | n.d. |
| 80 | 2.27 | 480 | 8 | 235.1 |
| 81 | 2.68 | 534 | 8 | 160.6 |
| 82 | 2.51 | 452 | 8 | 233.6 |
| 83 | 1.96 | 443 | 8 | n.d. |
| 84 | 1.23 | 432 | 8 | 108.2 |
| 85 | 1.87 | 466 | 9 | n.d. |
| 86 | 1.97 | 500 | 9 | 185.3 |
| 87 | 0.92 | 425 | 6 | n.d. |
| 88 | 2.48 | 445 | 8 | 136.5 |
| 89 | 4.33 | 335 | 7 | 146.5 |
| 90 | 4.05 | 497 | 10 | 138-143 |
| 91 | 2.13 | 436 | 8 | 246.3 |
| 92 | 2.47 | 485 | 8 | 242.2 |
| 93 | 1.71 | 407 | 8 | 192.2 |
| 94 | 2.30 | 399 | 8 | n.d. |
| 95 | 1.54 | 420 | 8 | 181.6 |
| 96 | 0.33 | 418 | 8 | 163.6 |
| 97 | 1.47 | 432 | 8 | 207.8 |
| 98 | 1.39 | 448 | 8 | n.d. |
| 99 | 1.42 | 432 | 8 | n.d. |
| 100 | 1.20 | 418 | 8 | 167.4 |
| 101 | 2.01 | 375 | 8 | 121.5 |
| 102 | 1.47 | 335 | 8 | 222.2 |
| 103 | 1.89 | 407 | 8 | 176.8 |
| 104 | 1.62 | 388 | 8 | n.d. |
| 105 | 2.28 | 429 | 8 | 253.5 |
| 106 | 2.35 | 443 | 8 | 189.4 |
| 107 | 2.40 | 443 | 8 | 257.3 |
| 108 | 2.27 | 411 | 8 | n.d. |
| 109 | 2.28 | 397 | 8 | n.d. |
| 110 | 2.68 | 471 | 8 | n.d. |
| 111 | 2.62 | 499 | 8 | 147.3 |
| 112 | 2.65 | 499 | 8 | 259.0 |
| 113 | 2.20 | 429 | 8 | 136.1 |
| 114 | 1.88 | 429 | 8 | 126.9 |
| 115 | 2.35 | 483 | 8 | 101.4 |
| 116 | 2.55 | 457 | 8 | n.d. |
| 117 | 2.57 | 511 | 8 | 221.5 |
| 118 | 3.72 | 505 | 8 | 157.9 |
| 119 | 0.77 | 366 | 4 | 151.2 |
| 120 | 1.25 | 404 | 2 | 194.9 |
| 121 | 0.92 | 417 | 1 | 173.4 |
| 122 | 0.90 | 417 | 1 | n.d. |
| 123 | 2.55 | 499 | 8 | n.d. |

TABLE 2a-continued

Retention time ($R_t$) in min., $[M + H]^+$ peak (protonated molecule), LCMS method and m.p. (melting point in ° C.). (n.d. means not determined)

| Co. No. | $R_t$ | $[M + H]^+$ | LCMS Method | m.p. (° C.) |
|---|---|---|---|---|
| 124 | 1.44 | 349 | 13 | 136.5 |
| 125 | 1.69 | 466 | 14 | n.d. |
| 126 | 2.62 | 465 | 8 | 206.5 |
| 127 | 2.64 | 465 | 8 | 218.5 |
| 128 | 2.60 | 476 | 8 | 116.9 |
| 129 | 1.90 | 465 | 14 | n.d. |
| 130 | 1.89 | 465 | 14 | n.d. |
| 131 | 0.99 | 417 | 6 | 170.7 |
| 132 | 0.81 | 379 | 6 | n.d. |
| 133 | 0.85 | 385 | 6 | 198.1 |
| 134 | 2.56 | 499 | 8 | 136.0 |
| 135 | 2.84 | 485 | 8 | 213.2 |
| 136 | 2.81 | 485 | 8 | n.d. |
| 137 | 1.72 | 436 | 13 | n.d. |
| 138 | 0.87 | 422 | 6 | n.d. |
| 139 | 1.61 | 451 | 9 | 195.9 |
| 140 | 1.99 | 501 | 9 | 115.2 |
| 141 | 1.94 | 475 | 9 | 146.2 |
| 142 | 1.96 | 475 | 9 | 141.4 |
| 143 | 1.94 | 475 | 9 | 229.3 |
| 144 | 1.94 | 475 | 9 | 194.4 |
| 145 | n.d. | n.d. | — | 204.5 |
| 146 | 1.79 | 447 | 9 | n.d. |
| 147 | 2.38 | 447 | 8 | 232.9 |
| 148 | 2.36 | 461 | 8 | n.d. |
| 149 | 2.37 | 461 | 8 | 122.0 |
| 150 | 1.36 | 519 | 11 | n.d. |
| 151 | 2.72 | 525 | 8 | 292.1 |
| 152 | 2.54 | 511 | 8 | n.d. |
| 153 | 2.72 | 570 | 8 | n.d. |
| 154 | 2.55 | 499 | 8 | n.d. |
| 155 | 1.09 | 486 | 6 | 160.9 |
| 156 | 2.70 | n.d. | 8 | n.d. |
| 157 | 1.38 | 563 | 11 | 147.7 |
| 158 | 2.95 | 503 | 12 | 137.1 |
| 159 | 3.22 | 519 | 12 | n.d. |
| 160 | 2.50 | 461 | 8 | 171.7 |
| 161 | 2.94 | 499 | 12 | n.d. |
| 163 | 2.48 | 459 | 8 | 103.1 |
| 164 | 2.76 | 525 | 8 | 213.7 |
| 165 | 1.02 | 439 | 6 | n.d. |
| 166 | 2.60 | 515 | 8 | 137.5 |
| 167 | 2.42 | 515 | 8 | n.d. |
| 168 | 2.15 | 435 | 8 | 225.6 |
| 169 | 2.58 | 499 | 8 | 181.9 |
| 170 | n.d. | n.d. | n.d. | 203.0 |
| 171 | 2.83 | 500 | 8 | 130.6 |
| 172 | 2.50 | 499 | 8 | 182.3 |
| 175 | 2.61 | 465 | 8 | n.d. |
| 176 | 0.81 | 363 | 6 | n.d. |
| 177 | 0.97 | 482 | 6 | n.d. |
| 178 | 0.94 | 436 | 6 | n.d. |
| 179 | 0.84 | 422 | 6 | n.d. |
| 180 | 1.73 | 470 | 14 | n.d. |
| 181 | 1.89 | 484 | 14 | n.d. |
| 182 | 1.97 | 498 | 14 | n.d. |
| 183 | 1.54 | 440 | 13 | n.d. |
| 184 | 1.55 | 440 | 13 | n.d. |
| 185 | 1.79 | 454 | 14 | 258 |
| 186 | 1.79 | 454 | 14 | 261 |
| 187 | 0.88 | 454 | 6 | n.d. |
| 188 | 0.89 | 454 | 6 | n.d. |
| 189 | 0.97 | 468 | 6 | 263 |
| 190 | 0.98 | 468 | 6 | 255 |
| 191 | 1.03 | 482 | 6 | n.d. |
| 192 | 1.03 | 482 | 6 | n.d. |
| 193 | 1.08 | 496 | 6 | n.d. |
| 194 | 1.10 | 496 | 6 | n.d. |
| 195 | 0.88 | 440 | 6 | n.d. |
| 196 | 0.96 | 454 | 6 | 187 |
| 197 | 1.71 | 514 | 14 | n.d. |
| 198 | 0.89 | 456 | 6 | n.d. |
| 199 | 1.17 | 542 | 6 | n.d. |
| 200 | 1.07 | 508 | 6 | 181 |

TABLE 2a-continued

Retention time ($R_t$) in min., $[M + H]^+$ peak (protonated molecule), LCMS method and m.p. (melting point in ° C.). (n.d. means not determined)

| Co. No. | $R_t$ | $[M + H]^+$ | LCMS Method | m.p. (° C.) |
|---|---|---|---|---|
| 201 | 0.74 | 418 | 6 | n.d. |
| 202 | 1.50 | 418 | 14 | n.d. |
| 203 | 0.90 | 456 | 6 | n.d. |
| 204 | 1.74 | 443 | 13 | n.d. |
| 205 | 1.73 | 443 | 13 | n.d. |
| 206 | 0.87 | 375 | 6 | n.d. |
| 207 | 0.87 | 375 | 6 | n.d. |
| 208 | 1.74 | 417 | 13 | 206 |
| 209 | 1.74 | 417 | 13 | 206 |
| 210 | 5.92 | 431 | 3 | n.d. |
| 211 | 6.03 | 431 | 3 | 146 |
| 212 | 1.72 | 470 | 14 | n.d. |
| 213 | 1.71 | 470 | 14 | n.d. |
| 214 | 1.77 | 484 | 13 | n.d. |
| 215 | 1.77 | 484 | 13 | n.d. |
| 216 | 1.86 | 498 | 13 | n.d. |
| 217 | 1.87 | 498 | 13 | n.d. |
| 218 | 0.91 | 454 | 6 | n.d. |
| 219 | 0.91 | 454 | 6 | 263 |
| 220 | 1.08 | 482 | 6 | n.d. |
| 221 | 1.09 | 482 | 6 | 194 |
| 222 | 1.80 | 460 | 14 | n.d. |
| 223 | 1.01 | 468 | 6 | 243 |
| 224 | 1.03 | 468 | 6 | n.d. |
| 225 | 1.03 | 484 | 6 | n.d. |
| 226 | 1.80 | 470 | 14 | n.d. |
| 227 | 1.03 | 484 | 6 | n.d. |
| 228 | 0.98 | 470 | 6 | 161 |
| 229 | 2.62 | 445 | 8 | 129 |
| 230 | 2.48 | 431 | 8 | 192 |
| 231 | 2.45 | 431 | 8 | 218 |
| 232 | 2.43 | 449 | 8 | 148 |
| 233 | 2.37 | 427 | 8 | 193 |
| 234 | 0.91 | 470 | 6 | n.d. |
| 235 | 1.05 | 498 | 6 | n.d. |
| 236 | 1.66 | 474 | 14 | n.d. |
| 237 | 1.62 | 484 | 14 | n.d. |
| 238 | 0.98 | 488 | 6 | n.d. |
| 239 | 0.96 | 498 | 6 | n.d. |
| 240 | 0.93 | 474 | 6 | n.d. |
| 241 | 1.03 | 488 | 6 | n.d. |
| 162 | n.d. | n.d. | n.d. | 171 |
| 173 | 1.00 | 471 | 6 | n.d. |
| 174 | 1.00 | 460 | 6 | n.d. |
| 242 | 0.88 | 420 | 6 | n.d. |
| 243 | 1.01 | 464 | 6 | n.d. |
| 244 | 1.05 | 498 | 6 | n.d. |
| 245 | 0.86 | 436 | 6 | n.d. |
| 246 | 0.97 | 442 | 6 | n.d. |
| 247 | 1.04 | 456 | 6 | n.d. |
| 248 | 1.93 | 494 | 13 | n.d. |
| 249 | 1.00 | 464 | 6 | n.d. |
| 250 | 0.96 | 430 | 6 | n.d. |

TABLE 2a-continued

Retention time ($R_t$) in min., $[M + H]^+$ peak (protonated molecule), LCMS method and m.p. (melting point in ° C.). (n.d. means not determined)

| Co. No. | $R_t$ | $[M + H]^+$ | LCMS Method | m.p. (° C.) |
|---|---|---|---|---|
| 251 | 1.75 | 480 | 13 | 150 |
| 252 | 2.55 | 472 | 8 | n.d. |
| 253 | 2.81 | 486 | 8 | 190 |
| 254 | 2.72 | 456 | 8 | 217 |
| 255 | 2.79 | 470 | 8 | 265 |
| 256 | 1.66 | 480 | 13 | n.d. |
| 257 | 1.65 | 474 | 14 | n.d. |
| 258 | 1.73 | 488 | 14 | n.d. |
| 259 | 2.86 | 456 | 8 | 230 |
| 260 | 2.52 | 442 | 8 | 208 |
| 261 | 1.79 | 488 | 14 | n.d. |
| 262 | 1.75 | 484 | 13 | n.d. |
| 263 | 0.93 | 474 | 6 | 223 |
| 264 | 0.98 | 488 | 6 | 193 |
| 265 | 0.92 | 488 | 6 | 260 |
| 266 | 0.96 | 488 | 6 | 258 |
| 267 | 1.53 | 474 | 14 | n.d. |
| 268 | 1.59 | 474 | 14 | n.d. |
| 269 | 2.58 | 474 | 8 | 138 |
| 270 | 2.72 | 488 | 8 | 138 |
| 271 | 0.95 | 470 | 6 | n.d. |
| 272 | 0.95 | 470 | 6 | n.d. |
| 273 | 1.02 | 484 | 6 | n.d. |
| 274 | 1.84 | 484 | 13 | n.d. |
| 276 | 0.87 | 436 | 6 | n.d. |
| 277 | 0.88 | 428 | 6 | n.d. |
| 278 | 0.81 | 402 | 6 | n.d. |
| 279 | 0.81 | 452 | 6 | n.d. |
| 282 | 0.82 | 466 | 6 | n.d. |
| 283 | 0.86 | 460 | 6 | n.d. |
| 284 | 0.89 | 474 | 6 | n.d. |
| 285 | 0.96 | 488 | 6 | n.d. |
| 286 | 0.86 | 456 | 6 | n.d. |
| 287 | 0.96 | 470 | 6 | n.d. |
| 288 | 0.88 | 456 | 6 | n.d. |
| 289 | 1.02 | 484 | 6 | n.d. |
| 293 | 0.82 | 422 | 6 | n.d. |
| 295 | 0.97 | 450 | 6 | n.d. |
| 296 | 0.97 | 450 | 6 | n.d. |

NMR

For a number of compounds, $^1H$ NMR spectra were recorded on a Bruker Avance III with a 300 MHz Ultrashield magnet, on a Bruker DPX-400 spectrometer operating at 400 MHz, on a Bruker DPX-360 operating at 360 MHz, or on a Bruker Avance 600 spectrometer operating at 600 MHz, using CHLOROFORM-d (deuterated chloroform, $CDCl_3$) or DMSO-$d_6$ (deuterated DMSO, dimethyl-d6 sulfoxide) as solvent. Chemical shifts (δ) are reported in parts per million (ppm) relative to tetramethylsilane (TMS), which was used as internal standard.

TABLE 2b $^1H$ NMR results

| Co. No. | $^1H$ NMR result |
|---|---|
| 1 | (300 MHz, DMSO-$d_6$) δ ppm 0.84 (t, J = 7.4 Hz, 3 H), 1.24-1.44 (m, 1 H), 1.63-1.79 (m, 1 H), 2.35 (br. s, 3 H), 3.84-4.00 (m, 2 H), 4.62 (d, J = 15.5 Hz, 1 H), 4.84 (dd, J = 15.7, 3.3 Hz, 1 H), 5.24 (d, J = 15.7 Hz, 1 H), 7.22 (d, J = 7.7 Hz, 1 H), 7.85-7.91 (m, 1 H), 8.02-8.18 (m, 4 H), 9.54 (d, J = 1.4 Hz, 1 H) |
| 2 | (300 MHz, DMSO-$d_6$) δ ppm 1.12 (d, J = 6.6 Hz, 3 H), 2.16 (s, 3 H), 3.89-4.02 (m, 2 H), 4.42 (d, J = 15.4 Hz, 1 H), 4.60 (d, J = 11.8 Hz, 1 H), 5.01 (d, J = 15.4 Hz, 1 H), 7.13 (d, J = 7.8 Hz, 1 H), 7.36-7.46 (m, 2 H), 7.60-7.70 (m, 2 H), 7.80-7.85 (m, 1 H), 8.28 (s, 1 H) |
| 3 | (300 MHz, DMSO-$d_6$) δ ppm 1.15 (d, J = 6.5 Hz, 3 H), 2.17 (d, J = 0.7 Hz, 3 H), 3.89-4.13 (m, 2 H), 4.61 (dd, J = 13.7, 2.3 Hz, 2 H), 5.18 (d, J = 15.7 Hz, 1 H), 7.15 (d, J = 7.8 Hz, 1 H), 7.43 (t, J = 1.2 Hz, 1 H), 7.83 (d, J = 7.7 Hz, 1 H), 8.02-8.17 (m, 3 H), 8.28 (d, J = 1.2 Hz, 1 H) |

TABLE 2b-continued

| $^1$H NMR results | |
|---|---|
| Co. No. | $^1$H NMR result |
| 4 | (300 MHz, DMSO-$d_6$) δ ppm 1.04 (d, J = 6.2 Hz, 3 H), 1.55 (br. s., 2 H), 1.65 (br. s., 4 H), 2.23 (s, 3 H), 2.31 (s, 3 H), 2.80 (t, J = 9.1 Hz, 4 H), 3.80-3.98 (m, 2 H), 4.34 (d, J = 14.8 Hz, 1 H), 4.61 (dd, J = 13.7, 1.6 Hz, 1 H), 5.01 (d, J = 14.8 Hz, 1 H), 6.92-7.03 (m, 2 H), 7.14 (d, J = 7.7 Hz, 1 H), 7.22 (d, J = 7.8 Hz, 1 H), 7.78 (s, 1 H), 8.05 (d, J = 7.8 Hz, 1 H), 9.26 (s, 1 H) |
| 4a | (300 MHz, CHLOROFORM-d) δ ppm 1.21 (d, J = 6.7 Hz, 3 H), 1.52-1.64 (m, 2 H), 1.65-1.80 (m, 4 H), 2.29 (s, 6 H), 2.72-2.93 (m, 4 H), 3.66 (dd, J = 14.1, 4.1 Hz, 1 H), 3.75-3.89 (m, 1 H), 4.05 (d, J = 14.7 Hz, 1 H), 4.76 (dd, J = 14.0, 2.1 Hz, 1 H), 5.36 (d, J = 14.7 Hz, 1 H), 6.81-6.98 (m, 2 H), 7.15 (d, J = 7.7 Hz, 2 H), 7.32 (d, J = 7.6 Hz, 1 H), 7.48 (d, J = 7.7 Hz, 1 H), 8.26 (br. s., 1 H) |
| 5 | (300 MHz, DMSO-$d_6$) δ ppm 2.16 (s, 3 H), 3.71 (t, J = 6.3 Hz, 2 H), 4.27 (t, J = 6.3 Hz, 2 H), 4.80 (s, 2 H), 7.15 (d, J = 7.7 Hz, 1 H), 7.27-7.55 (m, 6 H), 7.55-7.75 (m, 4 H), 7.81 (d, J = 7.7 Hz, 1 H), 8.26 (s, 1 H) |
| 6 | (300 MHz, DMSO-$d_6$) δ ppm 0.15-0.42 (m, 2 H), 0.42-0.72 (m, 2 H), 1.13 (d, J = 6.3 Hz, 3 H), 1.16-1.28 (m, 1 H), 2.33 (s, 3 H), 3.71-4.10 (m, 4 H), 4.48 (d, J = 15.4 Hz, 1 H), 4.60 (d, J = 12.4 Hz, 1 H), 5.07 (d, J = 15.5 Hz, 1 H), 7.02-7.42 (m, 4 H), 7.86 (s, 1 H), 8.10 (d, J = 7.7 Hz, 1 H), 9.48 (s, 1 H) |
| 7 | (300 MHz, DMSO-$d_6$) δ ppm 1.17 (d, J = 6.5 Hz, 3 H), 1.26 (t, J = 7.6 Hz, 3 H), 2.71 (q, J = 7.4 Hz, 2 H), 3.93-4.18 (m, 2 H), 4.57-4.69 (m, 2 H), 5.20 (d, J = 15.5 Hz, 1 H), 7.25 (d, J = 7.7 Hz, 1 H), 7.89 (d, J = 0.7 Hz, 1 H), 8.03-8.16 (m, 4 H), 9.48 (s, 1 H) |
| 9 | (300 MHz, DMSO-$d_6$) δ ppm 1.57 (d, J = 7.1 Hz, 3 H), 2.16 (s, 3 H), 3.35-3.49 (m, 1 H), 3.67 (ddd, J = 13.3, 8.6, 4.1 Hz, 1 H), 3.93-4.21 (m, 1 H), 4.30 (ddd, J = 14.1, 6.8, 4.1 Hz, 1 H), 5.59-5.90 (m, 1 H), 7.14 (d, J = 7.8 Hz, 1 H), 7.27-7.50 (m, 2 H), 7.50-7.69 (m, 2 H), 7.81 (d, J = 7.7 Hz, 1 H), 8.26 (d, J = 1.0 Hz, 1 H). |
| 9a | The NMR spectrum of 9a matches the one of compound 9 |
| 9b | The NMR spectrum of 9b matches the one of compound 9 |
| 10 | (300 MHz, DMSO-$d_6$) δ ppm 1.57 (d, J = 7.0 Hz, 3 H), 2.15 (br. s, 3 H), 3.19-3.30 (m, 1 H), 3.52-3.74 (m, 1 H), 4.08-4.27 (m, 2 H), 5.85 (q, J = 7.0 Hz, 1 H), 7.11 (d, J = 7.7 Hz, 1 H), 7.36-7.51 (m, 2 H), 7.60 (dd, J = 7.8, 1.4 Hz, 1 H), 7.66 (dd, J = 8.0, 1.6 Hz, 1 H), 7.79 (d, J = 7.8 Hz, 1 H), 8.25 (d, J = 1.2 Hz, 1 H) |
| 10a | The NMR spectrum of 10a matches the one of compound 10 |
| 10b | The NMR spectrum of 10b matches the one of compound 10 |
| 11a | (360 MHz, DMSO-$d_6$) δ ppm 1.61 (d, J = 7.0 Hz, 3 H), 2.15 (s, 3 H), 3.18-3.32 (m, 1 H), 3.69 (ddd, J = 13.2, 8.4, 4.0 Hz, 1 H), 4.08 (ddd, J = 12.4, 8.4, 4.0 Hz, 1 H), 4.29 (ddd, J = 14.1, 6.8, 3.7 Hz, 1 H), 5.87 (q, J = 7.0 Hz, 1 H), 7.14 (d, J = 7.7 Hz, 1 H), 7.43 (br. s., 1 H), 7.59-7.73 (m, 4 H), 7.81 (d, J = 7.7 Hz, 1 H), 8.27 (br. s., 1 H) |
| 11b | The NMR spectrum of 11b matches the one of compound 11a |
| 14 | The NMR spectrum of 14 matches the one of compound 14a |
| 14a | (600 MHz, CHLOROFORM-d) δ ppm 1.31 (d, J = 6.6 Hz, 3 H), 1.39 (d, J = 7.0 Hz, 3 H), 2.29 (d, J = 0.9 Hz, 3 H), 4.17 (qd, J = 6.9, 3.2 Hz, 1 H), 4.82 (d, J = 16.0 Hz, 1 H), 5.10 (qd, J = 6.6, 3.2 Hz, 1 H), 5.13 (d, J = 16.0 Hz, 1 H), 7.15 (s, 1 H), 7.36 (d, J = 7.6 Hz, 1 H), 7.49 (d, J = 7.8 Hz, 1 H), 7.72 (s, 2 H), 7.83 (s, 1 H), 8.27 (s, 1 H) |
| 14b | The NMR spectrum of 14b matches the one of compound 14a |
| 15 | (300 MHz, DMSO-$d_6$) δ ppm 0.88 (s, 9 H), 1.12-1.22 (m, 2 H), 1.47-1.60 (m, 2 H), 2.16 (s, 3 H), 3.45 (t, J = 7.3 Hz, 2 H), 3.63-3.76 (m, 2 H), 4.19-4.28 (m, 2 H), 7.08 (d, J = 7.7 Hz, 1 H), 7.38-7.43 (m, 1 H), 7.79 (d, J = 7.7 Hz, 1 H), 8.22-8.28 (m, 1 H) |
| 18 | (300 MHz, DMSO-$d_6$) δ ppm 0.77-1.03 (m, 2 H), 1.04-1.37 (m, 4 H), 1.46 (q, J = 7.0 Hz, 2 H), 1.54-1.82 (m, 5 H), 2.16 (s, 3 H), 3.50 (t, J = 7.6 Hz, 2 H), 3.69 (dd, J = 6.8, 5.0 Hz, 2 H), 4.11-4.40 (m, 2 H), 7.07 (d, J = 7.8 Hz, 1 H), 7.40 (s, 1 H), 7.78 (d, J = 7.7 Hz, 1 H), 8.14-8.36 (m, 1 H) |
| 19 | (400 MHz, DMSO-$d_6$) δ ppm 2.15 (s, 3 H), 3.64 (t, J = 6.1 Hz, 2 H), 4.22 (t, J = 5.7 Hz, 2 H), 4.71 (s, 2 H), 7.12 (d, J = 7.7 Hz, 1 H), 7.20-7.45 (m, 6 H), 7.70 (d, J = 7.7 Hz, 1 H), 8.17 (br. s., 1 H) |
| 20 | (300 MHz, DMSO-$d_6$) δ ppm 0.69-0.89 (m, 2 H), 1.01 (d, J = 6.7 Hz, 3 H), 1.04 (d, J = 6.0 Hz, 2 H), 2.15 (s, 3 H), 2.48 (s, 3 H), 3.08 (d, J = 13.2 Hz, 1 H), 3.39 (dd, J = 14.1, 4.1 Hz, 1 H), 3.46-3.68 (m, 1 H), 4.21 (br. s., 1 H), 4.51 (d, J = 14.2 Hz, 1 H), 7.01 (d, J = 7.7 Hz, 1 H), 7.06-7.20 (m, 3 H), 7.30 (d, J = 6.3 Hz, 1 H), 7.39 (s, 1 H), 7.76 (d, J = 7.7 Hz, 1 H), 8.23 (s, 1 H) |
| 21 | (300 MHz, DMSO-$d_6$) δ ppm 1.09 (d, J = 6.5 Hz, 3 H), 2.16 (s, 3 H), 2.30 (s, 3 H), 3.77-3.86 (m, 1 H), 3.86-3.96 (m, 1 H), 4.39 (d, J = 15.5 Hz, 1 H), 4.64 (dd, J = 13.9, 1.6 Hz, 1 H), 5.04 (d, J = 15.5 Hz, 1 H), 7.14 (d, J = 7.7 Hz, 1 H), 7.17-7.33 (m, 4 H), 7.43 (s, 1 H), 7.83 (d, J = 7.7 Hz, 1 H), 8.28 (s, 1 H) |
| 23 | (300 MHz, DMSO-$d_6$) δ ppm 1.09 (d, J = 6.5 Hz, 3 H), 1.29 (s, 9 H), 2.18 (s, 3 H), 3.78-3.90 (m, 1 H), 3.90-4.00 (m, 1 H), 4.43 (d, J = 15.1 Hz, 1 H), 4.63 (dd, J = 13.8, 2.0 Hz, 1 H), 5.03 (d, J = 15.3 Hz, 1 H), 7.11-7.22 (m, 2 H), 7.24-7.37 (m, 2 H), 7.39 (s, 1 H), 7.47 (s, 1 H), 7.85 (d, J = 7.7 Hz, 1 H), 8.40 (s, 1 H) |
| 24 | (300 MHz, DMSO-$d_6$) δ ppm 1.13 (d, J = 6.5 Hz, 3 H), 2.31 (s, 3 H), 3.90-4.10 (m, 2 H), 4.46 (d, J = 15.4 Hz, 1 H), 4.60 (d, J = 12.0 Hz, 1 H), 5.03 (d, J = 15.4 Hz, 1 H), 7.22 (d, J = 7.7 Hz, 1 H), 7.28-7.57 (m, 4 H), 7.78 (s, 1 H), 8.05 (d, J = 7.7 Hz, 1 H), 9.26 (s, 1 H) |

TABLE 2b-continued

| Co. No. | $^1$H NMR result |
|---|---|
| 25 | (300 MHz, DMSO-$d_6$) δ ppm 2.16 (s, 3 H), 3.64-3.74 (m, 2 H), 4.21-4.31 (m, 2 H), 4.72 (s, 2 H), 7.15 (d, J = 7.7 Hz, 1 H), 7.28-7.47 (m, 5 H), 7.81 (d, J = 7.8 Hz, 1 H), 8.26 (s, 1 H) |
| 29 | (300 MHz, DMSO-$d_6$) δ ppm 0.78-0.89 (m, 2 H), 0.95-1.04 (m, 2 H), 2.15 (s, 3 H), 3.55 (t, J = 5.6 Hz, 2 H), 3.73 (s, 2 H), 3.97-4.16 (m, 2 H), 6.96 (d, J = 7.7 Hz, 1 H), 7.28-7.35 (m, 2 H), 7.35-7.43 (m, 3 H), 7.74 (d, J = 7.7 Hz, 1 H), 8.22 (s, 1 H) |
| 29a | (400 MHz, DMSO-$d_6$) δ ppm 0.83-0.90 (m, 2 H), 0.97-1.03 (m, 2 H), 2.29 (s, 3 H), 3.52-3.60 (m, 2 H), 3.76 (s, 2 H), 4.02-4.12 (m, 2 H), 7.04 (d, J = 7.7 Hz, 1 H), 7.28 (m, J = 8.5 Hz, 2 H), 7.37 (m, J = 8.5 Hz, 2 H), 7.80 (br. s., 1 H), 7.93 (d, J = 7.7 Hz, 1 H), 9.18 (br. s., 1 H) |
| 30 | (300 MHz, DMSO-$d_6$) δ ppm 1.42 (q, J = 7.1 Hz, 1 H), 1.48-1.61 (m, 1 H), 2.21 (s, 3 H), 2.39 (ddd, J = 9.8, 6.6, 3.6 Hz, 1 H), 3.02-3.14 (m, 1 H), 3.77 (t, J = 6.0 Hz, 2 H), 4.14-4.30 (m, 1 H), 4.30-4.44 (m, 1 H), 7.16 (d, J = 7.7 Hz, 1 H), 7.33 (d, J = 8.5 Hz, 2 H), 7.42 (d, J = 8.5 Hz, 2 H), 7.47 (s, 1 H), 7.86 (d, J = 7.8 Hz, 1 H), 8.32 (s, 1 H) |
| 31 | (300 MHz, DMSO-$d_6$) δ ppm 2.17 (s, 3 H), 4.18 (d, J = 15.4 Hz, 1 H), 4.30 (dd, J = 14.2, 4.5 Hz, 1 H), 4.99 (dd, J = 14.2, 2.2 Hz, 1 H), 5.18-5.32 (m, 2 H), 7.15-7.23 (m, 2 H), 7.27 (d, J = 7.7 Hz, 1 H), 7.32-7.47 (m, 5 H), 7.65 (d, J = 8.2 Hz, 1 H), 7.70 (d, J = 2.1 Hz, 1 H), 7.86 (d, J = 7.7 Hz, 1 H), 8.21-8.27 (m, 1 H) |
| 34 | (300 MHz, DMSO-$d_6$) δ ppm 0.71 (d, J = 6.5 Hz, 3 H), 0.97 (d, J = 6.6 Hz, 3 H), 1.87 (dq, J = 13.1, 6.7 Hz, 1 H), 2.16 (s, 3 H), 3.66-3.88 (m, 2 H), 4.31 (d, J = 15.3 Hz, 1 H), 4.94 (d, J = 14.3 Hz, 1 H), 5.17 (d, J = 15.4 Hz, 1 H), 7.09 (d, J = 7.7 Hz, 1 H), 7.33-7.48 (m, 2 H), 7.61 (d, J = 8.2 Hz, 1 H), 7.69 (s, 1 H), 7.81 (d, J = 7.6 Hz, 1 H), 8.27 (s, 1 H) |
| 35 | (300 MHz, DMSO-$d_6$) δ ppm 1.15 (d, J = 6.5 Hz, 3 H), 2.16 (s, 3 H), 3.88-4.12 (m, 2 H), 4.54 (d, J = 15.7 Hz, 1 H), 4.64 (dd, J = 13.5, 1.7 Hz, 1 H), 5.04 (d, J = 15.7 Hz, 1 H), 7.12 (d, J = 7.7 Hz, 1 H), 7.17-7.31 (m, 1 H), 7.43 (t, J = 6.5 Hz, 2 H), 7.49-7.61 (m, 1 H), 7.82 (d, J = 7.7 Hz, 1 H), 8.29 (br. s., 1 H) |
| 36 | (300 MHz, DMSO-$d_6$) δ ppm 2.16 (s, 3 H), 3.75 (t, J = 5.6 Hz, 2 H), 4.32 (t, J = 5.6 Hz, 2 H), 4.82 (s, 2 H), 7.13 (d, J = 7.7 Hz, 1 H), 7.28-7.50 (m, 3 H), 7.62 (dd, J = 6.9, 2.3 Hz, 1 H), 7.82 (d, J = 7.7 Hz, 1 H), 8.28 (s, 1 H) |
| 37 | (400 MHz, CHLOROFORM-d) δ ppm 1.26 (d, J = 6.5 Hz, 3 H), 2.31 (br. s., 3 H), 3.69-3.90 (m, 2 H), 4.15 (d, J = 15.1 Hz, 1 H), 4.77 (d, J = 13.8 Hz, 1 H), 5.27 (d, J = 15.3 Hz, 1 H), 7.19 (d, J = 6.8 Hz, 2 H), 7.33 (d, J = 7.5 Hz, 1 H), 7.40-7.58 (m, 3 H), 8.29 (br. s., 1 H) |
| 38 | (360 MHz, DMSO-$d_6$) δ ppm 2.15 (s, 3 H), 3.66-3.74 (m, 2 H), 4.21-4.31 (m, 2 H), 4.71 (s, 2 H), 7.13 (d, J = 7.7 Hz, 1 H), 7.35 (dd, J = 8.2, 2.4 Hz, 1 H), 7.42 (s, 1 H), 7.59-7.67 (m, 2 H), 7.81 (d, J = 8.1 Hz, 1 H), 8.26 (s, 1 H) |
| 39 | (300 MHz, DMSO-$d_6$) δ ppm 2.16 (s, 3 H), 3.68-3.79 (m, 2 H), 4.23-4.33 (m, 2 H), 4.80 (s, 2 H), 7.12 (d, J = 7.7 Hz, 1 H), 7.19-7.28 (m, 1 H), 7.36-7.45 (m, 2 H), 7.50-7.60 (m, 1 H), 7.80 (d, J = 7.7 Hz, 1 H), 8.24-8.29 (m, 1 H) |
| 40 | (300 MHz, DMSO-$d_6$) δ ppm 1.11 (d, J = 6.6 Hz, 3 H), 2.17 (s, 3 H), 2.35 (s, 3 H), 3.78-3.88 (m, 1 H), 3.93 (dd, J = 14.1, 4.1 Hz, 1 H), 4.44 (d, J = 15.7 Hz, 1 H), 4.64 (dd, J = 14.0, 2.1 Hz, 1 H), 5.09 (d, J = 15.7 Hz, 1 H), 7.14 (d, J = 7.7 Hz, 1 H), 7.23 (t, J = 7.7 Hz, 1 H), 7.31 (d, J = 6.7 Hz, 1 H), 7.36-7.46 (m, 2 H), 7.83 (d, J = 7.8 Hz, 1 H), 8.28 (d, J = 1.2 Hz, 1 H) |
| 42 | (360 MHz, DMSO-$d_6$) δ ppm 2.15 (s, 3 H), 3.64-3.75 (m, 2 H), 4.21-4.30 (m, 2 H), 4.81 (s, 2 H), 7.14 (d, J = 7.7 Hz, 1 H), 7.42 (s, 1 H), 7.57-7.71 (m, 3 H), 7.73 (s, 1 H), 7.81 (d, J = 8.1 Hz, 1 H), 8.26 (s, 1 H) |
| 43 | (300 MHz, DMSO-$d_6$) δ ppm 1.14 (d, J = 6.6 Hz, 3 H), 2.16 (s, 3 H), 3.88-4.09 (m, 2 H), 4.47-4.71 (m, 2 H), 5.10 (d, J = 15.7 Hz, 1 H), 7.15 (d, J = 7.7 Hz, 1 H), 7.44 (s, 1 H), 7.61 (d, J = 8.1 Hz, 2 H), 7.73 (d, J = 8.2 Hz, 2 H), 7.84 (d, J = 7.7 Hz, 1 H), 8.28 (d, J = 1.1 Hz, 1 H) |
| 44 | (300 MHz, DMSO-$d_6$) δ ppm 1.15 (d, J = 6.6 Hz, 3 H), 2.16 (s, 3 H), 3.96 (dd, J = 13.8, 4.2 Hz, 1 H), 4.00-4.13 (m, 1 H), 4.53-4.66 (m, 2 H), 5.18 (d, J = 15.5 Hz, 1 H), 7.15 (d, J = 7.8 Hz, 1 H), 7.44 (s, 1 H), 7.83 (d, J = 7.8 Hz, 1 H), 8.02-8.16 (m, 3 H), 8.29 (s, 1 H) |
| 45 | (300 MHz, DMSO-$d_6$) δ ppm 2.16 (s, 3 H), 3.39-3.60 (m, 2 H), 3.83-3.98 (m, 2 H), 4.64 (d, J = 15.8 Hz, 1 H), 4.78-4.90 (m, 1 H), 5.07-5.17 (m, 1 H), 5.22 (d, J = 15.9 Hz, 1 H), 7.09 (d, J = 7.7 Hz, 1 H), 7.43 (t, J = 1.2 Hz, 1 H), 7.79 (d, J = 7.8 Hz, 1 H), 8.05 (s, 1 H), 8.12 (s, 2 H), 8.28 (d, J = 1.2 Hz, 1 H) |
| 48 | (300 MHz, DMSO-$d_6$) δ ppm 2.14 (s, 6 H), 2.22 (s, 3 H), 2.29 (d, J = 7.4 Hz, 2 H), 3.93 (dd, J = 14.0, 4.3 Hz, 1 H), 4.05-4.21 (m, 1 H), 4.76 (d, J = 15.8 Hz, 1 H), 4.95 (d, J = 13.2 Hz, 1 H), 5.19 (d, J = 15.5 Hz, 1 H), 7.18 (d, J = 7.7 Hz, 1 H), 7.50 (s, 1 H), 7.87 (d, J = 7.7 Hz, 1 H), 8.11 (s, 1 H), 8.18 (s, 2 H), 8.34 (d, J = 1.1 Hz, 1 H) |
| 50 | (300 MHz, DMSO-$d_6$) δ ppm 1.13 (d, J = 6.7 Hz, 3 H), 2.16 (s, 3 H), 3.07-3.19 (m, 2 H), 3.37-3.51 (m, 1 H), 3.77 (dd, J = 14.1, 4.2 Hz, 1 H), 3.97-4.17 (m, 2 H), 4.62 (dd, J = 14.0, 2.3 Hz, 1 H), 7.04 (d, J = 7.7 Hz, 1 H), 7.38-7.45 (m, 1 H), 7.80 (d, J = 7.8 Hz, 1 H), 7.96 (s, 1 H), 8.08 (s, 2 H), 8.27 (d, J = 1.1 Hz, 1 H) |
| 53 | (360 MHz, DMSO-$d_6$) δ ppm 2.15 (s, 3 H), 3.67-3.85 (m, 2 H), 4.17-4.37 (m, 2 H), 4.89 (s, 2 H), 7.15 (d, J = 7.7 Hz, 1 H), 7.43 (br. s., 1 H), 7.81 (d, J = 7.7 Hz, 1 H), 7.98-8.15 (m, 3 H), 8.27 (br. s., 1 H) |

TABLE 2b-continued

| $^1H$ NMR results | |
|---|---|
| Co. No. | $^1H$ NMR result |
| 55 | (300 MHz, DMSO-$d_6$) δ ppm 2.17 (s, 3 H), 4.11-4.19 (m, 2 H), 4.44 (t, J = 5.6 Hz, 2 H), 7.21 (d, J = 7.8 Hz, 1 H), 7.46 (s, 1 H), 7.50-7.60 (m, 1 H), 7.78-7.96 (m, 3 H), 8.32 (s, 1 H) |
| 57 | (300 MHz, DMSO-$d_6$) δ ppm 2.17 (s, 3 H), 2.31 (s, 3 H), 3.84-3.98 (m, 1 H), 4.08-4.22 (m, 1 H), 4.25-4.40 (m, 1 H), 4.61 (dt, J = 14.1, 4.6 Hz, 1 H), 7.17 (d, J = 7.7 Hz, 1 H), 7.45 (s, 1 H), 7.48-7.60 (m, 1 H), 7.68 (d, J = 7.8 Hz, 1 H), 7.70 (d, J = 7.8 Hz, 1 H), 7.84 (d, J = 7.8 Hz, 1 H), 8.30 (s, 1 H) |
| 59 | (300 MHz, DMSO-$d_6$) δ ppm 1.13 (d, J = 6.5 Hz, 3 H), 2.16 (s, 3 H), 2.40 (s, 3 H), 3.84-4.02 (m, 2 H), 4.46 (d, J = 15.4 Hz, 1 H), 4.61 (d, J = 11.8 Hz, 1 H), 5.09 (d, J = 15.4 Hz, 1 H), 7.15 (d, J = 7.7 Hz, 1 H), 7.43 (s, 1 H), 7.50 (d, J = 5.5 Hz, 2 H), 7.54 (s, 1 H), 7.83 (d, J = 7.7 Hz, 1 H), 8.28 (d, J = 1.1 Hz, 1 H) |
| 60 | (300 MHz, DMSO-$d_6$) δ ppm 2.16 (s, 3 H), 2.40 (s, 3 H), 3.63-3.76 (m, 2 H), 4.20-4.33 (m, 2 H), 4.77 (s, 2 H), 7.15 (d, J = 7.7 Hz, 1 H), 7.38-7.44 (m, 1 H), 7.44-7.55 (m, 3 H), 7.81 (d, J = 7.7 Hz, 1 H), 8.22-8.29 (m, 1 H) |
| 61 | (300 MHz, DMSO-$d_6$) δ ppm 1.14 (d, J = 6.6 Hz, 3 H), 2.17 (s, 3 H), 2.41 (s, 3 H), 3.89 (br. s., 1 H), 4.01 (dd, J = 14.2, 4.0 Hz, 1 H), 4.50 (d, J = 15.9 Hz, 1 H), 4.65 (dd, J = 14.1, 2.1 Hz, 1 H), 5.10 (d, J = 15.9 Hz, 1 H), 7.14 (d, J = 7.7 Hz, 1 H), 7.36-7.48 (m, 2 H), 7.61 (d, J = 7.6 Hz, 1 H), 7.66 (d, J = 7.8 Hz, 1 H), 7.84 (d, J = 7.7 Hz, 1 H), 8.29 (d, J = 1.1 Hz, 1 H) |
| 62 | (300 MHz, CHLOROFORM-d) δ ppm 1.28 (d, J = 6.6 Hz, 3 H), 2.30 (s, 3 H), 3.70-3.92 (m, 2 H), 4.23 (d, J = 15.1 Hz, 1 H), 4.80 (dd, J = 14.0, 2.3 Hz, 1 H), 5.31 (d, J = 15.1 Hz, 1 H), 7.16 (s, 1 H), 7.33 (d, J = 7.7 Hz, 1 H), 7.44-7.57 (m, 3 H), 7.62-7.69 (m, 1 H), 8.26 (d, J = 1.1 Hz, 1 H) |
| 63 | (300 MHz, CHLOROFORM-d) δ ppm 1.30 (d, J = 6.7 Hz, 3 H), 2.31 (s, 3 H), 3.75-3.92 (m, 2 H), 4.24 (d, J = 15.3 Hz, 1 H), 4.82 (dd, J = 13.7, 1.9 Hz, 1 H), 5.36 (d, J = 15.3 Hz, 1 H), 7.17 (s, 1 H), 7.35 (d, J = 7.7 Hz, 1 H), 7.46-7.58 (m, 3 H), 7.62 (s, 1 H), 8.28 (s, 1 H) |
| 64 | (300 MHz, DMSO-$d_6$) δ ppm 2.17 (s, 3 H), 3.73-3.87 (m, 2 H), 4.28-4.41 (m, 2 H), 4.86 (s, 2 H), 7.14 (d, J = 7.8 Hz, 1 H), 7.43 (s, 1 H), 7.56 (t, J = 7.8 Hz, 1 H), 7.74 (d, J = 7.7 Hz, 1 H), 7.80-7.86 (m, 2 H), 8.28 (s, 1 H) |
| 65 | (300 MHz, DMSO-$d_6$) δ ppm 2.16 (s, 3 H), 3.66-3.79 (m, 2 H), 4.18-4.33 (m, 2 H), 4.79 (s, 2 H), 7.14 (d, J = 7.7 Hz, 1 H), 7.42 (s, 1 H), 7.64-7.76 (m, 2 H), 7.81 (d, J = 7.7 Hz, 1 H), 7.85 (s, 1 H), 8.26 (s, 1 H) |
| 67 | (300 MHz, DMSO-$d_6$) δ ppm 1.10 (d, J = 6.6 Hz, 3 H), 2.16 (s, 3 H), 3.84 (dd, J = 14.0, 4.1 Hz, 1 H), 3.89 (s, 3 H), 3.91-4.04 (m, 1 H), 4.43 (d, J = 15.0 Hz, 1 H), 4.61 (dd, J = 14.0, 2.2 Hz, 1 H), 4.99 (d, J = 15.0 Hz, 1 H), 7.14 (d, J = 7.7 Hz, 1 H), 7.26 (d, J = 9.2 Hz, 1 H), 7.43 (s, 1 H), 7.57-7.74 (m, 2 H), 7.82 (d, J = 7.8 Hz, 1 H), 8.27 (d, J = 1.2 Hz, 1 H) |
| 68 | (300 MHz, DMSO-$d_6$) δ ppm 1.13 (d, J = 6.5 Hz, 3 H), 2.16 (s, 3 H), 3.85 (s, 3 H), 3.87-3.95 (m, 1 H), 3.95-4.04 (m, 1 H), 4.48 (d, J = 15.5 Hz, 1 H), 4.61 (dd, J = 13.8, 2.0 Hz, 1 H), 5.08 (d, J = 15.3 Hz, 1 H), 7.15 (d, J = 7.7 Hz, 1 H), 7.18 (s, 1 H), 7.25 (s, 1 H), 7.32 (s, 1 H), 7.43 (s, 1 H), 7.83 (d, J = 7.7 Hz, 1 H), 8.28 (d, J = 1.2 Hz, 1 H) |
| 69 | (300 MHz, DMSO-$d_6$) δ ppm 2.16 (s, 3 H), 3.61-3.73 (m, 2 H), 3.89 (s, 3 H), 4.16-4.29 (m, 2 H), 4.71 (s, 2 H), 7.14 (d, J = 7.7 Hz, 1 H), 7.26 (d, J = 8.5 Hz, 1 H), 7.41 (s, 1 H), 7.57-7.67 (m, 2 H), 7.80 (d, J = 7.7 Hz, 1 H), 8.26 (s, 1 H) |
| 70 | (300 MHz, DMSO-$d_6$) δ ppm 1.15 (d, J = 6.5 Hz, 3 H), 2.16 (s, 3 H), 3.93 (dd, J = 13.8, 3.5 Hz, 1 H), 4.05 (br. s., 1 H), 4.57 (d, J = 15.5 Hz, 1 H), 4.64 (d, J = 13.7 Hz, 1 H), 5.06 (d, J = 15.5 Hz, 1 H), 7.13 (d, J = 7.7 Hz, 1 H), 7.44 (s, 1 H), 7.51 (t, J = 9.1 Hz, 1 H), 7.64-8.01 (m, 3 H), 8.28 (s, 1 H) |
| 71 | (300 MHz, DMSO-$d_6$) δ ppm 1.16 (d, J = 6.3 Hz, 3 H), 2.16 (s, 3 H), 3.92-4.11 (m, 2 H), 4.58 (d, J = 16.1 Hz, 1 H), 4.62-4.71 (m, 1 H), 5.10 (d, J = 15.9 Hz, 1 H), 7.14 (d, J = 7.8 Hz, 1 H), 7.44 (s, 1 H), 7.70-7.89 (m, 4 H), 8.29 (s, 1 H) |
| 72 | (300 MHz, DMSO-$d_6$) δ ppm 1.13 (d, J = 6.5 Hz, 3 H), 2.35 (s, 3 H), 2.40 (s, 3 H), 3.82-4.02 (m, 2 H), 4.54 (d, J = 15.7 Hz, 1 H), 4.64 (d, J = 12.2 Hz, 1 H), 5.09 (d, J = 15.7 Hz, 1 H), 7.25 (d, J = 7.8 Hz, 1 H), 7.48 (d, J = 7.8 Hz, 1 H), 7.54-7.70 (m, 2 H), 7.88 (s, 1 H), 8.11 (d, J = 7.7 Hz, 1 H), 9.52 (s, 1 H) |
| 74 | (360 MHz, DMSO-$d_6$) δ ppm 2.15 (s, 3 H), 3.64-3.74 (m, 2 H), 4.21-4.30 (m, 2 H), 4.77 (s, 2 H), 7.14 (d, J = 7.7 Hz, 1 H), 7.31 (d, J = 8.1 Hz, 1 H), 7.34-7.44 (m, 3 H), 7.47-7.55 (m, 1 H), 7.81 (d, J = 7.7 Hz, 1 H), 8.26 (d, J = 1.5 Hz, 1 H) |
| 75 | (300 MHz, DMSO-$d_6$) δ ppm 2.16 (s, 3 H), 2.34 (s, 3 H), 3.64 (t, J = 5.7 Hz, 2 H), 4.28 (t, J = 5.7 Hz, 2 H), 4.73 (s, 2 H), 7.10-7.21 (m, 2 H), 7.25 (s, 1 H), 7.36 (d, J = 8.4 Hz, 1 H), 7.42 (s, 1 H), 7.81 (d, J = 7.8 Hz, 1 H), 8.26 (s, 1 H) |
| 76 | (300 MHz, DMSO-$d_6$) δ ppm 1.07-1.25 (m, 6 H), 2.35 (s, 3 H), 3.52 (q, J = 7.0 Hz, 2 H), 3.89-4.09 (m, 2 H), 4.51-4.69 (m, 4 H), 5.12 (d, J = 15.5 Hz, 1 H), 7.25 (d, J = 7.7 Hz, 1 H), 7.58-7.72 (m, 3 H), 7.87 (s, 1 H), 8.12 (d, J = 7.7 Hz, 1 H), 9.51 (d, J = 1.4 Hz, 1 H) |
| 77 | (300 MHz, DMSO-$d_6$) δ ppm 1.07-1.21 (m, 6 H), 2.27 (s, 3 H), 2.34 (s, 3 H), 3.16-3.23 (m, 1 H), 3.57 (s, 3H), 3.67-3.90 (m, 5 H), 4.41 (d, J = 14.8 Hz, 1 H), 4.55-4.74 (m, 1 H), 4.98 (d, J = 14.8 Hz, 1 H), 6.83 (s, 1 H), 7.11 (s, 1 H), 7.25 (d, J = 7.7 Hz, 1 H), 7.87 (s, 1 H), 8.11 (d, J = 7.8 Hz, 1 H), 9.51 (s, 1 H) |
| 78 | (300 MHz, DMSO-$d_6$) δ ppm 1.13 (d, J = 6.5 Hz, 3 H), 1.28 (d, J = 5.9 Hz, 6 H), 2.34 (s, 3 H), 3.85-3.99 (m, 1 H), 3.99-4.10 (m, 1 H), 4.50 (d, J = 15.4 Hz, 1 H), 4.61 (dd, J = 13.8, 1.7 Hz, 1 H), 4.76 (dt, J = 12.0, 6.0 Hz, 1 H), 5.06 (d, J = 15.4 Hz, 1 H), 7.15 (s, 1 H), 7.19-7.28 (m, 2 H), 7.29 (s, 1 H), 7.87 (s, 1 H), 8.11 (d, J = 7.7 Hz, 1 H), 9.51 (s, 1 H) |

TABLE 2b-continued

| $^1H$ NMR results | |
|---|---|
| Co. No. | $^1H$ NMR result |
| 79 | (300 MHz, DMSO-$d_6$) δ ppm 1.11 (d, J = 6.6 Hz, 3 H), 2.16 (s, 3 H), 3.87-4.05 (m, 2 H), 4.50 (d, J = 15.4 Hz, 1 H), 4.60 (d, J = 11.7 Hz, 1 H), 5.04 (d, J = 15.4 Hz, 1 H), 7.13 (d, J = 7.7 Hz, 1 H), 7.30 (d, J = 7.0 Hz, 1 H), 7.36-7.46 (m, 3 H), 7.46-7.55 (m, 1 H), 7.82 (d, J = 7.7 Hz, 1 H), 8.27 (s, 1 H) |
| 83 | (300 MHz, DMSO-$d_6$) δ ppm 1.18 (d, J = 6.5 Hz, 3 H), 2.22 (s, 3 H), 2.24 (s, 3 H), 2.35 (s, 3 H), 3.96 (dd, J = 14.0, 4.1 Hz, 1 H), 4.01-4.13 (m, 1 H), 4.57 (d, J = 15.3 Hz, 1 H), 4.68 (dd, J = 13.9, 2.2 Hz, 1 H), 5.13 (d, J = 15.3 Hz, 1 H), 6.13 (s, 1 H), 7.20 (d, J = 7.7 Hz, 1 H), 7.40-7.59 (m, 5 H), 7.89 (d, J = 7.7 Hz, 1 H), 8.33 (d, J = 1.2 Hz, 1 H) |
| 84 | (300 MHz, DMSO-$d_6$) δ ppm 1.15 (d, J = 6.5 Hz, 3 H), 1.50-1.76 (m, 6 H), 2.22 (s, 3 H), 3.12-3.26 (m, 4 H), 3.82-3.92 (m, 1 H), 3.92-4.01 (m, 1 H), 4.36 (d, J = 15.0 Hz, 1 H), 4.68 (dd, J = 13.8, 2.1 Hz, 1 H), 5.06 (d, J = 14.8 Hz, 1 H), 6.80 (d, J = 7.4 Hz, 1 H), 6.91 (dd, J = 8.0, 2.2 Hz, 1 H), 6.97 (s, 1 H), 7.13-7.30 (m, 2 H), 7.48 (s, 1 H), 7.88 (d, J = 7.7 Hz, 1 H), 8.33 (s, 1 H) |
| 85 | (300 MHz, DMSO-$d_6$) δ ppm 1.10 (d, J = 6.6 Hz, 3 H), 1.48-1.60 (m, 2 H), 1.60-1.74 (m, 4 H), 2.16 (s, 3 H), 2.85-3.02 (m, 4 H), 3.77-3.99 (m, 2 H), 4.36 (d, J = 15.3 Hz, 1 H), 4.61 (dd, J = 13.7, 1.8 Hz, 1 H), 5.01 (d, J = 15.1 Hz, 1 H), 7.02 (dd, J = 8.2, 1.9 Hz, 1 H), 7.09-7.18 (m, 2 H), 7.37 (d, J = 8.1 Hz, 1 H), 7.40-7.46 (m, 1 H), 7.83 (d, J = 7.7 Hz, 1 H), 8.28 (d, J = 1.1 Hz, 1 H) |
| 88 | (300 MHz, DMSO-$d_6$) δ ppm 2.16 (s, 3 H), 3.60-3.80 (m, 2 H), 4.11-4.38 (m, 2 H), 4.79 (s, 2 H), 7.32-7.72 (m, 10 H), 7.92 (s, 1 H), 8.36 (s, 1 H) |
| 89 | (360 MHz, DMSO-$d_6$) δ ppm 2.08 (s, 3 H), 3.66 (t, J = 5.7 Hz, 2 H), 4.21 (t, J = 5.7 Hz, 2 H), 4.73 (s, 2 H), 6.77 (br. s., 1 H), 7.13 (d, J = 7.7 Hz, 1 H), 7.26-7.43 (m, 5 H), 7.62 (br. s., 1 H), 7.75 (d, J = 7.3 Hz, 1 H) |
| 91 | (300 MHz, DMSO-$d_6$) δ ppm 2.04-2.17 (m, 3 H), 3.76-3.95 (m, 2 H), 4.18-4.34 (m, 2 H), 4.87 (s, 2 H), 7.07 (d, J = 7.7 Hz, 1 H), 7.36 (t, J = 1.3 Hz, 1 H), 7.43-7.52 (m, 2 H), 7.60-7.70 (m, 3 H), 7.74 (d, J = 7.8 Hz, 1 H), 8.21 (d, J = 1.1 Hz, 1 H) |
| 92 | (300 MHz, DMSO-$d_6$) δ ppm 2.18 (s, 3 H), 3.13 (t, J = 7.2 Hz, 2 H), 3.61-3.97 (m, 4 H), 4.15-4.33 (m, 2 H), 7.03 (d, J = 7.7 Hz, 1 H), 7.43 (br. s., 1 H), 7.80 (d, J = 7.7 Hz, 1 H), 7.98 (s, 1 H), 8.08 (s, 2 H), 8.29 (br. s., 1 H) |
| 93 | (300 MHz, DMSO-$d_6$) δ ppm 1.99-2.21 (m, 5 H), 3.56-3.77 (m, 2 H), 4.13 (q, J = 5.9 Hz, 4 H), 4.19-4.37 (m, 2 H), 4.68 (s, 2 H), 6.84-7.02 (m, 3 H), 7.12 (d, J = 7.7 Hz, 1 H), 7.42 (br. s., 1 H), 7.80 (d, J = 7.7 Hz, 1 H), 8.26 (br. s., 1 H) |
| 94 | (300 MHz, DMSO-$d_6$) δ ppm 2.16 (s, 3 H), 2.47 (s, 3 H), 3.59-3.80 (m, 2 H), 4.27 (t, J = 5.8 Hz, 2 H), 4.87 (s, 2 H), 7.18 (d, J = 7.8 Hz, 1 H), 7.27-7.51 (m, 3 H), 7.68 (s, 1 H), 7.75-7.93 (m, 4 H), 8.26 (s, 1 H) |
| 97 | (300 MHz, DMSO-$d_6$) δ ppm 1.54 (br. s., 2 H), 1.59-1.72 (m, 4 H), 2.16 (s, 3 H), 2.19 (s, 3 H), 2.76 (br. s., 4 H), 3.49-3.60 (m, 2 H), 4.18-4.30 (m, 2 H), 4.70 (s, 2 H), 6.93 (d, J = 7.4 Hz, 1 H), 7.00 (d, J = 7.7 Hz, 1 H), 7.08-7.20 (m, 2 H), 7.42 (s, 1 H), 7.81 (d, J = 7.8 Hz, 1 H), 8.26 (s, 1 H) |
| 98 | (300 MHz, DMSO-$d_6$) δ ppm 2.12-2.17 (m, 3 H), 2.18 (s, 3 H), 3.66-3.81 (m, 2 H), 4.23-4.35 (m, 2 H), 4.85 (s, 2 H), 4.91 (q, J = 8.8 Hz, 2 H), 7.06-7.14 (m, 2 H), 7.41 (t, J = 1.2 Hz, 1 H), 7.80 (d, J = 7.8 Hz, 1 H), 8.26 (d, J = 1.1 Hz, 1 H), 8.30 (d, J = 5.6 Hz, 1 H) |
| 99 | (300 MHz, DMSO-$d_6$) δ ppm 1.42-1.59 (m, 2 H), 1.59-1.74 (m, 4 H), 2.16 (s, 3 H), 2.21 (s, 3 H), 2.69-2.88 (m, 4 H), 3.46-3.72 (m, 2 H), 4.12-4.32 (m, 2 H), 4.64 (s, 2 H), 6.89 (d, J = 7.6 Hz, 1 H), 6.95 (s, 1 H), 7.13 (dd, J = 7.8, 4.5 Hz, 2 H), 7.41 (s, 1 H), 7.80 (d, J = 7.7 Hz, 1 H), 8.25 (s, 1 H) |
| 103 | (300 MHz, DMSO-$d_6$) δ ppm 1.86-2.02 (m, 2 H), 2.16 (s, 3 H), 3.62 (dt, J = 13.6, 6.9 Hz, 1 H), 3.71-3.85 (m, 3 H), 3.93 (dd, J = 11.3, 7.4 Hz, 1 H), 4.18-4.30 (m, 3 H), 4.34 (dd, J = 11.3, 2.1 Hz, 1 H), 6.78-6.91 (m, 4 H), 7.08 (d, J = 7.7 Hz, 1 H), 7.41 (s, 1 H), 7.79 (d, J = 7.7 Hz, 1 H), 8.25 (d, J = 1.1 Hz, 1 H) |
| 104 | (300 MHz, DMSO-$d_6$) δ ppm 2.18 (s, 3 H), 2.89-3.04 (m, 2 H), 3.54-3.63 (m, 2 H), 3.68 (t, J = 7.6 Hz, 2 H), 3.92-4.05 (m, 2 H), 6.62 (dd, J = 9.1, 1.3 Hz, 1 H), 6.95 (dd, J = 6.9, 1.2 Hz, 1 H), 7.04-7.13 (m, 1 H), 7.18 (td, J = 7.5, 1.1 Hz, 1 H), 7.23 (s, 1 H), 7.35 (d, J = 8.0 Hz, 1 H), 7.55 (dd, J = 9.1, 6.9 Hz, 1 H), 7.70 (d, J = 7.7 Hz, 1 H), 7.91 (d, J = 1.2 Hz, 1 H), 11.62 (s, 1 H) |
| 105 | (300 MHz, DMSO-$d_6$) δ ppm 2.04-2.15 (m, 1 H), 2.16 (s, 3 H), 2.40-2.48 (m, 1 H), 2.97-3.28 (m, 3 H), 3.54 (ddd, J = 13.0, 8.5, 4.1 Hz, 1 H), 4.06-4.23 (m, 1 H), 4.24-4.37 (m, 1 H), 6.18 (t, J = 8.4 Hz, 1 H), 7.18 (d, J = 7.8 Hz, 1 H), 7.43 (s, 1 H), 7.44-7.52 (m, 1 H), 7.63 (t, J = 8.8 Hz, 2 H), 7.84 (d, J = 7.7 Hz, 1 H), 8.27 (d, J = 1.1 Hz, 1 H) |
| 108 | (300 MHz, DMSO-$d_6$) δ ppm 2.19 (s, 3 H), 3.72 (t, J = 5.8 Hz, 2 H), 4.23 (t, J = 5.8 Hz, 2 H), 4.80 (s, 2 H), 6.87 (s, 1 H), 7.08-7.17 (m, 2 H), 7.31-7.42 (m, 2 H), 7.42-7.53 (m, 3 H), 7.57-7.71 (m, 4 H), 7.74 (d, J = 7.6 Hz, 1 H) |
| 109 | (300 MHz, DMSO-$d_6$) δ ppm 3.65-3.80 (m, 2 H), 4.20-4.37 (m, 2 H), 4.80 (s, 2 H), 7.08 (s, 1 H), 7.17 (d, J = 7.7 Hz, 1 H), 7.31-7.43 (m, 2 H), 7.48 (t, J = 7.4 Hz, 3 H), 7.55-7.76 (m, 5 H), 7.88 (d, J = 7.7 Hz, 1 H), 8.33 (s, 1 H) |
| 111 | (300 MHz, DMSO-$d_6$) δ ppm 1.20 (d, J = 6.6 Hz, 3 H), 1.73 (d, J = 7.1 Hz, 3 H), 2.33 (s, 3 H), 3.71 (dd, J = 14.0, 3.7 Hz, 1 H), 4.06-4.19 (m, 1 H), 4.53-4.69 (m, 1 H), 5.74 (q, J = 6.9 Hz, 1 H), 7.19 (d, J = 7.7 Hz, 1 H), 7.81-7.89 (m, 1 H), 8.02-8.17 (m, 4 H), 9.40-9.51 (m, 1 H) |

TABLE 2b-continued

| $^1H$ NMR results | |
|---|---|
| Co. No. | $^1H$ NMR result |
| 112 | (300 MHz, DMSO-$d_6$) δ ppm 0.82 (d, J = 6.5 Hz, 3 H), 1.79 (d, J = 7.0 Hz, 3 H), 2.33 (s, 3 H), 3.95 (dd, J = 14.0, 3.8 Hz, 1 H), 4.27-4.48 (m, 1 H), 4.65 (d, J = 12.8 Hz, 1 H), 5.64 (q, J = 6.8 Hz, 1 H), 7.21 (d, J = 7.7 Hz, 1 H), 7.85 (s, 1 H), 7.99-8.28 (m, 4 H), 9.47 (s, 1 H) |
| 119 | (600 MHz, DMSO-$d_6$) δ ppm 2.37 (s, 3 H), 3.64-3.68 (m, 2 H), 3.75 (3 H), 4.27-4.30 (m, 2 H), 4.69 (s, 2 H), 6.87 (ddd, J = 8.2, 2.6, 1.0 Hz, 1 H), 6.90-6.92 (m, 2 H), 7.25 (d, J = 7.8 Hz, 1 H), 7.28 (t, J = 7.8 Hz, 1 H), 8.13 (d, J = 7.9 Hz, 1 H), 9.40 (d, J = 0.6 Hz, 1 H) |
| 120 | (600 MHz, DMSO-$d_6$) δ ppm 2.37 (s, 3 H), 3.71-3.74 (m, 2 H), 4.30-4.32 (m, 2 H), 4.82 (s, 2 H), 7.26 (d, J = 7.9 Hz, 1 H), 7.60-7.63 (m, 1 H), 7.67 (d, J = 7.9 Hz, 2 H), 7.73 (s, 1 H), 8.13 (d, J = 7.9 Hz, 1 H), 9.40 (s, 1 H) |
| 121 | (400 MHz, CHLOROFORM-d) δ ppm 2.00 (quin, J = 6.4 Hz, 2 H), 2.29 (s, 3 H), 3.34 (t, J = 6.1 Hz, 2 H), 4.33 (br. s., 2 H), 4.70 (s, 2 H), 6.79 (d, J = 7.5 Hz, 1 H), 7.11 (br. s., 1 H), 7.21 (d, J = 8.0 Hz, 1 H), 7.41 (d, J = 7.5 Hz, 1 H), 7.43-7.51 (m, 2 H), 8.16 (br. s., 1 H) |
| 122 | (360 MHz, DMSO-$d_6$) δ ppm 1.90 (quin, J = 6.2 Hz, 2 H), 2.07 (s, 3 H), 3.36-3.41 (m, 2 H), 4.17 (br. s., 2 H), 4.70 (s, 2 H), 6.70 (d, J = 7.7 Hz, 1 H), 6.75 (s, 1 H), 7.38 (dd, J = 8.4, 1.8 Hz, 1 H), 7.60 (s, 1 H), 7.62-7.74 (m, 3 H) |
| 176 | (360 MHz, CHLOROFORM-d) δ ppm 1.15 (d, J = 6.6 Hz, 3 H), 2.28 (d, J = 1.1 Hz, 3 H), 2.94-3.07 (m, 2 H), 3.11-3.21 (m, 1 H), 3.36-3.51 (m, 2 H), 4.28-4.38 (m, 1 H), 4.60 (dd, J = 13.9, 2.2 Hz, 1 H), 7.13 (t, J = 1.5 Hz, 1 H), 7.20-7.26 (m, 4 H), 7.27-7.37 (m, 2 H), 7.45 (d, J = 7.7 Hz, 1 H), 8.22 (d, J = 1.5 Hz, 1 H) |
| 177 | (360 MHz, CHLOROFORM-d) δ ppm 1.19 (d, J = 7.0 Hz, 3 H), 2.28 (s, 3 H), 3.49 (dd, J = 14.1, 4.2 Hz, 1 H), 3.77 (s, 3 H), 3.82-3.95 (m, 1 H), 4.28 (d, J = 15.0 Hz, 1 H), 4.72 (dd, J = 14.3, 2.2 Hz, 1 H), 5.48 (d, J = 15.0 Hz, 1 H), 7.12 (d, J = 8.8 Hz, 2 H), 7.18-7.25 (m, 1 H), 7.33 (d, J = 7.7 Hz, 1 H), 7.43-7.58 (m, 3 H), 8.22 (s, 1 H) |
| 179 | (360 MHz, DMSO-$d_6$) δ ppm 1.62 (d, J = 6.6 Hz, 3 H), 2.65 (d, J = 1.1 Hz, 3 H), 4.03-4.16 (m, 1 H), 4.48-4.60 (m, 1 H), 5.06 (d, J = 14.6 Hz, 1 H), 5.20 (dd, J = 14.3, 2.2 Hz, 1 H), 5.80 (dd, J = 15.0, 0.7 Hz, 1 H), 7.51 (dd, J = 8.6, 2.0 Hz, 1 H), 7.72 (d, J = 7.7 Hz, 1 H), 7.82 (t, J = 1.3 Hz, 1 H), 7.95 (d, J = 1.8 Hz, 1 H), 8.03-8.09 (m, 1 H), 8.18 (d, J = 8.8 Hz, 1 H), 8.24 (d, J = 7.7 Hz, 1 H), 8.77 (d, J = 1.5 Hz, 1 H), 11.03 (br. s., 1 H) |
| 124 | (360 MHz, CHLOROFORM-d) δ ppm 1.23 (d, J = 6.6 Hz, 3 H), 2.24-2.36 (m, 3 H), 3.71 (dd, J = 14.1, 4.2 Hz, 1 H), 3.77-3.90 (m, 1 H), 4.15 (d, J = 15.0 Hz, 1 H), 4.75 (dd, J = 14.1, 2.4 Hz, 1 H), 5.38 (d, J = 15.0 Hz, 1 H), 7.15 (s, 1 H), 7.29-7.44 (m, 6 H), 7.48 (d, J = 7.7 Hz, 1 H), 8.20-8.30 (m, 1 H) |
| 125 | (400 MHz, CHLOROFORM-d) δ ppm 1.17 (d, J = 6.9 Hz, 3 H), 2.28 (s, 3 H), 3.50 (dd, J = 14.1, 4.0 Hz, 1 H), 3.81-3.90 (m, 1 H), 4.33 (d, J = 14.9 Hz, 1 H), 4.70 (dd, J = 14.1, 2.0 Hz, 1 H), 5.49 (d, J = 14.9 Hz, 1 H), 7.13 (s, 1 H), 7.18-7.26 (m, 2 H), 7.34 (d, J = 7.7 Hz, 1 H), 7.46-7.57 (m, 3 H), 8.19-8.29 (m, 1 H), 9.05 (br. s., 1 H) |
| 126 | (300 MHz, DMSO-$d_6$) δ ppm 0.80 (d, J = 6.6 Hz, 3 H), 1.74 (d, J = 7.0 Hz, 3 H), 2.39 (s, 3 H), 4.00 (dd, J = 14.0, 3.7 Hz, 1 H), 4.32 (br. s., 1 H), 4.68 (d, J = 13.6 Hz, 1 H), 5.67 (q, J = 6.8 Hz, 1 H), 7.27 (d, J = 7.8 Hz, 1 H), 7.36 (s, 1 H), 7.39-7.53 (m, 2 H), 7.92 (s, 1 H), 8.16 (d, J = 7.7 Hz, 1 H), 9.58 (d, J = 1.0 Hz, 1 H) |
| 127 | (300 MHz, DMSO-$d_6$) δ ppm 1.24 (d, J = 6.5 Hz, 3 H), 1.71 (d, J = 7.1 Hz, 3 H), 2.41 (s, 3 H), 3.76 (dd, J = 14.0, 3.6 Hz, 1 H), 3.95-4.14 (m, 1 H), 4.65 (d, J = 13.6 Hz, 1 H), 5.73 (q, J = 7.0 Hz, 1 H), 7.25 (d, J = 7.7 Hz, 1 H), 7.31-7.50 (m, 3 H), 7.94 (s, 1 H), 8.18 (d, J = 7.7 Hz, 1 H), 9.62 (d, J = 1.0 Hz, 1 H) |
| 129 | (360 MHz, CHLOROFORM-d) δ ppm 0.75 (d, J = 7.0 Hz, 3 H), 1.73 (d, J = 7.3 Hz, 3 H), 2.28 (s, 3 H), 3.71 (dd, J = 14.1, 3.8 Hz, 1 H), 3.92-4.02 (m, 1 H), 4.87 (dd, J = 13.9, 1.8 Hz, 1 H), 6.00 (q, J = 7.0 Hz, 1 H), 7.14 (s, 1 H), 7.31 (d, J = 7.7 Hz, 1 H), 7.49 (d, J = 7.7 Hz, 1 H), 7.58 (s, 1 H), 7.60 (s, 1 H), 7.65 (s, 1 H), 8.25 (s, 1 H) |
| 130 | (360 MHz, CHLOROFORM-d) δ ppm 1.32 (d, J = 6.6 Hz, 3 H), 1.72 (d, J = 7.3 Hz, 3 H), 2.28 (s, 3 H), 3.38 (dd, J = 14.3, 3.7 Hz, 1 H), 3.64-3.76 (m, 1 H), 4.77 (dd, J = 13.9, 1.5 Hz, 1 H), 6.06 (q, J = 7.2 Hz, 1 H), 7.15 (s, 1 H), 7.30 (d, J = 7.7 Hz, 1 H), 7.45-7.52 (m, 2 H), 7.56 (s, 1 H), 7.61 (s, 1 H), 8.23 (s, 1 H) |
| 131 | (400 MHz, CHLOROFORM-d) δ ppm 1.27 (d, J = 6.9 Hz, 3 H), 2.29 (d, J = 1.2 Hz, 3 H), 3.76-3.87 (m, 2 H), 4.12 (d, J = 15.3 Hz, 1 H), 4.78 (dd, J = 13.9, 2.2 Hz, 1 H), 5.27 (d, J = 15.7 Hz, 1 H), 7.15 (t, J = 1.2 Hz, 1 H), 7.22 (d, J = 2.0 Hz, 2 H), 7.32 (d, J = 7.7 Hz, 1 H), 7.34 (t, J = 1.8 Hz, 1 H), 7.48 (d, J = 7.7 Hz, 1 H), 8.25 (d, J = 1.2 Hz, 1 H) |
| 132 | (360 MHz, CHLOROFORM-d) δ ppm 1.23 (d, J = 6.6 Hz, 3 H), 2.29 (d, J = 0.7 Hz, 3 H), 3.71 (dd, J = 14.1, 4.2 Hz, 1 H), 3.77-3.87 (m, 4 H), 4.10 (d, J = 14.6 Hz, 1 H), 4.76 (dd, J = 14.1, 2.4 Hz, 1 H), 5.37 (d, J = 15.0 Hz, 1 H), 6.81-6.93 (m, 3 H), 7.15 (t, J = 1.1 Hz, 1 H), 7.27-7.35 (m, 2 H), 7.48 (d, J = 7.7 Hz, 1 H), 8.24 (d, J = 1.5 Hz, 1 H) |
| 133 | (360 MHz, CHLOROFORM-d) δ ppm 1.24 (d, J = 7.0 Hz, 3 H), 2.29 (s, 3 H), 3.75 (dd, J = 14.1, 4.2 Hz, 1 H), 3.79-3.89 (m, 1 H), 4.16 (d, J = 15.0 Hz, 1 H), 4.78 (dd, J = 14.3, 2.6 Hz, 1 H), 5.24 (d, J = 14.6 Hz, 1 H), 7.02-7.11 (m, 1 H), 7.11-7.22 (m, 3 H), 7.32 (d, J = 7.7 Hz, 1 H), 7.48 (d, J = 7.7 Hz, 1 H), 8.21-8.28 (m, 1 H) |

TABLE 2b-continued

| $^1H$ NMR results | |
|---|---|
| Co. No. | $^1H$ NMR result |
| 135 | (300 MHz, DMSO-$d_6$) δ ppm 0.12-0.29 (m, 2 H), 0.39-0.55 (m, 2 H), 0.63 (d, J = 6.5 Hz, 3 H), 0.88-1.07 (m, 1 H), 1.70 (d, J = 7.3 Hz, 3 H), 2.33 (s, 3 H), 2.62 (d, J = 6.9 Hz, 2 H), 3.90 (dd, J = 14.0, 3.4 Hz, 1 H), 4.25 (br. s., 1 H), 4.61 (d, J = 13.6 Hz, 1 H), 5.60-5.92 (m, 1 H), 7.23 (d, J = 7.7 Hz, 1 H), 7.59 (s, 2 H), 7.66 (s, 1 H), 7.85 (s, 1 H), 8.09 (d, J = 7.8 Hz, 1 H), 9.49 (s, 1 H) |
| 136 | (300 MHz, DMSO-$d_6$) δ ppm 0.09-0.32 (m, 2 H), 0.35-0.54 (m, 2 H), 0.89-1.08 (m, 1 H), 1.19 (d, J = 6.5 Hz, 3 H), 1.68 (d, J = 6.9 Hz, 3 H), 2.34 (s, 3 H), 2.62 (d, J = 6.7 Hz, 2 H), 3.62 (dd, J = 14.0, 3.1 Hz, 1 H), 3.93 (br. s., 1 H), 4.60 (d, J = 13.6 Hz, 1 H), 5.69-5.82 (m, 1 H), 7.21 (d, J = 7.7 Hz, 1 H), 7.57 (br. s., 2 H), 7.62 (br. s., 1 H), 7.86 (s, 1 H), 8.11 (d, J = 7.8 Hz, 1 H), 9.49 (s, 1 H) |
| 137 | (360 MHz, DMSO-$d_6$) δ ppm 1.05 (d, J = 6.6 Hz, 3 H), 2.15 (s, 3 H), 3.64 (dd, J = 14.3, 4.0 Hz, 1 H), 3.78 (s, 3 H), 3.90-4.03 (m, 1 H), 4.51 (d, J = 15.0 Hz, 1 H), 4.59 (dd, J = 14.1, 1.6 Hz, 1 H), 5.10 (d, J = 15.0 Hz, 1 H), 7.17 (d, J = 7.3 Hz, 2 H), 7.41 (s, 1 H), 7.47 (d, J = 8.8 Hz, 1 H), 7.55 (s, 1 H), 7.69 (d, J = 1.8 Hz, 1 H), 7.82 (d, J = 7.7 Hz, 1 H), 8.25 (s, 1 H) |
| 138 | (360 MHz, DMSO-$d_6$) δ ppm 1.02-1.05 (m, 3 H), 2.15 (s, 3 H), 3.57-3.66 (m, 1 H), 3.96 (ddd, J = 6.7, 4.3, 2.2 Hz, 1 H), 4.54 (d, J = 15.0 Hz, 1 H), 4.59 (dd, J = 14.1, 2.0 Hz, 1 H), 5.10 (d, J = 14.6 Hz, 1 H), 7.08-7.12 (m, 1 H), 7.18 (d, J = 7.7 Hz, 1 H), 7.38-7.43 (m, 2 H), 7.58 (d, J = 2.6 Hz, 1 H), 7.67 (d, J = 2.2 Hz, 1 H), 7.82 (d, J = 7.7 Hz, 1 H), 8.25 (d, J = 1.5 Hz, 1 H), 11.29-11.34 (m, 1 H) |
| 139 | (300 MHz, DMSO-$d_6$) δ ppm 1.17 (d, J = 6.6 Hz, 3 H), 2.38 (s, 3 H), 3.80 (dd, J = 14.3, 4.1 Hz, 1 H), 3.95-4.05 (m, 1 H), 4.61 (d, J = 14.7 Hz, 1 H), 4.66-4.77 (m, 1 H), 5.20 (d, J = 14.6 Hz, 1 H), 7.27 (d, J = 7.7 Hz, 1 H), 7.33-7.49 (m, 2 H), 7.58-7.69 (m, 1 H), 7.89 (s, 1 H), 8.13 (d, J = 7.8 Hz, 1 H), 9.50 (s, 1 H) |
| 140 | (300 MHz, DMSO-$d_6$) δ ppm 1.19 (d, J = 6.5 Hz, 3 H), 2.38 (s, 3 H), 3.93-4.20 (m, 2 H), 4.52-4.78 (m, 2 H), 5.17 (d, J = 15.7 Hz, 1 H), 7.28 (d, J = 7.7 Hz, 1 H), 7.80 (d, J = 8.0 Hz, 2 H), 7.90 (d, J = 5.8 Hz, 2 H), 8.15 (d, J = 7.7 Hz, 1 H), 9.56 (s, 1 H) |
| 141 | (300 MHz, DMSO-$d_6$) δ ppm 0.55 (d, J = 6.2 Hz, 3 H), 0.91 (t, J = 6.9 Hz, 3 H), 2.03-2.42 (m, 5 H), 3.76-4.01 (m, 4 H), 4.24 (br. s., 1 H), 4.61 (d, J = 13.9 Hz, 1 H), 5.53 (t, J = 7.5 Hz, 1 H), 7.17-7.30 (m, 2 H), 7.33 (br. s., 1 H), 7.36 (br. s., 1 H), 7.83 (s, 1 H), 8.08 (d, J = 7.7 Hz, 1 H), 9.43 (s, 1 H) |
| 142 | (300 MHz, DMSO-$d_6$) δ ppm 0.94 (t, J = 6.8 Hz, 3 H), 1.16 (d, J = 6.2 Hz, 3 H), 2.03-2.29 (m, 2 H), 2.33 (s, 3 H), 3.52 (dd, J = 13.9, 2.7 Hz, 1 H), 3.87 (s, 3 H), 3.92 (br. s., 1 H), 4.58 (d, J = 13.6 Hz, 1 H), 5.43 (t, J = 7.6 Hz, 1 H), 7.08-7.26 (m, 2 H), 7.30 (br. s., 1 H), 7.35 (s, 1 H), 7.83 (s, 1 H), 8.09 (d, J = 7.6 Hz, 1 H), 9.41 (s, 1 H) |
| 143 | (300 MHz, DMSO-$d_6$) δ ppm 0.66 (d, J = 6.6 Hz, 3 H), 1.35 (t, J = 6.9 Hz, 3 H), 1.69 (d, J = 7.1 Hz, 3 H), 2.34 (s, 3 H), 3.90 (dd, J = 14.1, 3.2 Hz, 1 H), 4.14 (q, J = 6.9 Hz, 2 H), 4.29 (br. s., 1 H), 4.62 (d, J = 13.7 Hz, 1 H), 5.72 (q, J = 7.0 Hz, 1 H), 7.21 (br. s., 1 H), 7.23 (d, J = 7.7 Hz, 1 H), 7.28-7.44 (m, 2 H), 7.85 (s, 1 H), 8.10 (d, J = 7.8 Hz, 1 H), 9.49 (s, 1 H) |
| 144 | (300 MHz, DMSO-$d_6$) δ ppm 1.19 (d, J = 6.5 Hz, 3 H), 1.35 (t, J = 6.9 Hz, 3 H), 1.67 (d, J = 7.1 Hz, 3 H), 2.35 (s, 3 H), 3.62 (dd, J = 14.0, 3.4 Hz, 1 H), 3.98 (br. s., 1 H), 4.14 (q, J = 6.9 Hz, 2 H), 4.60 (d, J = 13.6 Hz, 1 H), 5.65-5.75 (m, 1 H), 7.18 (br. s., 1 H), 7.21 (d, J = 7.7 Hz, 1 H), 7.26 (s, 1 H), 7.31 (s, 1 H), 7.87 (s, 1 H), 8.11 (d, J = 7.7 Hz, 1 H), 9.51 (s, 1 H) |
| 145 | (300 MHz, DMSO-$d_6$) δ ppm 1.21 (d, J = 6.3 Hz, 3 H), 2.39 (s, 3 H), 3.96-4.18 (m, 2 H), 4.51-4.72 (m, 2 H), 5.16 (d, J = 15.5 Hz, 1 H), 7.30 (d, J = 7.7 Hz, 1 H), 7.91 (s, 1 H), 7.86 (s, 1 H), 8.00 (d, J = 9.5 Hz, 2 H), 8.15 (d, J = 7.7 Hz, 1 H), 9.53 (s, 1 H) |
| 146 | (300 MHz, DMSO-$d_6$) δ ppm 0.68 (d, J = 6.6 Hz, 3 H), 1.74 (d, J = 7.0 Hz, 3 H), 2.38 (s, 3 H), 3.96 (dd, J = 14.0, 3.6 Hz, 1 H), 4.22-4.38 (m, 1 H), 4.67 (d, J = 13.3 Hz, 1 H), 5.81 (q, J = 7.0 Hz, 1 H), 7.05-7.05 (m, 1 H), 7.28 (d, J = 7.8 Hz, 1 H), 7.42 (d, J = 7.6 Hz, 1 H), 7.49 (s, 1 H), 7.54-7.65 (m, 2 H), 7.89 (s, 1 H), 8.13 (d, J = 7.7 Hz, 1 H), 9.48 (s, 1 H) |
| 147 | (300 MHz, DMSO-$d_6$) δ ppm 1.19 (d, J = 6.6 Hz, 3 H), 1.67 (d, J = 7.3 Hz, 3 H), 2.34 (s, 3 H), 3.64 (dd, J = 13.9, 4.0 Hz, 1 H), 3.85-4.00 (m, 1 H), 4.60 (d, J = 12.9 Hz, 1 H), 5.74 (q, J = 7.1 Hz, 1 H), 7.22 (d, J = 7.8 Hz, 1 H), 7.34 (d, J = 7.6 Hz, 1 H), 7.43 (s, 1 H), 7.45-7.60 (m, 2 H), 7.87 (s, 1 H), 8.11 (d, J = 7.7 Hz, 1 H), 9.46-9.54 (m, 1 H) |
| 148 | (300 MHz, DMSO-$d_6$) δ ppm 0.68 (d, J = 6.2 Hz, 3 H), 1.70 (d, J = 6.9 Hz, 3 H), 2.35 (s, 3 H), 3.80-3.99 (m, 4 H), 4.29 (br. s., 1 H), 4.62 (d, J = 13.6 Hz, 1 H), 5.72 (q, J = 7.0 Hz, 1 H), 7.06-7.29 (m, 2 H), 7.33 (br. s., 1 H), 7.35 (br. s., 1 H), 7.87 (s, 1 H), 8.11 (d, J = 7.7 Hz, 1 H), 9.53 (s, 1 H) |
| 149 | (300 MHz, DMSO-$d_6$) δ ppm 1.19 (d, J = 6.5 Hz, 3 H), 1.67 (d, J = 7.1 Hz, 3 H), 2.34 (s, 3 H), 3.63 (dd, J = 14.4, 3.3 Hz, 1 H), 3.86 (s, 3 H), 3.91-4.03 (m, 1 H), 4.61 (d, J = 13.7 Hz, 1 H), 5.72 (q, J = 7.2 Hz, 1 H), 7.15-7.25 (m, 2 H), 7.33 (s, 1 H), 7.27 (s, 1 H), 7.86 (s, 1 H), 8.10 (d, J = 7.7 Hz, 1 H), 9.48 (s, 1 H) |
| 155 | (360 MHz, DMSO-$d_6$) δ ppm 1.15 (d, J = 6.2 Hz, 3 H), 2.38 (s, 3 H), 3.93-4.03 (m, 1 H), 4.06 (ddd, J = 6.3, 4.1, 2.0 Hz, 1 H), 4.60 (d, J = 15.7 Hz, 1 H), 4.66 (dd, J = 13.7, 2.0 Hz, 1 H), 5.19 (d, J = 15.7 Hz, 1 H), 7.26 (d, J = 8.1 Hz, 1 H), 8.06 (s, 1 H), 8.10-8.19 (m, 3 H), 9.42 (s, 1 H) |

TABLE 2b-continued

<sup>1</sup>H NMR results

| Co. No. | <sup>1</sup>H NMR result |
|---|---|
| 160 | (300 MHz, DMSO-d$_6$) δ ppm 1.28 (d, J = 5.9 Hz, 6 H), 2.16 (s, 3 H), 3.65-3.77 (m, 2 H), 4.19-4.31 (m, 2 H), 4.70-4.81 (m, 3 H), 7.10-7.21 (m, 3 H), 7.24 (s, 1 H), 7.42 (t, J = 1.2 Hz, 1 H), 7.81 (d, J = 7.7 Hz, 1 H), 8.26 (dd, J = 1.2, 0.3 Hz, 1 H) |
| 163 | (300 MHz, DMSO-d$_6$) δ ppm 1.14 (d, J = 6.5 Hz, 3 H), 1.28 (d, J = 5.9 Hz, 6 H), 2.34 (s, 3 H), 3.90-4.11 (m, 2 H), 4.44-4.55 (m, 1 H), 4.57-4.72 (m, 2 H), 4.99 (d, J = 15.3 Hz, 1 H), 7.14-7.29 (m, 2 H), 7.48 (d, J = 9.5 Hz, 1 H), 7.87 (s, 1 H), 8.10 (d, J = 7.8 Hz, 1 H), 9.45-9.55 (m, 1 H) |
| 165 | (360 MHz, DMSO-d$_6$) δ ppm 1.06 (d, J = 6.2 Hz, 3 H), 2.15 (s, 3 H), 3.84 (dd, J = 13.9, 2.9 Hz, 1 H), 3.93-4.10 (m, 1 H), 4.56-4.80 (m, 2 H), 5.19 (d, J = 15.4 Hz, 1 H), 7.19 (dd, J = 7.7, 1.8 Hz, 1 H), 7.39-7.50 (m, 2 H), 7.83 (dd, J = 7.9, 1.6 Hz, 1 H), 7.94 (s, 1 H), 8.00-8.12 (m, 2 H), 8.27 (s, 1 H) |
| 168 | (300 MHz, DMSO-d$_6$) δ ppm 1.62 (d, J = 7.1 Hz, 3 H), 2.15 (s, 3 H), 3.35-3.51 (m, 1 H), 3.61-3.84 (m, 1 H), 4.06-4.30 (m, 2 H), 5.93 (q, J = 7.0 Hz, 1 H), 7.11 (d, J = 7.8 Hz, 1 H), 7.33-7.55 (m, 2 H), 7.73-7.95 (m, 3 H), 8.18-8.33 (m, 1 H) |
| 169 | (300 MHz, DMSO-d$_6$) δ ppm 1.33 (d, J = 7.0 Hz, 3 H), 2.15 (s, 3 H), 3.40-3.78 (m, 4 H), 3.78-3.91 (m, 1 H), 4.10-4.18 (m, 2 H), 6.98 (d, J = 7.7 Hz, 1 H), 7.38 (s, 1 H), 7.76 (d, J = 7.8 Hz, 1 H), 7.94 (s, 1 H), 8.06 (s, 2 H), 8.23 (s, 1 H) |
| 171 | (300 MHz, DMSO-d$_6$) δ ppm 1.14 (d, J = 6.6 Hz, 3 H), 1.42-1.77 (m, 6 H), 2.35 (s, 3 H), 2.83 (t, J = 5.2 Hz, 4 H), 3.90-4.09 (m, 2 H), 4.50 (d, J = 15.9 Hz, 1 H), 4.57-4.72 (m, 1 H), 5.10 (d, J = 15.9 Hz, 1 H), 7.15-7.39 (m, 2 H), 7.49 (s, 1 H), 7.64 (d, J = 8.2 Hz, 1 H), 7.81-7.96 (m, 1 H), 8.13 (d, J = 7.7 Hz, 1 H), 9.42-9.68 (m, 1 H) |
| 172 | (300 MHz, DMSO-d$_6$) δ ppm 1.26 (d, J = 6.7 Hz, 3 H), 2.15 (s, 3 H), 3.05-3.15 (m, 2 H), 3.55-3.77 (m, 2 H), 3.80-3.97 (m, 1 H), 4.21-4.35 (m, 1 H), 4.88-5.08 (m, 1 H), 6.94 (d, J = 7.8 Hz, 1 H), 7.33-7.45 (m, 1 H), 7.74 (d, J = 7.7 Hz, 1 H), 7.91 (s, 1 H), 8.01 (s, 2 H), 8.19-8.28 (m, 1 H) |
| 187 | (360 MHz, DMSO-d$_6$) δ ppm 1.13 (d, J = 6.6 Hz, 3 H), 1.66 (d, J = 7.0 Hz, 3 H), 2.11-2.18 (m, 3 H), 3.07 (dd, J = 14.1, 3.8 Hz, 1 H), 3.68-3.80 (m, 1 H), 4.49 (dd, J = 13.9, 1.5 Hz, 1 H), 6.00 (q, J = 7.0 Hz, 1 H), 7.18 (d, J = 7.7 Hz, 1 H), 7.38-7.45 (m, 2 H), 7.52 (d, J = 7.3 Hz, 1 H), 7.66 (d, J = 1.8 Hz, 1 H), 7.83 (d, J = 7.7 Hz, 1 H), 8.24 (d, J = 1.5 Hz, 1 H), 11.48 (d, J = 1.8 Hz, 1 H) |
| 188 | (360 MHz, DMSO-d$_6$) δ ppm 0.25 (d, J = 6.6 Hz, 3 H), 1.65 (d, J = 7.0 Hz, 3 H), 2.10-2.17 (m, 3 H), 3.78 (dd, J = 13.9, 3.7 Hz, 1 H), 4.10 (ddd, J = 6.3, 3.9, 1.8 Hz, 1 H), 4.56-4.66 (m, 1 H), 6.10 (q, J = 7.1 Hz, 1 H), 7.22 (d, J = 7.7 Hz, 1 H), 7.36-7.44 (m, 2 H), 7.54 (d, J = 7.3 Hz, 1 H), 7.63 (d, J = 1.8 Hz, 1 H), 7.82 (d, J = 7.7 Hz, 1 H), 8.25 (d, J = 1.1 Hz, 1 H), 11.43 (d, J = 1.8 Hz, 1 H) |
| 189 | (360 MHz, DMSO-d$_6$) δ ppm 1.13 (d, J = 7.0 Hz, 3 H), 1.64 (d, J = 7.0 Hz, 3 H), 2.14 (s, 3 H), 3.10 (dd, J = 13.7, 3.8 Hz, 1 H), 3.68-3.77 (m, 1 H), 3.80 (s, 3 H), 4.49 (dd, J = 13.7, 1.6 Hz, 1 H), 5.99 (q, J = 7.0 Hz, 1 H), 7.17 (d, J = 7.7 Hz, 1 H), 7.41 (s, 1 H), 7.52 (d, J = 7.3 Hz, 1 H), 7.62 (d, J = 10.2 Hz, 1 H), 7.66 (s, 1 H), 7.83 (d, J = 7.7 Hz, 1 H), 8.24 (d, J = 1.1 Hz, 1 H) |
| 190 | (360 MHz, DMSO-d$_6$) δ ppm 0.29 (d, J = 6.6 Hz, 3 H), 1.65 (d, J = 7.0 Hz, 3 H), 2.15 (s, 3 H), 3.72-3.83 (m, 4 H), 4.04-4.14 (m, 1 H), 4.56-4.65 (m, 1 H), 6.07 (q, J = 6.8 Hz, 1 H), 7.22 (d, J = 8.1 Hz, 1 H), 7.41 (t, J = 1.1 Hz, 1 H), 7.55 (d, J = 7.3 Hz, 1 H), 7.58-7.65 (m, 2 H), 7.82 (d, J = 8.1 Hz, 1 H), 8.26 (d, J = 1.1 Hz, 1 H) |
| 191 | (360 MHz, DMSO-d$_6$) δ ppm 1.13 (d, J = 7.0 Hz, 3 H), 1.38 (t, J = 7.3 Hz, 3 H), 1.65 (d, J = 7.3 Hz, 3 H), 2.16 (s, 3 H), 3.09 (dd, J = 13.9, 3.7 Hz, 1 H), 3.74 (dt, J = 4.6, 2.1 Hz, 1 H), 4.14-4.27 (m, 2 H), 4.50 (dd, J = 13.7, 1.6 Hz, 1 H), 5.99 (q, J = 6.8 Hz, 1 H), 7.18 (d, J = 7.7 Hz, 1 H), 7.45 (s, 1 H), 7.52 (d, J = 7.3 Hz, 1 H), 7.68 (d, J = 10.6 Hz, 1 H), 7.73 (s, 1 H), 7.85 (d, J = 7.7 Hz, 1 H), 8.35 (s, 1 H) |
| 192 | (360 MHz, DMSO-d$_6$) δ ppm 0.27 (d, J = 6.6 Hz, 3 H), 1.34 (t, J = 7.1 Hz, 3 H), 1.65 (d, J = 7.0 Hz, 3 H), 2.14 (s, 3 H), 3.79 (dd, J = 13.9, 3.7 Hz, 1 H), 4.05-4.15 (m, 1 H), 4.20 (q, J = 7.1 Hz, 2 H), 4.57-4.66 (m, 1 H), 6.09 (q, J = 7.0 Hz, 1 H), 7.22 (d, J = 7.7 Hz, 1 H), 7.41 (s, 1 H), 7.55 (d, J = 7.3 Hz, 1 H), 7.64-7.72 (m, 2 H), 7.82 (d, J = 7.7 Hz, 1 H), 8.22-8.29 (m, 1 H) |
| 193 | (360 MHz, DMSO-d$_6$) δ ppm 1.14 (d, J = 6.6 Hz, 3 H), 1.45 (d, J = 6.6 Hz, 3 H), 1.51 (d, J = 6.6 Hz, 3 H), 1.66 (d, J = 7.0 Hz, 3 H), 2.14 (d, J = 0.7 Hz, 3 H), 3.06 (dd, J = 13.9, 3.7 Hz, 1 H), 3.68-3.81 (m, 1 H), 4.50 (dd, J = 14.1, 1.6 Hz, 1 H), 4.74 (quin, J = 6.7 Hz, 1 H), 6.01 (q, J = 7.2 Hz, 1 H), 7.17 (d, J = 7.7 Hz, 1 H), 7.40 (s, 1 H), 7.51 (d, J = 7.7 Hz, 1 H), 7.71 (d, J = 11.0 Hz, 1 H), 7.79-7.86 (m, 2 H), 8.24 (d, J = 1.1 Hz, 1 H) |
| 194 | (360 MHz, DMSO-d$_6$) δ ppm 0.24 (d, J = 6.6 Hz, 3 H), 1.46 (d, J = 4.4 Hz, 3 H), 1.44 (d, J = 4.4 Hz, 3 H), 1.67 (d, J = 7.0 Hz, 3 H), 2.14 (s, 3 H), 3.79 (dd, J = 13.7, 3.5 Hz, 1 H), 4.05-4.16 (m, 1 H), 4.55-4.66 (m, 1 H), 4.74 (quin, J = 6.7 Hz, 1 H), 6.11 (q, J = 7.1 Hz, 1 H), 7.21 (d, J = 7.7 Hz, 1 H), 7.41 (s, 1 H), 7.56 (d, J = 7.3 Hz, 1 H), 7.70 (d, J = 11.0 Hz, 1 H), 7.77-7.85 (m, 2 H), 8.26 (d, J = 1.1 Hz, 1 H) |
| 204 | (360 MHz, CHLOROFORM-d) δ ppm 0.97 (d, J = 6.6 Hz, 3 H), 2.24 (ddd, J = 14.5, 9.3, 4.8 Hz, 1 H), 2.32 (s, 3 H), 2.61-2.73 (m, 1 H), 3.03-3.13 (m, 1 H), 3.22-3.33 (m, 1 H), 3.74-3.89 (m, 2 H), 4.82-4.88 (m, 1 H), 6.11 (dd, J = 8.8, 5.1 Hz, 1 H), 7.17 (br. s, 1 H), 7.32 (d, J = 7.7 Hz, 1 H), 7.42 (d, J = 8.4 Hz, 1 H), 7.51-7.59 (m, 3 H) 8.43 (br. s., 1 H) |

TABLE 2b-continued

| $^1$H NMR results | |
|---|---|
| Co. No. | $^1$H NMR result |
| 205 | (400 MHz, CHLOROFORM-d, 55° C.) δ ppm 1.27-1.31 (m, 3 H), 2.21 (dd, J = 13.3, 8.5 Hz, 1 H), 2.33 (s, 3 H), 2.61-2.65 (m, 1 H), 3.03 (d, J = 8.1 Hz, 1 H), 3.08-3.22 (m, 1 H), 3.61 (dd, J = 14.1, 4.0 Hz, 1 H), 3.64-3.73 (m, 1 H), 4.76-4.86 (m, 1 H), 6.22 (t, J = 8.1 Hz, 1 H), 7.19 (s, 1 H), 7.30 (d, J = 7.7 Hz, 1 H), 7.38 (s, 1 H), 7.43 (d, J = 7.7 Hz, 1 H), 7.52 (d, J = 7.7 Hz, 1 H), 7.54-7.60 (m, 1 H), 8.45 (s, 1 H) |
| 206 | (600 MHz, CHLOROFORM-d) δ ppm 1.17 (d, J = 6.7 Hz, 3 H), 2.28 (d, J = 1.0 Hz, 3 H), 3.10 (dd, J = 16.1, 6.2 Hz, 1 H), 3.18 (dd, J = 16.1, 6.4 Hz, 1 H), 3.28-3.39 (m, 2 H), 3.69 (dd, J = 13.9, 4.0 Hz, 1 H), 3.88-3.98 (m, 1 H), 4.79-4.87 (m, 1 H), 5.25-5.33 (m, 1 H), 7.14 (t, J = 1.2 Hz, 1 H), 7.18-7.24 (m, 2 H), 7.24-7.30 (m, 3 H), 7.46 (d, J = 7.6 Hz, 1 H), 8.21-8.25 (m, 1 H) |
| 207 | The NMR spectrum of 207 matches the one of compound 206 |
| 210 | (400 MHz, DMSO-$d_6$) δ ppm 1.17 (d, J = 6.5 Hz, 3 H), 1.62 (d, J = 6.9 Hz, 3 H), 2.15 (s, 3 H), 3.63 (dd, J = 13.9, 3.8 Hz, 1 H), 3.98 (br. s., 1 H), 4.61 (dd, J = 13.7, 1.6 Hz, 1 H), 5.64 (q, J = 6.9 Hz, 1 H), 7.09 (d, J = 7.7 Hz, 1 H), 7.42 (s, 1 H), 7.48 (d, J = 2.0 Hz, 2 H), 7.55 (t, J = 1.8 Hz, 1 H), 7.81 (d, J = 7.7 Hz, 1 H), 8.27 (s, 1 H) |
| 211 | (400 MHz, DMSO-$d_6$) δ ppm 0.75 (d, J = 6.5 Hz, 3 H), 1.66 (d, J = 7.3 Hz, 3 H), 2.15 (s, 3 H), 3.87 (dd, J = 14.1, 4.0 Hz, 1 H), 4.19-4.30 (m, 1 H), 4.64 (dd, J = 13.9, 1.8 Hz, 1 H), 5.56 (q, J = 6.9 Hz, 1 H), 7.11 (d, J = 7.7 Hz, 1 H), 7.42 (s, 1 H), 7.50 (d, J = 1.6 Hz, 2 H), 7.58 (t, J = 1.6 Hz, 1 H), 7.81 (d, J = 7.7 Hz, 1 H), 8.27 (d, J = 1.2 Hz, 1 H) |
| 212 | (360 MHz, CHLOROFORM-d) δ ppm 1.23 (s, 3 H), 1.77 (d, J = 7.0 Hz, 3 H), 2.28 (s, 3 H), 3.11 (dd, J = 13.9, 3.7 Hz, 1 H), 3.70 (ddd, J = 6.5, 4.1, 1.8 Hz, 1 H), 4.57 (dd, J = 14.1, 2.0 Hz, 1 H), 6.26-6.36 (m, 1 H), 7.13 (s, 1 H), 7.37 (d, J = 7.7 Hz, 1 H), 7.42 (s, 1 H), 7.44-7.54 (m, 3 H), 7.77 (s, 1 H), 8.22 (d, J = 1.1 Hz, 1 H), 8.87 (br. s., 1 H) |
| 213 | (360 MHz, CHLOROFORM-d) δ ppm 0.43 (d, J = 6.6 Hz, 3 H), 1.74 (d, J = 7.0 Hz, 3 H), 2.28 (s, 3 H), 3.65 (dd, J = 13.9, 3.7 Hz, 1 H), 3.96 (ddd, J = 6.7, 4.1, 2.0 Hz, 1 H), 4.83 (dd, J = 13.9, 1.8 Hz, 1 H), 6.40 (q, J = 7.1 Hz, 1 H), 7.12 (s, 1 H), 7.36-7.40 (m, 1 H), 7.40 (d, J = 2.6 Hz, 1 H), 7.45-7.51 (m, 3 H), 7.96 (s, 1 H), 8.15-8.29 (m, 1 H), 8.52 (br. s., 1 H) |
| 214 | (360 MHz, CHLOROFORM-d) δ ppm 1.24 (d, J = 6.6 Hz, 3 H), 1.75 (d, J = 7.0 Hz, 3 H), 2.28 (d, J = 0.7 Hz, 3 H), 3.11 (dd, J = 13.9, 4.0 Hz, 1 H), 3.65-3.76 (m, 1 H), 3.88 (s, 3 H), 4.57 (dd, J = 14.1, 2.0 Hz, 1 H), 6.29 (q, J = 6.8 Hz, 1 H), 7.13 (t, J = 1.1 Hz, 1 H), 7.25 (d, J = 0.7 Hz, 1 H), 7.36 (d, J = 7.7 Hz, 1 H), 7.39-7.44 (m, 1 H), 7.47-7.53 (m, 2 H), 7.73-7.77 (m, 1 H), 8.20 (d, J = 1.1 Hz, 1 H) |
| 215 | (360 MHz, CHLOROFORM-d) δ ppm 0.45 (d, J = 7.0 Hz, 3 H), 1.72 (d, J = 7.3 Hz, 3 H), 2.30 (s, 3 H), 3.65 (dd, J = 13.5, 3.7 Hz, 1 H), 3.87 (s, 3 H), 3.90-4.01 (m, 1 H), 4.82 (dd, J = 13.9, 1.8 Hz, 1 H), 6.35 (q, J = 6.8 Hz, 1 H), 7.11 (br. s., 1 H), 7.24 (s, 1 H), 7.34-7.42 (m, 2 H), 7.44-7.53 (m, 2 H), 7.92 (s, 1 H), 8.29 (s, 1 H) |
| 216 | (360 MHz, CHLOROFORM-d) δ ppm 1.24 (d, J = 6.6 Hz, 3 H), 1.54 (t, J = 7.3 Hz, 3 H), 1.75 (d, J = 7.0 Hz, 3 H), 2.28 (d, J = 0.7 Hz, 3 H), 3.12 (dd, J = 13.9, 3.7 Hz, 1 H), 3.64-3.74 (m, 1 H), 4.21-4.30 (m, 2 H), 4.57 (dd, J = 14.1, 2.0 Hz, 1 H), 6.23-6.33 (m, 1 H), 7.13 (s, 1 H), 7.30 (s, 1 H), 7.36 (d, J = 7.7 Hz, 1 H), 7.41-7.52 (m, 3 H), 7.75 (s, 1 H), 8.20 (s, 1 H) |
| 217 | (360 MHz, CHLOROFORM-d) δ ppm 0.42 (d, J = 6.6 Hz, 3 H), 1.50 (t, J = 7.3 Hz, 3 H), 1.72 (d, J = 7.0 Hz, 3 H), 2.28 (d, J = 0.7 Hz, 3 H), 3.65 (dd, J = 13.9, 3.7 Hz, 1 H), 3.95 (td, J = 4.2, 1.8 Hz, 1 H), 4.23 (q, J = 7.3 Hz, 2 H), 4.83 (dd, J = 13.7, 1.6 Hz, 1 H), 6.37 (q, J = 7.2 Hz, 1 H), 7.12 (s, 1 H), 7.29 (s, 1 H), 7.34-7.44 (m, 2 H), 7.44-7.52 (m, 2 H), 7.94 (s, 1 H), 8.22 (s, 1 H) |
| 218 | (360 MHz, DMSO-$d_6$) δ ppm 1.13 (d, J = 6.6 Hz, 3 H), 1.67 (d, J = 7.0 Hz, 3 H), 2.14 (s, 3 H), 3.04 (dd, J = 13.9, 3.7 Hz, 1 H), 3.71-3.80 (m, 1 H), 4.49 (dd, J = 13.9, 1.5 Hz, 1 H), 6.01 (q, J = 7.0 Hz, 1 H), 7.12 (dd, J = 11.0, 1.5 Hz, 1 H), 7.18 (d, J = 8.1 Hz, 1 H), 7.27 (d, J = 1.8 Hz, 1 H), 7.41 (s, 1 H), 7.75 (d, J = 2.2 Hz, 1 H), 7.83 (d, J = 7.7 Hz, 1 H), 8.24 (d, J = 1.1 Hz, 1 H), 11.83-12.05 (m, 1 H) |
| 219 | (360 MHz, DMSO-$d_6$) δ ppm 0.26 (d, J = 6.6 Hz, 3 H), 1.67 (d, J = 7.3 Hz, 3 H), 2.14 (s, 3 H), 3.79 (dd, J = 13.7, 3.5 Hz, 1 H), 4.05-4.16 (m, 1 H), 4.55-4.67 (m, 1 H), 6.10 (q, J = 6.8 Hz, 1 H), 7.11 (dd, J = 10.8, 1.6 Hz, 1 H), 7.21 (d, J = 7.7 Hz, 1 H), 7.31 (d, J = 1.8 Hz, 1 H), 7.41 (s, 1 H), 7.72 (d, J = 2.2 Hz, 1 H), 7.82 (d, J = 7.7 Hz, 1 H), 8.26 (d, J = 1.1 Hz, 1 H), 11.95 (d, J = 2.2 Hz, 1 H) |
| 220 | (360 MHz, DMSO-$d_6$) δ ppm 1.14 (d, J = 6.6 Hz, 3 H), 1.40 (t, J = 7.1 Hz, 3 H), 1.65 (d, J = 7.3 Hz, 3 H), 2.17 (s, 3 H), 3.08 (dd, J = 13.9, 3.7 Hz, 1 H), 3.71-3.80 (m, 1 H), 4.27-4.37 (m, 2 H), 4.50 (dd, J = 13.7, 1.6 Hz, 1 H), 5.98 (q, J = 7.0 Hz, 1 H), 7.14 (dd, J = 12.3, 1.6 Hz, 1 H), 7.19 (d, J = 7.7 Hz, 1 H), 7.26 (d, J = 1.8 Hz, 1 H), 7.49 (s, 1 H), 7.78 (s, 1 H), 7.88 (d, J = 7.7 Hz, 1 H), 8.46 (s, 1 H) |
| 221 | (360 MHz, DMSO-$d_6$) δ ppm 0.28 (d, J = 6.6 Hz, 3 H), 1.36 (t, J = 7.1 Hz, 3 H), 1.65 (d, J = 7.3 Hz, 3 H), 2.15 (s, 3 H), 3.80 (dd, J = 14.1, 3.8 Hz, 1 H), 4.10 (dt, J = 4.5, 2.3 Hz, 1 H), 4.31 (q, J = 7.4 Hz, 2 H), 4.53-4.67 (m, 1 H), 6.07 (q, J = 7.3 Hz, 1 H), 7.13 (dd, J = 12.1, 1.8 Hz, 1 H), 7.21 (d, J = 7.7 Hz, 1 H), 7.31 (d, J = 1.5 Hz, 1 H), 7.43 (s, 1 H), 7.75 (s, 1 H), 7.83 (d, J = 7.7 Hz, 1 H), 8.32 (s, 1 H) |

TABLE 2b-continued

| $^1$H NMR results | |
|---|---|
| Co. No. | $^1$H NMR result |
| 223 | (360 MHz, DMSO-$d_6$) δ ppm 1.13 (d, J = 6.6 Hz, 3 H), 1.64 (d, J = 7.0 Hz, 3 H), 2.14 (s, 3 H), 3.08 (dd, J = 14.1, 3.8 Hz, 1 H), 3.70-3.82 (m, 1 H), 3.97 (d, J = 2.2 Hz, 3 H), 4.50 (dd, J = 13.9, 1.8 Hz, 1 H), 5.97 (q, J = 7.0 Hz, 1 H), 7.12 (dd, J = 12.1, 1.8 Hz, 1 H), 7.17 (d, J = 7.7 Hz, 1 H), 7.24 (d, J = 1.5 Hz, 1 H), 7.41 (s, 1 H), 7.70 (s, 1 H), 7.83 (d, J = 7.7 Hz, 1 H), 8.25 (d, J = 1.1 Hz, 1 H) |
| 224 | (360 MHz, DMSO-$d_6$) δ ppm 0.31 (d, J = 6.6 Hz, 3 H), 1.64 (d, J = 7.0 Hz, 3 H), 2.15 (s, 3 H), 3.79 (dd, J = 13.9, 3.7 Hz, 1 H), 3.96 (d, J = 1.8 Hz, 3 H), 4.03-4.13 (m, 1 H), 4.62 (d, J = 15.0 Hz, 1 H), 6.05 (q, J = 7.1 Hz, 1 H), 7.12 (dd, J = 12.1, 1.8 Hz, 1 H), 7.21 (d, J = 7.7 Hz, 1 H), 7.29 (d, J = 1.8 Hz, 1 H), 7.42 (s, 1 H), 7.67 (s, 1 H), 7.82 (d, J = 7.7 Hz, 1 H), 8.28 (s, 1 H) |
| 243 | (360 MHz, CHLOROFORM-d) δ ppm 0.45 (d, J = 6.6 Hz, 3 H), 1.48 (t, J = 7.3 Hz, 3 H), 1.69 (d, J = 7.3 Hz, 3 H), 2.28 (s, 3 H), 3.63 (dd, J = 13.7, 3.8 Hz, 1 H), 3.88-4.00 (m, 1 H), 4.18 (q, J = 7.1 Hz, 2 H), 4.82 (dd, J = 14.1, 1.6 Hz, 1 H), 6.30 (q, J = 6.7 Hz, 1 H), 7.12 (s, 1 H), 7.18 (dd, J = 8.8, 1.8 Hz, 1 H), 7.23 (d, J = 10.2 Hz, 2 H), 7.37 (d, J = 7.7 Hz, 1 H), 7.49 (d, J = 7.7 Hz, 1 H), 7.60 (d, J = 1.5 Hz, 1 H), 8.22 (s, 1 H) |
| 244 | (360 MHz, CHLOROFORM-d) δ ppm 1.25 (d, J = 7.0 Hz, 3 H), 1.56 (t, J = 7.3 Hz, 3 H), 1.75 (d, J = 7.0 Hz, 3 H), 2.28 (s, 3 H), 3.09 (dd, J = 13.9, 3.7 Hz, 1 H), 3.64-3.74 (m, 1 H), 4.26 (qd, J = 7.2, 2.9 Hz, 2 H), 4.53 (dd, J = 13.9, 1.8 Hz, 1 H), 6.33 (q, J = 7.2 Hz, 1 H), 7.13 (s, 1 H), 7.29 (d, J = 7.3 Hz, 1 H), 7.33 (s, 1 H), 7.35 (d, J = 8.1 Hz, 1 H), 7.49 (d, J = 7.7 Hz, 1 H), 7.52 (d, J = 8.4 Hz, 1 H), 7.64 (s, 1 H), 8.19 (d, J = 0.7 Hz, 1 H) |
| 245 | (360 MHz, DMSO-$d_6$) δ ppm 1.14 (d, J = 6.6 Hz, 3 H), 1.68 (d, J = 7.3 Hz, 3 H), 2.30 (d, J = 0.7 Hz, 3 H), 3.07 (dd, J = 13.9, 3.7 Hz, 1 H), 3.72-3.83 (m, 1 H), 4.42-4.54 (m, 1 H), 6.02 (q, J = 7.0 Hz, 1 H), 7.12 (dd, J = 8.6, 2.0 Hz, 1 H), 7.28 (d, J = 8.1 Hz, 1 H), 7.40 (d, J = 1.8 Hz, 1 H), 7.43 (d, J = 8.8 Hz, 1 H), 7.68 (d, J = 2.2 Hz, 1 H), 7.80 (s, 1 H), 8.08 (d, J = 7.7 Hz, 1 H), 9.34 (s, 1 H), 11.47 (s, 1 H) |
| 276 | (360 MHz, CHLOROFORM-d) δ ppm 0.45 (d, J = 7.0 Hz, 3 H), 1.71 (d, J = 7.0 Hz, 3 H), 2.42-2.50 (m, 3 H), 3.69 (dd, J = 13.9, 3.7 Hz, 1 H), 3.91-4.04 (m, 1 H), 4.79 (dd, J = 14.1, 1.6 Hz, 1 H), 6.30 (q, J = 6.8 Hz, 1 H), 7.17 (dd, J = 8.6, 2.0 Hz, 1 H), 7.25 (m, 1 H), 7.32 (d, J = 8.8 Hz, 1 H), 7.35 (d, J = 2.2 Hz, 1 H), 7.43 (d, J = 8.1 Hz, 1 H), 7.57 (d, J = 1.8 Hz, 1 H), 7.70 (d, J = 7.7 Hz, 1 H), 8.65 (br. s., 1 H), 9.12 (s, 1 H) |
| 247 | (360 MHz, CHLOROFORM-d) δ ppm 0.59-0.76 (m, 2 H), 0.83-1.00 (m, 2 H), 1.19 (d, J = 7.0 Hz, 3 H), 1.46 (t, J = 7.3 Hz, 3 H), 1.92-2.08 (m, 1 H), 2.28 (s, 3 H), 3.54 (dd, J = 14.3, 4.0 Hz, 1 H), 3.90 (ddd, J = 6.7, 4.3, 2.2 Hz, 1 H), 4.14 (q, J = 7.3 Hz, 2 H), 4.30 (d, J = 15.0 Hz, 1 H), 4.64-4.77 (m, 1 H), 5.50 (d, J = 14.6 Hz, 1 H), 6.98 (dd, J = 8.4, 1.8 Hz, 1 H), 7.10-7.17 (m, 2 H), 7.26 (d, J = 7.3 Hz, 1 H), 7.31-7.39 (m, 2 H), 7.48 (d, J = 7.7 Hz, 1 H), 8.22 (s, 1 H) |
| 248 | (360 MHz, CHLOROFORM-d) δ ppm 0.45 (d, J = 6.6 Hz, 3 H), 0.97-1.04 (m, H), 1.08-1.16 (m, 2 H), 1.66 (d, J = 7.0 Hz, 3 H), 2.28 (s, 3 H), 3.32 (tt, J = 6.9, 3.7 Hz, 1 H), 3.63 (dd, J = 13.9, 4.0 Hz, 1 H), 3.84-3.97 (m, 1 H), 4.82 (dd, J = 13.7, 1.6 Hz, 1 H), 6.25 (q, J = 7.0 Hz, 1 H), 7.13 (s, 1 H), 7.19 (d, J = 1.1 Hz, 1 H), 7.31 (d, J = 9.1 Hz, 1 H), 7.37 (d, J = 7.7 Hz, 1 H), 7.49 (d, J = 7.7 Hz, 1 H), 7.60 (d, J = 7.3 Hz, 1 H), 8.23 (s, 1 H) |
| 249 | (360 MHz, CHLOROFORM-d) δ ppm 1.23 (d, J = 6.6 Hz, 3 H), 1.51 (t, J = 7.1 Hz, 3 H), 1.72 (d, J = 7.0 Hz, 3 H), 2.28 (s, 3 H), 3.17 (dd, J = 13.9, 3.7 Hz, 1 H), 3.65-3.76 (m, 1 H), 4.19 (qd, J = 7.3, 2.0 Hz, 2 H), 4.56 (dd, J = 13.9, 1.8 Hz, 1 H), 6.22 (q, J = 7.0 Hz, 1 H), 7.14 (s, 1 H), 7.16-7.22 (m, 2 H), 7.28 (d, J = 9.0 Hz, 1 H), 7.35 (d, J = 7.7 Hz, 1 H), 7.41 (d, J = 1.8 Hz, 1 H), 7.49 (d, J = 7.7 Hz, 1 H), 8.20 (s, 1 H) |
| 256 | (360 MHz, CHLOROFORM-d) δ ppm 0.47 (d, J = 6.6 Hz, 3 H), 1.66 (d, J = 7.0 Hz, 3 H), 2.28 (s, 3 H), 3.63 (dd, J = 13.7, 3.8 Hz, 1 H), 3.78 (s, 3 H), 3.87-3.98 (m, 4 H), 4.81 (dd, J = 13.7, 1.6 Hz, 1 H), 6.21-6.31 (m, 1 H), 6.77 (s, 1 H), 7.04 (s, 1 H), 7.13 (s, 1 H), 7.37 (d, J = 7.7 Hz, 1 H), 7.49 (d, J = 7.7 Hz, 1 H), 7.60 (s, 1 H), 8.22 (s, 1 H) |

SFC-MS

For SFC-MS, an analytical SFC system from Berger Instruments (Newark, Del., USA) was used comprising a dual pump control module (FCM-1200) for delivery of $CO_2$ and modifier, a thermal control module for column heating (TCM2100) with temperature control in the range 1-150° C. and column selection valves (Valco, VICI, Houston, Tex., USA) for 6 different columns. The photodiode array detector (Agilent 1100, Waldbronn, Germany) is equipped with a high-pressure flow cell (up to 400 bar) and configured with a CTC LC Mini PAL auto sampler (Leap Technologies, Carrboro, N.C., USA). A ZQ mass spectrometer (Waters, Milford, Mass., USA) with an orthogonal Z-electrospray interface is coupled with the SFC-system. Instrument control, data collection and processing were performed with an integrated platform consisting of the SFC ProNTo software and Masslynx software.

Co. No. 11a-11b: SFC-MS was carried out on a OD-H column (500×4.6 mm) (Daicel Chemical Industries Ltd) with a flow rate of 3 ml/min. Two mobile phases (mobile phase A: $CO_2$; mobile phase B: MeOH containing 0.2% $iPrNH_2$) were employed. First 30% B was hold for 18.5 min. Then a gradient was applied from 30% B to 50% B in 2 min and hold for 4.1 min. Column temperature was set at 50° C. Under these conditions, Co. No. 11a ('enantiomer A') had a shorter retention time ($R_t$) on the column than Co. No. 11b ('enantiomer B'). The measurement was compared against the racemic mixture.

Co. No. 14a-14b: SFC-MS was carried out on a OD-H column (250×4.6 mm) (Daicel Chemical Industries Ltd) with a flow rate of 3 ml/min. Two mobile phases (mobile phase A: $CO_2$; mobile phase B: MeOH containing 0.2% $iPrNH_2$) were employed. 20% B was hold for 15 min. Column temperature was set at 30° C. Under these conditions, Co. No. 14a ('Cis A') had a shorter $R_t$ on the column than Co. No. 14b ('Cis B'). The measurement was compared against the mixture of the compounds.

Co. No. 111-112: SFC-MS was carried out on a AD-H column (250×4.6 mm) (Daicel Chemical Industries Ltd) with a flow rate of 3 ml/min. Two mobile phases (mobile phase A: $CO_2$; mobile phase B: MeOH containing 0.2% $iPrNH_2$) were employed. 8% B was hold for 15 min. Column temperature was set at 30° C. Under these conditions, Co. No. 111 (diastereomer A') had a shorter $R_t$ on the column than Co. No. 112 (diastereomer B'). The measurement was compared against the mixture of the compounds.

Co. No. 129-130: SFC-MS was carried out on a AD-H column (250×4.6 mm) (Daicel Chemical Industries Ltd) with a flow rate of 3 ml/min. Two mobile phases (mobile phase A: $CO_2$; mobile phase B: EtOH containing 0.2% $iPrNH_2$) were employed. 25% B was hold for 15 min. Column temperature was set at 30° C. Under these conditions, Co. No. 130 (diastereomer A') had a shorter $R_t$ on the column than Co. No. 129 (diastereomer B'). The measurement was compared against the mixture of the compounds.

Co. No. 183-184: SFC-MS was carried out on an OD-H column (250×4.6 mm) (Daicel Chemical Industries Ltd) with a flow rate of 3 ml/min. Two mobile phases (mobile phase A: $CO_2$; mobile phase B: EtOH containing 0.2% $iPrNH_2$) were employed. 35% B was hold for 15 min. Column temperature was set at 30° C. Under these conditions, Co. No. 183 ('enantiomer A') had a shorter $R_t$ on the column than Co. No. 184 ('enantiomer B'). The measurement was compared against the racemic mixture.

Co. No. 185-186: The same SFC-MS conditions as for Co. No. 183-184 were used. Under these conditions, Co. No. 185 ('enantiomer A') had a shorter $R_t$ on the column than Co. No. 186 ('enantiomer B'). The measurement was compared against the racemic mixture.

Co. No. 206-207: SFC-MS was carried out on a OJ-H column (250×4.6 mm) (Daicel Chemical Industries Ltd) with a flow rate of 3 ml/min. Two mobile phases (mobile phase A: $CO_2$; mobile phase B: MeOH containing 0.2% $iPrNH_2$) were employed. First 25% B was hold for 18 min. Then a gradient was applied from 25% B to 50% B in 2.5 min, and 50% B was hold for 4.1 min. Column temperature was set at 30° C. Under these conditions, Co. No. 207 ('enantiomer A') had a shorter retention time ($R_t$) on the column than Co. No. 206 ('enantiomer B'). The measurement was compared against the racemic mixture.

Co. No. 208-209: SFC-MS was carried out on a OD-H column (250×4.6 mm) (Daicel Chemical Industries Ltd) with a flow rate of 3 ml/min. Two mobile phases (mobile phase A: $CO_2$; mobile phase B: MeOH containing 0.2% $iPrNH_2$) were employed. 35% B was hold for 15 min. Column temperature was set at 30° C. Under these conditions, Co. No. 209 ('enantiomer A') had a shorter retention time ($R_t$) on the column than Co. No. 208 ('enantiomer B'). The measurement was compared against the racemic mixture.

Co. No. 212-213: SFC-MS was carried out on a AD-H column (250×4.6 mm) (Daicel Chemical Industries Ltd) with a flow rate of 3 ml/min. Two mobile phases (mobile phase A: $CO_2$; mobile phase B: MeOH containing 0.2% $iPrNH_2$) were employed. 30% B was hold for 15 min. Column temperature was set at 40° C. Under these conditions, Co. No. 212 ('enantiomer A') had a shorter retention time ($R_t$) on the column than Co. No. 213 ('enantiomer B'). The measurement was compared against the racemic mixture.

Co. No. 236-237: SFC-MS was carried out on a OJ-H column (250×4.6 mm) (Daicel Chemical Industries Ltd) with a flow rate of 5 ml/min. Two mobile phases (mobile phase A: $CO_2$; mobile phase B: MeOH containing 0.2% $iPrNH_2$) were employed. 25% B was hold for 7 min. Column temperature was set at 40° C. Under these conditions, Co. No. 236 had a shorter $R_t$ on the column than Co. No. 237. The measurement was compared against the mixture of the compounds.

Co. No. 265-266: SFC-MS was carried out on a AD-H column (250×4.6 mm) (Daicel Chemical Industries Ltd) with a flow rate of 5 ml/min. Two mobile phases (mobile phase A: $CO_2$; mobile phase B: EtOH (containing 0.2% $iPrNH_2$) were employed. 35% B was hold for 4 min, increased up to 50% B in 1 min and hold for 2 min at 50% B. Column temperature was set at 40° C. Under these conditions, Co. No. 265 ('enantiomer A') had a shorter $R_t$ on the column than Co. No. 266 ('enantiomer B'). The measurement was compared against the mixture.

Co. No. 267-268: SFC-MS was carried out on a AD-H column (250×4.6 mm) (Daicel Chemical Industries Ltd) with a flow rate of 5 ml/min. Two mobile phases (mobile phase A: $CO_2$; mobile phase B: EtOH (containing 0.2% $iPrNH_2$) were employed. 40% B was hold for 4 min, increased up to 50% B in 1 min and hold for 2 min at 50% B. Column temperature was set at 40° C. Under these conditions, Co. No. 267 ('enantiomer A') had a shorter $R_t$ on the column than Co. No. 268 ('enantiomer B'). The measurement was compared against the mixture.

Co. No. 271-272: SFC-MS was carried out on a OD-H column (250×4.6 mm) (Daicel Chemical Industries Ltd) with a flow rate of 5 ml/min. Two mobile phases (mobile phase A: $CO_2$; mobile phase B: EtOH (containing 0.2% $iPrNH_2$) were employed. 35% B was hold for 4 min, increased up to 50% B in 1 min and hold for 2 min at 50% B. Column temperature was set at 40° C. Under these conditions, Co. No. 271 ('enantiomer A') had a shorter $R_t$ on the column than Co. No. 272 ('enantiomer B'). The measurement was compared against the mixture.

Co. No. 273-274: SFC-MS was carried out on a AD-H column (250×4.6 mm) (Daicel Chemical Industries Ltd) with a flow rate of 5 ml/min. Two mobile phases (mobile phase A: $CO_2$; mobile phase B: EtOH (containing 0.2% $iPrNH_2$) were employed. 35% B was hold for 4 min, increased up to 50% B in 1 min and hold for 2 min at 50% B. Column temperature was set at 40° C. Under these conditions, Co. No. 273 ('enantiomer A') had a shorter $R_t$ on the column than Co. No. 274 ('enantiomer B'). The measurement was compared against the mixture.

Co. No. 295-296: SFC-MS was carried out on a OD-H column (250×4.6 mm) (Daicel Chemical Industries Ltd) with a flow rate of 5 ml/min. Two mobile phases (mobile phase A: $CO_2$; mobile phase B: EtOH (containing 0.2% $iPrNH_2$) were employed. 40% B was hold for 4 min, increased up to 50% B in 1 min and hold for 2 min at 50% B. Column temperature was set at 40° C. Under these conditions, Co. No. 295 ('enantiomer A') had a shorter $R_t$ on the column than Co. No. 296 ('enantiomer B'). The measurement was compared against the mixture.

Pharmacology

A) Screening of the Compounds of the Invention for γ-Secretase-Modulating Activity Screening was carried out using SKNBE2 human neuroblastoma cells carrying the hAPP 695—wild type, grown in Dulbecco's Modified Eagle's Medium/Nutrient mixture F-12

(DMEM/NUT-mix F-12) (HAM) provided by Invitrogen (cat no. 10371-029) containing 5% Serum/Fe supplemented with 1% non-essential amino acids, 1-glutamine 2 mM, Hepes 15 mM, penicillin 50 U/ml (units/ml) en streptomycin 50 μg/ml. Cells were grown to near confluency.

The screening was performed using a modification of the assay as described in Citron et al (1997) Nature Medicine 3: 67. Briefly, cells were plated in a 384-well plate at $10^4$ cells/well in Ultraculture (Lonza, BE12-725F) supplemented with 1% glutamine (Invitrogen, 25030-024), 1% non-essential amino acid (NEAA), penicillin 50 U/ml en streptomycin 50 μg/ml in the presence of test compound at different test concentrations. The cell/compound mixture was incubated overnight at 37° C., 5% $CO_2$. The next day the media were assayed by two sandwich immuno-assays, for Aβ42 and Aβ total.

Aβtotal and Aβ42 concentrations were quantified in the cell supernatant using the Aphalisa technology (Perkin Elmer). Alphalisa is a sandwich assay using biotinylated antibody attached to streptavidin coated donorbeads and antibody conjugated to acceptor beads. In the presence of antigen, the beads come into close proximity. The excitation of the donor beads provokes the release of singlet oxygen molecules that trigger a cascade of energy transfer in the acceptor beads, resulting in light emission. To quantify the amount of Aβ42 in the cell supernatant, monoclonal antibody specific to the C-terminus of Aβ42 (JRF/cAβ42/26) was coupled to the receptor beads and biotinylated antibody specific to the N-terminus of Aβ (JRF/AβN/25) was used to react with the donor beads. To quantify the amount of Aβtotal in the cell supernatant, monoclonal antibody specific to the N-terminus of Aβ (JRF/AβN/25) was coupled to the receptor beads and biotinylated antibody specific to the mid region of Aβ (biotinylated 4G8) was used to react with the donor beads.

To obtain the values reported in Table 3, the data are calculated as percentage of the maximum amount of amyloid Beta 42 measured in the absence of the test compound. The sigmoidal dose response curves were analyzed using non-linear regression analysis with percentage of the control plotted against the log concentration of the compound. A 4-parameter equation was used to determine the $IC_{50}$.

TABLE 3

| Co. No. | IC50 Aβ42 (μM) | IC50 Aβtotal (μM) |
|---|---|---|
| 112 | 0.07 | >10 |
| 104 | >10 | >10 |
| 57 | >10 | >10 |
| 41 | >10 | >10 |
| 102 | >10 | >10 |
| 17 | >10 | >10 |
| 16 | >10 | >10 |
| 122 | >10 | >10 |
| 89 | >10 | >10 |
| 119 | >10 | >10 |
| 86 | 0.03 | >10 |
| 117 | 0.04 | >10 |
| 110 | 0.04 | >10 |
| 50 | 0.04 | >10 |
| 111 | 0.07 | >10 |
| 85 | 0.06 | >10 |
| 78 | 0.07 | >10 |
| 6 | 0.07 | >10 |
| 4 | 0.08 | >10 |
| 4a | 0.07 | >10 |
| 90 | 0.07 | >10 |
| 116 | 0.08 | >10 |
| 5 | 0.08 | >10 |
| 80 | 0.10 | >10 |
| 3 | 0.10 | >10 |

TABLE 3-continued

| Co. No. | IC50 Aβ42 (μM) | IC50 Aβtotal (μM) |
|---|---|---|
| 82 | 0.11 | >10 |
| 1 | 0.11 | >10 |
| 92 | 0.13 | >10 |
| 62 | 0.13 | >10 |
| 115 | 0.14 | >10 |
| 7 | 0.14 | >10 |
| 46 | 0.14 | >10 |
| 10a | 0.14 | >10 |
| 23 | 0.14 | >10 |
| 99 | 0.17 | >10 |
| 2 | 0.17 | >10 |
| 59 | 0.18 | >10 |
| 118 | 0.19 | >10 |
| 77 | 0.19 | >10 |
| 76 | 0.19 | >10 |
| 72 | 0.19 | >10 |
| 123 | 0.19 | >10 |
| 63 | 0.19 | >10 |
| 68 | 0.19 | >10 |
| 53 | 0.21 | >10 |
| 81 | 0.22 | >10 |
| 10 | 0.22 | >10 |
| 84 | 0.23 | >10 |
| 47 | 0.26 | >10 |
| 29 | 0.27 | >10 |
| 71 | 0.28 | >10 |
| 79 | 0.28 | >10 |
| 28 | 0.28 | >10 |
| 38 | 0.33 | 3.63 |
| 65 | 0.37 | >10 |
| 9b | 0.38 | >10 |
| 121 | 0.38 | >10 |
| 74 | 0.38 | >10 |
| 113 | 0.40 | >10 |
| 97 | 0.44 | >10 |
| 61 | 0.48 | >10 |
| 94 | 0.49 | >10 |
| 34 | 0.49 | >10 |
| 51 | 0.5 | >10 |
| 36 | 0.51 | >10 |
| 40 | 0.51 | >10 |
| 45 | 0.54 | >10 |
| 67 | 0.56 | >10 |
| 70 | 0.58 | >10 |
| 48 | 0.58 | >10 |
| 27 | 0.59 | >10 |
| 43 | 0.62 | >10 |
| 44 | 0.63 | >10 |
| 14b | 0.65 | >10 |
| 60 | 0.66 | >10 |
| 11a | 0.66 | >10 |
| 9 | 0.68 | >10 |
| 64 | 0.69 | >10 |
| 106 | 0.72 | >10 |
| 101 | 0.74 | >10 |
| 42 | 0.74 | >10 |
| 100 | 0.76 | >10 |
| 96 | 0.76 | >10 |
| 58 | 0.83 | >10 |
| 91 | 0.91 | >6.03 |
| 8 | 0.93 | >10 |
| 39 | 0.95 | >10 |
| 52 | 0.98 | >10 |
| 75 | 0.98 | >10 |
| 69 | 1.02 | >10 |
| 35 | 1.02 | >10 |
| 24 | 1.10 | >10 |
| 37 | 1.15 | >10 |
| 54 | 1.26 | >10 |
| 83 | 1.35 | >10 |
| 20 | 1.55 | >10 |
| 31 | 1.62 | >10 |
| 33 | 1.66 | >10 |
| 26 | 1.66 | >10 |
| 25 | 1.70 | >10 |
| 18 | 1.70 | >10 |

TABLE 3-continued

| Co. No. | IC50 Aβ42 (μM) | IC50 Aβtotal (μM) |
|---|---|---|
| 56 | 1.70 | >10 |
| 14a | 1.78 | >10 |
| 88 | 1.86 | >10 |
| 114 | 1.91 | >10 |
| 21 | 1.95 | >10 |
| 30 | 2.04 | >10 |
| 109 | 2.09 | >10 |
| 15 | 2.29 | >10 |
| 107 | 2.45 | >10 |
| 103 | 2.45 | >10 |
| 73 | 2.57 | >10 |
| 22 | 2.57 | >10 |
| 105 | 2.82 | >10 |
| 98 | 2.88 | >10 |
| 49 | 3.39 | >10 |
| 55 | 3.80 | >10 |
| 66 | 3.89 | >10 |
| 9a | 4.47 | >10 |
| 108 | 4.79 | >10 |
| 120 | 6.17 | >10 |
| 10b | 6.61 | >10 |
| 93 | 6.76 | >10 |
| 19 | 6.76 | >10 |
| 95 | 7.59 | >10 |
| 87 | 7.76 | >10 |
| 11b | 7.76 | >10 |
| 32 | 9.55 | 9.77 |
| 14 | n.d. | n.d. |
| 13 | n.d. | n.d. |
| 12 | n.d. | n.d. |
| 124 | 2.34 | >10 |
| 125 | 0.05 | >10 |
| 126 | 0.11 | >10 |
| 127 | 0.18 | >10 |
| 128 | 0.09 | >10 |
| 129 | 0.11 | >10 |
| 130 | 0.16 | >10 |
| 131 | 0.20 | >10 |
| 132 | 2.14 | >10 |
| 133 | 1.51 | >10 |
| 134 | 0.10 | >10 |
| 135 | 0.02 | >10 |
| 136 | 0.04 | >10 |
| 137 | 0.03 | >10 |
| 138 | 0.04 | >10 |
| 139 | 0.95 | >10 |
| 140 | 0.06 | >10 |
| 141 | 0.11 | >10 |
| 142 | 0.21 | >10 |
| 143 | 0.06 | >10 |
| 144 | 0.13 | >10 |
| 145 | 0.11 | >10 |
| 146 | 0.15 | >10 |
| 147 | 0.33 | >10 |
| 148 | 0.14 | >10 |
| 149 | 0.30 | >10 |
| 150 | n.d. | n.d. |
| 151 | 0.03 | >10 |
| 152 | 0.07 | >10 |
| 153 | 0.06 | >10 |
| 154 | 0.05 | >10 |
| 155 | 0.51 | >10 |
| 156 | 0.03 | >10 |
| 157 | 2.04 | 8.71 |
| 158 | 0.46 | >10 |
| 159 | 0.28 | >10 |
| 160 | 0.19 | >10 |
| 161 | 0.79 | >10 |
| 163 | 0.17 | >10 |
| 164 | 0.03 | >10 |
| 165 | 0.02 | >10 |
| 166 | 0.05 | >10 |
| 167 | 1.20 | >10 |
| 168 | 1.41 | >10 |
| 169 | 0.13 | >10 |
| 170 | 0.17 | >10 |

TABLE 3-continued

| Co. No. | IC50 Aβ42 (μM) | IC50 Aβtotal (μM) |
|---|---|---|
| 171 | 0.04 | >10 |
| 172 | 0.25 | >10 |
| 175 | 0.14 | >10 |
| 176 | 1.55 | >10 |
| 177 | 0.04 | >10 |
| 178 | n.d. | n.d. |
| 179 | 0.07 | >10 |
| 180 | 0.01 | 6.61 |
| 181 | 0.01 | 4.57 |
| 182 | 0.01 | 2.51 |
| 183 | 0.03 | 6.76 |
| 184 | 0.65 | 9.12 |
| 185 | 0.02 | 5.89 |
| 186 | 0.78 | >10 |
| 187 | 0.19 | 6.92 |
| 188 | 0.01 | 4.57 |
| 189 | 0.22 | 10 |
| 190 | 0.01 | 3.31 |
| 191 | 0.20 | >10 |
| 192 | 0.01 | 1.82 |
| 193 | 0.20 | >10 |
| 194 | 0.01 | 1.55 |
| 195 | 0.03 | 6.46 |
| 196 | 0.02 | 7.41 |
| 197 | 0.06 | >10 |
| 198 | n.d. | n.d. |
| 199 | 0.02 | 9.78 |
| 200 | 0.02 | >10 |
| 201 | n.d. | n.d. |
| 202 | n.d. | n.d. |
| 203 | n.d. | n.d. |
| 204 | 0.12 | >10 |
| 205 | 0.24 | >10 |
| 206 | >10 | >10 |
| 207 | 0.93 | >10 |
| 208 | 3.89 | >10 |
| 209 | 0.38 | >10 |
| 210 | 0.26 | >10 |
| 211 | 0.09 | >10 |
| 212 | n.d. | n.d. |
| 213 | n.d. | n.d. |
| 214 | 0.24 | 6.46 |
| 215 | 0.01 | 1.44 |
| 216 | 0.12 | 6.46 |
| 217 | 0.003 | 0.48 |
| 218 | 0.14 | 3.80 |
| 219 | 0.02 | 3.09 |
| 220 | 0.17 | 6.03 |
| 221 | 0.005 | 0.79 |
| 222 | 0.06 | >10 |
| 223 | 0.22 | 6.61 |
| 224 | 0.01 | 1.86 |
| 225 | 0.02 | >10 |
| 226 | 0.01 | 4.79 |
| 227 | 0.01 | 2.19 |
| 228 | 0.05 | >10 |
| 229 | 0.13 | >10 |
| 230 | 0.21 | >10 |
| 231 | 0.26 | >10 |
| 232 | 0.21 | >10 |
| 233 | 0.26 | >10 |
| 234 | n.d. | n.d. |
| 235 | 0.01 | 6 |
| 236 | n.d. | n.d. |
| 237 | n.d. | n.d. |
| 238 | 0.009 | 4 |
| 239 | n.d. | n.d. |
| 240 | n.d. | n.d. |
| 241 | 0.006 | 4 |
| 162 | 0.10 | >10 |
| 173 | 1.26 | >10 |
| 174 | 0.01 | 5 |
| 242 | 0.26 | >10 |
| 243 | 0.01 | 2 |
| 244 | 0.37 | >10 |
| 245 | 0.93 | 7 |

TABLE 3-continued

| Co. No. | IC50 Aβ42 (μM) | IC50 Aβtotal (μM) |
|---|---|---|
| 246 | 0.02 | 7 |
| 247 | 0.01 | 6 |
| 248 | 0.008 | 1 |
| 249 | 0.49 | 8 |
| 250 | 0.05 | >10 |
| 251 | 0.02 | 6 |
| 252 | 0.01 | 5 |
| 253 | 0.009 | 5 |
| 254 | 0.02 | 6 |
| 255 | 0.01 | 3 |
| 256 | 0.04 | 4 |
| 257 | 0.04 | >10 |
| 258 | 0.02 | 9 |
| 259 | 0.02 | 6 |
| 260 | 0.03 | 10 |
| 261 | 0.06 | >10 |
| 262 | 0.02 | >10 |
| 263 | n.d. | n.d. |

("n.d." means not determined)

B) Demonstration of In Vivo Efficacy

B-1) Aβ42

Aβ42 lowering agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ42 lowering agents can be administered in any standard form using any standard method. For example, but not limited to, Aβ42 lowering agents can be in the form of liquid, tablets or capsules that are taken orally or by injection. Aβ42 lowering agents can be administered at any dose that is sufficient to significantly reduce levels of Aβ42 in the blood, blood plasma, serum, cerebrospinal fluid (CSF), or brain.

To determine whether acute administration of an Aβ42 lowering agent would reduce Aβ42 levels in vivo, non-transgenic rodents, e.g. mice or rats were used. Animals treated with the Aβ42 lowering agent were examined and compared to those untreated or treated with vehicle and brain levels of soluble Aβ42 and total Aβ were quantitated by standard techniques, for example, using ELISA. Treatment periods varied from hours (h) to days and were adjusted based on the results of the Aβ42 lowering once a time course of onset of effect could be established.

A typical protocol for measuring Aβ42 lowering in vivo is shown but it is only one of many variations that could be used to optimize the levels of detectable Aβ. For example, Aβ42 lowering compounds were formulated in 20% of Captisol® (a sulfobutyl ether of β-cyclodextrin) in water or 20% hydroxypropyl β cyclodextrin. The Aβ42 lowering agents were administered as a single oral dose or by any acceptable route of administration to overnight fasted animals. After 4 h, the animals were sacrificed and Aβ42 levels were analysed.

Blood was collected by decapitation and exsanguinations in EDTA-treated collection tubes. Blood was centrifuged at 1900 g for 10 minutes (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains from non-transgenic animals were resuspended in 8 volumes of 0.4% DEA (diethylamine)/50 mM NaCl containing protease inhibitors (Roche-11873580001 or 04693159001) per gram of tissue, e.g. for 0.158 g brain, add 1.264 ml of 0.4% DEA. All samples were homogenized in the FastPrep-24 system (MP Biomedicals) using lysing matrix D (MPBio #6913-100) at 6 m/s for 20 seconds. Homogenates were centrifuged at 221.300×g for 50 min. The resulting high speed supernatants were then transferred to fresh eppendorf tubes. Nine parts of supernatant were neutralized with 1 part 0.5 M Tris-HCl pH 6.8 and used to quantify Aβtotal and Aβ42.

To quantify the amount of Aβtotal and Aβ42 in the soluble fraction of the brain homogenates, Enzyme-Linked-Immunosorbent-Assays were used. Briefly, the standards (a dilution of synthetic Aβ1-40 and Aβ1-42, Bachem) were prepared in 1.5 ml Eppendorf tube in Ultraculture, with final concentrations ranging from 10000 to 0.3 pg/ml. The samples and standards were co-incubated with HRPO-labelled N-terminal antibody for Aβ42 detection and with the biotinylated mid-domain antibody 4G8 for Aβtotal detection. 50 μl of conjugate/sample or conjugate/standards mixtures were then added to the antibody-coated plate (the capture antibodies selectively recognize the C-terminal end of Aβ42, antibody JRF/cAβ42/26, for Aβ42 detection and the N-terminus of Aβ, antibody JRF/rAβ/2, for Aβtotal detection). The plate was allowed to incubate overnight at 4° C. in order to allow formation of the antibody-amyloid complex. Following this incubation and subsequent wash steps the ELISA for Aβ42 quantification was finished by addition of Quanta Blu fluorogenic peroxidase substrate according to the manufacturer's instructions (Pierce Corp., Rockford, Ill.). A reading was performed after 10 to 15 min (excitation 320 nm/emission 420 nm).

For Aβtotal detection, a Streptavidine-Peroxidase-Conjugate was added, followed 60 min later by an additional wash step and addition of Quanta Blu fluorogenic peroxidase substrate according to the manufacturer's instructions (Pierce Corp., Rockford, Ill.). A reading was performed after 10 to 15 min (excitation 320 nm/emission 420 nm).

In this model a Aβ42 lowering compared to untreated animals would be advantageous, in particular a Aβ42 lowering with at least 10%, more in particular a Aβ42 lowering with at least 20%.

B-2) Aβ38

Aβ38 increasing agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ38 increasing agents can be administered in any standard form using any standard method. For example, but not limited to, Aβ38 increasing agents can be in the form of liquid, tablets or capsules that are taken orally or by injection. Aβ38 increasing agents can be administered at any dose that is sufficient to significantly increase levels of Aβ38 in the blood, plasma, serum, cerebrospinal fluid (CSF), or brain.

To determine whether acute administration of an Aβ38 increasing agents would increase Aβ38 levels in vivo, non-transgenic rodents, e.g. mice or rats were used. Animals treated with the Aβ38 increasing agents were examined and compared to those untreated or treated with vehicle and brain levels of soluble Aβ38 and total Aβ were quantitated by standard techniques, for example, using ELISA. Treatment periods varied from hours (h) to days and were adjusted based on the results of the Aβ38 increase once a time course of onset of effect could be established.

A typical protocol for measuring Aβ38 increase in vivo is shown but it is only one of many variations that could be used to optimize the levels of detectable Aβ. For example, Aβ38 increasing agents were formulated in 20% of Captisol® (a sulfobutyl ether of β-cyclodextrin) in water or 20% hydroxypropyl βcyclodextrin. The Aβ38 increasing agents were administered as a single oral dose or by any acceptable route of administration to overnight fasted animals. After 4 h, the animals were sacrificed and Aβ38 levels were analysed.

Blood was collected by decapitation and exsanguinations in EDTA-treated collection tubes. Blood was centrifuged at 1900 g for 10 minutes (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains from non-transgenic animals were resuspended in 8 volumes of 0.4% DEA (diethylamine)/50 mM NaCl containing protease inhibitors (Roche-11873580001 or 04693159001) per gram of tissue, e.g. for 0.158 g brain, add 1.264 ml of 0.4% DEA. All samples were homogenized in the FastPrep-24 system (MP Biomedicals) using lysing matrix D (MPBio #6913-100) at 6 m/s for 20 seconds. Homogenates were centrifuged at 221.300×g for 50 min. The resulting high speed supernatants were then transferred to fresh eppendorf tubes. Nine parts of supernatant were neutralized with 1 part 0.5 M Tris-HCl pH 6.8 and used to quantify Aβ total and Aβ38.

To quantify the amount of Aβtotal and Aβ38 in the soluble fraction of the brain homogenates, Enzyme-Linked-Immunosorbent-Assays were used. Briefly, the standards (a dilution of synthetic Aβ1-40 and Aβ1-38, ANASPEC) were prepared in 1.5 ml Eppendorf tube in Ultraculture, with final concentrations ranging from 10000 to 0.3 pg/ml. The samples and standards were co-incubated with HRPO-labelled N-terminal antibody for Aβ38 detection and with the biotinylated mid-domain antibody 4G8 for Aβtotal detection. 50 μl of conjugate/sample or conjugate/standards mixtures were then added to the antibody-coated plate (the capture antibodies selectively recognize the C-terminal end of Aβ38, antibody J&JPRD/Aβ38/5, for Aβ38 detection and the N-terminus of Aβ, antibody JRF/rAβ/2, for Aβtotal detection). The plate was allowed to incubate overnight at 4° C. in order to allow formation of the antibody-amyloid complex. Following this incubation and subsequent wash steps the ELISA for Aβ38 quantification was finished by addition of Quanta Blu fluorogenic peroxidase substrate according to the manufacturer's instructions (Pierce Corp., Rockford, Ill.). A reading was performed after 10 to 15 min (excitation 320 nm/emission 420 nm).

For Aβtotal detection, a Streptavidine-Peroxidase-Conjugate was added, followed 60 min later by an additional wash step and addition of Quanta Blu fluorogenic peroxidase substrate according to the manufacturer's instructions (Pierce Corp., Rockford, Ill.). A reading was performed after 10 to 15 min (excitation 320 nm/emission 420 nm).

In this model a Aβ38 increase compared to untreated animals would be advantageous, in particular a Aβ38 increase with at least 10%, more in particular a Aβ38 increase with at least 20%.

B-3) Results

The results are shown in Table 4 (dose 30 mg/kg oral dosing) (value for untreated animals as control (Ctrl) was set at 100):

| Co. No. | Aβ38 (% vs Ctrl)_Mean | Aβ42 (% vs Ctrl)_Mean | Aβtotal (% vs Ctrl)_Mean |
|---|---|---|---|
| 6 | 129 | 85 | 102 |
| 7 | 80 | 73 | 94 |
| 10a | 85 | 87 | 118 |
| 63 | 133 | 82 | 124 |
| 59 | 126 | 82 | 126 |
| 65 | 132 | 104 | 114 |
| 3 | 137 | 55 | 98 |
| 99 | 92 | 111 | 113 |
| 22 | 105 | 106 | 92 |
| 2 | 129 | 82 | 100 |
| 37 | 83 | 76 | 98 |
| 5 | 110 | 78 | 87 |
| 23 | 132 | 122 | 122 |
| 1 | 103 | 61 | 89 |
| 62 | 160 | 68 | 98 |
| 46 | 62 | 60 | 87 |
| 92 | 115 | 94 | 96 |
| 78 | 106 | 92 | 98 |
| 50 | 110 | 88 | 91 |
| 80 | 118 | 119 | 119 |
| 82 | 120 | 78 | 125 |

B-1b) Aβ42

Aβ42 lowering agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ42 lowering agents can be administered in any standard form using any standard method. For example, but not limited to, Aβ42 lowering agents can be in the form of liquid, tablets or capsules that are taken orally or by injection. Aβ42 lowering agents can be administered at any dose that is sufficient to significantly reduce levels of Aβ42 in the blood, blood plasma, serum, cerebrospinal fluid (CSF), or brain.

To determine whether acute administration of an Aβ42 lowering agent would reduce Aβ42 levels in vivo, non-transgenic rodents, e.g. mice or rats were used. Animals treated with the Aβ42 lowering agent were examined and compared to those untreated or treated with vehicle and brain levels of soluble Aβ42, Aβ40, Aβ38, and Aβ37 were quantitated by Meso Scale Discovery's (MSD) electrochemiluminescence detection technology. Treatment periods varied from hours (h) to days and were adjusted based on the results of the Aβ42 lowering once a time course of onset of effect could be established.

A typical protocol for measuring Aβ42 lowering in vivo is shown but it is only one of many variations that could be used to optimize the levels of detectable Aβ. For example, Aβ42 lowering compounds were formulated in 20% of Captisol® (a sulfo-butyl ether of β-cyclodextrin) in water or 20% hydroxypropyl βcyclodextrin. The Aβ42 lowering agents were administered as a single oral dose or by any acceptable route of administration to overnight fasted animals. After 4 h, the animals were sacrificed and Aβ42 levels were analysed.

Blood was collected by decapitation and exsanguinations in EDTA-treated collection tubes. Blood was centrifuged at 1900 g for 10 minutes (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains from non-transgenic animals were resuspended in 8 volumes of 0.4% DEA (diethylamine)/50 mM NaCl containing protease inhibitors (Roche-11873580001 or 04693159001) per gram of tissue, e.g. for 0.158 g brain, add 1.264 ml of 0.4% DEA. All samples were homogenized in the FastPrep-24 system (MP Biomedicals) using lysing matrix D (MPBio #6913-100) at 6 m/s for 20 seconds. Homogenates were centrifuged at 20800×g for 5 min and supernatants collected. Supernatants were centrifuged at 221.300×g for 50 min. The resulting high speed supernatants were then transferred to fresh eppendorf tubes. Nine parts of supernatant were neutralized with 1 part 0.5 M Tris-HCl pH 6.8 and used to quantify Aβ.

To quantify the amount of Aβ42, Aβ40, Aβ38, and Aβ37 in the soluble fraction of the brain homogenates, simultaneous specific detection of Aβ42, Aβ40, Aβ38, and Aβ37 was performed using MSD's electro-chemiluminescence multiplex detection technology. In this assay purified monoclonal antibodies specific for Abeta37 (JRD/Aβ37/3), Abeta38 (J&JPRD/Aβ38/5), Abeta40 (JRF/cAβ40/28), and Abeta42 (JRF/cAβ42/26) were coated on MSD 4-plex plates. Briefly, the standards (a dilution of synthetic Aβ42, Aβ40, Aβ38, and Aβ37) were prepared in 1.5 ml Eppendorf tube in Ultraculture, with final concentrations ranging from 10000 to 0.3 pg/m. The samples and standards were co-incubated with Sulfo-tag labelled JRF/rAβ/2 antibody to the N-terminus of Aβ as detector antibody. 50 μl of conjugate/sample or conjugate/standards mixtures were then added to the antibody-coated plate. The plate was allowed to incubate overnight at 4° C. in order to allow formation of the antibody-amyloid complex. Following this incubation and subsequent wash steps the assay was finished by adding read buffer according to the manufacturer's instructions (Meso Scale Discovery, Gaitherburg, Md.).

The SULFO-TAG emits light upon electrochemical stimulation initiated at the electrode. MSD Sector instrument SI6000 was used for signal read-out.

In this model a Aβ42 lowering compared to untreated animals would be advantageous, in particular a Aβ42 lowering with at least 10%, more in particular a Aβ42 lowering with at least 20%.

B-2b) Aβ38

Aβ38 increasing agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ38 increasing agents can be administered in any standard form using any standard method. For example, but not limited to, Aβ38 increasing agents can be in the form of liquid, tablets or capsules that are taken orally or by injection. Aβ38 increasing agents can be administered at any dose that is sufficient to significantly increase levels of Aβ38 in the blood, plasma, serum, cerebrospinal fluid (CSF), or brain.

To determine whether acute administration of an Aβ38 increasing agents would increase Aβ38 levels in vivo, non-transgenic rodents, e.g. mice or rats were used. Animals treated with the Aβ38 increasing agents were examined and compared to those untreated or treated with vehicle and brain levels of soluble Aβ42, Aβ40, Aβ38, and Aβ37 were quantitated by MSD electrochemiluminescence detection technology. Treatment periods varied from hours (h) to days and were adjusted based on the results of the Aβ38 increase once a time course of onset of effect could be established.

A typical protocol for measuring Aβ38 increase in vivo is shown but it is only one of many variations that could be used to optimize the levels of detectable Aβ. For example, Aβ38 increasing agents were formulated in 20% of Captisol® (a sulfobutyl ether of β-cyclodextrin) in water or 20% hydroxypropyl βcyclodextrin. The Aβ38 increasing agents were administered as a single oral dose or by any acceptable route of administration to overnight fasted animals. After 4 h, the animals were sacrificed and Aβ38 levels were analysed.

Blood was collected by decapitation and exsanguinations in EDTA-treated collection tubes. Blood was centrifuged at 1900 g for 10 minutes (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains from non-transgenic animals were resuspended in 8 volumes of 0.4% DEA (diethylamine)/50 mM NaCl containing protease inhibitors (Roche-11873580001 or 04693159001) per gram of tissue, e.g. for 0.158 g brain, add 1.264 ml of 0.4% DEA. All samples were homogenized in the FastPrep-24 system (MP Biomedicals) using lysing matrix D (MPBio #6913-100) at 6 m/s for 20 seconds. Homogenates were centrifuged at 20800×g for 5 min and supernatants collected. Supernatants were centrifuged at 221.300×g for 50 min. The resulting high speed supernatants were then transferred to fresh eppendorf tubes. Nine parts of supernatant were neutralized with 1 part 0.5 M Tris-HCl pH 6.8 and used to quantify Aβ.

To quantify the amount of Aβ42, Aβ40, Aβ38, and Aβ37 in the soluble fraction of the brain homogenates, simultaneous specific detection of Aβ42, Aβ40, Aβ38, and Aβ37 was performed using MSD's electro-chemiluminescence multiplex detection technology. In this assay purified monoclonal antibodies specific for Abeta37 (JRD/Aβ37/3), Abeta38 (J&JPRD/Aβ38/5), Abeta40 (JRF/cAβ40/28), and Abeta42 (JRF/cAβ42/26) were coated on MSD 4-plex plates. Briefly, the standards (a dilution of synthetic Aβ42, Aβ40, Aβ38, and Aβ37) were prepared in 1.5 ml Eppendorf tube in Ultraculture, with final concentrations ranging from 10000 to 0.3 pg/m. The samples and standards were co-incubated with Sulfo-tag labelled JRF/rAβ/2 antibody to the N-terminus of Aβ as detector antibody. 50 μl of conjugate/sample or conjugate/standards mixtures were then added to the antibody-coated plate. The plate was allowed to incubate overnight at 4° C. in order to allow formation of the antibody-amyloid complex. Following this incubation and subsequent wash steps the assay was finished by adding read buffer according to the manufacturer's instructions (MesoScale Discovery, Gaitherburg, Md.).

The SULFO-TAG emits light upon electrochemical stimulation initiated at the electrode. MSD Sector instrument SI6000 was used for signal read-out.

In this model a Aβ38 increase compared to untreated animals would be advantageous, in particular a Aβ38 increase with at least 10%, more in particular a Aβ38 increase with at least 20%.

B-3b) Results

The results are shown in Table 5 (dose 30 mg/kg oral dosing) (value for untreated animals as control (Ctrl) was set at 100):

| Co. No. | Aβ40 (% vs Ctrl)_Mean | Aβ42 (% vs Ctrl)_Mean | Aβ38 (% vs Ctrl)_Mean |
|---|---|---|---|
| 3 | 85 | 51 | 133 |
| 92 | 100 | 87 | 124 |
| 6 | 108 | 73 | 118 |
| 78 | 114 | 89 | 100 |
| 50 | 112 | 99 | 160 |
| 80* | 164 | 148 | 133 |
| 82 | 125 | 103 | 118 |
| 110 | 103 | 88 | 102 |
| 111 | 52 | 35 | 136 |
| 112 | 82 | 55 | 153 |
| 116 | 105 | 75 | 182 |
| 117 | 84 | 66 | 154 |
| 118 | 115 | 92 | 140 |
| 166 | 107 | 64 | 127 |
| 164 | 97 | 80 | 185 |
| 158 | 98 | 97 | 120 |
| 153 | 128 | 100 | 108 |
| 151 | 57 | 41 | 153 |
| 145 | 92 | 71 | 102 |
| 143 | 129 | 123 | 122 |
| 141 | 122 | 85 | 145 |
| 140 | 71 | 42 | 96 |
| 134 | 115 | 97 | 138 |
| 133 | 77 | 87 | 84 |
| 132 | 121 | 104 | 84 |
| 130 | 114 | 67 | 182 |
| 128 | 116 | 60 | 162 |
| 189 | 118 | 116 | 116 |
| 192 | 44 | 39 | 147 |
| 194 | 43 | 39 | 197 |
| 183 | 133 | 97 | 141 |
| 185 | 89 | 68 | 170 |
| 195 | 135 | 105 | 123 |
| 203 | 137 | 67 | 133 |
| 219 | 95 | 76 | 119 |

*For compound 80 the test was not fully validated.

Composition Examples

"Active ingredient" (a.i.) as used throughout these examples relates to a compound of Formula (I), including any tautomer or stereoisomeric form thereof, or a pharmaceutically acceptable addition salt or a solvate thereof; in particular to any one of the exemplified compounds.

Typical examples of recipes for the formulation of the invention are as follows:

1. Tablets

| | |
|---|---|
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| | |
|---|---|
| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

The invention claimed is:

1. A compound of Formula (I)

(I)

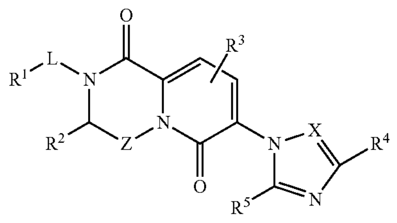

wherein $R^1$ is hydrogen, $C_{1-4}$alkyl or Ar;

provided however that $R^1$ is $C_{1-4}$alkyl or Ar when L is a covalent bond;

$R^2$ is hydrogen, phenyl, cyclo$C_{3-7}$alkyl, tetrahydro-2H-pyranyl, tetrahydro-2H -thiopyranyl, piperidinyl, or $C_{1-4}$alkyl optionally substituted with one or more substituents each independently selected from the group consisting of halo, hydroxy, $C_{1-4}$alkyloxy and $NR^7R^8$;

Z is methylene or 1,2-ethanediyl, wherein methylene or 1,2-ethanediyl is optionally substituted with one or two $C_{1-4}$alkyl substituents ;

L is a covalent bond, $—(CH_2)_{m-n}—Y—(CH_2)_n—$, 1,2-cyclopropanediyl, $C_{1-6}$alkanediyl optionally substituted with one or more substituents selected from the group consisting of tetrahydro-2H-pyranyl, phenyl and $C_{1-4}$alkyloxy$C_{1-4}$alkyl, or $C_{1-6}$alkanediyl wherein two geminal hydrogen atoms are replaced by $C_{2-6}$alkanediyl;

m is 3, 4, 5, 6 or 7;

n is 1, 2 or 3;

Y is O or NH;

Ar is a ring system selected from the group consisting of phenyl, indolyl, oxazolyl, benzo[b]thienyl, 1,3-benzodioxolyl, 1,4-benzodioxanyl, 3,4-dihydro-2H-1,5-benzodioxepinyl, pyridyl, indanyl, 1,2,3,4-tetrahydro-1-naphthalenyl, and naphthalenyl;

wherein said ring system is optionally substituted with one or more substituents each independently selected from the group consisting of halo, $Ar^2$, $R^0$, $C_{1-4}$alkyl optionally substituted with one or more substituents each independently selected from the group consisting of halo, $C_{1-4}$alkyloxy and cyclo$C_{3-7}$alkyl, and $C_{1-4}$alkyloxy optionally substituted with one or more substituents each independently selected from the group consisting of halo and cyclo$C_{3-7}$alkyl;

$Ar^2$ is phenyl optionally substituted with one or more substituents each independently selected from the group consisting of halo and $C_{1-4}$alkyl optionally substituted with one or more halo substituents;

$R^3$ is hydrogen, halo or $C_{1-4}$alkyl;

$R^4$ is hydrogen, halo or $C_{1-4}$alkyl;

$R^5$ is hydrogen or $C_{1-4}$alkyl;

X is $CR^6$ or N;

$R^6$ is hydrogen or $C_{1-4}$alkyl;

$R^7$ is hydrogen or $C_{1-4}$alkyl;

$R^8$ is hydrogen or $C_{1-4}$alkyl; and, $R^0$ is a ring system selected from the group consisting of piperidinyl, morpholinyl, cyclo$C_{3-7}$alkyl, pyrazolyl and pyrrolidinyl; wherein said ring system is optionally substituted with one or more substituents each independently selected from the group consisting of halo or $C_{1-4}$alkyl optionally substituted with one or more halo atoms;

or a tautomer, stereoisomer or pharmaceutically acceptable addition salt thereof.

2. The compound according to claim 1, wherein $R^2$ is hydrogen, phenyl, cyclo$C_{3-7}$alkyl, tetrahydro-2H-pyranyl, or $C_{1-4}$alkyl optionally substituted with one or more substituents each independently selected from the group consisting of hydroxy, $C_{1-4}$alkyloxy and $NR^7R^8$;

m is 3;

n is 2;

Y is 0;

$R^3$ is hydrogen or halo;

$R^4$ is hydrogen, halo or $C_{1-4}$alkyl;

$R^8$ is $C_{1-4}$alkyl; and, $R^0$ is a ring system selected from the group consisting of piperidinyl, morpholinyl, cyclo$C_{3-7}$alkyl, pyrazolyl and pyrrolidinyl; wherein said ring system is optionally substituted with one or more $C_{1-4}$alkyl groups optionally substituted with one or more halo atoms.

3. The compound according to claim 1, wherein $R^1$ is Ar.

4. The compound according to claim 1, wherein X is CH.

5. The compound according to claim 1, wherein n is 1 or 2.

6. The compound according to claim 1, wherein $R^1$ is Ar;

$R^2$ is hydrogen or $C_{1-4}$alkyl;

Z is methylene;

L is a $C_{1-6}$alkanediyl;

Ar is a ring system selected from the group consisting of phenyl optionally substituted with one or more substituents each independently selected from the group consisting of halo, $Ar^2$, $R^0$, $C_{1-4}$alkyl optionally substituted with one or more substituents each independently selected from the group consisting of halo, $C_{1-4}$alkyloxy and cyclo$C_{3-7}$alkyl, and $C_{1-4}$alkyloxy optionally substituted with one or more substituents each independently selected from the group consisting of halo and cyclo$C_{3-7}$alkyl;

$Ar^2$ is phenyl optionally substituted with one or more substituents each independently selected from the group consisting of halo and $C_{i-4}$alkyl optionally substituted with one or more halo substituents;

$R^3$ is hydrogen;

$R^4$ is $C_{1-4}$alkyl;

$R^5$ is hydrogen;

X is CH; and, $R^0$ is a ring system selected from the group consisting of piperidinyl, morpholinyl, cyclo$C_{3-7}$alkyl, pyrazolyl and pyrrolidinyl; wherein said ring system is optionally substituted with one or more substituents each independently selected from the group consisting of halo or $C_{1-4}$alkyl optionally substituted with one or more halo atoms.

7. The compound according to claim 1, wherein

L is a covalent bond, 1,2-cyclopropanediyl, $C_{1-6}$alkanediyl optionally substituted with one or more substituents selected from the group consisting of tetrahydro-2H-pyranyl, phenyl and $C_{1-4}$alkyloxy$C_{1-4}$alkyl, or $C_{1-6}$alkanediyl wherein two geminal hydrogen atoms are replaced by $C_{2-6}$alkanediyl.

8. The compound according to claim 1, wherein

L is a covalent bond or $C_{1-6}$alkanediyl;

$R^1$ is Ar; and,

Ar is indolyl optionally substituted with one or more substituents each independently selected from the group consisting of halo, $Ar^2$, $R^0$, $C_{1-4}$alkyl optionally substituted with one or more substituents each independently selected from the group consisting of halo, $C_{1-4}$alkyloxy and cyclo$C_{3-7}$alkyl, and $C_{1-4}$alkyloxy optionally substituted with one or more substituents each independently selected from the group consisting of halo and cyclo$C_{3-7}$alkyl.

9. The compound according to claim 1, wherein $R^2$ is $C_{1-4}$alkyl and L is $C_{1-6}$alkanediyl.

10. The compound according to claim 1, wherein the position of $R^3$ is fixed as shown in formula (I-x)

(I-x)

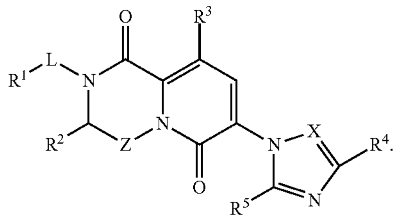

11. The compound according to claim 1, wherein the compound is selected from the group consisting of 2-[1-[1-ethyl-5-(trifluoromethyl)-1H-indol-3-yl]ethyl]-3,4-dihydro-3-methyl-7-(4-methyl-1H-imidazol-1-yl)-2H-pyrido[1,2-a]pyrazine-1,6-dione, and, 2-[1-(5-chloro-1-ethyl-7-fluoro-1H-indol-3-yl)ethyl]-3,4-dihydro-3-methyl-7-(4-methyl-1H-imidazol-1-yl)-2H-pyrido[1,2-a]pyrazine-1,6-dione, or a tautomer, stereoisomer or pharmaceutically acceptable addition salt thereof.

12. A pharmaceutical composition comprising a therapeutically effective amount of a compound according to claim 1 and a pharmaceutically acceptable carrier.

13. A method for treating a disease or condition in a subject selected from the group consisting of Alzheimer's disease, traumatic brain injury, mild cognitive impairment, senility, dementia, dementia with Lewy bodies, cerebral amyloid angiopathy, multi-infarct dementia, dementia pugilistica, Down's syndrome, dementia associated with Parkinson's disease and dementia associated with beta-amyloid, comprising administering to said subject a therapeutically effective amount of a compound according to claim 1.

14. The method according to claim 13, wherein the disease is Alzheimer's disease.

* * * * *